(12) United States Patent
Sauerberg et al.

(10) Patent No.: US 10,266,577 B2
(45) Date of Patent: Apr. 23, 2019

(54) GLP-1 DERIVATIVES, AND USES THEREOF

(71) Applicant: Novo Nordisk A/S, Bagsvaerd (DK)

(72) Inventors: Per Sauerberg, Farum (DK); Jacob Kofoed, Vaerloese (DK)

(73) Assignee: Novo Nordisk A/S, Bagsvaerd (DK)

( * ) Notice: Subject to any disclaimer, the term of this patent is extended or adjusted under 35 U.S.C. 154(b) by 72 days.

(21) Appl. No.: 14/909,543

(22) PCT Filed: Aug. 14, 2014

(86) PCT No.: PCT/EP2014/067413
§ 371 (c)(1),
(2) Date: Feb. 2, 2016

(87) PCT Pub. No.: WO2015/022400
PCT Pub. Date: Feb. 19, 2015

(65) Prior Publication Data
US 2016/0200791 A1  Jul. 14, 2016

Related U.S. Application Data

(60) Provisional application No. 61/866,169, filed on Aug. 15, 2013.

(30) Foreign Application Priority Data

Aug. 15, 2013 (EP) ..................... 13180558

(51) Int. Cl.
| | | |
|---|---|---|
| *A61K 38/00* | (2006.01) | |
| *A61K 47/54* | (2017.01) | |
| *A61K 47/58* | (2017.01) | |
| *A61K 47/60* | (2017.01) | |
| *C07K 14/605* | (2006.01) | |

(52) U.S. Cl.
CPC ............ *C07K 14/605* (2013.01); *A61K 47/54* (2017.08); *A61K 47/58* (2017.08); *A61K 47/60* (2017.08); *A61K 38/00* (2013.01)

(58) Field of Classification Search
None
See application file for complete search history.

(56) References Cited

U.S. PATENT DOCUMENTS

| | | | |
|---|---|---|---|
| 2010/0016229 A1 | 1/2010 | Sarubbi | |
| 2013/0288960 A1* | 10/2013 | Madsen | A61K 47/542 514/7.2 |
| 2015/0133374 A1* | 5/2015 | Kofoed | A61K 38/26 514/7.2 |

FOREIGN PATENT DOCUMENTS

| | | |
|---|---|---|
| CN | 1232470 A | 10/1999 |
| WO | 00/07617 A1 | 2/2000 |
| WO | 02/098348 A2 | 12/2002 |
| WO | 03/072195 A2 | 9/2003 |
| WO | 2005/027978 A2 | 3/2005 |
| WO | 2006097537 A2 | 9/2006 |
| WO | 2008/028974 A1 | 3/2008 |
| WO | 2011/080103 A1 | 7/2011 |
| WO | 2012062803 A1 | 5/2012 |
| WO | 2012062804 A1 | 5/2012 |
| WO | 2012140117 A1 | 10/2012 |

OTHER PUBLICATIONS

Wermuth, et al "Glossary of Terms used in Medicinal Chemistry," Pure and Appl. Chem., vol. 70, No. 5, pp. 1129-1143, (1998). (Year: 1998).*
Knudsen, L et al. "Potent derivatives of glucagon-like peptide-1 with pharmacokinetic properties suitable for once daily administration." Journal of Medicinal Chemistry 2000 vol. 43 (9) pp. 1664-1669.

* cited by examiner

*Primary Examiner* — Thomas S Heard
(74) *Attorney, Agent, or Firm* — Jianjie Hu

(57) ABSTRACT

The present invention relates to tri-acylated GLP-1 derivatives, acylated at positions corresponding to positions (18, 22, 30), (18, 26, 37), (18, 27, 37), (26, 30, 37), or (27, 30, 37) of the native human glucagon-like peptide 1 (GLP-1 (7-37) (SEQ ID NO: 1); or pharmaceutically acceptable salts, amides, or esters thereof. The acylated side chains comprise a protracting moiety selected from Chem. 1: HOOC—$(CH_2)_{16}$—CO—*, Chem. 1a: HOOC—$(CH_2)_{18}$—CO—*, and Chem. 2: $HO_3S$—$(CH_2)_{15}$—CO—*, and the protracting moieties are connected, via a linker, to a Lys residue of the GLP-1 peptide. The GLP-1 peptide has a maximum of seven amino acid changes as compared to GLP-1 (7-37) (SEQ ID NO: 1). The invention also relates to intermediate products in the form of novel GLP-1 analogs, as well as to pharmaceutical compositions and uses of the derivatives and analogs, in particular for the treatment of type 2 diabetes. The derivatives have very long half-lives while maintaining a satisfactory potency, which makes them potentially suitable for once-monthly administration.

13 Claims, No Drawings
Specification includes a Sequence Listing.

SEQUENCE LISTING

```
<160> NUMBER OF SEQ ID NOS: 8

<210> SEQ ID NO 1
<211> LENGTH: 31
<212> TYPE: PRT
<213> ORGANISM: Homo sapiens

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 2
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (2)..(2)
<223> OTHER INFORMATION: Aib

<400> SEQUENCE: 2

His Xaa Glu Gly Thr Phe Thr Ser Asp Val Ser Lys Tyr Leu Glu Lys
1               5                   10                  15

Gln Ala Ala Arg Glu Phe Ile Lys Trp Leu Val Arg Gly Arg Gly
            20                  25                  30

<210> SEQ ID NO 3
<211> LENGTH: 31
<212> TYPE: PRT
<213> ORGANISM: Artificial Sequence
```

```
<220> FEATURE:
<223> OTHER INFORMATION: GLP-1 analogue
<220> FEATURE:
<221> NAME/KEY: MOD_RES
<222> LOCATION: (2)..(2)
<223> OTHER INFORMATION: Aib

<400> SEQUENCE: 3

His Xaa Glu Gly Thr Phe Thr Ser Asp Val Ser Lys Tyr Leu Glu Gly
 1               5                  10                  15

Gln Ala Ala Arg Glu Phe Ile Ala Trp Leu Val Arg Gly Arg Lys
            20                  25                  30

<210> SEQ ID NO 4
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (2)..(2)
<223> OTHER INFORMATION: Aib

<400> SEQUENCE: 4

His Xaa Glu Gly Thr Phe Thr Ser Asp Val Ser Lys Tyr Leu Glu Glu
 1               5                  10                  15

Gln Ala Ala Arg Lys Phe Ile Ala Trp Leu Val Arg Gly Arg Lys
            20                  25                  30

<210> SEQ ID NO 5
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (2)..(2)
<223> OTHER INFORMATION: Aib

<400> SEQUENCE: 5

His Xaa Glu Gly Thr Phe Thr Ser Asp Val Ser Lys Tyr Leu Glu Gly
 1               5                  10                  15

Gln Ala Ala Arg Lys Phe Ile Ala Trp Leu Val Arg Gly Arg Lys
            20                  25                  30

<210> SEQ ID NO 6
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (2)..(2)
<223> OTHER INFORMATION: Aib

<400> SEQUENCE: 6

His Xaa Glu Gly Thr Phe Thr Ser Asp Val Ser Ser Tyr Leu Glu Glu
 1               5                  10                  15

Gln Ala Ala Arg Lys Phe Ile Lys Trp Leu Val Arg Gly Arg Lys
            20                  25                  30
```

```
<210> SEQ ID NO 7
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (2)..(2)
<223> OTHER INFORMATION: Aib

<400> SEQUENCE: 7

His Xaa Glu Gly Thr Phe Thr Ser Asp Val Ser Ser Tyr Leu Glu Glu
1               5                   10                  15

Gln Ala Ala Lys Glu Phe Ile Lys Trp Leu Val Arg Gly Arg Lys
            20                  25                  30

<210> SEQ ID NO 8
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: MISC_FEATURE
<222> LOCATION: (1)..(1)
<223> OTHER INFORMATION: X is L-histidine, (S)-2-Hydroxy-3-(1H-imidazol-
      4-yl)-propionic acid, D-histidine, desamino-histidine,
      homohistidine, N?-acetyl-histidine, N?-formyl-histidine, N?-methyl
      -histidine, 3-pyridylalanine, 2-pyridylalanine, or 4-
      pyridylalanine
<220> FEATURE:
<221> NAME/KEY: MISC_FEATURE
<222> LOCATION: (2)..(2)
<223> OTHER INFORMATION: X is Ala, Gly, Ser, Aib, (1-aminocyclopropyl)
      carboxylic acid, or (1-aminocyclobutyl) carboxylic acid
<220> FEATURE:
<221> NAME/KEY: MISC_FEATURE
<222> LOCATION: (6)..(6)
<223> OTHER INFORMATION: X is Phe or Leu
<220> FEATURE:
<221> NAME/KEY: MISC_FEATURE
<222> LOCATION: (10)..(10)
<223> OTHER INFORMATION: X is Val or Leu
<220> FEATURE:
<221> NAME/KEY: MISC_FEATURE
<222> LOCATION: (12)..(12)
<223> OTHER INFORMATION: X is Ser, Arg, Lys, Val, or Leu
<220> FEATURE:
<221> NAME/KEY: MISC_FEATURE
<222> LOCATION: (13)..(13)
<223> OTHER INFORMATION: X is Tyr or Gln
<220> FEATURE:
<221> NAME/KEY: MISC_FEATURE
<222> LOCATION: (14)..(14)
<223> OTHER INFORMATION: X is Leu or Met
<220> FEATURE:
<221> NAME/KEY: MISC_FEATURE
<222> LOCATION: (16)..(16)
<223> OTHER INFORMATION: X is Gly, Lys or Glu
<220> FEATURE:
<221> NAME/KEY: MISC_FEATURE
<222> LOCATION: (17)..(17)
<223> OTHER INFORMATION: X is Gln, Glu, Lys, or Arg
<220> FEATURE:
<221> NAME/KEY: MISC_FEATURE
<222> LOCATION: (19)..(19)
<223> OTHER INFORMATION: X is Ala or Val
<220> FEATURE:
<221> NAME/KEY: MISC_FEATURE
<222> LOCATION: (20)..(20)
<223> OTHER INFORMATION: X is Arg or Lys
<220> FEATURE:
<221> NAME/KEY: MISC_FEATURE
<222> LOCATION: (21)..(21)
<223> OTHER INFORMATION: X is Glu, Lys, or Leu
```

```
<220> FEATURE:
<221> NAME/KEY: MISC_FEATURE
<222> LOCATION: (24)..(24)
<223> OTHER INFORMATION: X is Ala, Glu, or Lys
<220> FEATURE:
<221> NAME/KEY: MISC_FEATURE
<222> LOCATION: (25)..(25)
<223> OTHER INFORMATION: X is Trp or His
<220> FEATURE:
<221> NAME/KEY: MISC_FEATURE
<222> LOCATION: (27)..(27)
<223> OTHER INFORMATION: X is Val, Lys, or Arg
<220> FEATURE:
<221> NAME/KEY: MISC_FEATURE
<222> LOCATION: (28)..(28)
<223> OTHER INFORMATION: X is Lys, Arg, His, Asn, or Gln
<220> FEATURE:
<221> NAME/KEY: MISC_FEATURE
<222> LOCATION: (29)..(29)
<223> OTHER INFORMATION: X is Gly or Ala
<220> FEATURE:
<221> NAME/KEY: MISC_FEATURE
<222> LOCATION: (30)..(30)
<223> OTHER INFORMATION: X is Arg or Gly
<220> FEATURE:
<221> NAME/KEY: MISC_FEATURE
<222> LOCATION: (31)..(31)
<223> OTHER INFORMATION: X is Gly, Pro, or Lys

<400> SEQUENCE: 8

Xaa Xaa Glu Gly Thr Xaa Thr Ser Asp Xaa Ser Xaa Xaa Xaa Glu Xaa
1               5                   10                  15

Xaa Ala Xaa Xaa Xaa Phe Ile Xaa Xaa Leu Xaa Xaa Xaa Xaa Xaa
            20                  25                  30
```

GLP-1 DERIVATIVES, AND USES THEREOF

CROSS-REFERENCE TO RELATED APPLICATIONS

This application is a 35 U.S.C. § 371 National Stage application of International Application PCT/EP2014/067413 (WO 2015/022400), filed Aug. 14, 2014, which claims priority to European Patent Application 13180558.2, filed Aug. 15, 2013 and to U.S. Provisional Application 61/866,169, filed Aug. 15, 2013, the contents of which are incorporated herein by reference.

TECHNICAL FIELD

The present invention relates to tri-acylated GLP-1 derivatives. The derivatives comprise a first, a second, and a third protracting moiety selected from certain carboxylic and sulfonic acids. The acylation may be at positions corresponding to positions (18, 22, 30), (18, 26, 37), (18, 27, 37), (26, 30, 37), or (27, 30, 37) of the native human glucagon-like peptide 1 (GLP-1(7-37); (SEQ ID NO: 1)). Each protracting moiety may be attached to the peptide via a linker. The invention also relates to the pharmaceutical use of these derivatives.

INCORPORATION-BY-REFERENCE OF THE SEQUENCE LISTING

The Sequence Listing, entitled "SEQUENCE LISTING", is 3109 bytes, was created on Jul. 7, 2014 and is incorporated herein by reference.

SEQUENCE LISTING

The instant application contains a Sequence Listing which has been submitted in ASCII format via EFS-Web and is hereby incorporated by reference in its entirety. Said ASCII copy, created on Feb. 2, 2016 and amended on Jan. 20, 2017, is named "8715US02_SL_NEW_ST25.TXT" and is 6 kilobytes in size.

BACKGROUND

WO 2005/027978 A2 discloses a number of mono-acylated GLP-1 derivatives including some that are acylated with carboxylic or sulfonic acid.

WO 2011/080103 A1, WO 2012/140117 A1, WO 2012/062803 A1, and WO 2012/062804 A1 disclose a number of double-acylated GLP-1 derivatives including some that are acylated with carboxylic acids.

WO2008/028974 A1 discloses methods for simulating chromatographic separation of mixtures containing a target peptide and related impurities. In Example 1 experiments are carried out with the monoacylated GLP-1 compound liraglutide as the target peptide, in admixture with some impurities believed to be two diacylated, and one tri-acylated variant thereof. These impurities are not further described in the WO publication, as they were not isolated and characterised.

SUMMARY

Liraglutide is a GLP-1 derivative for once daily administration. It is marketed under the trade name of VICTOZA® by Novo Nordisk A/S.

Semaglutide is a GLP-1 derivative for once weekly administration. It is under development by Novo Nordisk A/S. This compound is disclosed in WO 2006/097537 A2, Example 4.

The invention relates to derivatives of GLP-1 peptides which have potential for once monthly administration.

In one aspect the invention relates to tri-acylated GLP-1 derivatives. The derivatives comprise a first, a second, and a third protracting moiety selected from certain long carboxylic and sulfonic acids, such as C18 or C20 diacid (Chem. 1 or Chem. 1a, respectively) and C16 sulfonic acid (Chem. 2). The acylation may be at positions corresponding to positions (18, 22, 30), (18, 26, 37), (18, 27, 37), (26, 30, 37), or (27, 30, 37) of the native human glucagon-like peptide 1 (GLP-1(7-37); (SEQ ID NO: 1)). Each protracting moiety may be attached to the peptide via a linker.

In a second aspect the invention relates to pharmaceutical compositions comprising such derivatives and pharmaceutically acceptable excipients, as well as the medical use of the derivatives.

In a third aspect, the invention relates to intermediate products in the form of novel GLP-1 analogues, which can be incorporated in the derivatives of the invention. Such analogues may comprise the following amino acid changes when compared to GLP-1(7-37) (SEQ ID NO: 1): i) (8Aib, 18K, 22K, 26R, 30K, 34R); ii) (8Aib, 18K, 34R, 37K); iii) (8Aib, 18K, 22E, 26R, 27K, 34R, 37K); iv) (8Aib, 18K, 26R, 27K, 34R, 37K); v) (8Aib, 22E, 26R, 27K, 30K, 34R, 37K); vi) (8Aib, 22E, 30K, 34R, 37K); vii) (18K, 22K, 30K); iix) (18K, 37K); ix) (18K, 27K, 37K); x) (27K, 30K, 37K); or xi) (30K, 37K); wherein in embodiment iix) and xi) the amino acid at the position corresponding to position 26 in GLP-1(7-37) (SEQ ID NO: 1) is K.

The amino acid sequence of native human GLP-1(7-37) is included in the sequence listing as SEQ ID NO: 1. The amino acid sequences of the GLP-1 analogues of the derivatives that are exemplified herein are included in the sequence listing as SEQ ID NO: 2 to SEQ ID NO: 7.

The derivatives of the invention represent a remarkable leap in the search for GLP-1 derivatives of very long half-lives and still with a very good potency.

DESCRIPTION

In what follows, Greek letters may be represented by their symbol or the corresponding written name, for example: α=alpha; β=beta; ε=epsilon; γ=gamma; δ=delta; ω=omega; etc. Also, the Greek letter of μ may be represented by "u", e.g. in μl=ul, or in μM=uM.

An asterisk (*) in a chemical formula designates i) a point of attachment, ii) a radical, and/or iii) an unshared electron.

In its first aspect the invention relates to a derivative of a GLP-1 peptide, wherein the GLP-1 peptide comprises a first, a second, and a third K residue at positions corresponding to positions (18, 22, 30), (18, 26, 37), (18, 27, 37), (26, 30, 37), or (27, 30, 37) of GLP-1(7-37) (SEQ ID NO: 1), respectively, and has a maximum of seven amino acid changes as compared to GLP-1(7-37) (SEQ ID NO: 1); which derivative comprises a first, a second, and a third protracting moiety of formula Chem. 1: HOOC—$(CH_2)_{16}$—CO—* (C18 diacid), Chem. 1a: HOOC—$(CH_2)_{18}$—CO—* (C20 diacid), or formula Chem. 2: $HO_3S$—$(CH_2)_{15}$—CO—* (C16 sulfonic acid); and a first, a second, and a third linker, each linker comprising a *—CO group and an *—NH group; wherein each protracting moiety is attached at its *—CO end to the *—NH end of the respective linker, and each linker is attached at its *—CO end to the epsilon amino group of the respective K residue of the GLP-1 peptide; or a pharmaceutically acceptable salt, amide, or ester thereof.

In its second aspect, the invention relates to a pharmaceutical composition comprising a derivative of the invention and a pharmaceutically acceptable excipient; and the use of the derivative or analogue of the invention as a medicament, in particular for use in the (i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C; (ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes; (iii) improving β-cell function, such as decreasing β-cell apoptosis, increasing β-cell function and/or β-cell mass, and/or for restoring glucose sensitivity to β-cells; (iv) prevention and/or treatment of cognitive disorders and/or neurodegenerative disorders, such as Alzheimer's disease, Parkinson's disease, and/or multiple sclerosis; (v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence; (vi) prevention and/or treatment of diabetic complications, such as angiopathy; neuropathy, including peripheral neuropathy; nephropathy; and/or retinopathy; (vii) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo(a)) in vitro and/or in vivo; (viii) prevention and/or treatment of cardiovascular diseases, such as syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis obliterens), diastolic dysfunction, and/or systolic dysfunction; and/or reduction of blood pressure, such as reduction of systolic blood pressure; (ix) prevention and/or treatment of gastrointestinal diseases, such as inflammatory bowel disease, short bowel syndrome, or Crohn's disease or colitis; dyspepsia, and/or gastric ulcers; and/or inflammation, such as psoriasis, psoriactic arthritis, rheumatoid arthritis, and/or systemic lupus erythematosus; (x) prevention and/or treatment of critical illness, such as treatment of a critically ill patient, a critical illness poly-nephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteraemia, septicaemia, and/or septic shock during hospitalisation; and/or stabilising blood glucose, insulin balance and optionally metabolism in intensive care unit patients with acute illness; (xi) prevention and/or treatment of polycystic ovary syndrome (PCOS); (xii) prevention and/or treatment of cerebral disease, such as cerebral ischemia, cerebral haemorrhage, and/or traumatic brain injury; (xiii) prevention and/or treatment of sleep apnoea; and/or (xiv) prevention and/or treatment of abuse, such as alcohol abuse and/or drug abuse.

In its third aspect, the invention relates to an intermediate product in the form of a GLP-1 analogue, which comprises the following amino acid changes when compared to GLP-1(7-37): i) (8Aib, 18K, 22K, 26K, 30K, 34R); ii) (8Aib, 18K, 34R, 37K); iii) (8Aib, 18K, 22E, 26R, 27K, 34R, 37K); iv) (8Aib, 18K, 26R, 27K, 34R, 37K); v) (8Aib, 22E, 26R, 27K, 30K, 34R, 37K); vi) (8Aib, 22E, 30K, 34R, 37K); vii) (18K, 22K, 30K); iix) (18K, 37K); ix) (18K, 27K, 37K); x) (27K, 30K, 37K); or xi) (30K, 37K); wherein in embodiment iix) and xi) the amino acid at the position corresponding to position 26 in GLP-1(7-37) (SEQ ID NO: 1) is K; wherein the intermediate product may be selected from the analogues of i)-xi).

GLP-1 Receptor Agonist

A receptor agonist may be defined as an analogue that binds to a receptor and elicits a response typical of the natural ligand. A full agonist may be defined as one that elicits a response of the same magnitude as the natural ligand (see e.g. "Principles of Biochemistry", A L Lehninger, D L Nelson, M M Cox, Second Edition, Worth Publishers, 1993, page 763).

Thus, for example, a "GLP-1 receptor agonist" may be defined as a compound which is capable of binding to the GLP-1 receptor and capable of activating it. And a "full" GLP-1 receptor agonist may be defined as a GLP-1 receptor agonist which is capable of eliciting a magnitude of GLP-1 receptor response that is similar to native GLP-1.

Structural Features

GLP-1 Peptide and Analogues

The term "GLP-1 peptide" as used herein may be referred to as an analogue (or variant) of the human glucagon-like peptide-1 (GLP-1(7-37)), the sequence of which is included in the sequence listing as SEQ ID NO: 1. The peptide having the sequence of SEQ ID NO: 1 may also be designated "native" GLP-1.

The GLP-1 peptide of the invention comprises a first, a second, and a third K residue at positions corresponding to positions (18, 22, 30), (18, 26, 37), (18, 27, 37), (26, 30, 37), or (27, 30, 37) of GLP-1(7-37) (SEQ ID NO: 1), and has a maximum of seven amino acid changes as compared to GLP-1(7-37) (SEQ ID NO: 1).

In a particular embodiment the first, second, and third K residues are designated K1, K2, and K3, respectively. In another particular embodiment K1, K2, and K3 are at positions corresponding to positions p1, p2, and p3, respectively, of GLP-1(7-37) (SEQ ID NO: 1). Positions (p1, p2, p3) may be selected from the following sets of positions of GLP-1 (7-37) (SEQ ID NO: 1): (18, 22, 30), (18, 26, 37), (18, 27, 37), (26, 30, 37), and (27, 30, 37).

In a still further particular embodiment, the GLP-1 peptide has the general formula I: $Xaa_7$-$Xaa_8$-Glu-Gly-Thr-$Xaa_{12}$-Thr-Ser-Asp-$Xaa_{16}$-Ser-$Xaa_{18}$-$Xaa_{19}$-$Xaa_{20}$-Glu-$Xaa_{22}$-$Xaa_{23}$-Ala-$Xaa_{25}$-$Xaa_{26}$-$Xaa_{27}$-Phe-Ile-$Xaa_{30}$-$Xaa_{31}$-Leu-$Xaa_{33}$-$Xaa_{34}$-$Xaa_{35}$-$Xaa_{36}$-$Xaa_{37}$, wherein $Xaa_7$ is L-histidine, (S)-2-Hydroxy-3-(1H-imidazol-4-yl)-propionic acid, D-histidine, desamino-histidine, homohistidine, N$^\alpha$-acetyl-histidine, N$^\alpha$-formyl-histidine, N$^\alpha$-methyl-histidine, 3-pyridylalanine, 2-pyridylalanine, or 4-pyridylalanine; $Xaa_8$ is Ala, Gly, Ser, Aib, (1-aminocyclopropyl)

carboxylic acid, or (1-aminocyclobutyl) carboxylic acid; $Xaa_{12}$ is Phe or Leu; $Xaa_{16}$ is Val or Leu; $Xaa_{18}$ is Ser, Arg, Lys, Val, or Leu; $Xaa_{19}$ is Tyr or Gln; $Xaa_{20}$ is Leu or Met; $Xaa_{22}$ is Gly, Lys or Glu; $Xaa_{23}$ is Gln, Glu, Lys, or Arg; $Xaa_{25}$ is Ala or Val; $Xaa_{26}$ is Arg or Lys; $Xaa_{27}$ is Glu, Lys, or Leu; $Xaa_{30}$ is Ala, Glu, or Lys; $Xaa_{31}$ is Trp or His; $Xaa_{33}$ is Val, Lys, or Arg; $Xaa_{34}$ is Lys, Arg, His, Asn, or Gln; $Xaa_{35}$ is Gly or Ala; $Xaa_{36}$ is Arg or Gly; and $Xaa_{37}$ is Gly, Pro, or Lys.

In this formula the numbering of the amino acid residues follows the established practice in the art for native GLP-1, namely that the first (N-terminal) amino acid residue is numbered or accorded position no. 7, and the subsequent amino acid residues downstream towards the C-terminus are numbered 8, 9, 10, and so on, until the last (C-terminal) amino acid residue, which in native GLP-1 is Gly with number 37.

The numbering is done differently in the sequence listing, where the first amino acid residue of SEQ ID NO: 1 (His) is assigned no. 1, and the last (Gly) no. 31, and vice versa for the other GLP-1 sequences of the sequence listing. However, herein we follow the established numbering practice in the art, as explained above.

Each of the GLP-1 analogues of the derivatives of the invention may be described by reference to i) the number of the amino acid residue in native GLP-1(7-37) which corresponds to the amino acid residue which is changed (i.e., the corresponding position in native GLP-1), and to ii) the actual change.

In other words, the GLP-1 analogue of the invention may be described by reference to the native GLP-1(7-37) peptide, namely as a variant thereof in which a number of amino acid residues have been changed when compared to native GLP-1(7-37) (SEQ ID NO: 1).

These changes may represent, independently, one or more amino acid substitutions, additions, and/or deletions.

The following are non-limiting examples of suitable analogue nomenclature:

The GLP-1 peptide incorporated in the derivative of Example 1 herein may be referred to as the following GLP-1 analogue: (8Aib, 18K, 22K, 26R, 30K, 34R) GLP-1(7-37). This means that when this analogue is aligned with native GLP-1, it has i) an Aib at the position in the analogue which corresponds, according to the alignment, to position 8 in native GLP-1, ii) a K at the position in the analogue which corresponds to position 18 in native GLP-1, iii) a K at the position in the analogue which corresponds to position 22 in native GLP-1, iv) an R at the position in the analogue which corresponds to position 26 in native GLP-1, v) a K at the position in the analogue which corresponds to position 30 in native GLP-1, and vi) an R at the position in the analogue which corresponds to position 34 in native GLP-1. All other amino acids in this analogue are identical to the corresponding amino acid in native GLP-1.

The GLP-1 peptide of the invention may be defined by amino acid changes when and/or as compared to native GLP-1. The amino acid changes discussed above may be thought of as amino acid substitutions, relative to native GLP-1.

Analogues "comprising" certain specified changes may comprise further changes, when compared to SEQ ID NO: 1. In a particular embodiment, the analogue "has" the specified changes.

As is apparent from the above examples, amino acid residues may be identified by their full name, their one-letter code, and/or their three-letter code. These three ways are fully equivalent.

The expressions "a position equivalent to" or "corresponding position" may be used to characterise the site of change in a variant GLP-1 (7-37) sequence by reference to a reference sequence such as native GLP-1(7-37) (SEQ ID NO: 1). Equivalent or corresponding positions, as well as the number of changes, are easily deduced, e.g. by simple handwriting and eyeballing; and/or a standard protein or peptide alignment program may be used, such as "align" which is based on a Needleman-Wunsch algorithm. This algorithm is described in Needleman, S. B. and Wunsch, C. D., (1970), Journal of Molecular Biology, 48: 443-453, and the align program by Myers and W. Miller in "Optimal Alignments in Linear Space" CABIOS (computer applications in the biosciences) (1988) 4:11-17. For the alignment, the default scoring matrix BLOSUM62 and the default identity matrix may be used, and the penalty for the first residue in a gap may be set at −12, or preferably at −10, and the penalties for additional residues in a gap at −2, or preferably at −0.5.

An example of such alignment is inserted below, in which sequence no. 1 is SEQ ID NO: 1, and sequence no. 2 is the analogue (8Aib, 18K, 22K, 26R, 30K, 34R) (SEQ ID NO: 2) thereof:

```
Aligned_sequences:    2 sequence no. 1:       1 sequence no. 2:       2

Matrix:               EBLOSUM62

Gap_penalty:          10.0

Extend_penalty:       0.5

Length:               31

Identity:             25/31 (80.6%)

Similarity:           27/31 (87.1%)

Gaps:                 0/31 ( 0.0%)

Score:                134.0

1       1 HAEGTFTSDVSSYLEGQAAKEFIAWLVKGRG 31
          |.||||||||.|||.|||:|||.|||:|||
2       1 HXEGTFTSDVSKYLEKQAAREFIKWLVRGRG 31
```

When 6 is added to the position numbers shown in this alignment (i.e., to "1" and "31" in sequence 1, and to "1" and "31" in sequence 2) one gets the position numbering as used herein. For example, in sequence 1 (which is identical to SEQ ID NO: 1), the N-terminal amino acid (H) has position number 7, and the C-terminal amino acid (G) has number 37.

In case specific amino acid residues or the like with no one-letter codon (such as Aib) are included in the sequence these may, for alignment purposes, be replaced with, e.g., X, as shown in the above alignment. If desired, X can later be manually corrected.

The following are non-limiting examples of what can be inferred from the above alignment:

As one example it can be inferred that sequence 2 has 6 amino acid changes as compared to sequence 1 (namely at all those positions where a full stop ("."), a colon (":"), or a horizontal hyphen ("-") is shown in the alignment).

As another example it can be inferred that, e.g., sequence no. 2 comprises 18K, since it has a K at the position which corresponds, according to the alignment, to position 18 in the reference sequence (sequence no. 1, SEQ ID NO: 1).

And similarly all other changes in sequence 2 as compared to sequence 1 can be deduced from the alignment.

The term "peptide", as e.g. used in the context of the GLP-1 peptide of the derivatives of the invention, refers to a compound which comprises a series of amino acids interconnected by amide (or peptide) bonds.

The peptide of the invention comprises at least 31 amino acids. In a particular embodiment the peptide is composed of 31 amino acids. In an additional particular embodiment the peptide consists of 31 amino acids.

In a still further particular embodiment the peptide consists of amino acids interconnected by peptide bonds.

Amino acids are molecules containing an amine group and a carboxylic acid group, and, optionally, one or more additional groups, often referred to as a side chain.

The term "amino acid" includes proteinogenic (or natural) amino acids (amongst those the 20 standard amino acids), as well as non-proteinogenic (or non-natural) amino acids. Proteinogenic amino acids are those which are naturally incorporated into proteins.

The standard amino acids are those encoded by the genetic code. Non-proteinogenic amino acids are either not found in proteins, or not produced by standard cellular machinery (e.g., they may have been subject to post-translational modification). Non-limiting examples of non-proteinogenic amino acids are Aib (α-aminoisobutyric acid (or 2-Aminoisobutyric acid)), des-amino-histidine (alternative name imidazopropionic acid or 3-(Imidazol-5-yl)propanoic acid, abbreviated Imp), as well as the D-isomers of the proteinogenic amino acids.

In what follows, each amino acid of the GLP-1 peptide for which the optical isomer is not stated is to be understood to mean the L-isomer (unless otherwise specified).

The GLP-1 derivatives and analogues of the invention have GLP-1 activity. This term refers to the ability to bind to the GLP-1 receptor and initiate a signal transduction pathway resulting in insulinotropic action or other physiological effects as is known in the art. For example, the analogues and derivatives of the invention can be tested for GLP-1 activity using the assays described in Examples 22, 23, 25, or 26 herein.

GLP-1 Derivatives

The term "GLP-1 derivative" generally refers to a compound which may be prepared from the native GLP-1 peptide or an analogue thereof by chemical modification, in particular by covalent attachment of one or more substituents. The GLP-1 derivative according to the invention comprises three such substituents. Each of these may, also or alternatively, be referred to as a side chain.

In a particular embodiment, the side chain is capable of forming non-covalent complexes with albumin, thereby promoting the circulation of the derivative with the blood stream, and also having the effect of protracting the time of action of the derivative, due to the fact that the complex of the GLP-1-derivative and albumin is only slowly disintegrated to release the active pharmaceutical ingredient. Thus, the substituent, or side chain, as a whole is preferably referred to as an albumin binding moiety.

In another particular embodiment the albumin binding moiety comprises a portion which is particularly relevant for the albumin binding and thereby the protraction, which portion may accordingly be referred to as a protracting moiety. The protracting moiety may be, preferably at, the terminal (or distal, or free) end of the albumin binding moiety, relative to its point of attachment to the peptide. The albumin binding moiety is attached to the peptide by acylation of a lysine residue of the peptide, in particular by acylation to the epsilon-amino group of the lysine residue.

In a still further particular embodiment the albumin binding moiety comprises a portion between the protracting moiety and the point of attachment to the peptide, which portion may be referred to as a linker, linker moiety, spacer, or the like.

The derivative of the invention comprises a first, a second, and a third protracting moiety of formula Chem. 1 or Chem. 1a, or formula Chem. 2:

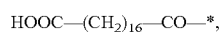    Chem. 1:

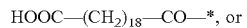    Chem. 1a:

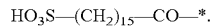    Chem. 2:

Chem. 1 may also be referred to as C18 diacid, Chem. 1a may be referred to as C20 diacid, and Chem. 2 may be referred to as C16 sulfonic acid. In a particular embodiment the first, second, and third protracting moieties are designated Pr1, Pr2, and Pr3, respectively.

The derivative of the invention also comprises a first, a second, and a third linker.

In another particular embodiment the first, second, and third linker are designated Ln1, Ln2, and Ln3, respectively.

Each linker comprises a *—CO group and an *—NH group.

In a still further particular embodiment Pr1 is attached at its *—CO group to the *—NH group of Ln1 which is attached at its *—CO group to the epsilon amino group of K1; Pr2 is attached at its *—CO group to the *—NH group of Ln2 which is attached at its *—CO group to the epsilon amino group of K2; and Pr3 is attached at its *—CO group to the *—NH group of Ln3 which is attached at its *—CO group to the epsilon amino group of K3.

The linkers (Ln1, Ln2, and Ln3) may comprise an element_1 of formula Chem. 3:

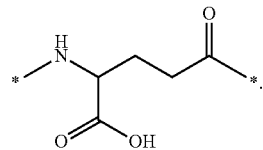    Chem. 3

This element may be referred to as gamma-Glu, or briefly gGlu, due to the fact that it is the gamma carboxy group of the amino acid glutamic acid which is here used for connection to another linker element, or to the epsilon-amino group of lysine, as the case may be.

Also, or alternatively, the linkers (Ln1, Ln2, and Ln3) may comprise an element_2 of formula Chem. 4:

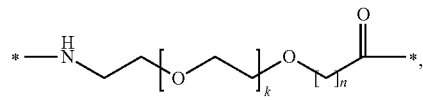    Chem. 4 wherein k is an integer in the range of 1-5, and n is an integer in the range of 1-5.

In a particular embodiment, when k=1 and n=1, the Chem. 4 element_2 may be designated OEG, or a di-radical of 8-amino-3,6-dioxaoctanoic acid.

Also, or alternatively, the linkers (Ln1, Ln2, and Ln3) may comprise an element_3 of formula Chem. 5, which may be referred to as Trx (for tranexamic acid):

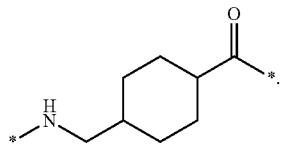

Chem. 5

Also, or alternatively, the linkers (Ln1, Ln2, and Ln3) may comprise an element_4 of formula Chem. 6:

*—NH—(CH$_2$)$_q$—CH[(CH$_2$)$_w$—NH$_2$]—CO—*,    Chem. 6:

wherein q is an integer in the range of 0-5, and w is an integer in the range of 0-5, with the provisos that when w is 0 q is an integer in the range of 1-5, and when q is 0 w is an integer in the range of 1-5. In a particular embodiment (q is 4 and w is 0, or w is 4 and q is 0), Chem. 6 represents an eps-Lys residue, where eps means epsilon and refers to the fact that it is the epsilon-amino group of lysine which is used for connection to the carboxy group of the protracting moiety, or of another linker element, as the case may be.

Also, or alternatively, the linkers (Ln1, Ln2, and Ln3) may comprise an element_5 of formula Chem. 7, which is a Ser residue:

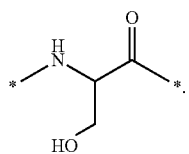

Chem. 7

Also, or alternatively, the linkers (Ln1, Ln2, and Ln3) may comprise an element_6 of formula Chem. 8, which is a Cysteic acid (3-sulfo-Ala) residue:

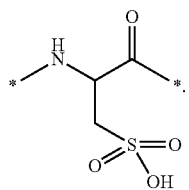

Chem. 8

Also, or alternatively, the linkers (Ln1, Ln2, and Ln3) may comprise an element_7 of formula Chem. 9, which is an amino carboxylic acid residue:

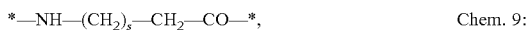

*—NH—(CH$_2$)$_s$—CH$_2$—CO—*,    Chem. 9:

in which s is an integer in the range of 2-4. In Chem. 9, the group *—(CH$_2$)$_s$—* may represent straight or branched, preferably straight, alkylene. In a particular embodiment (s=2) Chem. 9 represents 4-amino butanoic acid (Abu). In another particular embodiment (s=4) Chem. 9 represents 6-amino hexanoic acid (Ahx).

The first, second, and third protracting moieties are connected to the first, second, and third linkers, respectively, and in turn to the first, second, and third K residues, respectively, of the GLP-1 peptide via amide bonds.

The first, second, and third linker may comprise one or more of the various elements as defined above (element_1 to element_7), each element may occur one or more times, and also the sequence of the elements may vary.

Whenever a linker is said to "comprise" a certain element, it may in addition contain other elements, whereas the term "incorporates" is intended to mean the same as "has" or "includes only". Therefore, a linker which "incorporates" two elements_2 of formula Chem. 4 has only two of these elements in its structure.

Various particular combinations of linker elements are described in more detail below in the section headed "Particular embodiments". The sequence in which the elements are indicated here is generally from the N-terminus to the C-terminus.

In a particular embodiment, the three albumin binding moieties (i.e. the three side chains) are similar, preferably substantially identical, or, most preferably, identical.

In another particular embodiment, the first, second, and third protracting moieties are similar, preferably substantially identical, or, most preferably, identical.

In a still further particular embodiment, the first, second, and third linkers are similar, preferably substantially identical, or, most preferably identical.

The term "substantially identical" includes differences from identity which are due to formation of one or more esters and/or amides; preferably formation of one or more methyl esters, and simple amides; more preferably formation of no more than two methyl esters, and/or simple amides; or most preferably formation of no more than one methyl ester, and/or simple amide.

In the context of chemical compounds such as the albumin binding moieties, protracting moieties, and linkers, similarity and/or identity may be determined using any suitable computer program and/or algorithm known in the art.

For example, the similarity of protracting moieties, linkers, and/or entire side chains may suitably be determined using molecular fingerprints. Fingerprints is a mathematical method of representing a chemical structure (see e.g. Chemoinformatics: A textbook, Johann Gasteiger and Thomas Engel (Eds), Wiley-VCH Verlag, 2003).

Examples of suitable fingerprints include, without limitation, UNITY fingerprints, MDL fingerprints, and/or ECFP fingerprints, such as ECFP_6 fingerprints (ECFP stands for extended-connectivity fingerprints).

In particular embodiments, the protracting moieties, the linkers, and/or the entire side chains are represented as a) ECFP_6 fingerprints; b) UNITY fingerprints; and/or c) MDL fingerprints.

The Tanimoto coefficient is preferably used for calculating the similarity of the fingerprints, whether a), b), or c) is used.

In particular embodiments, whether a), b), or c) is used, the protracting moieties, the linkers, and/or the entire side chains, respectively, have a similarity of at least 0.5 (50%); preferably at least 0.6 (60%); more preferably at least 0.7 (70%), or at least 0.8 (80%); even more preferably at least 0.9 (90%); or most preferably at least 0.99 (99%), such as a similarity of 1.0 (100%).

UNITY fingerprints may be calculated using the programme SYBYL (available from Tripos, 1699 South Hanley Road, St. Louis, Mo. 63144-2319 USA). ECFP_6 and MDL fingerprints may be calculated using the programme Pipeline Pilot (available from Accelrys Inc., 10188 Telesis Court, Suite 100, San Diego, Calif. 92121, USA).

For more details, see for example J. Chem. Inf. Model. 2008, 48, 542-549; J. Chem. Inf. Comput. Sci. 2004, 44, 170-178; J. Med. Chem. 2004, 47, 2743-2749; J. Chem. Inf. Model. 2010, 50, 742-754; as well as SciTegic Pipeline Pilot Chemistry Collection: Basic Chemistry User Guide, March 2008, SciTegic Pipeline Pilot Data Modeling Collection, 2008—both from Accelrys Software Inc., San Diego, US, and the guides http://www.tripos.com/tripos_resources/fileroot/pdfs/Unity_111408.pdf, and http://www.tripos.com/data/SYBYL/SYBYL_072505.pdf.

An example of a similarity calculation is inserted below, in which a known entire side chain of a known GLP-1 derivative was compared with a methyl ester thereof:

was measured in an Envision plate reader. The amount of light was proportional to the concentration of the compound.

Pharmaceutically Acceptable Salt, Amide, or Ester

The derivatives, analogues, and intermediate products of the invention may be in the form of a pharmaceutically acceptable salt, amide, or ester.

Salts are e.g. formed by a chemical reaction between a base and an acid, e.g.: $2NH_3+H_2SO_4 \rightarrow (NH_4)_2SO_4$.

The salt may be a basic salt, an acid salt, or it may be neither nor (i.e. a neutral salt). Basic salts produce hydroxide ions and acid salts hydronium ions in water.

The salts of the derivatives of the invention may be formed with cations or anions, between anionic or cationic

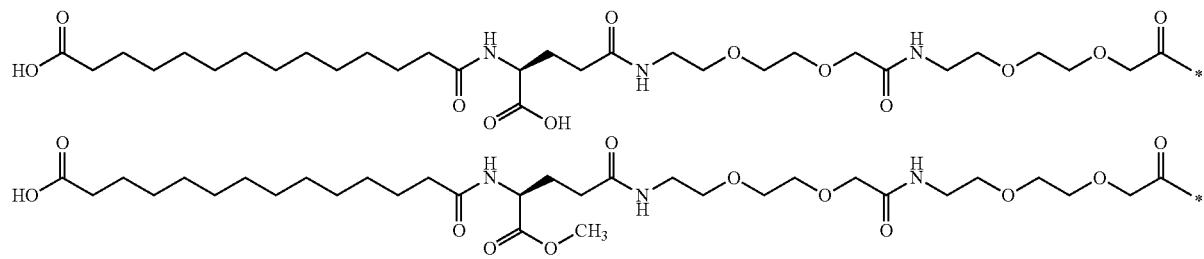

Using a) ECFP_6 fingerprints the similarity is 0.798, using b) UNITY fingerprints the similarity is 0.957; and using MDL fingerprints the similarity is 0.905.

In case of three identical side chains (albumin binding moieties) the derivative may be designated symmetrical.

In particular embodiments, the similarity coefficient is at least 0.80, preferably at least 0.85, more preferably at least 0.90, even more preferably at least 0.95, or most preferably at least 0.99.

The derivatives of the invention may exist in different stereoisomeric forms having the same molecular formula and sequence of bonded atoms, but differing only in the three-dimensional orientation of their atoms in space. The stereoisomerism of the exemplified derivatives of the invention is indicated in the experimental section, in the names as well as the structures, using standard nomenclature. Unless otherwise stated the invention relates to all stereoisomeric forms of the claimed derivative.

The concentration in plasma of the GLP-1 derivatives of the invention may be determined using any suitable method. For example, LC-MS (Liquid Chromatography Mass Spectroscopy) may be used, or immunoassays such as RIA (Radio Immuno Assay), ELISA (Enzyme-Linked Immuno Sorbent Assay), and LOCI (Luminescence Oxygen Channeling Immunoasssay). General protocols for suitable RIA and ELISA assays are found in, e.g., WO 2009/030738 on p. 116-118. A preferred assay is the LOCI assay, where LOCI refers to Luminescence Oxygen Channeling Immunoasssay, which is generally described for the determination of insulin by Poulsen and Jensen in Journal of Biomolecular Screening 2007, vol. 12, p. 240-247. The donor beads were coated with streptavidin, while acceptor beads were conjugated with a monoclonal antibody recognising a mid-/C-terminal epitope of the peptide. Another monoclonal antibody, specific for the N-terminus, was biotinylated. The three reactants were combined with the analyte and formed a two-sited immunocomplex. Illumination of the complex released singlet oxygen atoms from the donor beads, which were channelled into the acceptor beads and triggered chemiluminescence which groups, respectively. These groups may be situated in the peptide moiety, and/or in the side chain of the derivatives of the invention.

Non-limiting examples of anionic groups of the derivatives of the invention include free carboxylic groups in the side chain, if any, as well as in the peptide moiety. The peptide moiety often includes a free carboxylic acid group at the C-terminus, and it may also include free carboxylic groups at internal acid amino acid residues such as Asp and Glu.

Non-limiting examples of cationic groups in the peptide moiety include the free amino group at the N-terminus, if present, as well as any free amino group of internal basic amino acid residues such as His, Arg, and Lys.

In a particular embodiment the derivatives and analogues of the invention are basic salts. These salts may, e.g., be formed between anionic groups in the peptide moiety and sodium or potassium cations.

In another particular embodiment the derivatives and analogues of the invention are acid salts. These salts may, e.g., be formed between cationic groups in the peptide moiety and chloride or acetate anions.

The ester of the derivatives of the invention may, e.g., be formed by the reaction of a free carboxylic acid group with an alcohol or a phenol, which leads to replacement of at least one hydroxyl group by an alkoxy or aryloxy group The ester formation may involve the free carboxylic group at the C-terminus of the peptide, and/or any free carboxylic group in the side chain.

The amide of the derivatives of the invention may, e.g., be formed by the reaction of a free carboxylic acid group with an amine or a substituted amine, or by reaction of a free or substituted amino group with a carboxylic acid.

The amide formation may involve the free carboxylic group at the C-terminus of the peptide, any free carboxylic group in the side chain, the free amino group at the N-terminus of the peptide, and/or any free or substituted amino group of the peptide in the peptide and/or the side chain.

In a particular embodiment, the peptide or derivative is in the form of a pharmaceutically acceptable salt. In another particular embodiment, the derivative is in the form of a pharmaceutically acceptable amide, preferably with an amide group at the C-terminus of the peptide. In a still further particular embodiment, the peptide or derivative is in the form a pharmaceutically acceptable ester.

Functional Properties

In a particular embodiment the derivatives of the invention have a very long half-life and at the same time a very good potency in vitro and in vivo, which makes them potentially suitable for once-monthly administration.

Thus, in a first functional aspect, the derivatives of the invention have a good potency. Also, or alternatively, in a second aspect, they bind very well to the GLP-1 receptor, e.g. at a high concentration of albumin. Preferably they are potent GLP-1 receptor agonists as is reflected by their ability to bind strongly to the GLP-1 receptor combined with the capacity to activate the receptor. Also, or alternatively, in a third functional aspect, they have improved pharmacokinetic properties.

Biological Activity—In Vitro Potency

According to the first functional aspect, the derivatives of the invention, as well as the constituent GLP-1 peptides as such, are biologically active, or potent.

In a particular embodiment, potency and/or activity refers to in vitro potency, i.e. performance in a functional GLP-1 receptor assay, more in particular to the capability of activating the human GLP-1 receptor.

The in vitro potency may, e.g., be determined in a medium containing membranes expressing the human GLP-1 receptor, and/or in an assay with whole cells expressing the human GLP-1 receptor.

For example, the response of the human GLP-1 receptor may be measured in a reporter gene assay, e.g. in a stably transfected BHK cell line that expresses the human GLP-1 receptor and contains the DNA for the cAMP response element (CRE) coupled to a promoter and the gene for firefly luciferase (CRE luciferase). When cAMP is produced as a result of activation of the GLP-1 receptor this in turn results in the luciferase being expressed. Luciferase may be determined by adding luciferin, which by the enzyme is converted to oxyluciferin and produces bioluminescence, which is measured and is a measure of the in vitro potency. One non-limiting example of such an assay is described in Example 22.

The term half maximal effective concentration ($EC_{50}$) generally refers to the concentration which induces a response halfway between the baseline and maximum, by reference to the dose response curve. $EC_{50}$ is used as a measure of the potency of a compound and represents the concentration where 50% of its maximal effect is observed.

The in vitro potency of the derivatives of the invention may be determined as described above, and the $EC_{50}$ of the derivative in question determined. The lower the $EC_{50}$ value, the better the potency.

In a particular embodiment, the derivatives of the invention are very potent, despite the fact that they have very long half-lives. In a particular embodiment, the derivative of the invention has an in vitro potency determined using the method of Example 22 corresponding to an $EC_{50}$ at or below 300 pM.

Biological Activity—In Vivo Pharmacology

In another particular embodiment the derivatives of the invention as well as the constituent GLP-1 peptides as such are potent in vivo, which may be determined as is known in the art in any suitable animal model, as well as in clinical trials.

The diabetic db/db mouse is one example of a suitable animal model, and the blood glucose and/or body weight lowering effect may be determined in such mice in vivo, e.g. as described in Example 25. In a particular embodiment the derivatives of the invention are capable of lowering blood glucose and body weight in db/db mice for at least up to 48 hours.

The LYD pig is another example of a suitable animal model, and the reduction in food intake may be determined in a PD study in such pigs in vivo, e.g. as described in Example 26.

In a particular embodiment the derivatives of the invention are very potent in vivo and over a long time, which is evidenced by the results found in the experimental part and also referred to in the section headed "Particular embodiments".

Biological Activity—In Vitro Receptor Binding

According to the second functional aspect, the derivatives of the invention, as well as the constituent GLP-1 peptides as such bind very well to the GLP-1 receptor, e.g. at a high concentration of albumin. This may be determined as described in Example 23.

Generally, the binding to the GLP-1 receptor at low albumin concentration should be as good as possible, corresponding to a low $IC_{50}$ value.

The $IC_{50}$ value at high albumin concentration reflects the influence of serum albumin on the binding of the derivative to the GLP-1 receptor. As is known, the GLP-1 derivatives can bind to serum albumin and if this is the case then the $IC_{50}$ value at high serum albumin will be higher than the $IC_{50}$ value at low albumin. An increased $IC_{50}$ value at high serum albumin represents a reduced binding to the GLP-1 receptor caused by serum albumin binding competing with the binding to the GLP-1 receptor.

In a particular embodiment, the derivatives of the invention bind very well to the GLP-1 receptor at a low albumin concentration, but they also bind very well at a high albumin concentration.

As an example, in a particular embodiment, the GLP-1 receptor binding affinity ($IC_{50}$) of the derivatives of the invention in the presence of a low concentration of HSA (max. 0.001% final assay concentration) is at 15 nM or below.

Pharmacokinetics Profile

According to the third functional aspect, the derivatives of the invention have improved pharmacokinetic properties such as increased terminal half-life, and/or decreased clearance.

Increasing terminal half-life and/or decreasing of the clearance means that the compound in question is eliminated slower from the body. For the derivatives of the invention this entails an extended duration of pharmacological effect.

The pharmacokinetic properties of the derivatives of the invention may suitably be determined in-vivo in pharmacokinetic (PK) studies. Such studies are conducted to evaluate how pharmaceutical compounds are absorbed, distributed, and eliminated in the body, and how these processes affect the concentration of the compound in the body, over the course of time.

In the discovery and preclinical phase of pharmaceutical drug development, animal models such as the mouse, rat, monkey, dog, or pig, may be used to perform this characterisation. Any of these models can be used to test the pharmacokinetic properties of the derivatives of the invention.

In such studies, animals are typically administered with a single dose of the drug, either intravenously (i.v.), subcutaneously (s.c.), or orally (p.o.) in a relevant formulation. Blood samples are drawn at predefined time points after dosing, and samples are analysed for concentration of drug with a relevant quantitative assay. Based on these measurements, time-plasma concentration profiles for the compound of study are plotted and a so-called non-compartmental pharmacokinetic analysis of the data is performed.

For most compounds, the terminal part of the plasma-concentration profiles will be linear when drawn in a semi-logarithmic plot, reflecting that after the initial absorption and distribution, drug is removed from the body at a constant fractional rate. The rate (lambda Z or $\lambda_z$) is equal to minus the slope of the terminal part of the plot. From this rate, also a terminal half-life may be calculated, as $t\frac{1}{2}=\ln(2)/\lambda_z$ (see, e.g., Johan Gabrielsson and Daniel Weiner: Pharmacokinetics and Pharmacodynamic Data Analysis. Concepts & Applications, 3rd Ed., Swedish Pharmaceutical Press, Stockholm (2000)).

Clearance can be determined after i.v. administration and is defined as the dose (D) divided by area under the curve (AUC) on the plasma concentration versus time profile (Rowland, M and Tozer T N: Clinical Pharmacokinetics: Concepts and Applications, $3^{rd}$ edition, 1995 Williams Wilkins).

The estimate of terminal half-life and/or clearance is relevant for evaluation of dosing regimens and an important parameter in drug development, in the evaluation of new drug compounds.

Pharmacokinetics Profile—Half Life In Vivo in Minipigs

According to the third functional aspect, the derivatives of the invention have improved pharmacokinetic properties.

In a particular embodiment, the pharmacokinetic properties may be determined as terminal half-life ($T_{1/2}$) in vivo in minipigs after i.v. administration, e.g. as described in Example 24 herein.

In a particular embodiment the derivatives of the invention have an excellent terminal half-life in minipigs which makes them suitable for once-monthly administration. In a particular embodiment, the terminal half-life of the derivatives of the invention in minipigs after i.v. administration is at least 90 hours.

Additional particular embodiments of the derivatives of the invention are described in the section headed "Particular embodiments" before the experimental section.

Production Processes

The production of peptides like GLP-1(7-37) and GLP-1 analogues is well known in the art.

The GLP-1 peptide moiety of the derivatives of the invention (or fragments thereof) may for instance be produced by classical peptide synthesis, e.g., solid phase peptide synthesis using t-Boc or Fmoc chemistry or other well established techniques, see, e.g., Greene and Wuts, "Protective Groups in Organic Synthesis", John Wiley & Sons, 1999, Florencio Zaragoza Dörwald, "Organic Synthesis on solid Phase", Wiley-VCH Verlag GmbH, 2000, and "Fmoc Solid Phase Peptide Synthesis", Edited by W. C. Chan and P. D. White, Oxford University Press, 2000.

Also, or alternatively, they may be produced by recombinant methods, viz. by culturing a host cell containing a DNA sequence encoding the analogue and capable of expressing the peptide in a suitable nutrient medium under conditions permitting the expression of the peptide. Non-limiting examples of host cells suitable for expression of these peptides are: *Escherichia coli, Saccharomyces cerevisiae*, as well as mammalian BHK or CHO cell lines.

Those derivatives of the invention which include non-natural amino acids and/or a covalently attached N-terminal mono- or dipeptide mimetic may e.g. be produced as described in the experimental part. Or see e.g., Hodgson et al: "The synthesis of peptides and proteins containing non-natural amino acids", Chemical Society Reviews, vol. 33, no. 7 (2004), p. 422-430; and WO 2009/083549 A1 entitled "Semi-recombinant preparation of GLP-1 analogues".

Specific examples of methods of preparing a number of the derivatives of the invention are included in the experimental part.

Pharmaceutical Compositions

The invention also relates to pharmaceutical compositions comprising a derivative of the invention or a pharmaceutically acceptable salt, amide, or ester thereof, and a pharmaceutically acceptable excipient. Such compositions may be prepared as is known in the art.

The term "excipient" broadly refers to any component other than the active therapeutic ingredient(s). The excipient may be an inert substance, an inactive substance, and/or a not medicinally active substance.

The excipient may serve various purposes, e.g. as a carrier, vehicle, diluent, tablet aid, and/or to improve administration, and/or absorption of the active substance.

The formulation of pharmaceutically active ingredients with various excipients is known in the art, see e.g. Remington: The Science and Practice of Pharmacy (e.g. $19^{th}$ edition (1995), and any later editions).

Non-limiting examples of excipients are: Solvents, diluents, buffers, preservatives, tonicity regulating agents, chelating agents, and stabilisers.

Examples of formulations include liquid formulations, i.e. aqueous formulations comprising water. A liquid formulation may be a solution, or a suspension. An aqueous formulation typically comprises at least 50% w/w water, or at least 60%, 70%, 80%, or even at least 90% w/w of water.

Alternatively, a pharmaceutical composition may be a solid formulation, e.g. a freeze-dried or spray-dried composition, which may be used as is, or whereto the physician or the patient adds solvents, and/or diluents prior to use.

The pH in an aqueous formulation may be anything between pH 3 and pH 10, for example from about 7.0 to about 9.5; or from about 3.0 to about 7.0.

A pharmaceutical composition may comprise a buffer. The buffer may e.g. be selected from sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid, and mixtures thereof.

A pharmaceutical composition may comprise a preservative. The preservative may e.g. be selected from phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1,2-diol), and mixtures thereof. The preservative may be present in a concentration from 0.1 mg/ml to 20 mg/ml. A pharmaceutical composition may comprise an isotonic agent. The isotonic agent may e.g. be selected from a salt (e.g. sodium chloride), a sugar or sugar alcohol, an amino acid (e.g. glycine, histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), and mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, alfa and beta HPCD, soluble starch, hydroxyethyl starch and carboxymethylcellulose-Na may be used. Sugar alcohol is defined as a C4-C8 hydrocarbon having at least one —OH group and includes, for example, mannitol, sorbitol, inositol, galactitol, dulcitol, xylitol, and arabitol. In one embodiment, the sugar alcohol additive is mannitol.

A pharmaceutical composition may comprise a chelating agent. The chelating agent may e.g. be selected from salts of ethylenediaminetetraacetic acid (EDTA), citric acid, and aspartic acid, and mixtures thereof.

A pharmaceutical composition may comprise a stabiliser. The stabiliser may e.g. be one or more oxidation inhibitors, aggregation inhibitors, surfactants, and/or one or more protease inhibitors. Non-limiting examples of these various kinds of stabilisers are disclosed in the following.

The term "aggregate formation" refers to a physical interaction between the polypeptide molecules resulting in formation of oligomers, which may remain soluble, or large visible aggregates that precipitate from the solution. Aggregate formation by a polypeptide during storage of a liquid pharmaceutical composition can adversely affect biological activity of that polypeptide, resulting in loss of therapeutic efficacy of the pharmaceutical composition. Furthermore, aggregate formation may cause other problems such as blockage of tubing, membranes, or pumps when the polypeptide-containing pharmaceutical composition is administered using an infusion system.

A pharmaceutical composition may comprise an amount of an amino acid base sufficient to decrease aggregate formation of the polypeptide during storage of the composition. The term "amino acid base" refers to one or more amino acids (such as methionine, histidine, imidazole, arginine, lysine, isoleucine, aspartic acid, tryptophan, threonine), or analogues thereof. Any amino acid may be present either in its free base form or in its salt form. Any stereoisomer (i.e., L, D, or a mixture thereof) of the amino acid base may be present.

Methionine (or other sulphuric amino acids or amino acid analogous) may be added to inhibit oxidation of methionine residues to methionine sulfoxide when the polypeptide acting as the therapeutic agent is a polypeptide comprising at least one methionine residue susceptible to such oxidation. Any stereoisomer of methionine (L or D) or combinations thereof can be used.

A pharmaceutical composition may comprise a stabiliser selected from high molecular weight polymers or low molecular compounds. The stabiliser may e.g. be selected from polyethylene glycol (e.g. PEG 3350), polyvinyl alcohol (PVA), polyvinylpyrrolidone, carboxy-/hydroxycellulose or derivates thereof (e.g. HPC, HPC-SL, HPC-L and HPMC), cyclodextrins, sulphur-containing substances as monothioglycerol, thioglycolic acid and 2-methylthioethanol, and different salts (e.g. sodium chloride). A pharmaceutical composition may comprise additional stabilising agents such as, but not limited to, methionine and EDTA, which protect the polypeptide against methionine oxidation, and a nonionic surfactant, which protects the polypeptide against aggregation associated with freeze-thawing or mechanical shearing.

A pharmaceutical composition may comprise one or more surfactants. The term "surfactant" refers to any molecules or ions that are comprised of a water-soluble (hydrophilic) part, and a fat-soluble (lipophilic) part. The surfactant may e.g. be selected from anionic surfactants, cationic surfactants, nonionic surfactants, and/or zwitterionic surfactants.

A pharmaceutical composition may comprise one or more protease inhibitors, such as, e.g., EDTA (ethylenediamine tetraacetic acid), and/or benzamidineHCl.

Additional, optional, ingredients of a pharmaceutical composition include, e.g., wetting agents, emulsifiers, antioxidants, bulking agents, metal ions, oily vehicles, proteins (e.g., human serum albumin, gelatine), and/or a zwitterion (e.g., an amino acid such as betaine, taurine, arginine, glycine, lysine and histidine).

Still further, a pharmaceutical composition may be formulated as is known in the art of oral formulations of insulinotropic compounds, e.g. using any one or more of the formulations described in WO 2008/145728.

An administered dose may contain from 0.1 mg-100 mg of the derivative, from 1-100 mg of the derivative, or from 1-50 mg of the derivative.

The derivative may be administered in the form of a pharmaceutical composition. It may be administered to a patient in need thereof at several sites, for example, at topical sites such as skin or mucosal sites; at sites which bypass absorption such as in an artery, in a vein, or in the heart; and at sites which involve absorption, such as in the skin, under the skin, in a muscle, or in the abdomen.

The route of administration may be, for example, lingual; sublingual; buccal; in the mouth; oral; in the stomach; in the intestine; nasal; pulmonary, such as through the bronchioles, the alveoli, or a combination thereof; parenteral, epidermal; dermal; transdermal; conjunctival; uretal; vaginal; rectal; and/or ocular. A composition may be an oral composition, and the route of administration is per oral.

A composition may be administered in several dosage forms, for example as a solution; a suspension; an emulsion; a microemulsion; multiple emulsions; a foam; a salve; a paste; a plaster; an ointment; a tablet; a coated tablet; a chewing gum; a rinse; a capsule such as hard or soft gelatine capsules; a suppositorium; a rectal capsule; drops; a gel; a spray; a powder; an aerosol; an inhalant; eye drops; an ophthalmic ointment; an ophthalmic rinse; a vaginal pessary; a vaginal ring; a vaginal ointment; an injection solution; an in situ transforming solution such as in situ gelling, setting, precipitating, and in situ crystallisation; an infusion solution; or as an implant.

A composition may be a tablet, optionally coated, a capsule, or a chewing gum.

A composition may further be compounded in a drug carrier or drug delivery system, e.g. in order to improve stability, bioavailability, and/or solubility. In a particular embodiment a composition may be attached to such system through covalent, hydrophobic, and/or electrostatic interactions. The purpose of such compounding may be, e.g., to decrease adverse effects, achieve chronotherapy, and/or increase patient compliance.

A composition may also be used in the formulation of controlled, sustained, protracting, retarded, and/or slow release drug delivery systems.

Parenteral administration may be performed by subcutaneous, intramuscular, intraperitoneal, or intravenous injection by means of a syringe, optionally a pen-like syringe, or by means of an infusion pump.

A composition may be administered nasally in the form of a solution, a suspension, or a powder; or it may be administered pulmonally in the form of a liquid or powder spray.

Transdermal administration is a still further option, e.g. by needle-free injection, from a patch such as an iontophoretic patch, or via a transmucosal route, e.g. buccally.

A composition may be a stabilised formulation. The term "stabilised formulation" refers to a formulation with increased physical and/or chemical stability, preferably both. In general, a formulation must be stable during use and storage (in compliance with recommended use and storage conditions) until the expiration date is reached.

The term "physical stability" refers to the tendency of the polypeptide to form biologically inactive and/or insoluble aggregates as a result of exposure to thermo-mechanical stress, and/or interaction with destabilising interfaces and surfaces (such as hydrophobic surfaces). The physical stability of an aqueous polypeptide formulation may be evaluated by means of visual inspection, and/or by turbidity measurements after exposure to mechanical/physical stress (e.g. agitation) at different temperatures for various time periods. Alternatively, the physical stability may be evaluated using a spectroscopic agent or probe of the conformational status of the polypeptide such as e.g. Thioflavin T or "hydrophobic patch" probes.

The term "chemical stability" refers to chemical (in particular covalent) changes in the polypeptide structure leading to formation of chemical degradation products potentially having a reduced biological potency, and/or increased immunogenic effect as compared to the intact polypeptide. The chemical stability can be evaluated by measuring the amount of chemical degradation products at various time-points after exposure to different environmental conditions, e.g. by SEC-HPLC, and/or RP-HPLC.

The treatment with a derivative according to the present invention may also be combined with one or more additional pharmacologically active substances, e.g. selected from antidiabetic agents, antiobesity agents, appetite regulating agents, antihypertensive agents, agents for the treatment and/or prevention of complications resulting from or associated with diabetes and agents for the treatment and/or prevention of complications and disorders resulting from or associated with obesity. Examples of these pharmacologically active substances are: Insulin, sulphonylureas, biguanides, meglitinides, glucosidase inhibitors, glucagon agonists, glucagon antagonists, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents as HMG CoA inhibitors (statins), Gastric Inhibitory Polypeptides (GIP analogs), compounds lowering food intake, RXR agonists and agents acting on the ATP-dependent potassium channel of the β-cells; Cholestyramine, colestipol, clofibrate, gemfibrozil, lovastatin, pravastatin, simvastatin, probucol, dextrothyroxine, neteglinide, repaglinide; β-blockers such as alprenolol, atenolol, timolol, pindolol, propranolol and metoprolol, ACE (angiotensin converting enzyme) inhibitors such as benazepril, captopril, enalapril, fosinopril, lisinopril, alatriopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin; CART (cocaine amphetamine regulated transcript) agonists, NPY (neuropeptide Y) antagonists, PYY agonists, Y2 receptor agonists, Y4 receptor agonits, mixed Y2/Y4 receptor agonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, O3 agonists, oxyntomodulin and analogues, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, fibroblast growth factor 21 (FGF-21), galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, RXR (retinoid X receptor) modulators, TR β agonists; histamine H3 antagonists, Gastric Inhibitory Polypeptide agonists or antagonists (GIP analogs), gastrin and gastrin analogs.

The treatment with a derivative according to this invention may also be combined with a surgery that influences the glucose levels, and/or lipid homeostasis such as gastric banding or gastric bypass.

Pharmaceutical Indications

The present invention also relates to a derivative of the invention, for use as a medicament.

In particular embodiments, the derivative of the invention may be used for the following medical treatments:

(i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells;

(iv) prevention and/or treatment of cognitive disorders and/or neurodegenerative disorders, such as Alzheimer's disease, Parkinson's disease, and/or multiple sclerosis;

(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence;

(vi) prevention and/or treatment of diabetic complications, such as angiopathy; neuropathy, including peripheral neuropathy; nephropathy; and/or retinopathy;

(vii) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo(a)) in vitro and/or in vivo;

(viii) prevention and/or treatment of cardiovascular diseases, such as syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis oblitterens), diastolic dysfunction, and/or systolic dysfunction; and/or reduction of blood pressure, such as reduction of systolic blood pressure;

(ix) prevention and/or treatment of gastrointestinal diseases, such as inflammatory bowel disease, short bowel syndrome, or Crohn's disease or colitis; dyspepsia, and/or gastric ulcers; and/or inflammation, such as psoriasis, psoriactic arthritis, rheumatoid arthritis, and/or systemic lupus erythematosus;

(x) prevention and/or treatment of critical illness, such as treatment of a critically ill patient, a critical illness polynephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteraemia, septicaemia, and/or septic shock during hospitalisation; and/or stabilising blood glucose, insulin balance and optionally metabolism in intensive care unit patients with acute illness;

(xi) prevention and/or treatment of polycystic ovary syndrome (PCOS);

(xii) prevention and/or treatment of cerebral disease, such as cerebral ischemia, cerebral haemorrhage, and/or traumatic brain injury;

(xiii) prevention and/or treatment of sleep apnoea; and/or (xiv) prevention and/or treatment of abuse, such as alcohol abuse and/or drug abuse.

In a particular embodiment the indication is selected from the group consisting of (i)-(xiv), such as indications (i)-(viii), (x)-(xiii), and/or (xiv), and relates in one way or the other to diabetes.

In another particular embodiment, the indication is selected from the group consisting of (i)-(iii) and (v)-(viii), such as indications (i), (ii), and/or (iii); or indication (v), indication (vi), indication (vii), and/or indication (viii).

In a still further particular embodiment, the indication is (i). In a further particular embodiment the indication is (v). In a still further particular embodiment the indication is (viii).

The following indications are particularly preferred: Type 2 diabetes, and/or obesity.

Particular Embodiments

The following are particular embodiments of the invention:

1. A derivative of a GLP-1 peptide,
wherein the GLP-1 peptide comprises a first, a second, and a third K residue at positions corresponding to positions (18, 22, 30), (18, 26, 37), (18, 27, 37), (26, 30, 37), or (27, 30, 37) of GLP-1(7-37) (SEQ ID NO: 1), and has a maximum of seven amino acid changes as compared to GLP-1 (7-37) (SEQ ID NO: 1);
which derivative comprises
a first, a second, and a third protracting moiety selected from formula Chem. 1, Chem. 1a, andChem. 2:

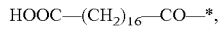  Chem. 1:

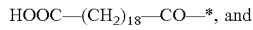  Chem. 1a:

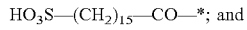  Chem. 2:

a first, a second, and a third linker, each linker comprising a *—CO group and an *—NH group;
wherein each protracting moiety is attached at its *—CO end to the *—NH end of the respective linker, and each linker is attached at its *—CO end to the epsilon amino group of the respective K residue of the GLP-1 peptide;
or a pharmaceutically acceptable salt, amide, or ester thereof.

2. The derivative of embodiment 1, wherein the first, second, and third K residues are designated K1, K2, and K3, respectively.

3. The derivative of any of embodiments 1-2, wherein the first K residue (K1) is at a position corresponding to position p1 of GLP-1(7-37) (SEQ ID NO: 1), the second K residue (K2) is at a position corresponding to position p2 of GLP-1(7-37) (SEQ ID NO: 1), and the third K residue (K3) is at a position corresponding to position p3 of GLP-1(7-37) (SEQ ID NO: 1).

4. The derivative of embodiment 3, wherein p1, p2, and p3 are selected from the following sets of positions of GLP-1 (7-37) (SEQ ID NO: 1): (18, 22, 30), (18, 26, 37), (18, 27, 37), (26, 30, 37), and (27, 30, 37).

5. The derivative of any of embodiments 1-4, wherein the first, second, and third protracting moieties are designated Pr1, Pr2, and Pr3, respectively.

6. The derivative of any of embodiments 1-5, wherein the first, second, and third linker are designated Ln1, Ln2, and Ln3, respectively.

7. The derivative of any of embodiments 1-6, wherein the first protracting moiety (Pr1) is attached at its *—CO group to the *—NH group of the first linker (Ln1) which is attached at its *—CO group to the epsilon amino group of the first K residue (K1); the second protracting moiety (Pr2) is attached at its *—CO group to the *—NH group of the second linker (Ln2) which is attached at its *—CO group to the epsilon amino group of the second K residue (K2); and the third protracting moiety (Pr3) is attached at its *—CO group to the *—NH group of the third linker (Ln3) which is attached at its *—CO group to the epsilon amino group of the third K residue (K3).

8. A derivative of a GLP-1 peptide,
wherein the GLP-1 peptide comprises a first K residue (K1), a second K residue (K2), and a third K residue (K3) at positions (p) corresponding to positions (p1, p2, p3), respectively, of GLP-1(7-37) (SEQ ID NO: 1), where (p1, p2, p3) are selected from (18, 22, 30), (18, 26, 37), (18, 27, 37), (26, 30, 37), and (27, 30, 37); and
wherein the GLP-1 peptide has a maximum of seven amino acid changes as compared to GLP-1(7-37) (SEQ ID NO: 1);
which derivative comprises a first protracting moiety (Pr1), a second protracting moiety (Pr2), and a third protracting moiety (Pr3), wherein each of Pr1, Pr2 and Pr3 is selected from formula Chem. 1, Chem. 1a, and Chem. 2:

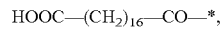  Chem. 1:

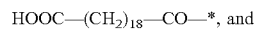  Chem. 1a:

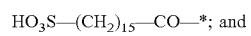  Chem. 2:

a first linker (Ln1), a second linker (Ln2), and a third linker (Ln3), wherein each of Ln1, Ln2 and Ln3 comprises a *—CO group and an *—NH group;
wherein
Pr1 is attached at its *—CO group to the *—NH group of Ln1 and Ln1 is attached at its *—CO group to the epsilon amino group of K1,
Pr2 is attached at its *—CO group to the *—NH group of Ln2 and Ln2 is attached at its *—CO group to the epsilon amino group of K2, and Pr3 is attached at its *—CO group to the *—NH group of Ln3 and Ln3 is attached at its *—CO group to the epsilon amino group of K3;

or a pharmaceutically acceptable salt, amide, or ester thereof.

9. The derivative of any of embodiments 1-8, wherein the first, second, and third K residues (K1, K2, K3) are at positions (p1, p2, p3) corresponding to positions (18, 22, 30) of GLP-1(7-37) (SEQ ID NO: 1), respectively.

10. The derivative of any of embodiments 1-8, wherein the first, second, and third K residues (K1, K2, K3) are at positions (p1, p2, p3) corresponding to positions (18, 26, 37) of GLP-1(7-37) (SEQ ID NO: 1), respectively.

11. The derivative of any of embodiments 1-8, wherein the first, second, and third K residues (K1, K2, K3) are at positions (p1, p2, p3) corresponding to positions (18, 27, 37) of GLP-1(7-37) (SEQ ID NO: 1), respectively.

12. The derivative of any of embodiments 1-8, wherein the first, second, and third K residues (K1, K2, K3) are at positions (p1, p2, p3) corresponding to positions (26, 30, 37) of GLP-1(7-37) (SEQ ID NO: 1), respectively.

13. The derivative of any of embodiments 1-8, wherein the first, second, and third K residues (K1, K2, K3) are at positions (p1, p2, p3) corresponding to positions (27, 30, 37) of GLP-1(7-37) (SEQ ID NO: 1), respectively.

14. The derivative of any of embodiments 1-13, wherein each of the first, second, and third protracting moiety (Pr1, Pr2, and Pr3, respectively) is of formula Chem. 1.

15. The derivative of any of embodiments 1-13, wherein each of the first, second, and third protracting moiety (Pr1, Pr2, and Pr3, respectively) is of formula Chem. 1a.

16. The derivative of any of embodiments 1-13, wherein each of the first, second, and third protracting moiety (Pr1, Pr2, and Pr3, respectively) is of formula Chem. 2.

17. The derivative of any of embodiments 1-16, wherein each of the first, second, and third linker (Ln1, Ln2, and Ln3, respectively) comprises an element_1 of formula Chem. 3:

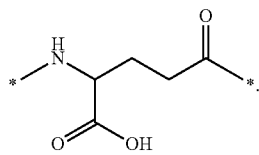

Chem. 3

18. The derivative of any of embodiments 1-17, wherein each of the first, second, and third linker (Ln1, Ln2, and Ln3, respectively) incorporates one element_1 of formula Chem. 3.

19. The derivative of any of embodiments 1-18, wherein Chem. 3 represents a gGlu residue.

20. The derivative of any of embodiments 1-19, wherein element_1 is an L-gGlu residue.

21. The derivative of any of embodiments 1-20, wherein each of the first, second, and third linker (Ln1, Ln2, and Ln3, respectively) comprises an element_2 of formula Chem. 4:

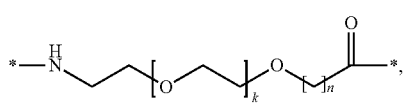

Chem. 4 wherein k is an integer in the range of 1-5, and n is an integer in the range of 1-5.

22. The derivative of any of embodiments 1-21, wherein each of the first, second, and third linker (Ln1, Ln2, and Ln3, respectively) comprises at least one element_2 of formula Chem. 4.

23. The derivative of any of embodiments 1-22, wherein each of the first, second, and third linker (Ln1, Ln2, and Ln3, respectively) comprises at least two elements_2 of formula Chem. 4.

24. The derivative of any of embodiments 1-23, wherein each of the first, second, and third linker (Ln1, Ln2, and Ln3, respectively) comprises at least four elements_2 of formula Chem. 4.

25. The derivative of any of embodiments 1-24, wherein each of the first, second, and third linker (Ln1, Ln2, and Ln3, respectively) comprises at least five elements_2 of formula Chem. 4.

26. The derivative of any of embodiments 1-25, wherein each of the first, second, and third linker (Ln1, Ln2, and Ln3, respectively) comprises two elements_2 of formula Chem. 4.

27. The derivative of any of embodiments 1-26, wherein each of the first, second, and third linker incorporates two elements_2 of formula Chem. 4.

28. The derivative of any of embodiments 1-27, wherein each of the first, second, and third linker (Ln1, Ln2, and Ln3, respectively) comprises four elements_2 of formula Chem. 4.

29. The derivative of any of embodiments 15-18, wherein each of the first, second, and third linker incorporates four elements_2 of formula Chem. 4.

30. The derivative of any of embodiments 15-17, wherein each of the first, second, and third linker (Ln1, Ln2, and Ln3, respectively) comprises five elements_2 of formula Chem. 4.

31. The derivative of any of embodiments 15-18, wherein each of the first, second, and third linker incorporates five elements_2 of formula Chem. 4.

32. The derivative of any of embodiments 1-31, wherein k=1 and n=1.

33. The derivative of any of embodiments 1-32, wherein Chem. 4 represents OEG.

34. The derivative of any of embodiments 1-21, wherein each of the first, second, and third linker (Ln1, Ln2, and Ln3, respectively) comprises an element_3 of formula Chem. 5:

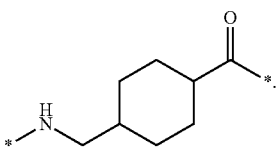

Chem. 5

35. The derivative of any of embodiments 1-34, wherein each of the first, second, and third linker (Ln1, Ln2, and Ln3, respectively) incorporates one element_3 of formula Chem. 5.

36. The derivative of any of embodiments 1-35, wherein Chem. 5 represents Trx.

37. The derivative of any of embodiments 1-36, wherein each of the first, second, and third linker (Ln1, Ln2, and Ln3, respectively) comprises an element_4 of formula Chem. 6:

*—NH—$(CH_2)_q$—CH[$(CH_2)_w$—$NH_2$]—CO—*,  Chem. 6:

wherein q is an integer in the range of 0-5, and w is an integer in the range of 0-5, with the provisos that when w is 0 q is an integer in the range of 1-5, and when q is 0 w is an integer in the range of 1-5.

38. The derivative of any of embodiments 1-37, wherein each of the first, second, and third linker (Ln1, Ln2, and Ln3, respectively) comprises at least one element_4 of formula Chem. 6.

39. The derivative of any of embodiments 1-38, wherein each of the first, second, and third linker (Ln1, Ln2, and Ln3, respectively) comprises at least two elements_4 of formula Chem. 6.

40. The derivative of any of embodiments 1-39, wherein each of the first, second, and third linker (Ln1, Ln2, and Ln3, respectively) comprises two elements_4 of formula Chem. 6.

41. The derivative of any of embodiments 1-40, wherein each of the first, second, and third linker (Ln1, Ln2, and Ln3, respectively) incorporates two elements_4 of formula Chem. 6.

42. The derivative of any of embodiments 1-41, wherein each of the first, second, and third linker (Ln1, Ln2, and Ln3, respectively) comprises three elements_4 of formula Chem. 6.

43. The derivative of any of embodiments 1-42, wherein each of the first, second, and third linker (Ln1, Ln2, and Ln3, respectively) incorporates three elements_4 of formula Chem. 6.

44. The derivative of any of embodiments 1-43, wherein q is 4 and w is 0.

45. The derivative of any of embodiments 1-43, wherein w is 4 and q is 0.

46. The derivative of any of embodiments 1-45, wherein Chem. 6 represents an eps-Lys residue.

47. The derivative of any of embodiments 1-46, wherein element_4 is an L-eps-Lys residue.

48. The derivative of any of embodiments 1-47, wherein each of the first, second, and third linker (Ln1, Ln2, and Ln3, respectively) comprises an element_5 of formula Chem. 7:

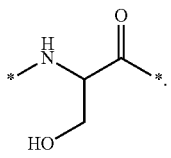

Chem. 7

49. The derivative of any of embodiments 1-48, wherein each of the first, second, and third linker (Ln1, Ln2, and Ln3, respectively) comprises at least one element_5 of formula Chem. 7.

50. The derivative of any of embodiments 1-49, wherein each of the first, second, and third linker (Ln1, Ln2, and Ln3, respectively) comprises at least five elements_5 of formula Chem. 7.

51. The derivative of any of embodiments 1-50, wherein each of the first, second, and third linker (Ln1, Ln2, and Ln3, respectively) comprises five elements_5 of formula Chem. 7.

52. The derivative of any of embodiments 1-51, wherein each of the first, second, and third linker (Ln1, Ln2, and Ln3, respectively) comprises six elements_5 of formula Chem. 7.

53. The derivative of any of embodiments 1-52, wherein each of the first, second, and third linker (Ln1, Ln2, and Ln3, respectively) incorporates five elements_5 of formula Chem. 7.

54. The derivative of any of embodiments 1-53, wherein each of the first, second, and third linker (Ln1, Ln2, and Ln3, respectively) incorporates six elements_5 of formula Chem. 7.

55. The derivative of any of embodiments 1-54, wherein element_5 is a Ser residue.

56. The derivative of any of embodiments 1-55, wherein element_5 is an L-Ser residue.

57. The derivative of any of embodiments 1-56, wherein each of the first, second, and third linker (Ln1, Ln2, and Ln3, respectively) comprises an element_6 of formula Chem. 8:

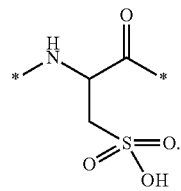

Chem. 8

58. The derivative of any of embodiments 1-57, wherein each of the first, second, and third linker (Ln1, Ln2, and Ln3, respectively) incorporates one element_6 of formula Chem. 8.

59. The derivative of any of embodiments 1-58, wherein Chem. 8 represents a cysteic acid residue.

60. The derivative of any of embodiments 1-59, wherein element_6 is an L-Cysteic acid.

61. The derivative of any of embodiments 1-59, wherein each of the first, second, and third linker (Ln1, Ln2, and Ln3, respectively) comprises an element_7 of formula Chem. 9:

$$*-NH-(CH_2)_s-CH_2-CO-*,\qquad \text{Chem. 9:}$$

in which s is an integer in the range of 2-4.

62. The derivative of any of embodiments 1-61, wherein in Chem. 9 $*-(CH_2)_s-*$ represents straight or branched alkylene.

63. The derivative of any of embodiments 1-62, wherein in Chem. 9 $*-(CH_2)_s-*$ represents straight alkylene.

64. The derivative of any of embodiments 1-63, wherein s is 2.

65. The derivative of any of embodiments 1-64, wherein Chem. 9 represents 4-amino butanoic acid (Abu).

66. The derivative of any of embodiments 1-64, wherein s is 4.

67. The derivative of any of embodiments 1-66, wherein Chem. 9 represents 6-amino hexanoic acid (Ahx).

68. The derivative of any of embodiments 1-67, wherein each of the first, second, and third linker (Ln1, Ln2, and Ln3, respectively) consists of one element_3 of formula Chem. 5, one element_1 of formula Chem. 3, and two elements_2 of formula Chem. 4 wherein k=1 and n=1, interconnected via amide bonds and in the sequence indicated.

69. The derivative of any of embodiments 1-68, wherein each of the first, second, and third linker (Ln1, Ln2, and Ln3, respectively) consists of one element_6 of formula Chem. 8, and two elements_2 of formula Chem. 4 wherein k=1 and n=1, interconnected via amide bonds and in the sequence indicated.

70. The derivative of any of embodiments 1-69, wherein each of the first, second, and third linker (Ln1, Ln2, and Ln3, respectively) consists of one element_1 of formula Chem. 3, five elements_5 of formula Chem. 7, and one element_4 of formula Chem. 6 wherein q=4 and w=0 (or w=4 and q=0), interconnected via amide bonds and in the sequence indicated.

71. The derivative of any of embodiments 1-70, wherein each of the first, second, and third linker (Ln1, Ln2, and Ln3, respectively) consists of one element_3 of formula Chem. 5, one element_6 of formula Chem. 8, and two elements_2 of formula Chem. 4 wherein k=1 and n=1, interconnected via amide bonds and in the sequence indicated.

72. The derivative of any of embodiments 1-71, wherein each of the first, second, and third linker (Ln1, Ln2, and Ln3, respectively) consists of one element_1 of formula Chem. 3, and two elements_2 of formula Chem. 4 wherein k=1 and n=1, interconnected via amide bonds and in the sequence indicated.

73. The derivative of any of embodiments 1-72, wherein each of the first, second, and third linker (Ln1, Ln2, and Ln3, respectively) consists of one element_1 of formula Chem. 3, two elements_2 of formula Chem. 4 wherein k=1 and n=1, and one element_4 of formula Chem. 6 wherein q=4 and w=0 (or w=4 and q=0), interconnected via amide bonds and in the sequence indicated.

74. The derivative of any of embodiments 1-73, wherein each of the first, second, and third linker (Ln1, Ln2, and Ln3, respectively) consists of one element_2 of formula Chem. 4 wherein k=1 and n=1, one element_1 of formula Chem. 3, and one element_2 of formula Chem. 4 wherein k=1 and n=1, interconnected via amide bonds and in the sequence indicated.

75. The derivative of any of embodiments 1-74, wherein each of the first, second, and third linker (Ln1, Ln2, and Ln3, respectively) consists of one element_1 of formula Chem. 3, and six elements_5 of formula Chem. 7, interconnected via amide bonds and in the sequence indicated.

76. The derivative of any of embodiments 1-75, wherein each of the first, second, and third linker (Ln1, Ln2, and Ln3, respectively) consists of one element_6 of formula Chem. 8, two elements_2 of formula Chem. 4 wherein k=1 and n=1, and one element_4 of formula Chem. 6 wherein q=4 and w=0 (or w=4 and q=0), interconnected via amide bonds and in the sequence indicated.

77. The derivative of any of embodiments 1-76, wherein each of the first, second, and third linker (Ln1, Ln2, and Ln3, respectively) consists of one element_4 of formula Chem. 6 wherein q=4 and w=0 (or w=4 and q=0), and two elements_2 of formula Chem. 4 wherein k=1 and n=1, and interconnected via amide bonds and in the sequence indicated.

78. The derivative of any of embodiments 1-77, wherein each of the first, second, and third linker (Ln1, Ln2, and Ln3, respectively) consists of two elements_4 of formula Chem. 6 wherein q=4 and w=0 (or w=4 and q=0), and two elements_2 of formula Chem. 4 wherein k=1 and n=1, and interconnected via amide bonds and in the sequence indicated.

79. The derivative of any of embodiments 1-78, wherein each of the first, second, and third linker (Ln1, Ln2, and Ln3, respectively) consists of two elements_4 of formula Chem. 6 wherein q=4 and w=0 (or w=4 and q=0), and five elements_2 of formula Chem. 4 wherein k=1 and n=1, and interconnected via amide bonds and in the sequence indicated.

80. The derivative of any of embodiments 1-79, wherein each of the first, second, and third linker (Ln1, Ln2, and Ln3, respectively) consists of three elements_4 of formula Chem. 6 wherein q=4 and w=0 (or w=4 and q=0), and five elements_2 of formula Chem. 4 wherein k=1 and n=1, and interconnected via amide bonds and in the sequence indicated.

81. The derivative of any of embodiments 1-80, wherein each of the first, second, and third linker (Ln1, Ln2, and Ln3, respectively) consists of one element_7 of formula Chem. 9 wherein s=2, two elements_4 of formula Chem. 6 wherein q=4 and w=0 (or w=4 and q=0), and four elements_2 of formula Chem. 4 wherein k=1 and n=1, and interconnected via amide bonds and in the sequence indicated.

82. The derivative of any of embodiments 1-81, wherein each of the first, second, and third linker (Ln1, Ln2, and Ln3, respectively) consists of one element_7 of formula Chem. 9 wherein s=4, two elements_4 of formula Chem. 6 wherein q=4 and w=0 (or w=4 and q=0), and four elements_2 of formula Chem. 4 wherein k=1 and n=1, and interconnected via amide bonds and in the sequence indicated.

83. The derivative of any of embodiments 1-82, wherein each of the first, second, and third linker (Ln1, Ln2, and Ln3, respectively) consists of one element_7 of formula Chem. 9 wherein s=4, two elements_4 of formula Chem. 6 wherein q=4 and w=0 (or w=4 and q=0), and five elements_2 of formula Chem. 4 wherein k=1 and n=1, and interconnected via amide bonds and in the sequence indicated.

84. The derivative of any of embodiments 1-83, wherein each of the first, second, and third linker (Ln1, Ln2, and Ln3, respectively) consists of one element_7 of formula Chem. 9 wherein s=2, two elements_4 of formula Chem. 6 wherein q=4 and w=0 (or w=4 and q=0), and five elements_2 of formula Chem. 4 wherein k=1 and n=1, and interconnected via amide bonds and in the sequence indicated.

85. The derivative of any of embodiments 1-84, wherein the GLP-1 peptide has a maximum of 7 amino acid changes, when compared with GLP-1(7-37) (SEQ ID NO: 1).

86. The derivative of any of embodiments 1-85, wherein the GLP-1 peptide has a maximum of 6 amino acid changes, when compared with GLP-1(7-37) (SEQ ID NO: 1).

87. The derivative of any of embodiments 1-86, wherein the GLP-1 peptide has a maximum of 5 amino acid changes, when compared with GLP-1(7-37) (SEQ ID NO: 1).

88. The derivative of any of embodiments 1-87, wherein the GLP-1 peptide has a maximum of 4 amino acid changes, when compared with GLP-1(7-37) (SEQ ID NO: 1).

89. The derivative of any of embodiments 1-88, wherein the GLP-1 peptide has a minimum of 2 amino acid changes, when compared with GLP-1(7-37) (SEQ ID NO: 1).

90. The derivative of any of embodiments 1-89, wherein the GLP-1 peptide has a minimum of 3 amino acid changes, when compared with GLP-1(7-37) (SEQ ID NO: 1).

91. The derivative of any of embodiments 1-90, wherein the GLP-1 peptide has a minimum of 4 amino acid changes, when compared with GLP-1(7-37) (SEQ ID NO: 1).

92. The derivative of any of embodiments 1-91, wherein the GLP-1 peptide has a minimum of 5 amino acid changes, when compared with GLP-1(7-37) (SEQ ID NO: 1).

93. The derivative of any of embodiments 1-92, wherein the GLP-1 peptide has a minimum of 6 amino acid changes, when compared with GLP-1(7-37) (SEQ ID NO: 1).

94. The derivative of any of embodiments 1-93, wherein the GLP-1 peptide has a minimum of 7 amino acid changes, when compared with GLP-1(7-37) (SEQ ID NO: 1).

95. The derivative of any of embodiments 1-94, wherein the GLP-1 peptide has 4 amino acid changes, when compared with GLP-1(7-37) (SEQ ID NO: 1).

96. The derivative of any of embodiments 1-95, wherein the GLP-1 peptide has 5 amino acid changes, when compared with GLP-1(7-37) (SEQ ID NO: 1).

97. The derivative of any of embodiments 1-96, wherein the GLP-1 peptide has 6 amino acid changes, when compared with GLP-1(7-37) (SEQ ID NO: 1).
98. The derivative of any of embodiments 1-97, wherein the GLP-1 peptide has 7 amino acid changes, when compared with GLP-1(7-37) (SEQ ID NO: 1).
99. The derivative of any of embodiments 1-98, wherein the GLP-1 peptide comprises at least three Lys residues.
100. The derivative of any of embodiments 1-99, wherein the GLP-1 peptide comprises three Lys residues.
101. The derivative of any of embodiments 1-100, wherein the GLP-1 peptide has three Lys residues.
102. The derivative of any of embodiments 1-101, wherein the GLP-1 peptide has only three Lys residues.
103. The derivative of any of embodiments 1-102, wherein the GLP-1 peptide has the general formula I:

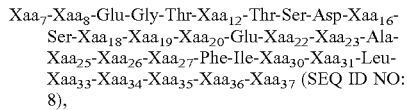

wherein
$Xaa_7$ is L-histidine, (S)-2-Hydroxy-3-(1H-imidazol-4-yl)-propionic acid, D-histidine, desamino-histidine, homohistidine, $N^\alpha$-acetyl-histidine, $N^\alpha$-formyl-histidine, $N^\alpha$-methyl-histidine, 3-pyridylalanine, 2-pyridylalanine, or 4-pyridylalanine;
$Xaa_8$ is Ala, Gly, Ser, Aib, (1-aminocyclopropyl) carboxylic acid, or (1-aminocyclobutyl) carboxylic acid;
$Xaa_{12}$ is Phe or Leu;
$Xaa_{16}$ is Val or Leu;
$Xaa_{18}$ is Ser, Arg, Lys, Val, or Leu;
$Xaa_{19}$ is Tyr or Gln;
$Xaa_{20}$ is Leu or Met;
$Xaa_{22}$ is Gly, Lys or Glu;
$Xaa_{23}$ is Gln, Glu, Lys, or Arg;
$Xaa_{25}$ is Ala or Val;
$Xaa_{26}$ is Arg or Lys;
$Xaa_{27}$ is Glu, Lys, or Leu;
$Xaa_{30}$ is Ala, Glu, or Lys;
$Xaa_{31}$ is Trp or His;
$Xaa_{33}$ is Val, Lys, or Arg;
$Xaa_{34}$ is Lys, Arg, His, Asn, or Gln;
$Xaa_{35}$ is Gly or Ala;
$Xaa_{36}$ is Arg or Gly; and
$Xaa_{37}$ is Gly, Pro, or Lys.
104. The derivative of any of embodiments 1-103, wherein in Formula I $Xaa_7$ is L-histidine, (S)-2-Hydroxy-3-(1H-imidazol-4-yl)-propionic acid, D-histidine, desamino-histidine, $N^\alpha$-acetyl-histidine, $N^\alpha$-formyl-histidine, $N^\alpha$-methyl-histidine; $Xaa_8$ is Ala, Gly, Ser, Aib, (1-aminocyclopropyl) carboxylic acid, or (1-aminocyclobutyl) carboxylic acid; $Xaa_{12}$ is Phe; $Xaa_{16}$ is Val or Leu; $Xaa_{18}$ is Ser, Arg, Lys; $Xaa_{19}$ is Tyr or Gln; $Xaa_{20}$ is Leu or Met; $Xaa_{22}$ is Gly, Lys or Glu; $Xaa_{23}$ is Gln, Glu, Lys, or Arg; $Xaa_{25}$ is Ala or Val; $Xaa_{26}$ is Arg or Lys; $Xaa_{27}$ is Glu, Lys, or Leu; $Xaa_{30}$ is Ala, Glu, or Lys; $Xaa_{31}$ is Trp or His; $Xaa_{33}$ is Val, Lys, or Arg; $Xaa_{34}$ is Lys, Arg, His, Asn, or Gln; $Xaa_{35}$ is Gly; $Xaa_{36}$ is Arg or Gly; and $Xaa_{37}$ is Gly, Pro, or Lys.
105. The derivative of any of embodiments 1-104, wherein the GLP-1 peptide has the general formula I:

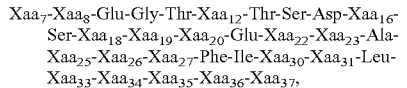

wherein $Xaa_7$ is L-histidine; $Xaa_8$ is Aib; $Xaa_{12}$ is Phe; $Xaa_{16}$ is Val; $Xaa_{18}$ is Ser or Lys; $Xaa_{19}$ is Tyr; $Xaa_{20}$ is Leu; $Xaa_{22}$ is Gly, Lys or Glu; $Xaa_{23}$ is Gln; $Xaa_{25}$ is Ala; $Xaa_{26}$ is Arg or Lys; $Xaa_{27}$ is Glu or Lys; $Xaa_{30}$ is Ala or Lys; $Xaa_{31}$ is Trp; $Xaa_{33}$ is Val, $Xaa_{34}$ is Arg; $Xaa_{35}$ is Gly; $Xaa_{36}$ is Arg; and $Xaa_{37}$ is Gly or Lys.
106. The derivative of any of embodiments 1-105, wherein $Xaa_7$ is His.
107. The derivative of any of embodiments 1-106, wherein $Xaa_8$ is Aib.
108. The derivative of any of embodiments 1-107, wherein $Xaa_{12}$ is Phe.
109. The derivative of any of embodiments 1-108, wherein $Xaa_{16}$ is Val.
110. The derivative of any of embodiments 1-109, wherein $Xaa_{18}$ is Ser.
111. The derivative of any of embodiments 1-110, wherein $Xaa_{18}$ is Lys.
112. The derivative of any of embodiments 1-111, wherein $Xaa_{19}$ is Tyr.
113. The derivative of any of embodiments 1-112, wherein $Xaa_{20}$ is Leu.
114. The derivative of any of embodiments 1-113, wherein $Xaa_{22}$ is Gly.
115. The derivative of any of embodiments 1-114, wherein $Xaa_{22}$ is Glu.
116. The derivative of any of embodiments 1-115, wherein $Xaa_{22}$ is Lys.
117. The derivative of any of embodiments 1-116, wherein $Xaa_{23}$ is Gln.
118. The derivative of any of embodiments 1-117, wherein $Xaa_{25}$ is Ala.
119. The derivative of any of embodiments 1-118, wherein $Xaa_{26}$ is Arg.
120. The derivative of any of embodiments 1-119, wherein $Xaa_{26}$ is Lys.
121. The derivative of any of embodiments 1-120, wherein $Xaa_{27}$ is Glu.
122. The derivative of any of embodiments 1-121, wherein $Xaa_{27}$ is Lys.
123. The derivative of any of embodiments 1-122, wherein $Xaa_{30}$ is Ala.
124. The derivative of any of embodiments 1-123, wherein $Xaa_{30}$ is Lys.
125. The derivative of any of embodiments 1-124, wherein $Xaa_{31}$ is Trp.
126. The derivative of any of embodiments 1-125, wherein $Xaa_{33}$ is Val.
127. The derivative of any of embodiments 1-126, wherein $Xaa_{34}$ is Arg.
128. The derivative of any of embodiments 1-127, wherein $Xaa_{35}$ is Gly.
129. The derivative of any of embodiments 1-128, wherein $Xaa_{36}$ is Arg.
130. The derivative of any of embodiments 1-129, wherein $Xaa_{37}$ is Gly.
131. The derivative of any of embodiments 1-130, wherein $Xaa_{37}$ is Lys.
132. The derivative of any of embodiments 1-131, wherein the GLP-1 peptide comprises the following amino acid changes when compared to GLP-1 (7-37) (SEQ ID NO: 1): vii) (18K, 22K, 30K); iix) (18K, 37K); ix) (18K, 27K, 37K); x) (27K, 30K, 37K); or xi) (30K, 37K); wherein in embodiment iix) and xi) the amino acid at the position corresponding to position 26 in GLP-1(7-37) (SEQ ID NO: 1) is K.
133. The derivative of any of embodiments 1-132, wherein the GLP-1 peptide comprises the following amino acid changes when compared to GLP-1 (7-37) (SEQ ID NO: 1):

i) (8Aib, 18K, 22K, 26R, 30K, 34R); ii) (8Aib, 18K, 34R, 37K); iii) (8Aib, 18K, 22E, 26R, 27K, 34R, 37K); iv) (8Aib, 18K, 26R, 27K, 34R, 37K); v) (8Aib, 22E, 26R, 27K, 30K, 34R, 37K); or vi) (8Aib, 22E, 30K, 34R, 37K).

134. The derivative of any of embodiments 1-133, wherein the GLP-1 peptide is selected from the following analogues of GLP-1 (7-37) (SEQ ID NO: 1):
i) (8Aib, 18K, 22K, 26R, 30K, 34R) (SEQ ID NO: 2); ii) (8Aib, 18K, 34R, 37K) (SEQ ID NO: 3); iii) (8Aib, 18K, 22E, 26R, 27K, 34R, 37K) (SEQ ID NO: 4); iv) (8Aib, 18K, 26R, 27K, 34R, 37K (SEQ ID NO: 5)); v) (8Aib, 22E, 26R, 27K, 30K, 34R, 37K) (SEQ ID NO: 6); and vi) (8Aib, 22E, 30K, 34R, 37K) (SEQ ID NO: 7).

135. The derivative of any of embodiments 1-134, in the form of an acid or basic salt.

136. The derivative of any of embodiments 1-135 in the form of an acid salt.

137. The derivative of any of embodiments 1-136 in the form of a chloride salt.

138. The derivative of any of embodiments 1-137 in the form of an acetate salt.

139. The derivative of any of embodiments 1-138 in the form of a basic salt

140. The derivative of any of embodiments 1-139 in the form of a sodium or potassium salt.

141. The derivative of any of embodiments 1-140 in the form of a sodium salt.

142. The derivative of any of embodiments 1-141 in the form of a potassium salt.

143. The derivative of any of embodiments 1-142 which is a GLP-1 receptor agonist.

144. The derivative of any of embodiments 1-143, which is a full GLP-1 receptor agonist.

145. The derivative of any of embodiments 1-144, which is biologically active in vitro.

146. The derivative of any of embodiments 1-145, which is potent in vitro.

147. The derivative of any of embodiments 1-146, which is capable of activating the human GLP-1 receptor.

148. The derivative of any of embodiments 1-147 which is capable of activating the human GLP-1 receptor in an assay with whole cells expressing the human GLP-1 receptor, wherein the assay is performed in the absence of HSA (0% HSA), and/or in the presence of HSA (1% HSA), preferably in the absence of HSA.

149. The derivative of any of embodiments 1-148, where the response of the human GLP-1 receptor is measured in a reporter gene assay, such as the assay of Example 22.

150. The derivative of any of embodiments 1-149, wherein the biological activity, or potency, in vitro is determined essentially as described in Example 22.

151. The derivative of any of embodiments 1-150, which has an in vitro potency corresponding to an $EC_{50}$ of 300 pM or below.

152. The derivative of any of embodiments 1-151, which has an in vitro potency corresponding to an $EC_{50}$ of 200 pM or below.

153. The derivative of any of embodiments 1-152, which has an in vitro potency corresponding to an $EC_{50}$ of 120 pM or below.

154. The derivative of any of embodiments 1-153, which has an in vitro potency corresponding to an $EC_{50}$ of 75 pM or below.

155. The derivative of any of embodiments 1-154, which has an in vitro potency corresponding to an $EC_{50}$ of 40 pM or below.

156. The derivative of any of embodiments 1-155, which has an in vitro potency corresponding to an $EC_{50}$ of 25 pM or below.

157. The derivative of any of embodiments 1-156, which has an in vitro potency corresponding to an $EC_{50}$ of 15 pM or below.

158. The derivative of any of embodiments 1-157, wherein the $EC_{50}$ is determined essentially as described in Example 22.

159. The derivative of any of embodiments 1-158, which has an in vitro potency corresponding to an $EC_{50}$ of less than 30 times the $EC_{50}$ of semaglutide, wherein the $EC_{50}$ of semaglutide is determined in the same way as the $EC_{50}$ of the derivative.

160. The derivative of any of embodiments 1-159, which has an in vitro potency corresponding to an $EC_{50}$ of less than 20 times the $EC_{50}$ of semaglutide, wherein the $EC_{50}$ of semaglutide is determined in the same way as the $EC_{50}$ of the derivative.

161. The derivative of any of embodiments 1-160, which has an in vitro potency corresponding to an $EC_{50}$ of less than 10 times the $EC_{50}$ of semaglutide, wherein the $EC_{50}$ of semaglutide is determined in the same way as the $EC_{50}$ of the derivative.

162. The derivative of any of embodiments 1-161, which has an in vitro potency corresponding to an $EC_{50}$ of less than 7 times the $EC_{50}$ of semaglutide, wherein the $EC_{50}$ of semaglutide is determined in the same way as the $EC_{50}$ of the derivative.

163. The derivative of any of embodiments 1-162, which has an in vitro potency corresponding to an $EC_{50}$ of less than 4 times the $EC_{50}$ of semaglutide, wherein the $EC_{50}$ of semaglutide is determined in the same way as the $EC_{50}$ of the derivative.

164. The derivative of any of embodiments 1-163, which has an in vitro potency corresponding to an $EC_{50}$ of less than 2 times the $EC_{50}$ of semaglutide, wherein the $EC_{50}$ of semaglutide is determined in the same way as the $EC_{50}$ of the derivative.

165. The derivative of any of embodiments 1-164, wherein the $EC_{50}$ is determined essentially as described in Example 22.

166. The derivative of any of embodiments 1-165, which is capable of binding to the GLP-1 receptor.

167. The derivative of any of embodiments 1-166, which is capable of binding to the GLP-1 receptor at a low concentration of HSA (max. 0.001% final assay concentration).

168. The derivative of any of embodiments 1-167, which is capable of binding to the GLP-1 receptor at a high concentration of HSA (2.0% final assay concentration).

169. The derivative of any of embodiments 1-168, wherein the binding to the human GLP-1 receptor is measured in a competitive binding assay, such as the assay of Example 23.

170. The derivative of any of embodiments 1-169, wherein the binding to the human GLP-1 receptor in vitro is determined essentially as described in Example 23.

171. The derivative of any of embodiments 1-170, which at a low concentration of HSA is capable of binding to the human GLP-1 receptor with an $IC_{50}$ of 15 nM or below.

172. The derivative of any of embodiments 1-171, which at a low concentration of HSA is capable of binding to the human GLP-1 receptor with an $IC_{50}$ of 10 nM or below.

173. The derivative of any of embodiments 1-172, which at a low concentration of HSA is capable of binding to the human GLP-1 receptor with an $IC_{50}$ of 3.0 nM or below.

174. The derivative of any of embodiments 1-173, which at a low concentration of HSA is capable of binding to the human GLP-1 receptor with an $IC_{50}$ of 1.4 nM or below.

175. The derivative of any of embodiments 1-174, which at a low concentration of HSA is capable of binding to the human GLP-1 receptor with an $IC_{50}$ of 0.50 nM or below.

176. The derivative of any of embodiments 1-175, which at a low concentration of HSA is capable of binding to the human GLP-1 receptor with an $IC_{50}$ of 0.30 nM or below.

177. The derivative of any of embodiments 1-176, wherein the $IC_{50}$ is determined essentially as described in Example 23, in a reaction with a low concentration of HSA, viz. max. 0.001% HSA (final assay concentration).

178. The derivative of any of embodiments 1-177, which at a low concentration of HSA is capable of binding to the human GLP-1 receptor with an $IC_{50}$ of less than 20 times the $IC_{50}$ of semaglutide, wherein the $IC_{50}$ of semaglutide is determined in the same way as the $IC_{50}$ of the derivative.

179. The derivative of any of embodiments 1-178, which at a low concentration of HSA is capable of binding to the human GLP-1 receptor with an $IC_{50}$ of less than 10 times the $IC_{50}$ of semaglutide, wherein the $IC_{50}$ of semaglutide is determined in the same way as the $IC_{50}$ of the derivative.

180. The derivative of any of embodiments 1-179, which at a low concentration of HSA is capable of binding to the human GLP-1 receptor with an $IC_{50}$ of less than 1.5 times the $IC_{50}$ of semaglutide, wherein the $IC_{50}$ of semaglutide is determined in the same way as the $IC_{50}$ of the derivative.

181. The derivative of any of embodiments 1-180, which at a low concentration of HSA is capable of binding to the human GLP-1 receptor with an $IC_{50}$ of less than 0.7 times the $IC_{50}$ of semaglutide, wherein the $IC_{50}$ of semaglutide is determined in the same way as the $IC_{50}$ of the derivative.

182. The derivative of any of embodiments 1-181, wherein the $IC_{50}$ is determined essentially as described in Example 23, in a reaction with a low concentration of HSA, viz. max. 0.001% HSA (final assay concentration).

183. The derivative of any of embodiments 1-182, which at 2.0% HSA (final assay concentration) is capable of binding to the human GLP-1 receptor with an $IC_{50}$ of 800 nM or below.

184. The derivative of any of embodiments 1-183, which at 2.0% HSA (final assay concentration) is capable of binding to the human GLP-1 receptor with an $IC_{50}$ of 500 nM or below.

185. The derivative of any of embodiments 1-184, which at 2.0% HSA (final assay concentration) is capable of binding to the human GLP-1 receptor with an $IC_{50}$ of 250 nM or below.

186. The derivative of any of embodiments 1-185, which at 2.0% HSA (final assay concentration) is capable of binding to the human GLP-1 receptor with an $IC_{50}$ of 100 nM or below.

187. The derivative of any of embodiments 1-186, wherein the $IC_{50}$ is determined essentially as described in Example 23, in a reaction with 2.0% HSA (final assay concentration).

188. The derivative of any of embodiments 1-187, which at 2.0% HSA (final assay concentration) is capable of binding to the human GLP-1 receptor with an $IC_{50}$ of less than 8 times the $IC_{50}$ of semaglutide, wherein the $IC_{50}$ of semaglutide is determined in the same way as the $IC_{50}$ of the derivative.

189. The derivative of any of embodiments 1-188, which at 2.0% HSA (final assay concentration) is capable of binding to the human GLP-1 receptor with an $IC_{50}$ of less than 2.5 times the $IC_{50}$ of semaglutide, wherein the $IC_{50}$ of semaglutide is determined in the same way as the $IC_{50}$ of the derivative.

190. The derivative of any of embodiments 1-187, which at 2.0% HSA (final assay concentration) is capable of binding to the human GLP-1 receptor with an $IC_{50}$ of less than 1 time the $IC_{50}$ of semaglutide, wherein the $IC_{50}$ of semaglutide is determined in the same way as the $IC_{50}$ of the derivative.

191. The derivative of any of embodiments 1-186, which at 2.0% HSA (final assay concentration) is capable of binding to the human GLP-1 receptor with an $IC_{50}$ of less than 0.4 times the $IC_{50}$ of semaglutide, wherein the $IC_{50}$ of semaglutide is determined in the same way as the $IC_{50}$ of the derivative.

192. The derivative of any of embodiments 1-187, wherein the $IC_{50}$ is determined essentially as described in Example 23, in a reaction with 2.0% HSA (final assay concentration).

193. The derivative of any of embodiments 1-192, which has improved pharmacokinetic properties.

194. The derivative of any of embodiments 1-193, which has an increased half-life and/or a decreased clearance.

195. The derivative of any of embodiments 1-194, which is suitable for once-monthly administration.

196. The derivative of any of embodiments 1-195, for s.c. administration.

197. The derivative of any of embodiments 1-196, wherein the derivative is tested in vivo in pharmacokinetic (PK) studies.

198. The derivative of any of embodiments 1-197, wherein the derivative is tested in any suitable animal model, such as mouse, rat, monkey, dog, or pig.

199. The derivative of any of embodiments 1-198, which is compared with semaglutide.

200. The derivative of any of embodiments 1-199, which has an improved terminal half-life (T½) in vivo in minipigs after i.v. administration as compared to semaglutide.

201. The derivative of any of embodiments 1-200, wherein the terminal half-life is determined in vivo in minipigs after i.v. administration using any suitable study protocol, such as the one described in Example 24.

202. The derivative of any of embodiments 1-201, wherein the terminal half-life is determined in vivo in minipigs after i.v. administration, essentially as described in Example 24.

203. The derivative of any of embodiments 1-202, which has a terminal half-life (T½) in vivo in minipigs after i.v. administration of at least 90 hours.

204. The derivative of any of embodiments 1-203, which has a terminal half-life (T½) in vivo in minipigs after i.v. administration of at least 100 hours.

205. The derivative of any of embodiments 1-204, which has a terminal half-life (T½) in vivo in minipigs after i.v. administration of at least 120 hours.

206. The derivative of any of embodiments 1-205, which has a terminal half-life (T½) in vivo in minipigs after i.v. administration of at least 140 hours.

207. The derivative of any of embodiments 1-206, which has a terminal half-life (T½) in vivo in minipigs after i.v. administration of at least 1.5 times the terminal half-life of semaglutide, determined in the same way.

208. The derivative of any of embodiments 1-207, which has a terminal half-life (T½) in vivo in minipigs after i.v. administration of at least 2 times the terminal half-life of semaglutide, determined in the same way.

209. The derivative of any of embodiments 1-208, which has a terminal half-life (T½) in vivo in minipigs after i.v. administration of at least 2.2 times the terminal half-life of semaglutide, determined in the same way.

210. The derivative of any of embodiments 1-209, which has a terminal half-life (T½) in vivo in minipigs after i.v. administration of at least 2.6 times the terminal half-life of semaglutide, determined in the same way.
211. The derivative of any of embodiments 1-210, which is potent in vivo.
212. The derivative of any of embodiments 1-211, which is potent in vivo when determined in any suitable animal model, such as mouse or pig.
213. The derivative of any of embodiments 1-212, wherein the animal model is db/db mouse.
214. The derivative of any of embodiments 1-213, wherein the blood glucose lowering effect is determined.
215. The derivative of any of embodiments 1-214, wherein the body weight lowering effect is determined.
216. The derivative of any of embodiments 1-215, wherein blood glucose lowering effect and/or body weight lowering effect is determined in vivo in db/db mouse using any suitable study protocol and methodology, e.g. as described in Example 25.
217. The derivative of any of embodiments 1-216, wherein the blood glucose lowering effect and/or the body weight lowering effect is determined in vivo in db/db mouse, essentially as described in Example 25.
218. The derivative of any of embodiments 1-217, which has the effect in vivo of decreasing blood glucose after 24 hours, or 48 hours, determined in a single-dose study in a db/db mouse model, in a suitable dose, such as 10, or 100 nmol/kg.
219. The derivative of any of embodiments 1-218, wherein the blood glucose is decreased by at least 10%, as compared to the blood glucose level before administration of the derivative.
220. The derivative of any of embodiments 1-219, wherein the blood glucose is decreased by at least 20%, as compared to the blood glucose level before administration of the derivative.
221. The derivative of any of embodiments 1-220 wherein the blood glucose is decreased by at least 40%, as compared to the blood glucose level before administration of the derivative.
222. The derivative of any of embodiments 1-221, wherein the blood glucose is decreased by at least 60%, as compared to the blood glucose level before administration of the derivative.
223. The derivative of any of embodiments 1-222, which has the effect in vivo of decreasing blood glucose after 72 hours, determined in a single-dose study in a db/db mouse model, in a suitable dose, such as 10 or 100 nmol/kg.
224. The derivative of any of embodiments 1-223, which has the effect in vivo of decreasing blood glucose after 96 hours, determined in a single-dose study in a db/db mouse model, in a suitable dose, such as 10 or 100 nmol/kg.
225. The derivative of any of embodiments 1-224, wherein the blood glucose is decreased by at least 0.5%, as compared to the blood glucose level before administration of the derivative.
226. The derivative of any of embodiments 1-225, wherein the blood glucose is decreased by at least 1%, as compared to the blood glucose level before administration of the derivative.
227. The derivative of any of embodiments 1-226, wherein the blood glucose is decreased by at least 5%, as compared to the blood glucose level before administration of the derivative.
228. The derivative of any of embodiments 1-227, wherein the blood glucose is decreased by at least 10%, as compared to the blood glucose level before administration of the derivative.
229. The derivative of any of embodiments 1-228, wherein the blood glucose is decreased by at least 15%, as compared to the blood glucose level before administration of the derivative.
230. The derivative of any of embodiments 1-229, which has the effect in vivo of decreasing body weight after 48 hours, determined in a single-dose study in a db/db mouse model, in a suitable dose, such as 10 or 100 nmol/kg.
231. The derivative of any of embodiments 1-230, wherein the body weight is decreased by at least 1%, as compared to the body weight before administration of the derivative.
232. The derivative of any of embodiments 1-231, wherein the body weight is decreased by at least 2%, as compared to the body weight before administration of the derivative.
233. The derivative of any of embodiments 1-232, wherein the body weight is decreased by at least 5%, as compared to the body weight before administration of the derivative.
234. The derivative of any of embodiments 1-233, wherein the body weight is decreased by at least 7%, as compared to the body weight before administration of the derivative.
235. The derivative of any of embodiments 1-234, which has the effect in vivo of decreasing body weight after 72 hours, determined in a single-dose study in a db/db mouse model, in a suitable dose, such as 10 or 100 nmol/kg.
236. The derivative of any of embodiments 1-235 which has the effect in vivo of decreasing body weight after 96 hours, determined in a single-dose study in a db/db mouse model, in a suitable dose, such as 10 or 100 nmol/kg.
237. The derivative of any of embodiments 1-236, wherein the body weight is decreased by at least 2%, as compared to the body weight before administration of the derivative.
238. The derivative of any of embodiments 1-237, wherein the body weight is decreased by at least 3%, as compared to the body weight before administration of the derivative.
239. The derivative of any of embodiments 1-238, wherein the body weight is decreased by at least 4%, as compared to the body weight before administration of the derivative.
240. The derivative of embodiment 170, wherein the animal model is pig.
241. The derivative of embodiment 198, wherein the animal model is LYD pig.
242. The derivative of any of embodiments 198-199, wherein the reduction in food intake is determined in an in vivo pharmacodynamic (PD) study.
243. The derivative of any of embodiments 198-200, wherein the reduction in food intake is determined in vivo in pig using any suitable study protocol and methodology, e.g. as described in Example 26.
244. The derivative of any of embodiments 198-201, wherein the reduction in food intake is determined in vivo in pig using any suitable study protocol and methodology, essentially as described in Example 26.
245. The derivative of any of embodiments 1-244, which has the effect in vivo of reducing food intake during a first period of 24 hours (0-24 hours) after administration of a single dose of the derivative, wherein food intake is determined in a single-dose study in a LYD pig model.
246. The derivative of any of embodiments 1-245, which has the effect in vivo of reducing food intake during a second period of 24 hours (24-48 hours) after administration of a single dose of the derivative, wherein food intake is determined in a single-dose study in a LYD pig model.

247. The derivative of any of embodiments 1-246, which has the effect in vivo of reducing food intake during a third period of 24 hours (48-72 hours) after administration of a single dose of the derivative, wherein food intake is determined in a single-dose study in a LYD pig model.

248. The derivative of any of embodiments 1-247, which has the effect in vivo of reducing food intake during a fourth period of 24 hours (72-96 hours) after administration of a single dose of the derivative, wherein food intake is determined in a single-dose study in a LYD pig model.

249. A GLP-1 derivative selected from the following: Chem. 21, Chem. 22, Chem. 23, Chem. 24, Chem. 25, Chem. 26, Chem. 27, Chem. 28, Chem. 29, Chem. 30, Chem. 31, Chem. 32, Chem. 33, Chem. 34, Chem. 35, Chem. 36, Chem. 37, Chem. 38, Chem. 39, Chem. 40, or Chem. 41; or a pharmaceutically acceptable salt, amide, or ester thereof.

250. A GLP-1 derivative selected from the chemical structures shown in any of Examples 1-21; or a pharmaceutically acceptable salt, amide, or ester thereof.

251. A GLP-1 derivative selected from the GLP-1 derivative names shown in any of Examples 1-21; or a pharmaceutically acceptable salt, amide, or ester thereof.

252. The derivative of any of embodiments 249-250, which is a derivative according to any of embodiments 1-248.

253. An intermediate product in the form of a GLP-1 analogue, which comprises the following amino acid changes when compared to GLP-1(7-37) (SEQ ID NO: 1):
vii) (18K, 22K, 30K);
iix) (18K, 37K);
ix) (18K, 27K, 37K);
x) (27K, 30K, 37K); or
xi) (30K, 37K);
wherein in embodiment iix) and xi) the amino acid at the position corresponding to position 26 in GLP-1(7-37) (SEQ ID NO: 1) is K.

254. An intermediate product in the form of a GLP-1 analogue, which comprises the following amino acid changes when compared to GLP-1 (7-37) (SEQ ID NO: 1):
i) (8Aib, 18K, 22K, 26R, 30K, 34R); ii) (8Aib, 18K, 34R, 37K); iii) (8Aib, 18K, 22E, 26R, 27K, 34R, 37K); iv) (8Aib, 18K, 26R, 27K, 34R, 37K); v) (8Aib, 22E, 26R, 27K, 30K, 34R, 37K); or vi) (8Aib, 22E, 30K, 34R, 37K).

255. An intermediate product in the form of a GLP-1 analogue, selected from the following analogues of GLP-1 (7-37) (SEQ ID NO: 1):
i) (8Aib, 18K, 22K, 26R, 30K, 34R) (SEQ ID NO: 2); ii) (8Aib, 18K, 34R, 37K) (SEQ ID NO: 3); iii) (8Aib, 18K, 22E, 26R, 27K, 34R, 37K) (SEQ ID NO: 4); iv) (8Aib, 18K, 26R, 27K, 34R, 37K (SEQ ID NO: 5)); v) (8Aib, 22E, 26R, 27K, 30K, 34R, 37K) (SEQ ID NO: 6); and vi) (8Aib, 22E, 30K, 34R, 37K) (SEQ ID NO: 7).

256. A pharmaceutical composition comprising a derivative according to any of embodiments 1-252, or an analogue according to any of embodiments 253-255, and a pharmaceutically acceptable excipient.

257. A derivative according to any of embodiments 1-252, or an analogue according to any of embodiments 253-255, for use as a medicament.

258. A derivative according to any of embodiments 1-252, or an analogue according to any of embodiments 253-255, for use in
(i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells;

(iv) prevention and/or treatment of cognitive disorders and/or neurodegenerative disorders, such as Alzheimer's disease, Parkinson's disease, and/or multiple sclerosis;

(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence;

(vi) prevention and/or treatment of diabetic complications, such as angiopathy; neuropathy, including peripheral neuropathy; nephropathy; and/or retinopathy;

(vii) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo(a)) in vitro and/or in vivo;

(viii) prevention and/or treatment of cardiovascular diseases, such as syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis obliterens), diastolic dysfunction, and/or systolic dysfunction; and/or reduction of blood pressure, such as reduction of systolic blood pressure;

(ix) prevention and/or treatment of gastrointestinal diseases, such as inflammatory bowel disease, short bowel syndrome, or Crohn's disease or colitis; dyspepsia, and/or gastric ulcers; and/or inflammation, such as psoriasis, psoriactic arthritis, rheumatoid arthritis, and/or systemic lupus erythematosus;

(x) prevention and/or treatment of critical illness, such as treatment of a critically ill patient, a critical illness polynephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteraemia, septicaemia, and/or septic shock during hospitalisation; and/or stabilising blood glucose, insulin balance and optionally metabolism in intensive care unit patients with acute illness;

(xi) prevention and/or treatment of polycystic ovary syndrome (PCOS);

(xii) prevention and/or treatment of cerebral disease, such as cerebral ischemia, cerebral haemorrhage, and/or traumatic brain injury;

(xiii) prevention and/or treatment of sleep apnoea; and/or (xiv) prevention and/or treatment of abuse, such as alcohol abuse and/or drug abuse.

259. Use of a derivative according to any of embodiments 1-252, or an analogue according to any of embodiments 253-255, in the manufacture of a medicament for (i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells;

(iv) prevention and/or treatment of cognitive disorders and/or neurodegenerative disorders, such as Alzheimer's disease, Parkinson's disease, and/or multiple sclerosis;

(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence;

(vi) prevention and/or treatment of diabetic complications, such as angiopathy; neuropathy, including peripheral neuropathy; nephropathy; and/or retinopathy;

(vii) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo(a)) in vitro and/or in vivo;

(viii) prevention and/or treatment of cardiovascular diseases, such as syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atherosclerosis oblitterens), diastolic dysfunction, and/or systolic dysfunction; and/or reduction of blood pressure, such as reduction of systolic blood pressure;

(ix) prevention and/or treatment of gastrointestinal diseases, such as inflammatory bowel disease, short bowel syndrome, or Crohn's disease or colitis; dyspepsia, and/or gastric ulcers; and/or inflammation, such as psoriasis, psoriactic arthritis, rheumatoid arthritis, and/or systemic lupus erythematosus;

(x) prevention and/or treatment of critical illness, such as treatment of a critically ill patient, a critical illness polynephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteraemia, septicaemia, and/or septic shock during hospitalisation; and/or stabilising blood glucose, insulin balance and optionally metabolism in intensive care unit patients with acute illness;

(xi) prevention and/or treatment of polycystic ovary syndrome (PCOS);

(xii) prevention and/or treatment of cerebral disease, such as cerebral ischemia, cerebral haemorrhage, and/or traumatic brain injury;

(xiii) prevention and/or treatment of sleep apnoea; and/or (xiv) prevention and/or treatment of abuse, such as alcohol abuse and/or drug abuse.

260. A method for (i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells;

(iv) prevention and/or treatment of cognitive disorders and/or neurodegenerative disorders, such as Alzheimer's disease, Parkinson's disease, and/or multiple sclerosis;

(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence;

(vi) prevention and/or treatment of diabetic complications, such as angiopathy; neuropathy, including peripheral neuropathy; nephropathy; and/or retinopathy;

(vii) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo(a)) in vitro and/or in vivo;

(viii) prevention and/or treatment of cardiovascular diseases, such as syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis oblitterens), diastolic dysfunction, and/or systolic dysfunction; and/or reduction of blood pressure, such as reduction of systolic blood pressure;

(ix) prevention and/or treatment of gastrointestinal diseases, such as inflammatory bowel disease, short bowel syndrome, or Crohn's disease or colitis; dyspepsia, and/or gastric ulcers; and/or inflammation, such as psoriasis, psoriactic arthritis, rheumatoid arthritis, and/or systemic lupus erythematosus;

(x) prevention and/or treatment of critical illness, such as treatment of a critically ill patient, a critical illness polynephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteraemia, septicaemia, and/or septic shock during hospitalisation; and/or stabilising blood glucose, insulin balance and optionally metabolism in intensive care unit patients with acute illness;

(xi) prevention and/or treatment of polycystic ovary syndrome (PCOS);

(xii) prevention and/or treatment of cerebral disease, such as cerebral ischemia, cerebral haemorrhage, and/or traumatic brain injury;

(xiii) prevention and/or treatment of sleep apnoea; and/or (xiv) prevention and/or treatment of abuse, such as alcohol abuse and/or drug abuse;

wherein a pharmaceutically active amount of a derivative according to any of embodiments 1-252, or an analogue according to any of embodiments 253-255, is administered.

Additional Particular Embodiments

The following are additional particular sets of embodiments of the invention:

1. A derivative of a GLP-1 peptide,
wherein the GLP-1 peptide comprises a first, a second, and a third K residue at positions corresponding to positions (18, 22, 30), (18, 26, 37), (18, 27, 37), (26, 30, 37), or (27, 30, 37) of GLP-1(7-37) (SEQ ID NO: 1), and has a maximum of seven amino acid changes as compared to GLP-1 (7-37) (SEQ ID NO: 1);
which derivative comprises
a first, a second, and a third protracting moiety of formula Chem. 1 or formula Chem. 2:

  Chem. 1:

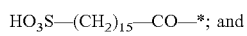  Chem. 2:

a first, a second, and a third linker, each linker comprising a *—CO group and an *—NH group;
wherein each protracting moiety is attached at its *—CO end to the *—NH end of the respective linker, and each linker is attached at its *—CO end to the epsilon amino group of the respective K residue of the GLP-1 peptide;
or a pharmaceutically acceptable salt, amide, or ester thereof.

2. The derivative of embodiment 1, wherein the first, second, and third K residues are designated K1, K2, and K3, respectively.

3. The derivative of any of embodiments 1-2, wherein the first K residue (K1) is at a position corresponding to position p1 of GLP-1 (7-37) (SEQ ID NO: 1), the second K residue (K2) is at a position corresponding to position p2 of GLP-1(7-37) (SEQ ID NO: 1), and the third K residue (K3) is at a position corresponding to position p3 of GLP-1(7-37) (SEQ ID NO: 1).

4. The derivative of embodiment 3, wherein p1, p2, and p3 are selected from the following sets of positions of GLP-1 (7-37) (SEQ ID NO: 1): (18, 22, 30), (18, 26, 37), (18, 27, 37), (26, 30, 37), and (27, 30, 37).

5. The derivative of any of embodiments 1-4, wherein the first, second, and third protracting moieties are designated Pr1, Pr2, and Pr3, respectively.

6. The derivative of any of embodiments 1-5, wherein the first, second, and third linker are designated Ln1, Ln2, and Ln3, respectively.

7. The derivative of any of embodiments 1-6, wherein the first protracting moiety (Pr1) is attached at its *—CO group to the *—NH group of the first linker (Ln1) which is attached at its *—CO group to the epsilon amino group of the first K residue (K1); the second protracting moiety (Pr2) is attached at its *—CO group to the *—NH group of the second linker (Ln2) which is attached at its *—CO group to the epsilon amino group of the second K residue (K2); and the third protracting moiety (Pr3) is attached at its *—CO group to the *—NH group of the third linker (Ln3) which is attached at its *—CO group to the epsilon amino group of the third K residue (K3).

8. A derivative of a GLP-1 peptide,
wherein the GLP-1 peptide comprises a first K residue (K1), a second K residue (K2), and a third K residue (K3) at positions (p) corresponding to positions (p1, p2, p3), respectively, of GLP-1(7-37) (SEQ ID NO: 1), where (p1, p2, p3) are selected from (18, 22, 30), (18, 26, 37), (18, 27, 37), (26, 30, 37), and (27, 30, 37); and
wherein the GLP-1 peptide has a maximum of seven amino acid changes as compared to GLP-1(7-37) (SEQ ID NO: 1);
which derivative comprises a first protracting moiety (Pr1), a second protracting moiety (Pr2), and a third protracting moiety (Pr3), wherein each of Pr1, Pr2 and Pr3 is of formula Chem. 1 or formula Chem. 2:

  Chem. 1:

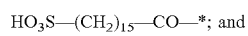  Chem. 2:

a first linker (Ln1), a second linker (Ln2), and a third linker (Ln3), wherein each of Ln1, Ln2 and Ln3 comprises a *—CO group and an *—NH group;
wherein
Pr1 is attached at its *—CO group to the *—NH group of Ln1 and Ln1 is attached at its *—CO group to the epsilon amino group of K1,
Pr2 is attached at its *—CO group to the *—NH group of Ln2 and Ln2 is attached at its *—CO group to the epsilon amino group of K2, and
Pr3 is attached at its *—CO group to the *—NH group of Ln3 and Ln3 is attached at its *—CO group to the epsilon amino group of K3;
or a pharmaceutically acceptable salt, amide, or ester thereof.

8a. The derivative of any of embodiments 1-8, wherein the first, second, and third K residues (K1, K2, K3) are at positions (p1, p2, p3) corresponding to positions (18, 22, 30) of GLP-1(7-37) (SEQ ID NO: 1), respectively.

8b. The derivative of any of embodiments 1-8, wherein the first, second, and third K residues (K1, K2, K3) are at positions (p1, p2, p3) corresponding to positions (18, 26, 37) of GLP-1(7-37) (SEQ ID NO: 1), respectively.

8c. The derivative of any of embodiments 1-8, wherein the first, second, and third K residues (K1, K2, K3) are at positions (p1, p2, p3) corresponding to positions (18, 27, 37) of GLP-1(7-37) (SEQ ID NO: 1), respectively.

8d. The derivative of any of embodiments 1-8, wherein the first, second, and third K residues (K1, K2, K3) are at positions (p1, p2, p3) corresponding to positions (26, 30, 37) of GLP-1(7-37) (SEQ ID NO: 1), respectively.

8e. The derivative of any of embodiments 1-8, wherein the first, second, and third K residues (K1, K2, K3) are at positions (p1, p2, p3) corresponding to positions (27, 30, 37) of GLP-1(7-37) (SEQ ID NO: 1), respectively.

9. The derivative of any of embodiments 1-8e, wherein each of the first, second, and third protracting moiety (Pr1, Pr2, and Pr3, respectively) is of formula Chem. 1.

10. The derivative of any of embodiments 1-8e, wherein each of the first, second, and third protracting moiety (Pr1, Pr2, and Pr3, respectively) is of formula Chem. 2.

11. The derivative of any of embodiments 1-10, wherein each of the first, second, and third linker (Ln1, Ln2, and Ln3, respectively) comprises an element_1 of formula Chem. 3:

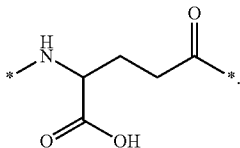

Chem. 3

12. The derivative of embodiment 11, wherein each of the first, second, and third linker (Ln1, Ln2, and Ln3, respectively) incorporates one element_1 of formula Chem. 3.

13. The derivative of any of embodiments 11-12, wherein Chem. 3 represents a gGlu residue.

14. The derivative of any of embodiments 11-13, wherein element_1 is an L-gGlu residue.

15. The derivative of any of embodiments 1-14, wherein each of the first, second, and third linker (Ln1, Ln2, and Ln3, respectively) comprises an element_2 of formula Chem. 4:

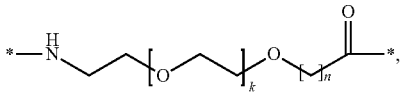

Chem. 4 wherein k is an integer in the range of 1-5, and n is an integer in the range of 1-5.

16. The derivative of embodiment 15, wherein each of the first, second, and third linker (Ln1, Ln2, and Ln3, respectively) comprises at least one element_2 of formula Chem. 4.

17. The derivative of any of embodiments 15-16, wherein each of the first, second, and third linker (Ln1, Ln2, and Ln3, respectively) comprises at least two elements_2 of formula Chem. 4.

18. The derivative of any of embodiments 15-17, wherein each of the first, second, and third linker (Ln1, Ln2, and Ln3, respectively) comprises two elements_2 of formula Chem. 4.

19. The derivative of any of embodiments 15-18, wherein each of the first, second, and third linker incorporates two elements_2 of formula Chem. 4.

20. The derivative of any of embodiments 15-19, wherein k=1 and n=1.

21. The derivative of any of embodiments 15-20, wherein Chem. 4 represents OEG.

22. The derivative of any of embodiments 1-21, wherein each of the first, second, and third linker (Ln1, Ln2, and Ln3, respectively) comprises an element_3 of formula Chem. 5:

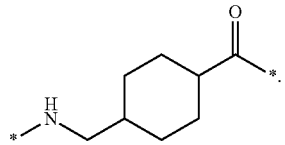

Chem. 5

23. The derivative of any of embodiments 1-22, wherein each of the first, second, and third linker (Ln1, Ln2, and Ln3, respectively) incorporates one element_3 of formula Chem. 5.

24. The derivative of any of embodiments 122-23, wherein Chem. 5 represents Trx.

25. The derivative of any of embodiments 1-24, wherein each of the first, second, and third linker (Ln1, Ln2, and Ln3, respectively) comprises an element_4 of formula Chem. 6:

$$*-NH-(CH_2)_q-CH[(CH_2)_w-NH_2]-CO-*,$$ Chem. 6:

wherein q is an integer in the range of 0-5, and w is an integer in the range of 0-5, with the provisos that when w is 0 q is an integer in the range of 1-5, and when q is 0 w is an integer in the range of 1-5.

26. The derivative of embodiment 25, wherein each of the first, second, and third linker (Ln1, Ln2, and Ln3, respectively) comprises at least one element_4 of formula Chem. 6.

27. The derivative of any of embodiments 25-26, wherein each of the first, second, and third linker (Ln1, Ln2, and Ln3, respectively) comprises at least two elements_4 of formula Chem. 6.

28. The derivative of any of embodiments 25-27, wherein each of the first, second, and third linker (Ln1, Ln2, and Ln3, respectively) comprises two elements_4 of formula Chem. 6.

29. The derivative of any of embodiments 25-28, wherein each of the first, second, and third linker (Ln1, Ln2, and Ln3, respectively) incorporates two elements_4 of formula Chem. 6.

30. The derivative of any of embodiments 25-29, wherein q is 4 and w is 0.

31. The derivative of any of embodiments 25-29, wherein w is 4 and q is 0.

32. The derivative of any of embodiments 25-31, wherein Chem. 6 represents an eps-Lys residue.

33. The derivative of any of embodiments 25-32, wherein element_4 is an L-eps-Lys residue.

34. The derivative of any of embodiments 1-33, wherein each of the first, second, and third linker (Ln1, Ln2, and Ln3, respectively) comprises an element_5 of formula Chem. 7:

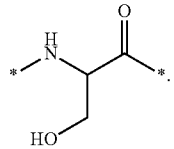

Chem. 7

35. The derivative of embodiment 34, wherein each of the first, second, and third linker (Ln1, Ln2, and Ln3, respectively) comprises at least one element_5 of formula Chem. 7.

36. The derivative of any of embodiments 34-35, wherein each of the first, second, and third linker (Ln1, Ln2, and Ln3, respectively) comprises at least five elements_5 of formula Chem. 7.
37. The derivative of any of embodiments 34-36, wherein each of the first, second, and third linker (Ln1, Ln2, and Ln3, respectively) comprises five elements_5 of formula Chem. 7.
38. The derivative of any of embodiments 34-37, wherein each of the first, second, and third linker (Ln1, Ln2, and Ln3, respectively) comprises six elements_5 of formula Chem. 7.
39. The derivative of any of embodiments 34-38, wherein each of the first, second, and third linker (Ln1, Ln2, and Ln3, respectively) incorporates five elements_5 of formula Chem. 7.
40. The derivative of any of embodiments 34-39, wherein each of the first, second, and third linker (Ln1, Ln2, and Ln3, respectively) incorporates six elements_5 of formula Chem. 7.
41. The derivative of any of embodiments 34-40, wherein element_5 is a Ser residue.
42. The derivative of any of embodiments 34-41, wherein element_5 is an L-Ser residue.
43. The derivative of any of embodiments 1-42, wherein each of the first, second, and third linker (Ln1, Ln2, and Ln3, respectively) comprises an element_6 of formula Chem. 8:

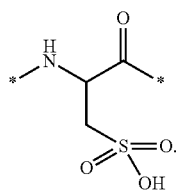

Chem. 8

44. The derivative of embodiment 43, wherein each of the first, second, and third linker (Ln1, Ln2, and Ln3, respectively) incorporates one element_6 of formula Chem. 8.
45. The derivative of any of embodiments 43-44, wherein Chem. 8 represents a Cysteic acid residue.
46. The derivative of any of embodiments 43-45, wherein element_6 is an L-Cysteic acid.
47. The derivative of any of embodiments 1-46, wherein each of the first, second, and third linker (Ln1, Ln2, and Ln3, respectively) consists of one element_3 of formula Chem. 5, one element_1 of formula Chem. 3, and two elements_2 of formula Chem. 4 wherein k=1 and n=1, interconnected via amide bonds and in the sequence indicated.
48. The derivative of any of embodiments 1-46, wherein each of the first, second, and third linker (Ln1, Ln2, and Ln3, respectively) consists of one element_6 of formula Chem. 8, and two elements_2 of formula Chem. 4 wherein k=1 and n=1, interconnected via amide bonds and in the sequence indicated.
49. The derivative of any of embodiments 1-46, wherein each of the first, second, and third linker (Ln1, Ln2, and Ln3, respectively) consists of one element_1 of formula Chem. 3, five elements_5 of formula Chem. 7, and one element_4 of formula Chem. 6 wherein q=4 and w=0 (or w=4 and q=0), interconnected via amide bonds and in the sequence indicated.
50. The derivative of any of embodiments 1-46, wherein each of the first, second, and third linker (Ln1, Ln2, and Ln3, respectively) consists of one element_3 of formula Chem. 5, one element_6 of formula Chem. 8, and two elements_2 of formula Chem. 4 wherein k=1 and n=1, interconnected via amide bonds and in the sequence indicated.
51. The derivative of any of embodiments 1-46, wherein each of the first, second, and third linker (Ln1, Ln2, and Ln3, respectively) consists of one element_1 of formula Chem. 3, and two elements_2 of formula Chem. 4 wherein k=1 and n=1, interconnected via amide bonds and in the sequence indicated.
52. The derivative of any of embodiments 1-46, wherein each of the first, second, and third linker (Ln1, Ln2, and Ln3, respectively) consists of one element_1 of formula Chem. 3, two elements_2 of formula Chem. 4 wherein k=1 and n=1, and one element_4 of formula Chem. 6 wherein q=4 and w=0 (or w=4 and q=0), interconnected via amide bonds and in the sequence indicated.
53. The derivative of any of embodiments 1-46, wherein each of the first, second, and third linker (Ln1, Ln2, and Ln3, respectively) consists of one element_2 of formula Chem. 4 wherein k=1 and n=1, one element_1 of formula Chem. 3, and one element_2 of formula Chem. 4 wherein k=1 and n=1, interconnected via amide bonds and in the sequence indicated.
54. The derivative of any of embodiments 1-46, wherein each of the first, second, and third linker (Ln1, Ln2, and Ln3, respectively) consists of one element_1 of formula Chem. 3, and six elements_5 of formula Chem. 7, interconnected via amide bonds and in the sequence indicated.
55. The derivative of any of embodiments 1-46, wherein each of the first, second, and third linker (Ln1, Ln2, and Ln3, respectively) consists of one element_6 of formula Chem. 8, two elements_2 of formula Chem. 4 wherein k=1 and n=1, and one element_4 of formula Chem. 6 wherein q=4 and w=0 (or w=4 and q=0), interconnected via amide bonds and in the sequence indicated.
56. The derivative of any of embodiments 1-46, wherein each of the first, second, and third linker (Ln1, Ln2, and Ln3, respectively) consists of one element_4 of formula Chem. 6 wherein q=4 and w=0 (or w=4 and q=0), and two elements_2 of formula Chem. 4 wherein k=1 and n=1, and interconnected via amide bonds and in the sequence indicated.
57. The derivative of any of embodiments 1-46, wherein each of the first, second, and third linker (Ln1, Ln2, and Ln3, respectively) consists of two elements_4 of formula Chem. 6 wherein q=4 and w=0 (or w=4 and q=0), and two elements_2 of formula Chem. 4 wherein k=1 and n=1, and interconnected via amide bonds and in the sequence indicated.
58. The derivative of any of embodiments 1-57, wherein the GLP-1 peptide has a maximum of 7 amino acid changes, when compared with GLP-1(7-37) (SEQ ID NO: 1).
59. The derivative of any of embodiments 1-58, wherein the GLP-1 peptide has a maximum of 6 amino acid changes, when compared with GLP-1(7-37) (SEQ ID NO: 1).
60. The derivative of any of embodiments 1-59, wherein the GLP-1 peptide has a maximum of 5 amino acid changes, when compared with GLP-1(7-37) (SEQ ID NO: 1).
61. The derivative of any of embodiments 1-60, wherein the GLP-1 peptide has a maximum of 4 amino acid changes, when compared with GLP-1(7-37) (SEQ ID NO: 1).
62. The derivative of any of embodiments 1-61, wherein the GLP-1 peptide has a minimum of 2 amino acid changes, when compared with GLP-1(7-37) (SEQ ID NO: 1).
63. The derivative of any of embodiments 1-62, wherein the GLP-1 peptide has a minimum of 3 amino acid changes, when compared with GLP-1(7-37) (SEQ ID NO: 1).

64. The derivative of any of embodiments 1-63, wherein the GLP-1 peptide has a minimum of 4 amino acid changes, when compared with GLP-1(7-37) (SEQ ID NO: 1).
65. The derivative of any of embodiments 1-64, wherein the GLP-1 peptide has a minimum of 5 amino acid changes, when compared with GLP-1(7-37) (SEQ ID NO: 1).
66. The derivative of any of embodiments 1-65, wherein the GLP-1 peptide has a minimum of 6 amino acid changes, when compared with GLP-1(7-37) (SEQ ID NO: 1).
67. The derivative of any of embodiments 1-66, wherein the GLP-1 peptide has a minimum of 7 amino acid changes, when compared with GLP-1(7-37) (SEQ ID NO: 1).
68. The derivative of any of embodiments 1-67, wherein the GLP-1 peptide has 4 amino acid changes, when compared with GLP-1(7-37) (SEQ ID NO: 1).
69. The derivative of any of embodiments 1-67, wherein the GLP-1 peptide has 5 amino acid changes, when compared with GLP-1(7-37) (SEQ ID NO: 1).
70. The derivative of any of embodiments 1-67, wherein the GLP-1 peptide has 6 amino acid changes, when compared with GLP-1(7-37) (SEQ ID NO: 1).
71. The derivative of any of embodiments 1-67, wherein the GLP-1 peptide has 7 amino acid changes, when compared with GLP-1(7-37) (SEQ ID NO: 1).
72. The derivative of any of embodiments 1-71, wherein the GLP-1 peptide comprises at least three Lys residues.
73. The derivative of any of embodiments 1-72, wherein the GLP-1 peptide comprises three Lys residues.
74. The derivative of any of embodiments 1-73, wherein the GLP-1 peptide has three Lys residues.
75. The derivative of any of embodiments 1-74, wherein the GLP-1 peptide has only three Lys residues.
76. The derivative of any of embodiments 1-75, wherein the GLP-1 peptide has the general formula I:

$Xaa_7$-$Xaa_8$-Glu-Gly-Thr-$Xaa_{12}$-Thr-Ser-Asp-$Xaa_{16}$-Ser-$Xaa_{18}$-$Xaa_{19}$-$Xaa_{20}$-Glu-$Xaa_{22}$-$Xaa_{23}$-Ala-$Xaa_{25}$-$Xaa_{26}$-$Xaa_{27}$-Phe-Ile-$Xaa_{30}$-$Xaa_{31}$-Leu-$Xaa_{33}$-$Xaa_{34}$-$Xaa_{35}$-$Xaa_{36}$-$Xaa_{37}$ (SEQ ID NO: 8), Formula I:

wherein
$Xaa_7$ is L-histidine, (S)-2-Hydroxy-3-(1H-imidazol-4-yl)-propionic acid, D-histidine, desamino-histidine, homohistidine, $N^\alpha$-acetyl-histidine, $N^\alpha$-formyl-histidine, α-methyl-histidine, 3-pyridylalanine, 2-pyridylalanine, or 4-pyridylalanine;
$Xaa_8$ is Ala, Gly, Ser, Aib, (1-aminocyclopropyl) carboxylic acid, or (1-aminocyclobutyl) carboxylic acid;
$Xaa_{12}$ is Phe or Leu;
$Xaa_{16}$ is Val or Leu;
$Xaa_{18}$ is Ser, Arg, Lys, Val, or Leu;
$Xaa_{19}$ is Tyr or Gin;
$Xaa_{20}$ is Leu or Met;
$Xaa_{22}$ is Gly, Lys or Glu;
$Xaa_{23}$ is Gin, Glu, Lys, or Arg;
$Xaa_{25}$ is Ala or Val;
$Xaa_{26}$ is Arg or Lys;
$Xaa_{27}$ is Glu, Lys, or Leu;
$Xaa_{30}$ is Ala, Glu, or Lys;
$Xaa_{31}$ is Trp or His;
$Xaa_{33}$ is Val, Lys, or Arg;
$Xaa_{34}$ is Lys, Arg, His, Asn, or Gin;
$Xaa_{35}$ is Gly or Ala;
$Xaa_{36}$ is Arg or Gly; and
$Xaa_{37}$ is Gly, Pro, or Lys.

77. The derivative of embodiment 76, wherein $Xaa_7$ is His.
78. The derivative of any of embodiments 76-77, wherein $Xaa_8$ is Aib.
79. The derivative of any of embodiments 76-78, wherein $Xaa_{12}$ is Phe.
80. The derivative of any of embodiments 76-79, wherein $Xaa_{16}$ is Val.
81. The derivative of any of embodiments 76-80, wherein $Xaa_{18}$ is Ser.
82. The derivative of any of embodiments 76-80, wherein $Xaa_{18}$ is Lys.
83. The derivative of any of embodiments 76-82, wherein $Xaa_{19}$ is Tyr.
84. The derivative of any of embodiments 76-83, wherein $Xaa_{20}$ is Leu.
85. The derivative of any of embodiments 76-84, wherein $Xaa_{22}$ is Gly.
86. The derivative of any of embodiments 76-84, wherein $Xaa_{22}$ is Lys.
87. The derivative of any of embodiments 76-86, wherein $Xaa_{23}$ is Gin.
88. The derivative of any of embodiments 76-87, wherein $Xaa_{25}$ is Ala.
89. The derivative of any of embodiments 76-88, wherein $Xaa_{26}$ is Arg.
90. The derivative of any of embodiments 76-88, wherein $Xaa_{26}$ is Lys.
91. The derivative of any of embodiments 76-90, wherein $Xaa_{27}$ is Glu.
92. The derivative of any of embodiments 76-90, wherein $Xaa_{27}$ is Lys.
93. The derivative of any of embodiments 76-92, wherein $Xaa_{30}$ is Ala.
94. The derivative of any of embodiments 76-92, wherein $Xaa_{30}$ is Lys.
95. The derivative of any of embodiments 76-94, wherein $Xaa_{31}$ is Trp.
96. The derivative of any of embodiments 76-95, wherein $Xaa_{33}$ is Val
97. The derivative of any of embodiments 76-96, wherein $Xaa_{34}$ is Arg.
98. The derivative of any of embodiments 76-97, wherein $Xaa_{35}$ is Gly.
99. The derivative of any of embodiments 76-98, wherein $Xaa_{36}$ is Arg.
100. The derivative of any of embodiments 76-99, wherein $Xaa_{37}$ is Gly.
101. The derivative of any of embodiments 76-99, wherein $Xaa_{37}$ is Lys.
102. The derivative of any of embodiments 1-101, wherein the GLP-1 peptide is selected from the following analogues of GLP-1 (7-37) (SEQ ID NO: 1):
i) (8Aib, 18K, 22K, 26R, 30K, 34R) (SEQ ID NO: 2); ii) (8Aib, 18K, 34R, 37K) (SEQ ID NO: 3); iii) (8Aib, 18K, 22E, 26R, 27K, 34R, 37K) (SEQ ID NO: 4); iv) (8Aib, 18K, 26R, 27K, 34R, 37K (SEQ ID NO: 5)); v) (8Aib, 22E, 26R, 27K, 30K, 34R, 37K) (SEQ ID NO: 6); and vi) (8Aib, 22E, 30K, 34R, 37K) (SEQ ID NO: 7).
103. The derivative of any of embodiments 1-102, in the form of a sodium, potassium, chloride, or acetate salt thereof.
104. The derivative of any of embodiments 1-103 which is a GLP-1 receptor agonist.
105. The derivative of embodiment 104, which is a full GLP-1 receptor agonist.
106. The derivative of any of embodiments 1-105, which is biologically active in vitro.
107. The derivative of any of embodiments 1-106, which is potent in vitro.

108. The derivative of any of embodiments 1-107, which is capable of activating the human GLP-1 receptor.
109. The derivative of any of embodiments 1-108 which is capable of activating the human GLP-1 receptor in an assay with whole cells expressing the human GLP-1 receptor, wherein the assay is performed in the absence of HSA (0% HSA), and/or in the presence of HSA (1% HSA), preferably in the absence of HSA.
110. The derivative of embodiment 109, where the response of the human GLP-1 receptor is measured in a reporter gene assay, such as the assay of Example 22.
111. The derivative of any of embodiments 106-110, wherein the biological activity, or potency, in vitro is determined essentially as described in Example 22.
112. The derivative of any of embodiments 1-109, which has an in vitro potency corresponding to an $EC_{50}$ of 300 pM or below.
113. The derivative of any of embodiments 1-110, which has an in vitro potency corresponding to an $EC_{50}$ of 200 pM or below.
114. The derivative of any of embodiments 1-111, which has an in vitro potency corresponding to an $EC_{50}$ of 105 pM or below.
115. The derivative of any of embodiments 1-112, which has an in vitro potency corresponding to an $EC_{50}$ of 75 pM or below.
116. The derivative of any of embodiments 1-113, which has an in vitro potency corresponding to an $EC_{50}$ of 40 pM or below.
117. The derivative of any of embodiments 1-114, which has an in vitro potency corresponding to an $EC_{50}$ of 25 pM or below.
118. The derivative of any of embodiments 112-117, wherein the $EC_{50}$ is determined essentially as described in Example 22.
119. The derivative of any of embodiments 1-118, which has an in vitro potency corresponding to an $EC_{50}$ of less than 30 times the $EC_{50}$ of semaglutide, wherein the $EC_{50}$ of semaglutide is determined in the same way as the $EC_{50}$ of the derivative.
120. The derivative of any of embodiments 1-119, which has an in vitro potency corresponding to an $EC_{50}$ of less than 20 times the $EC_{50}$ of semaglutide, wherein the $EC_{50}$ of semaglutide is determined in the same way as the $EC_{50}$ of the derivative.
121. The derivative of any of embodiments 1-120, which has an in vitro potency corresponding to an $EC_{50}$ of less than 10 times the $EC_{50}$ of semaglutide, wherein the $EC_{50}$ of semaglutide is determined in the same way as the $EC_{50}$ of the derivative.
122. The derivative of any of embodiments 1-121, which has an in vitro potency corresponding to an $EC_{50}$ of less than 7 times the $EC_{50}$ of semaglutide, wherein the $EC_{50}$ of semaglutide is determined in the same way as the $EC_{50}$ of the derivative.
123. The derivative of any of embodiments 1-122, which has an in vitro potency corresponding to an $EC_{50}$ of less than 4 times the $EC_{50}$ of semaglutide, wherein the $EC_{50}$ of semaglutide is determined in the same way as the $EC_{50}$ of the derivative.
124. The derivative of any of embodiments 1-123, which has an in vitro potency corresponding to an $EC_{50}$ of less than 2 times the $EC_{50}$ of semaglutide, wherein the $EC_{50}$ of semaglutide is determined in the same way as the $EC_{50}$ of the derivative.
125. The derivative of any of embodiments 119-124, wherein the $EC_{50}$ is determined essentially as described in Example 22.
126. The derivative of any of embodiments 1-125, which is capable of binding to the GLP-1 receptor.
127. The derivative of any of embodiments 1-126, which is capable of binding to the GLP-1 receptor at a low concentration of HSA (max. 0.001% final assay concentration).
128. The derivative of any of embodiments 1-127, which is capable of binding to the GLP-1 receptor at a high concentration of HSA (2.0% final assay concentration).
129. The derivative of any of embodiments 126-128, wherein the binding to the human GLP-1 receptor is measured in a competitive binding assay, such as the assay of Example 23.
130. The derivative of any of embodiments 126-129, wherein the binding to the human GLP-1 receptor in vitro is determined essentially as described in Example 23.
131. The derivative of any of embodiments 1-130, which at a very low concentration of HSA is capable of binding to the human GLP-1 receptor with an $IC_{50}$ of 10.0 nM or below.
132. The derivative of any of embodiments 1-131, which at a very low concentration of HSA is capable of binding to the human GLP-1 receptor with an $IC_{50}$ of 3.0 nM or below.
133. The derivative of any of embodiments 1-132, which at a very low concentration of HSA is capable of binding to the human GLP-1 receptor with an $IC_{50}$ of 1.0 nM or below.
134. The derivative of any of embodiments 1-133, which at a very low concentration of HSA is capable of binding to the human GLP-1 receptor with an $IC_{50}$ of 0.5 nM or below.
135. The derivative of any of embodiments 131-134, wherein the $IC_{50}$ is determined essentially as described in Example 23, in a reaction with max. 0.001% HSA (final assay concentration).
136. The derivative of any of embodiments 1-135, which at a very low concentration of HSA is capable of binding to the human GLP-1 receptor with an $IC_{50}$ of less than 11 times the $IC_{50}$ of semaglutide, wherein the $IC_{50}$ of semaglutide is determined in the same way as the $IC_{50}$ of the derivative.
137. The derivative of any of embodiments 1-136, which at a very low concentration of HSA is capable of binding to the human GLP-1 receptor with an $IC_{50}$ of less than 4 times the $IC_{50}$ of semaglutide, wherein the $IC_{50}$ of semaglutide is determined in the same way as the $IC_{50}$ of the derivative.
138. The derivative of any of embodiments 1-137, which at a very low concentration of HSA is capable of binding to the human GLP-1 receptor with an $IC_{50}$ of less than 1.5 times the $IC_{50}$ of semaglutide, wherein the $IC_{50}$ of semaglutide is determined in the same way as the $IC_{50}$ of the derivative.
139. The derivative of any of embodiments 1-138, which at a very low concentration of HSA is capable of binding to the human GLP-1 receptor with an $IC_{50}$ of less than 0.7 times the $IC_{50}$ of semaglutide, wherein the $IC_{50}$ of semaglutide is determined in the same way as the $IC_{50}$ of the derivative.
140. The derivative of any of embodiments 136-139, wherein the $IC_{50}$ is determined essentially as described in Example 23, in a reaction with max. 0.001% HSA (final assay concentration).
141. The derivative of any of embodiments 1-140, which at 2.0% HSA (final assay concentration) is capable of binding to the human GLP-1 receptor with an $IC_{50}$ of 800 nM or below.
142. The derivative of any of embodiments 1-141, which at 2.0% HSA (final assay concentration) is capable of binding to the human GLP-1 receptor with an $IC_{50}$ of 500 nM or below.

143. The derivative of any of embodiments 1-142, which at 2.0% HSA (final assay concentration) is capable of binding to the human GLP-1 receptor with an $IC_{50}$ of 300 nM or below.

144. The derivative of any of embodiments 1-143, which at 2.0% HSA (final assay concentration) is capable of binding to the human GLP-1 receptor with an $IC_{50}$ of 200 nM or below.

145. The derivative of any of embodiments 141-144, wherein the $IC_{50}$ is determined essentially as described in Example 23, in a reaction with 2.0% HSA (final assay concentration).

146. The derivative of any of embodiments 1-145, which at 2.0% HSA (final assay concentration) is capable of binding to the human GLP-1 receptor with an $IC_{50}$ of less than 10 times the $IC_{50}$ of semaglutide, wherein the $IC_{50}$ of semaglutide is determined in the same way as the $IC_{50}$ of the derivative.

147. The derivative of any of embodiments 1-146, which at 2.0% HSA (final assay concentration) is capable of binding to the human GLP-1 receptor with an $IC_{50}$ of less than 7 times the $IC_{50}$ of semaglutide, wherein the $IC_{50}$ of semaglutide is determined in the same way as the $IC_{50}$ of the derivative.

148. The derivative of any of embodiments 1-147, which at 2.0% HSA (final assay concentration) is capable of binding to the human GLP-1 receptor with an $IC_{50}$ of less than 1 time the $IC_{50}$ of semaglutide, wherein the $IC_{50}$ of semaglutide is determined in the same way as the $IC_{50}$ of the derivative.

149. The derivative of any of embodiments 1-148, which at 2.0% HSA (final assay concentration) is capable of binding to the human GLP-1 receptor with an $IC_{50}$ of less than 0.6 times the $IC_{50}$ of semaglutide, wherein the $IC_{50}$ of semaglutide is determined in the same way as the $IC_{50}$ of the derivative.

150. The derivative of any of embodiments 146-149, wherein the $IC_{50}$ is determined essentially as described in Example 23, in a reaction with 2.0% HSA (final assay concentration).

151. The derivative of any of embodiments 1-150, which has improved pharmacokinetic properties.

152. The derivative of any of embodiments 1-151, which has an increased half-life and/or a decreased clearance.

153. The derivative of any of embodiments 1-152, which is suitable for once-monthly administration.

154. The derivative of embodiment 153, for s.c. administration.

155. The derivative of any of embodiments 151-154, wherein the derivative is tested in vivo in pharmacokinetic (PK) studies.

156. The derivative of embodiment 155, wherein the derivative is tested in any suitable animal model, such as mouse, rat, monkey, dog, or pig.

157. The derivative of any of embodiments 151-156, which is compared with semaglutide.

158. The derivative of any of embodiments 1-157, which has an improved terminal half-life (T½) in vivo in minipigs after i.v. administration as compared to semaglutide.

159. The derivative of any of embodiments 151-158, wherein the terminal half-life is determined in vivo in minipigs after i.v. administration using any suitable study protocol, such as the one described in Example 24.

160. The derivative of any of embodiments 151-159, wherein the terminal half-life is determined in vivo in minipigs after i.v. administration, essentially as described in Example 24.

161. The derivative of any of embodiments 1-160, which has a terminal half-life (T½) in vivo in minipigs after i.v. administration of at least 90 hours.

162. The derivative of any of embodiments 1-161, which has a terminal half-life (T½) in vivo in minipigs after i.v. administration of at least 100 hours.

163. The derivative of any of embodiments 1-162, which has a terminal half-life (T½) in vivo in minipigs after i.v. administration of at least 120 hours.

164. The derivative of any of embodiments 1-163, which has a terminal half-life (T½) in vivo in minipigs after i.v. administration of at least 140 hours.

165. The derivative of any of embodiments 1-164, which has a terminal half-life (T½) in vivo in minipigs after i.v. administration of at least 1.5 times the terminal half-life of semaglutide, determined in the same way.

166. The derivative of any of embodiments 1-165, which has a terminal half-life (T½) in vivo in minipigs after i.v. administration of at least 2 times the terminal half-life of semaglutide, determined in the same way.

167. The derivative of any of embodiments 1-166, which has a terminal half-life (T½) in vivo in minipigs after i.v. administration of at least 2.2 times the terminal half-life of semaglutide, determined in the same way.

168. The derivative of any of embodiments 1-165, which has a terminal half-life (T½) in vivo in minipigs after i.v. administration of at least 2.6 times the terminal half-life of semaglutide, determined in the same way.

169. The derivative of any of embodiments 1-168, which is potent in vivo.

170. The derivative of any of embodiments 1-169, which is potent in vivo when determined in any suitable animal model, such as mouse or pig.

171. The derivative of embodiment 170, wherein the animal model is db/db mouse.

172. The derivative of any of embodiments 169-171, wherein the blood glucose lowering effect is determined.

173. The derivative of any of embodiments 167-172, wherein the body weight lowering effect is determined.

174. The derivative of any of embodiments 1-171, wherein blood glucose lowering effect and/or body weight lowering effect is determined in vivo in db/db mouse using any suitable study protocol and methodology, e.g. as described in Example 25.

175. The derivative of any of embodiments 1-172, wherein the blood glucose lowering effect and/or the body weight lowering effect is determined in vivo in db/db mouse, essentially as described in Example 25.

176. The derivative of any of embodiments 1-173, which has the effect in vivo of decreasing blood glucose after 48 hours, determined in a single-dose study in a db/db mouse model, in a suitable dose, such as 100 nmol/kg.

177. The derivative of embodiment 176, wherein the blood glucose is decreased by at least 10%, as compared to the blood glucose level before administration of the derivative.

178. The derivative of any of embodiments 176-177, wherein the blood glucose is decreased by at least 20%, as compared to the blood glucose level before administration of the derivative.

179. The derivative of any of embodiments 176-178 wherein the blood glucose is decreased by at least 40%, as compared to the blood glucose level before administration of the derivative.

180. The derivative of any of embodiments 176-179, wherein the blood glucose is decreased by at least 60%, as compared to the blood glucose level before administration of the derivative.

181. The derivative of any of embodiments 1-180, which has the effect in vivo of decreasing blood glucose after 72 hours, determined in a single-dose study in a db/db mouse model, in a suitable dose, such as 100 nmol/kg.

182. The derivative of any of embodiments 1-181, which has the effect in vivo of decreasing blood glucose after 96 hours, determined in a single-dose study in a db/db mouse model, in a suitable dose, such as 100 nmol/kg.

183. The derivative of embodiment 182, wherein the blood glucose is decreased by at least 0.5%, as compared to the blood glucose level before administration of the derivative.

184. The derivative of any of embodiments 182-183, wherein the blood glucose is decreased by at least 1%, as compared to the blood glucose level before administration of the derivative.

185. The derivative of any of embodiments 182-184, wherein the blood glucose is decreased by at least 5%, as compared to the blood glucose level before administration of the derivative.

186. The derivative of any of embodiments 182-185, wherein the blood glucose is decreased by at least 10%, as compared to the blood glucose level before administration of the derivative.

187. The derivative of any of embodiments 182-186, wherein the blood glucose is decreased by at least 15%, as compared to the blood glucose level before administration of the derivative.

188. The derivative of any of embodiments 1-187, which has the effect in vivo of decreasing body weight after 48 hours, determined in a single-dose study in a db/db mouse model, in a suitable dose, such as 100 nmol/kg.

189. The derivative of embodiment 188, wherein the body weight is decreased by at least 1%, as compared to the body weight before administration of the derivative.

190. The derivative of any of embodiments 188-189, wherein the body weight is decreased by at least 2%, as compared to the body weight before administration of the derivative.

191. The derivative of any of embodiments 188-190, wherein the body weight is decreased by at least 5%, as compared to the body weight before administration of the derivative.

192. The derivative of any of embodiments 188-191, wherein the body weight is decreased by at least 7%, as compared to the body weight before administration of the derivative.

193. The derivative of any of embodiments 1-192, which has the effect in vivo of decreasing body weight after 72 hours, determined in a single-dose study in a db/db mouse model, in a suitable dose, such as 100 nmol/kg.

194. The derivative of any of embodiments 1-193 which has the effect in vivo of decreasing body weight after 96 hours, determined in a single-dose study in a db/db mouse model, in a suitable dose, such as 100 nmol/kg.

195. The derivative of embodiment 194, wherein the body weight is decreased by at least 2%, as compared to the body weight before administration of the derivative.

196. The derivative of any of embodiments 194-195, wherein the body weight is decreased by at least 3%, as compared to the body weight before administration of the derivative.

197. The derivative of any of embodiments 194-196, wherein the body weight is decreased by at least 4%, as compared to the body weight before administration of the derivative.

198. The derivative of embodiment 170, wherein the animal model is pig.

199. The derivative of embodiment 198, wherein the animal model is LYD pig.

200. The derivative of any of embodiments 198-199, wherein the reduction in food intake is determined in an in vivo pharmacodynamic (PD) study.

201. The derivative of any of embodiments 198-200, wherein the reduction in food intake is determined in vivo in pig using any suitable study protocol and methodology, e.g. as described in Example 26.

202. The derivative of any of embodiments 198-201, wherein the reduction in food intake is determined in vivo in pig using any suitable study protocol and methodology, essentially as described in Example 26.

203. The derivative of any of embodiments 1-202, which has the effect in vivo of reducing food intake during a first period of 24 hours (0-24 hours) after administration of a single dose of the derivative, wherein food intake is determined in a single-dose study in a LYD pig model.

204. The derivative of any of embodiments 1-203, which has the effect in vivo of reducing food intake during a second period of 24 hours (24-48 hours) after administration of a single dose of the derivative, wherein food intake is determined in a single-dose study in a LYD pig model.

205. The derivative of any of embodiments 1-204, which has the effect in vivo of reducing food intake during a third period of 24 hours (48-72 hours) after administration of a single dose of the derivative, wherein food intake is determined in a single-dose study in a LYD pig model.

206. The derivative of any of embodiments 1-205, which has the effect in vivo of reducing food intake during a fourth period of 24 hours (72-96 hours) after administration of a single dose of the derivative, wherein food intake is determined in a single-dose study in a LYD pig model.

207. A GLP-1 derivative selected from the following: Chem. 21, Chem. 22, Chem. 23, Chem. 24, Chem. 25, Chem. 26, Chem. 27, Chem. 28, Chem. 29, Chem. 30, Chem. 31, Chem. 32, Chem. 33, or Chem. 34; or a pharmaceutically acceptable salt, amide, or ester thereof.

208. A GLP-1 derivative selected from the chemical structures shown in any of Examples 1-14; or a pharmaceutically acceptable salt, amide, or ester thereof.

209. A GLP-1 derivative selected from the GLP-1 derivative names shown in any of Examples 1-4; or a pharmaceutically acceptable salt, amide, or ester thereof.

210. The derivative of any of embodiments 207-209, which is a derivative according to any of embodiments 1-206.

211. An intermediate product in the form of a GLP-1 analogue, which comprises the following amino acid changes when compared to GLP-1(7-37) (SEQ ID NO: 1):
vii) (18K, 22K, 30K);
iix) (18K, 37K);
ix) (18K, 27K, 37K);
x) (27K, 30K, 37K); or
xi) (30K, 37K);
wherein in embodiment iix) and xi) the amino acid at the position corresponding to position 26 in GLP-1(7-37) (SEQ ID NO: 1) is K.

212. An intermediate product in the form of a GLP-1 analogue, which comprises the following amino acid changes when compared to GLP-1 (7-37) (SEQ ID NO: 1):
i) (8Aib, 18K, 22K, 26R, 30K, 34R); ii) (8Aib, 18K, 34R, 37K); iii) (8Aib, 18K, 22E, 26R, 27K, 34R, 37K); iv) (8Aib, 18K, 26R, 27K, 34R, 37K); v) (8Aib, 22E, 26R, 27K, 30K, 34R, 37K); or vi) (8Aib, 22E, 30K, 34R, 37K).

213. An intermediate product in the form of a GLP-1 analogue, selected from the following analogues of GLP-1 (7-37) (SEQ ID NO: 1):

i) (8Aib, 18K, 22K, 26R, 30K, 34R) (SEQ ID NO: 2); ii) (8Aib, 18K, 34R, 37K) (SEQ ID NO: 3); iii) (8Aib, 18K, 22E, 26R, 27K, 34R, 37K) (SEQ ID NO: 4); iv) (8Aib, 18K, 26R, 27K, 34R, 37K (SEQ ID NO: 5)); v) (8Aib, 22E, 26R, 27K, 30K, 34R, 37K) (SEQ ID NO: 6); and vi) (8Aib, 22E, 30K, 34R, 37K) (SEQ ID NO: 7).

214. A pharmaceutical composition comprising a derivative according to any of embodiments 1-210, or an analogue according to any of embodiments 211-213, and a pharmaceutically acceptable excipient.

215. A derivative according to any of embodiments 1-210, or an analogue according to any of embodiments 211-213, for use as a medicament.

216. A derivative according to any of embodiments 1-210, or an analogue according to any of embodiments 211-213, for use in (i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells;

(iv) prevention and/or treatment of cognitive disorders and/or neurodegenerative disorders, such as Alzheimer's disease, Parkinson's disease, and/or multiple sclerosis;

(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence;

(vi) prevention and/or treatment of diabetic complications, such as angiopathy; neuropathy, including peripheral neuropathy; nephropathy; and/or retinopathy;

(vii) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo(a)) in vitro and/or in vivo;

(viii) prevention and/or treatment of cardiovascular diseases, such as syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atherosclerosis obliterens), diastolic dysfunction, and/or systolic dysfunction; and/or reduction of blood pressure, such as reduction of systolic blood pressure;

(ix) prevention and/or treatment of gastrointestinal diseases, such as inflammatory bowel disease, short bowel syndrome, or Crohn's disease or colitis; dyspepsia, and/or gastric ulcers; and/or inflammation, such as psoriasis, psoriactic arthritis, rheumatoid arthritis, and/or systemic lupus erythematosus;

(x) prevention and/or treatment of critical illness, such as treatment of a critically ill patient, a critical illness polynephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteraemia, septicaemia, and/or septic shock during hospitalisation; and/or stabilising blood glucose, insulin balance and optionally metabolism in intensive care unit patients with acute illness;

(xi) prevention and/or treatment of polycystic ovary syndrome (PCOS);

(xii) prevention and/or treatment of cerebral disease, such as cerebral ischemia, cerebral haemorrhage, and/or traumatic brain injury;

(xiii) prevention and/or treatment of sleep apnoea; and/or (xiv) prevention and/or treatment of abuse, such as alcohol abuse and/or drug abuse.

217. Use of a derivative according to any of embodiments 1-210, or an analogue according to any of embodiments 211-213, in the manufacture of a medicament for (i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells;

(iv) prevention and/or treatment of cognitive disorders and/or neurodegenerative disorders, such as Alzheimer's disease, Parkinson's disease, and/or multiple sclerosis;

(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence;

(vi) prevention and/or treatment of diabetic complications, such as angiopathy; neuropathy, including peripheral neuropathy; nephropathy; and/or retinopathy;

(vii) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo(a)) in vitro and/or in vivo;

(viii) prevention and/or treatment of cardiovascular diseases, such as syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis oblitterens), diastolic dysfunction, and/or systolic dysfunction; and/or reduction of blood pressure, such as reduction of systolic blood pressure;

(ix) prevention and/or treatment of gastrointestinal diseases, such as inflammatory bowel disease, short bowel syndrome, or Crohn's disease or colitis; dyspepsia, and/or gastric ulcers; and/or inflammation, such as psoriasis, psoriactic arthritis, rheumatoid arthritis, and/or systemic lupus erythematosus;

(x) prevention and/or treatment of critical illness, such as treatment of a critically ill patient, a critical illness polynephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteraemia, septicaemia, and/or septic shock during hospitalisation; and/or stabilising blood glucose, insulin balance and optionally metabolism in intensive care unit patients with acute illness;

(xi) prevention and/or treatment of polycystic ovary syndrome (PCOS);

(xii) prevention and/or treatment of cerebral disease, such as cerebral ischemia, cerebral haemorrhage, and/or traumatic brain injury;

(xiii) prevention and/or treatment of sleep apnoea; and/or (xiv) prevention and/or treatment of abuse, such as alcohol abuse and/or drug abuse.

218. A method for (i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells;

(iv) prevention and/or treatment of cognitive disorders and/or neurodegenerative disorders, such as Alzheimer's disease, Parkinson's disease, and/or multiple sclerosis;

(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence;

(vi) prevention and/or treatment of diabetic complications, such as angiopathy; neuropathy, including peripheral neuropathy; nephropathy; and/or retinopathy;

(vii) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo(a)) in vitro and/or in vivo;

(viii) prevention and/or treatment of cardiovascular diseases, such as syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis oblitterens), diastolic dysfunction, and/or systolic dysfunction; and/or reduction of blood pressure, such as reduction of systolic blood pressure;

(ix) prevention and/or treatment of gastrointestinal diseases, such as inflammatory bowel disease, short bowel syndrome, or Crohn's disease or colitis; dyspepsia, and/or gastric ulcers; and/or inflammation, such as psoriasis, psoriactic arthritis, rheumatoid arthritis, and/or systemic lupus erythematosus;

(x) prevention and/or treatment of critical illness, such as treatment of a critically ill patient, a critical illness polynephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteraemia, septicaemia, and/or septic shock during hospitalisation; and/or stabilising blood glucose, insulin balance and optionally metabolism in intensive care unit patients with acute illness;

(xi) prevention and/or treatment of polycystic ovary syndrome (PCOS);

(xii) prevention and/or treatment of cerebral disease, such as cerebral ischemia, cerebral haemorrhage, and/or traumatic brain injury;

(xiii) prevention and/or treatment of sleep apnoea; and/or (xiv) prevention and/or treatment of abuse, such as alcohol abuse and/or drug abuse;

wherein a pharmaceutically active amount of a derivative according to any of embodiments 1-210, or an analogue according to any of embodiments 211-213, is administered. A still further set of particular embodiments are:

a). A derivative of a GLP-1 peptide, wherein the GLP-1 peptide comprises a first, a second, and a third K residue at positions corresponding to positions (18, 22, 30), (18, 26, 37), (18, 27, 37), (26, 30, 37), or (27, 30, 37) of GLP-1(7-37) (SEQ ID NO: 1), and has a maximum of seven amino acid changes as compared to GLP-1 (7-37) (SEQ ID NO: 1);

which derivative comprises a first, a second, and a third protracting moiety of formula Chem. 1 or formula Chem. 2:

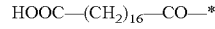   Chem. 1:

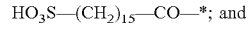; and   Chem. 2:

a first, a second, and a third linker, each linker comprising a *—CO group and an *—NH group;

wherein each protracting moiety is attached at its *—CO end to the *—NH end of the respective linker, and each linker is attached at its *—CO end to the epsilon amino group of the respective K residue of the GLP-1 peptide;

or a pharmaceutically acceptable salt, amide, or ester thereof.

b). The derivative of embodiment a), wherein each of the first, second, and third protracting moiety is of formula Chem. 1.

c). The derivative of embodiment a), wherein each of the first, second, and third protracting moiety is of formula Chem. 2.

d). The derivative of any of embodiments a)-c), wherein the linker comprises one or more linker elements selected from formula Chem. 3, Chem. 4, Chem. 5, Chem. 6, Chem. 7, and/or Chem. 8:

Chem. 3

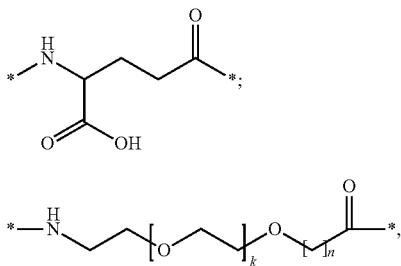

Chem. 4

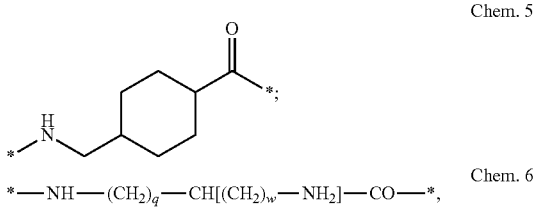

wherein k is an integer in the range of 1-5, and n is an integer in the range of 1-5;

Chem. 5

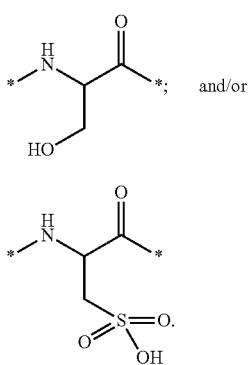

Chem. 6

*—NH—(CH$_2$)$_q$—CH[(CH$_2$)$_w$—NH$_2$]—CO—*, wherein q is an integer in the range of 0-5, and w is an integer in the range of 0-5, with the provisos that when w is 0 q is an integer in the range of 1-5, and when q is 0 w is an integer in the range of 1-5;

Chem. 7

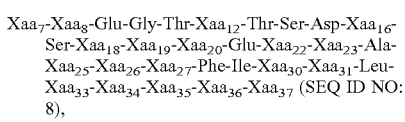   and/or

Chem. 8 e). The derivative of any of embodiments a)-d), wherein the GLP-1 peptide has the general formula I:

Xaa$_7$-Xaa$_8$-Glu-Gly-Thr-Xaa$_{12}$-Thr-Ser-Asp-Xaa$_{16}$-
Ser-Xaa$_{18}$-Xaa$_{19}$-Xaa$_{20}$-Glu-Xaa$_{22}$-Xaa$_{23}$-Ala-
Xaa$_{25}$-Xaa$_{26}$-Xaa$_{27}$-Phe-Ile-Xaa$_{30}$-Xaa$_{31}$-Leu-
Xaa$_{33}$-Xaa$_{34}$-Xaa$_{35}$-Xaa$_{36}$-Xaa$_{37}$ (SEQ ID NO: 8),

Formula I:

wherein

Xaa$_7$ is L-histidine, (S)-2-Hydroxy-3-(1H-imidazol-4-yl)-propionic acid, D-histidine, desamino-histidine, homohistidine, N$^\alpha$-acetyl-histidine, N$^\alpha$-formyl-histidine, α-methyl-histidine, 3-pyridylalanine, 2-pyridylalanine, or 4-pyridylalanine;

Xaa$_8$ is Ala, Gly, Ser, Aib, (1-aminocyclopropyl) carboxylic acid, or (1-aminocyclobutyl) carboxylic acid;

Xaa$_{12}$ is Phe or Leu;
Xaa$_{16}$ is Val or Leu;
Xaa$_{18}$ is Ser, Arg, Lys, Val, or Leu;
Xaa$_{19}$ is Tyr or Gln;
Xaa$_{20}$ is Leu or Met;
Xaa$_{22}$ is Gly, Lys or Glu;
Xaa$_{23}$ is Gln, Glu, Lys, or Arg;
Xaa$_{25}$ is Ala or Val;
Xaa$_{26}$ is Arg or Lys;
Xaa$_{27}$ is Glu, Lys, or Leu;
Xaa$_{30}$ is Ala, Glu, or Lys;
Xaa$_{31}$ is Trp or His;
Xaa$_{33}$ is Val, Lys, or Arg;
Xaa$_{34}$ is Lys, Arg, His, Asn, or Gln;
Xaa$_{35}$ is Gly or Ala;
Xaa$_{36}$ is Arg or Gly; and Xaa$_{37}$ is Gly, Pro, or Lys, f). The derivative of embodiment e), wherein Xaa$_8$ is Aib.

g). The derivative of any of embodiments a)-f), wherein the GLP-1 peptide comprises i) (8Aib, 18K, 22K, 26R, 30K, 34R); ii) (8Aib, 18K, 34R, 37K); iii) (8Aib, 18K, 22E, 26R, 27K, 34R, 37K); iv) (8Aib, 18K, 26R, 27K, 34R, 37K); v) (8Aib, 22E, 26R, 27K, 30K, 34R, 37K); vi) (8Aib, 22E, 30K, 34R, 37K); vii) (18K, 22K, 30K); iix) (18K, 37K); ix) (18K, 27K, 37K); x) (27K, 30K, 37K); or xi) (30K, 37K); wherein in embodiment iix) and xi) the amino acid at the position corresponding to position 26 in GLP-1(7-37) (SEQ ID NO: 1) is K.

h). The derivative of any of embodiments a)-g), wherein the GLP-1 peptide is selected from the following analogues of GLP-1 (7-37) (SEQ ID NO: 1):
i) (8Aib, 18K, 22K, 26R, 30K, 34R) (SEQ ID NO: 2); ii) (8Aib, 18K, 34R, 37K) (SEQ ID NO: 3); iii) (8Aib, 18K, 22E, 26R, 27K, 34R, 37K) (SEQ ID NO: 4); iv) (8Aib, 18K, 26R, 27K, 34R, 37K (SEQ ID NO: 5)); v) (8Aib, 22E, 26R, 27K, 30K, 34R, 37K) (SEQ ID NO: 6); and vi) (8Aib, 22E, 30K, 34R, 37K) (SEQ ID NO: 7).

j). A GLP-1 derivative selected from the following: Chem. 21, Chem. 22, Chem. 23, Chem. 24, Chem. 25, Chem. 26, Chem. 27, Chem. 28, Chem. 29, Chem. 30, Chem. 31, Chem. 32, Chem. 33, or Chem. 34; or a pharmaceutically acceptable salt, amide, or ester thereof.

k). An intermediate product in the form of a GLP-1 analogue, which comprises the following amino acid changes when compared to GLP-1(7-37) (SEQ ID NO: 1): vii) (18K, 22K, 30K); iix) (18K, 37K); ix) (18K, 27K, 37K); x) (27K, 30K, 37K); or xi) (30K, 37K); wherein in embodiment iix) and xi) the amino acid at the position corresponding to position 26 in GLP-1(7-37) (SEQ ID NO: 1) is K.

l). An intermediate product in the form of a GLP-1 analogue, which comprises the following amino acid changes when compared to GLP-1 (7-37) (SEQ ID NO: 1):
i) (8Aib, 18K, 22K, 26R, 30K, 34R); ii) (8Aib, 18K, 34R, 37K); iii) (8Aib, 18K, 22E, 26R, 27K, 34R, 37K); iv) (8Aib, 18K, 26R, 27K, 34R, 37K); v) (8Aib, 22E, 26R, 27K, 30K, 34R, 37K); or vi) (8Aib, 22E, 30K, 34R, 37K).

m). An intermediate product in the form of a GLP-1 analogue, selected from the following analogues of GLP-1 (7-37) (SEQ ID NO: 1):

i) (8Aib, 18K, 22K, 26R, 30K, 34R) (SEQ ID NO: 2); ii) (8Aib, 18K, 34R, 37K) (SEQ ID NO: 3); iii) (8Aib, 18K, 22E, 26R, 27K, 34R, 37K) (SEQ ID NO: 4); iv) (8Aib, 18K, 26R, 27K, 34R, 37K (SEQ ID NO: 5)); v) (8Aib, 22E, 26R, 27K, 30K, 34R, 37K) (SEQ ID NO: 6); and vi) (8Aib, 22E, 30K, 34R, 37K) (SEQ ID NO: 7).

n). A pharmaceutical composition comprising a derivative according to any of embodiments a)-h) or j), or an analogue according to any of embodiments k)-m), and a pharmaceutically acceptable excipient.

o). A derivative according to any of embodiments a)-h) or j), or an analogue according to any of embodiments k)-m), for use as a medicament.

p). A derivative according to any of embodiments a)-h) or j), or an analogue according to any of embodiments k)-m), for use in (i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells;

(iv) prevention and/or treatment of cognitive disorders and/or neurodegenerative disorders, such as Alzheimer's disease, Parkinson's disease, and/or multiple sclerosis;

(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence;

(vi) prevention and/or treatment of diabetic complications, such as angiopathy; neuropathy, including peripheral neuropathy; nephropathy; and/or retinopathy;

(vii) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo(a)) in vitro and/or in vivo;

(viii) prevention and/or treatment of cardiovascular diseases, such as syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis obliterens), diastolic dysfunction, and/or systolic dysfunction; and/or reduction of blood pressure, such as reduction of systolic blood pressure;

(ix) prevention and/or treatment of gastrointestinal diseases, such as inflammatory bowel disease, short bowel syndrome, or Crohn's disease or colitis; dyspepsia, and/or gastric ulcers; and/or inflammation, such as psoriasis, psoriactic arthritis, rheumatoid arthritis, and/or systemic lupus erythematosus;

(x) prevention and/or treatment of critical illness, such as treatment of a critically ill patient, a critical illness polynephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteraemia, septicaemia, and/or septic shock during hospitalisation; and/or stabilising blood glucose, insulin balance and optionally metabolism in intensive care unit patients with acute illness;

(xi) prevention and/or treatment of polycystic ovary syndrome (PCOS);

(xii) prevention and/or treatment of cerebral disease, such as cerebral ischemia, cerebral haemorrhage, and/or traumatic brain injury;

(xiii) prevention and/or treatment of sleep apnoea; and/or (xiv) prevention and/or treatment of abuse, such as alcohol abuse and/or drug abuse.

EXAMPLES

This experimental part starts with a list of abbreviations, and is followed by a section including general methods for synthesising and characterising analogues and derivatives of the invention. Then follows a number of examples which relate to the preparation of specific GLP-1 derivatives, and at the end a number of examples have been included relating to the activity and properties of these analogues and derivatives (section headed pharmacological methods). The examples serve to illustrate the invention.

Materials and Methods

List of Abbreviations

Aib: α-aminoisobutyric acid (2-Aminoisobutyric acid)
AcOH: acetic acid
API: Active Pharmaceutical Ingredient
AUC: Area Under the Curve
BG: Blood Glucose
BHK Baby Hamster Kidney
BW: Body Weight
Boc: t-butyloxycarbonyl
Bom: benzyloxymethyl
BSA: Bovine serum albumin
Bzl: benzyl
CAS: Chemical Abstracts Service
Clt: 2-chlorotrityl
collidine: 2,4,6-trimethylpyridine
DCM: dichloromethane
Dde: 1-(4,4-dimethyl-2,6-dioxocyclohexylidene)ethyl
DesH: des-amino histidine (may also be referred to as imidazopropionic acid or 3-(Imidazol-5-yl)propanoic acid, Imp)
DIC: diisopropylcarbodiimide
DIPEA: diisopropylethylamine
DMEM: Dulbecco's Modified Eagle's Medium (DMEM)
EDTA: ethylenediaminetetraacetic acid
EGTA: ethylene glycol tetraacetic acid
FCS: Fetal Calf Serum
Fmoc: 9-fluorenylmethyloxycarbonyl
HATU: (O-(7-azabenzotriazol-1-yl)-1,1,3,3-tetramethyluronium hexa fluorophosphate)
HBTU: (2-(1H-benzotriazol-1-yl-)-1,1,3,3 tetramethyluronium hexafluorophosphate)

HEPES: 4-(2-hydroxyethyl)-1-piperazineethanesulfonic acid
HFIP 1,1,1,3,3,3-hexafluoro-2-propanol or hexafluoroisopropanol
HOAt: 1-hydroxy-7-azabenzotriazole
HOBt: 1-hydroxybenzotriazole
HPLC: High Performance Liquid Chromatography
HSA: Human Serum Albumin
IBMX: 3-isobutyl-1-methylxanthine
Imp: Imidazopropionic acid (also referred to as 3-(Imidazol-5-yl)propanoic acid), see also DesH, des-amino histidine)
Inp: isonipecotic acid
i.v. intravenously
ivDde: 1-(4,4-dimethyl-2,6-dioxocyclohexylidene)-3-methylbutyl
IVGTT: Intravenous Glucose Tolerance Test
LCMS: Liquid Chromatography Mass Spectroscopy
LYD: Landrace Yorkshire Duroc
MALDI-MS: See MALDI-TOF MS
MALDI-TOF MS: Matrix-Assisted Laser Desorption/Ionisation Time of Flight Mass Spectroscopy
MeOH: methanol
Mmt: 4-methoxytrityl
Mtt: 4-methyltrityl
NMP: N-methyl pyrrolidone
OBz: benzoyl ester
OEG: 8-amino-3,6-dioxaoctanoic acid
OPfp: pentafluorophenoxy
OPnp: para-nitrophenoxy
OSu: O-succinimidyl esters (hydroxysuccinimide esters)
OtBu: tert butyl ester
Oxyma Pure®: Cyano-hydroxyimino-acetic acid ethyl ester
Pbf: 2,2,4,6,7-pentamethyldihydrobenzofuran-5-sulfonyl
PBS: Phosphate Buffered Saline
PD: Pharmacodynamic
Pen/Strep: Pencillin/Streptomycin
PK: Pharmacokinetic
PyBoP: (Benzotriazol-1-yloxy)tripyrrolidinophosphonium hexafluorophosphate
RP: Reverse Phase
RP-HPLC: Reverse Phase High Performance Liquid Chromatography
RT: Room Temperature
Rt: Retention time
s.c.: Subcutaneously
SD: Standard Deviation
SEC-HPLC: Size Exclusion High Performance Liquid Chromatography
SEM: Standard Error of Mean
SPA: Scintillation Proximity Assay
SPPS: Solid Phase Peptide Synthesis
tBu: tert. butyl
TFA: trifluoroacetic acid
TIS: triisopropylsilane
TLC: Thin Layer Chromatography
Tos: tosylate (or pare-toluenesulfonyl)
Tris: tris(hydroxymethyl)aminomethane or 2-amino-2-hydroxymethyl-propane-1,3-diol
Trt: triphenylmethyl (trityl)
Trx: tranexamic acid
UPLC: Ultra Performance Liquid Chromatography Special Materials Fmoc-L-cysteic acid
Fmoc-8-amino-3,6-dioxaoctanoic acid
Fmoc-tranexamic acid
Fmoc-Glu-OtBu
Boc-Lys(Fmoc)-OH
Octadecanedioic acid mono-tert-butyl ester
Eicosanedioic acid mono-tert-butyl ester
16-Sulfo-hexadecanoic acid The preparation of eicosanedioic acid mono-tert-butyl ester and 16-Sulfo-hexadecanoic acid is described in section 2 below, and the six first-mentioned materials are commercially available.

Chemical Methods

This section is divided in two: Section A relating to general methods (of preparation (A1); and of detection and characterisation (A2)), and section B, in which the preparation and characterisation of a number of specific example compounds is described.

A. General Methods

A1. Methods of Preparation

This section relates to methods for solid phase peptide synthesis (SPPS methods, including methods for de-protection of amino acids, methods for cleaving the peptide from the resin, and for its purification), as well as methods for detecting and characterising the resulting peptide (LCMS, MALDI, and UPLC methods). The solid phase synthesis of peptides may in some cases be improved by the use of di-peptides protected on the di-peptide amide bond with a group that can be cleaved under acidic conditions such as, but not limited to, 2-Fmoc-oxy-4-methoxybenzyl, or 2,4,6-trimethoxybenzyl. In cases where a serine or a threonine is present in the peptide, pseudoproline di-peptides may be used (available from, e.g., Novabiochem, see also W. R. Sampson (1999), J. Pep. Sci. 5, 403). The Fmoc-protected amino acid derivatives used were the standard recommended: Fmoc-Ala-OH, Fmoc-Arg(Pbf)-OH, Fmoc-Asn(Trt)-OH, Fmoc-Asp(OtBu)-OH, Fmoc-Cys(Trt)-OH, Fmoc-Gln(Trt)-OH, Fmoc-Glu(OtBu)-OH, Fmoc-Gly-OH, Fmoc-His(Trt)-OH, Fmoc-Ile-OH, Fmoc-Leu-OH, Fmoc-Lys(Boc)-OH, Fmoc-Met-OH, Fmoc-Phe-OH, Fmoc-Pro-OH, Fmoc-Ser(tBu)-OH, Fmoc-Thr(tBu)-OH, Fmoc-Trp(Boc)-OH, Fmoc-Tyr(tBu)-OH, or, Fmoc-Val-OH etc. supplied from e.g. Anaspec, Bachem, Iris Biotech, or Novabiochem. Where nothing else is specified the natural L-form of the amino acids are used. The N-terminal amino acid was Boc protected at the alpha amino group (e.g. Boc-His(Boc)-OH, or Boc-His(Trt)-OH for peptides with His at the N-terminus). In case of modular albumin binding moiety attachment using SPPS the following suitably protected building blocks such as but not limited to Fmoc-8-amino-3,6-dioxaoctanoic acid, Fmoc-tranexamic acid, Fmoc-isonipecotic acid, Fmoc-Glu-OtBu, Fmoc-Lys(Fmoc)-OH, and Boc-Lys(FMoc)-OH were used supplied from e.g. Anaspec, Bachem, Iris Biotech, or Novabiochem. Eicosanedioic acid mono-tert-butyl ester, and 16-Sulfo-hexadecanoic acid can be prepared as described below. All operations stated below were performed at 250-µmol synthesis scale.

1. Synthesis of Resin Bound Protected Peptide Backbone

Method: SPPS_P

SPPS_P was performed on a Prelude Solid Phase Peptide Synthesiser from Protein Technologies (Tucson, Ariz. 85714

U.S.A.) at 250-μmol scale using six fold excess of Fmoc-amino acids (300 mM in NMP with 300 mM HOAt or Oxyma Pure®) relative to resin loading, e.g. low load Fmoc-Gly-Wang (0.35 mmol/g). Fmoc-deprotection was performed using 20% piperidine in NMP. Coupling was performed using 3:3:3:4 amino acid/(HOAt or Oxyma Pure®)/DIC/collidine in NMP. NMP and DCM top washes (7 ml, 0.5 min, 2×2 each) were performed between deprotection and coupling steps. Coupling times were generally 60 minutes. Some amino acids including, but not limited to Fmoc-Arg(Pbf)-OH, Fmoc-Aib-OH or Boc-His(Trt)-OH were "double coupled", meaning that after the first coupling (e.g. 60 min), the resin is drained and more reagents are added (amino acid, (HOAt or Oxyma Pure®), DIC, and collidine), and the mixture allowed to react again (e.g. 60 min).

Method: SPPS_L

SPPS_L was performed on a microwave-based Liberty peptide synthesiser from CEM Corp. (Matthews, N.C. 28106, U.S.A.) e.g. at 250-μmol scale using six fold excess of Fmoc-amino acids (300 mM in NMP with 300 mM HOAt or Oxyma Pure®) relative to resin loading, e.g. low load Fmoc-Gly-Wang (0.35 mmol/g). Fmoc-deprotection was performed using 5% piperidine in NMP at up to 75° C. for 30 seconds where after the resin was drained and washed with NMP and the Fmoc-deprotection was repeated this time for 2 minutes at 75° C. Coupling was performed using 1:1:1 amino acid/(HOAt or Oxyma Pure®)/DIC in NMP. Coupling times and temperatures were generally 5 minutes at up to 75° C. Longer coupling times were used for larger scale reactions, for example 10 min. Histidine amino acids were double coupled at 50° C., or quadruple coupled if the previous amino acid was sterically hindered (e.g. Aib). Arginine amino acids were coupled at RT for 25 minutes and then heated to 75° C. for 5 min. Some amino acids such as but not limited to Aib, were "double coupled", meaning that after the first coupling (e.g. 5 min at 75° C.), the resin is drained and more reagents are added (amino acid, (HOAt or Oxyma Pure®) and DIC), and the mixture is heated again (e.g. 5 min at 75° C.). NMP washes (5×10 ml) were performed between deprotection and coupling steps.

2. Synthesis of Eicosanedioic Acid Mono-Tert-Butyl Ester and 16-Sulfo-Hexadecanoic Acid Eicosanedioic acid mono-tert-butyl ester can be prepared as is known in the art, e.g. as described in WO 2010102886 A1.

16-Sulfo-hexadecanoic acid can be prepared as follows:

16-Hexadecanolide (150 g, 589 mmol) was dissolved in MeOH (2500 mL) and toluene-4-sulfonic acid (13.5 g, 71.0 mmol) was added. Reaction mixture was heated to reflux for 16 hrs. After cooling down sodium hydrogencarbonate was added (8.40 g, 112 mmol) and the raction mixture was stirred 15 minutes. Solvents were evaporated, ethyl-acetate was added (2000 mL) and the mixture was extracted with water (400 mL), 10% solution of sodium hydrogencarbonate (2×400 mL) and brine (200 mL). After drying with anhydrous $MgSO_4$, filtration and evaporation of solvents crude product was obtained. It has been recrystallised from hexane (1500 mL). After filtration 16-hydroxyhexadecanoic acid methyl ester was obtained as a white solid.

Yield: 161.0 g (96%).

Above prepared ester was dissolved in DCM (1200 mL). Triethylamine was added (118 mL, 847.8 mmol), reaction mixture was cooled to 0° C. and mesylchloride (55 mL) was added slowly during 10 minutes. After one hour the reaction mixture was allowed to warm to room temperature and has been stirred overnight. After 16 hrs water was added (20 mL) and the mixture was stirred 30 minutes. Solvents were evaporated, ethyl-acetate was added (1600 mL) and the mixture was extracted with 1M HCl (2×600 mL), 5% solution of sodium carbonate (2×400 mL) and water (400 mL). After drying with anhydrous $MgSO_4$, filtration and evaporation of solvents 16-mesylhexadecanoic acid methyl ester was obtained as white solid.

Yield: 205.1 g (100%).

Above prepared mesylate was dissolved in ethanole (2000 mL), thiourea (81.0 g, 1.068 mol) and NaI (92.2 g, 0.616 mmol) were added and the reaction mixture was refluxed two days. After cooling down solvents were evaporated and solution of NaOH (184 g) in water (1600 mL) was added. Resulting suspension was heated 2 hrs to reflux and poured into 10% HCl (2000 mL). After 15 minutes another portion of conc. HCl was added (120 mL). White precipitate was filtered and washed with water, dried and evaporated several times with toluene. 16-Mercaptohexadecanoic acid was obtained as a white solid.

Yield: 165.1 g (100%).

16-Mercaptohexadecanoic acid (165.1 g, 0.572 mmol) was dissolved in DCM (1600 mL) and 2N HCl was added (800 mL). Bromine (200 mL) was slowly added, forming first white precipitate which has been dissolved after adding the whole bromine volume. The mixture was stirred 3 hrs at room temperature. Both DCM and bromine were evaporated, three more portions of DCM (3×500 mL) were added and evaporated to get rid of the rest of bromine. 2M NaOH was added until brown colour disappeared and the reaction mixture was heated to reflux for 1 hr. Conc. HCl was added to acidic pH, precipitate was filtered off and centrifuged and decanted six times with water. The title product was obtained as a white solid.

Yield: 151.6 g (74%).

$^1H$ NMR spectrum (300 MHz, DMSO, $δ_H$): 11.97 (bs, 1H); 2.39 (m, 2H); 2.18 (t, J=7.3 Hz, 2H); 1.49 (m, 4H); 1.23 (m, 22H).

3. Attachment of Side Chains to Resin Bound Protected Peptide Backbone

When an acylation is present on a lysine side chain, the epsilon amino group of lysine to be acylated was protected with either Mtt, Mmt, Dde, ivDde, or Boc, depending on the route for attachment of the protracting moiety and linker. Dde- or ivDde-deprotection was performed with 2% hydrazine in NMP (2×20 ml, each 10 min) followed by NMP washings (4×20 ml). Mtt- or Mmt-deprotection was performed with 2% TFA and 2-3% TIS in DCM (5×20 ml, each 10 min) followed by DCM (2×20 ml), 10% MeOH and 5% DIPEA in DCM (2×20 ml) and NMP (4×20 ml) washings, or by treatment with hexafluoroisopropanol/DCM (75:25, 5×20 ml, each 10 min) followed by washings as above. In some cases the Mtt group was removed by automated steps on the Liberty peptide synthesiser. Mtt deprotection was performed with hexafluoroisopropanol or hexafluoroisopropanol/DCM (75:25) at room temperature for 30 min followed by washing with DCM (7 ml×5), followed by washing with 5% piperidine (7 ml×5) and NMP washings. The protracting moiety and/or linker can be attached to the peptide either by acylation of the resin bound peptide or by acylation in solution of the unprotected peptide. In case of attachment of the protracting moiety and/or linker to the protected peptidyl resin the attachment can be modular using SPPS and suitably protected building blocks.

Method: SC_P

The N-ε-lysine protection group was removed as described above and the chemical modification of the lysine was performed by one or more automated steps on the Prelude peptide synthesiser using suitably protected building blocks as described above. Double couplings were performed as described in SPPS_P with 3 hours per coupling.

Method: SC_L

The N-ε-lysine protection group was removed as described above and the chemical modification of the lysine was performed by one or more automated steps on the Liberty peptide synthesiser using suitably protected building blocks as described above. Double couplings were performed as described in SPPS_L.

Method: SC_M_1

The N-ε-lysine protection group was removed as described above and the chemical modification of the lysine was performed by one or more manual steps using suitably protected building blocks as described above. The SC_M_1 was performed at 500-μmol scale using four or six fold excess of Fmoc-amino acids (300 mM in NMP with 300 mM HOAt, Oxyma Pure®) relative to resin loading. Fmoc-deprotection was performed using 20% piperidine in NMP for 5 minutes at room temperature where after the resin was drained and washed with NMP and the Fmoc-deprotection was repeated this time for 15 minutes at room temperature. Coupling was performed using 1:1:1 amino acid/Oxyma Pure®/DIC in NMP. Coupling times were generally 60 minutes at room temperature. Some building blocks were double coupled meaning that after the first coupling (e.g. 60 min), the resin is drained and more reagents are added (amino acid, (HOAt or Oxyma Pure®), DIC, and collidine), and the mixture allowed to react again (e.g. 60 min).

Method: SC_M_2

Coupling of Fmoc-L-cysteic acid at 250 μmol or 500-μmol scale using two to four fold excess of the above acid dissolved DMF and the solution was mixed with PyBoP dissolved in NMP for 5 min. (300 mM in DMF with 300 mM PyBOP in NMP). The solution was added to the resin followed by addition of DIPEA (Acid/PyBOP/DIPEA (1:1:4). The resin was shaken for 2 hours. Double coupled.

Method: SC_M_3

Coupling of 16-Sulfo-hexadecanoic acid was performed at 250-μmol or 500-μmol scale using tree to four fold excess of the acid dissolved in boiling DMF followed by slowly cooling until 50° C. and addition of PyBoP dissolved in DMF (40 mM in DMF with 300 mM PyBOP) before adding the solution to the resin. Slowly addition of DIPEA (Acid/PyBOP/DIPEA (1:1:4). The resin was shaken for 2 hours. Double or triple coupled.

4. Cleavage of Resin Bound Peptide with or without Attached Side Chains and Purification Method: CP_M1

After synthesis the resin was washed with DCM, and the peptide was cleaved from the resin by a 2-3 hour treatment with TFA/TIS/water (95/2.5/2.5 or 92.5/5/2.5) followed by precipitation with diethylether. The peptide was dissolved in a suitable solvent (such as, e.g., 30% aqueous acetic acid, or 2% aqueous $NH_4OH$, and purified by standard RP-HPLC on a C18, 5 μM column, using acetonitrile/water/TFA. The fractions were analysed by a combination of UPLC, MALDI and LCMS methods, and the appropriate fractions were pooled and lyophilised.

If needed the peptide counter ion can be exchanged to sodium using the methods known in the art. As an example approx. 2 g peptide was dissolved in 250 ml acetonitrile/water (50/50) and loaded onto a Waters X-Bridge C8, 5 pM, 50×250 mm column on a preparative RP-HPLC system. Following loading, the column was washed with water for 8 min at a flow rate of 60 ml/min and 0.01 N NaOH pH 11 at a flow rate of 60 ml/min for 2×8 min. The sodium salt of the peptide was eluted using an isocratic flow of water at 60 ml/min for 10 min followed by a linear gradient of 5% to 85% acetonitrile over 30 min. If needed the peptide counter ion can be exchanged to acetate using the methods known in the art. As an example approx. 0.5 g peptide was dissolved in 250 ml acetonitrile/water (50/50) and loaded onto a Waters X-Bridge C8, 5 pM, 50×250 mm column on a preparative RP-HPLC system. Following loading, the column was washed with water for 8 min at a flow rate of 60 ml/min, 0.01 N NaOH pH 11 at a flow rate of 60 ml/min for 2×8 min followed by 1% AcOH in water at a flow rate of 60 ml/min for 8 min. The acetate salt of the peptide was eluted using a linear gradient of 5% to 85% acetonitrile in water with 0.1 acetic acid over 30 min.

A2. General Methods for Detection and Characterisation

1. LC-MS Method

Method: LCMS01v01

LCMS01v01 was performed on a setup consisting of Waters Acquity UPLC system and LCT Premier XE mass spectrometer from Micromass. Eluents: A: 0.1% Formic acid in water; B: 0.1% Formic acid in acetonitrile. The analysis was performed at RT by injecting an appropriate volume of the sample (preferably 2-10 μl) onto the column which was eluted with a gradient of A and B. The UPLC conditions, detector settings and mass spectrometer settings were: Column: Waters Acquity UPLC BEH, C-18, 1.7 μm, 2.1 mm×50 mm. Gradient: Linear 5%-95% acetonitrile during 4.0 min (alternatively 8.0 min) at 0.4 ml/min. Detection: 214 nm (analogue output from TUV (Tunable UV detector)) MS ionisation mode: API-ES. Scan: 100-2000 amu (alternatively 500-2000 amu), step 0.1 amu.

2. UPLC Method

Method: UPLC02v01

The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing: A: 99.95% $H_2O$, 0.05% TFA; B: 99.95% $CH_3CN$, 0.05% TFA. The following linear gradient was used: 95% A, 5% B to 95% A, 5% B over 16 minutes at a flow-rate of 0.40 ml/min.

3. MALDI-MS Method

Method: MALDI01v01

Molecular weights were determined using matrix-assisted laser desorption and ionisation time-of-flight mass spectroscopy, recorded on a Microflex or Autoflex (Bruker). A matrix of alpha-cyano-4-hydroxy cinnamic acid was used.

B. Preparation of Example Compounds

Example 1

N{Epsilon-18}-[2-[2-[2-[[2-[2-[2-[[(4S)-4-carboxy-4-[[4-[(16-sulfohexadecanoylamino)methyl]cyclohexanecarbonyl]amino]butanoyl]amino]ethoxy]ethoxy]acetyl]amino]ethoxy]ethoxy]acetyl],
N{Epsilon-22}-[2-[2-[2-[[2-[2-[2-[[(4S)-4-carboxy-4-[[4-[(16-sulfohexadecanoylamino)methyl]cyclohexanecarbonyl]amino]butanoyl]amino]ethoxy]ethoxy]acetyl]amino]ethoxy]ethoxy]acetyl],
N{Epsilon-30}-[2-[2-[2-[[2-[2-[2-[[(4S)-4-carboxy-4-[[4-[(16-sulfohexadecanoylamino)methyl]cyclohexanecarbonyl]amino]butanoyl]amino]ethoxy]ethoxy]acetyl]amino]ethoxy]ethoxy]acetyl]-[Aib8,Lys18,Lys22,Arg26,Lys30,Arg34]-GLP-1-(7-37)-peptide Chem. 21

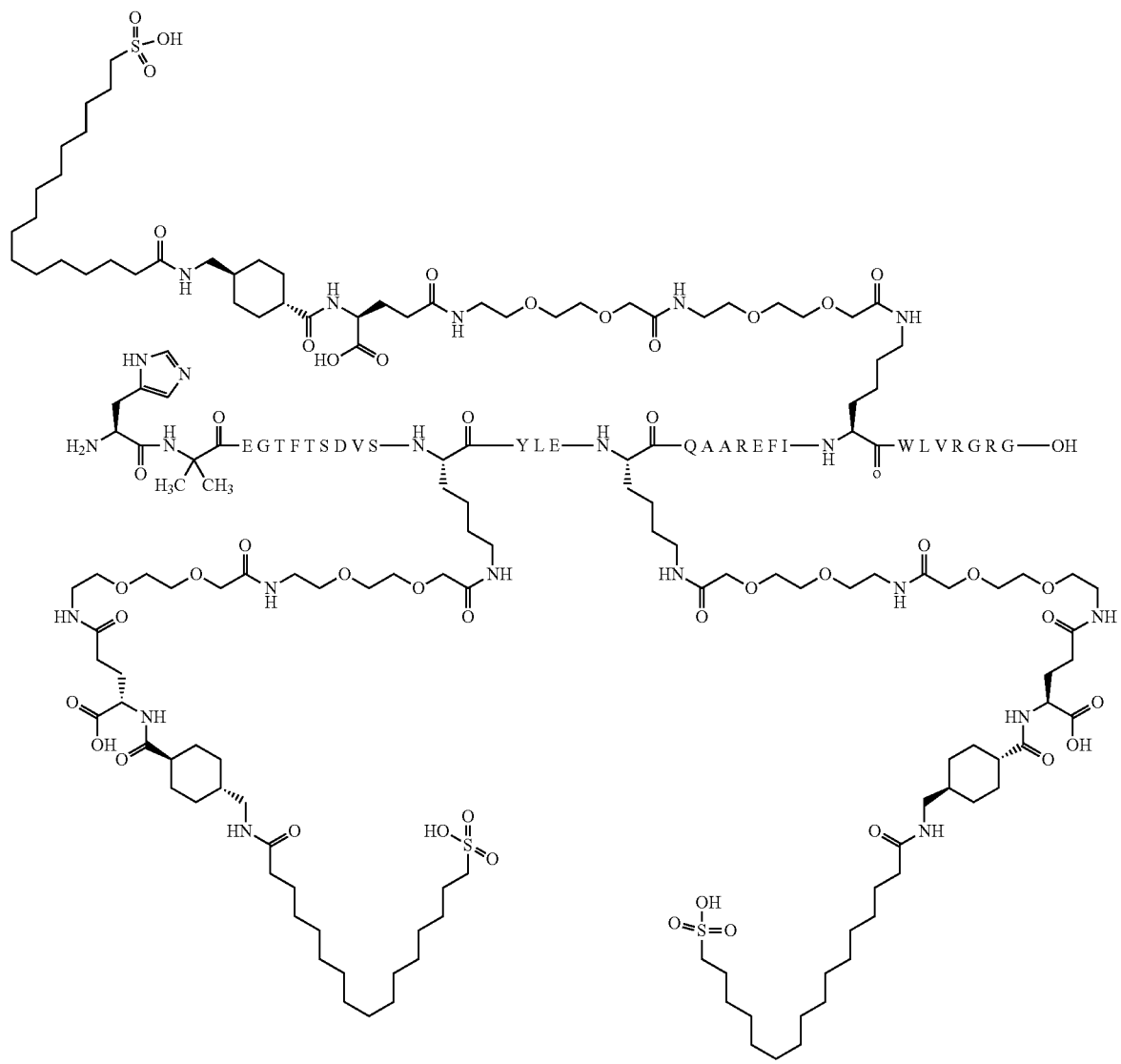

The peptide is SEQ ID NO: 2
Synthesis method: SPPS_P; SC_M_1; SC_M_3; CP_M1
LCMS01v01: Rt=2.5 min, m/4=1557; m/5=1246; m/6=1039; m/7=890
UPLC02v01: Rt=9.3 min Example 2

N{Epsilon-18}-[2-[2-[2-[[2-[2-[2-[[(2R)-3-sulfo-2-(16-sulfohexadecanoylamino)propanoyl]amino]ethoxy]ethoxy]acetyl]amino]ethoxy]ethoxy]acetyl], N{Epsilon-22}-[2-[2-[2-[[2-[2-[2-[[(2R)-3-sulfo-2-(16-sulfohexadecanoylamino)propanoyl]amino]ethoxy]ethoxy]acetyl]amino]ethoxy]ethoxy]acetyl], N{Epsilon-30}-[2-[2-[2-[[2-[2-[2-[[(2R)-3-sulfo-2-(16-sulfohexadecanoylamino)propanoyl]amino]ethoxy]ethoxy]acetyl]amino]ethoxy]ethoxy]acetyl]-[Aib8,Lys18,Lys22,Arg26,Lys30,Arg34]-GLP-1-(7-37)-peptide

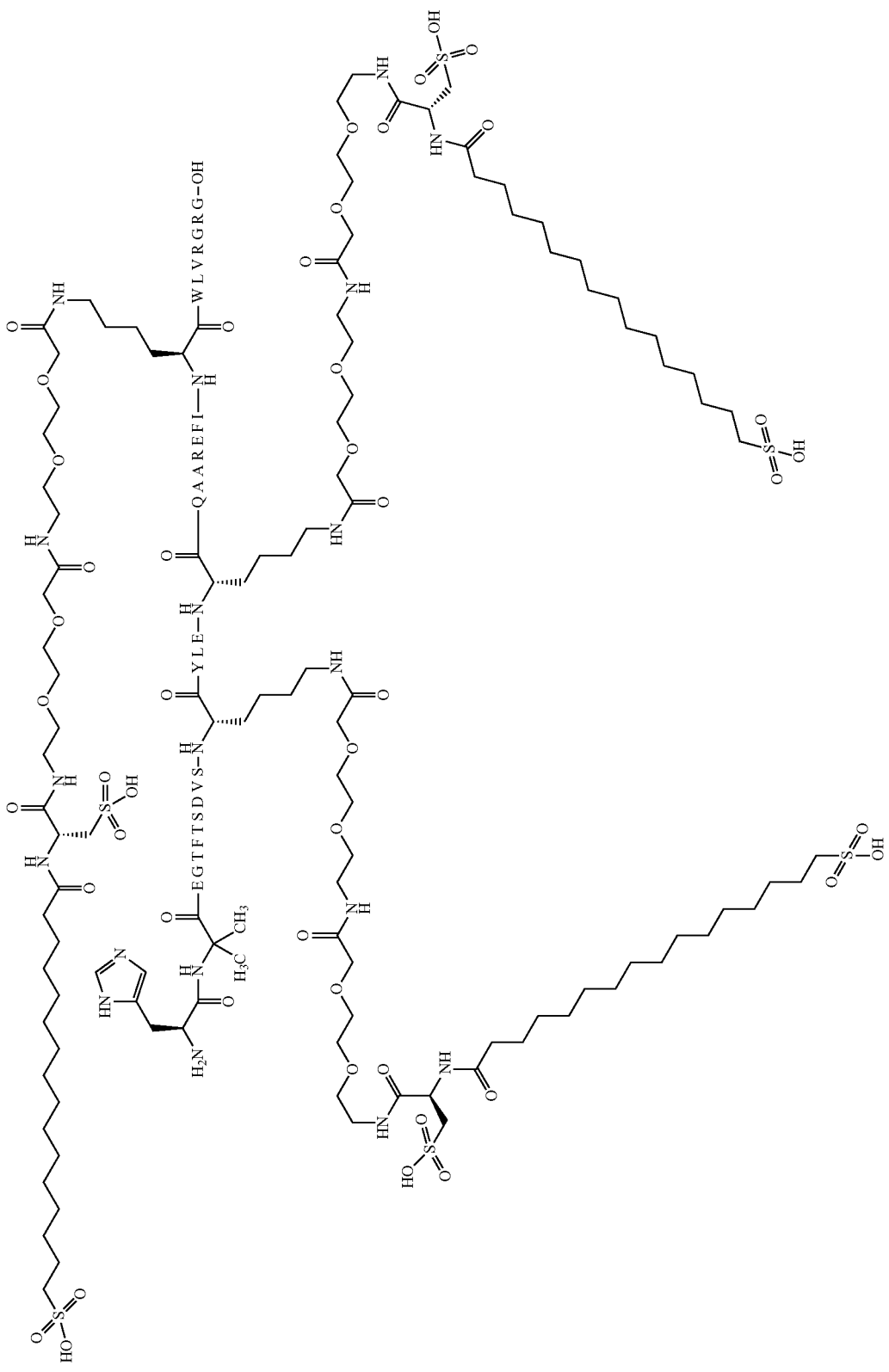
Chem. 22

The peptide is SEQ ID NO: 2.
Synthesis method: SPPS_L; SC_L; SC_M_1; SC_M_2; SC_M_3; CP_M1
LCMS01v01: Rt=2.8 min; m/3=1959; m/4=1469; m/5=1175; m/6=980
UPLC02v01: Rt=8.9 min

Example 3

N{Epsilon-18}-[(2S)-2-amino-6-[[(2S)-2-[[(2S)-2-[[(2S)-2-[[(2S)-2-[[(2S)-2-[[(4S)-4-carboxy-4-(17-carboxyheptadecanoylamino)butanoyl]amino]-3-hydroxypropanoyl]amino]-3-hydroxypropanoyl]amino]-3-hydroxypropanoyl]amino]-3-hydroxypropanoyl]amino]-3-hydroxypropanoyl]amino]hexanoyl], N{Epsilon-26}-[(2S)-2-amino-6-[[(2S)-2-[[(2S)-2-[[(2S)-2-[[(2S)-2-[[(2S)-2-[[(4S)-4-carboxy-4-(17-carboxyheptadecanoylamino)butanoyl]amino]-3-hydroxypropanoyl]amino]-3-hydroxypropanoyl]amino]-3-hydroxypropanoyl]amino]-3-hydroxypropanoyl]amino]-3-hydroxypropanoyl]amino]hexanoyl], N{Epsilon-37}-[(2S)-2-amino-6-[[(2S)-2-[[(2S)-2-[[(2S)-2-[[(2S)-2-[[(2S)-2-[[(4S)-4-carboxy-4-(17-carboxyheptadecanoylamino)butanoyl]amino]-3-hydroxypropanoyl]amino]-3-hydroxypropanoyl]amino]-3-hydroxypropanoyl]amino]-3-hydroxypropanoyl]amino]-3-hydroxypropanoyl]amino]hexanoyl]-[Aib8,Lys18,Arg34,Lys37]-GLP-1-(7-37)-peptide

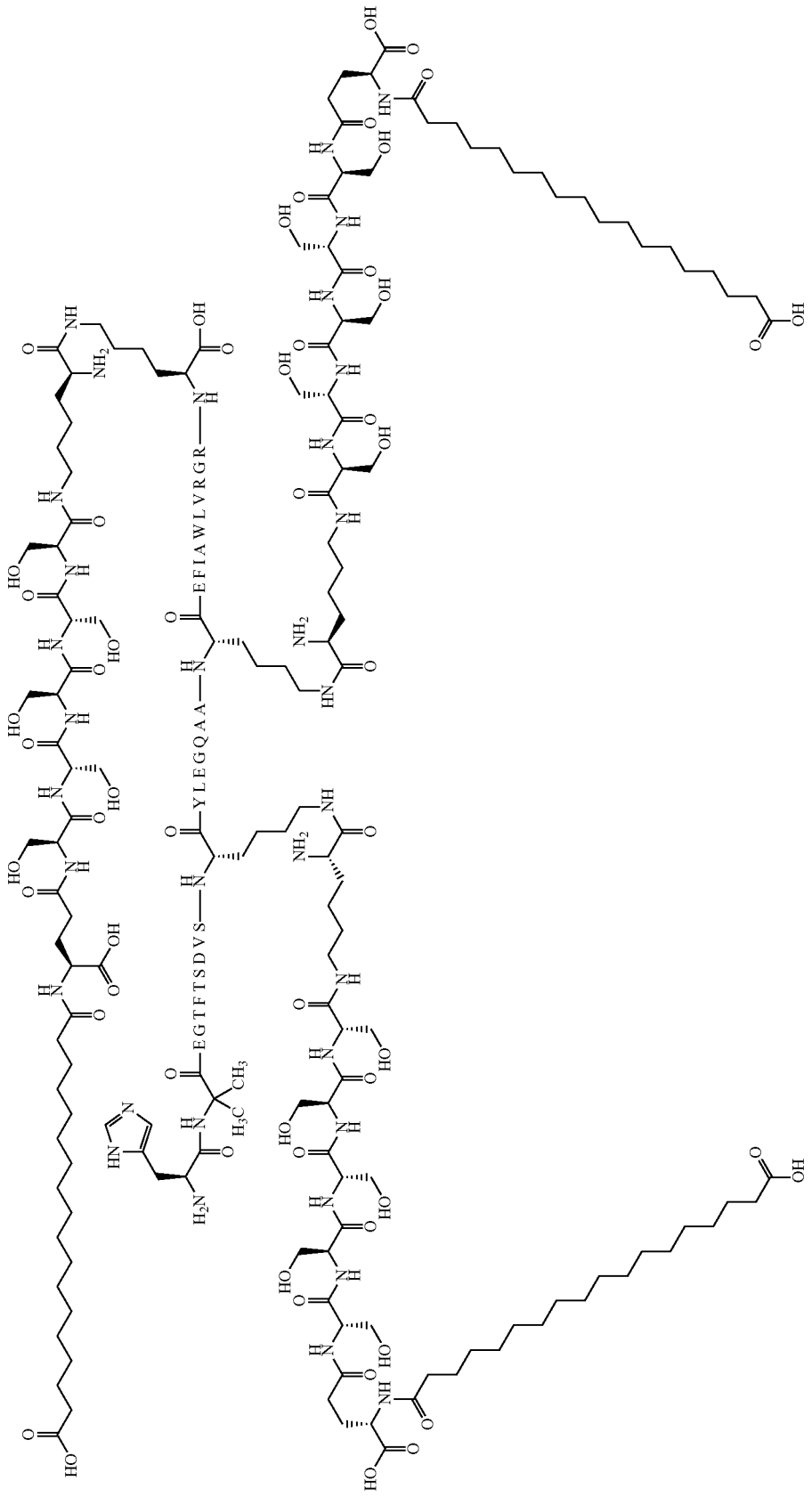
Chem. 23

The peptide is SEQ ID NO: 3.
Synthesis method: SPPS_P; SC_P; CP_M1
MALDI01v1: calc. m/z: 6477. found m/z: 6475.
UPLC02v01: Rt=9.30 min Example 4

N{Epsilon-18}-[2-[2-[2-[[2-[2-[2-[[(2R)-3-sulfo-2-[[4-[(16-sulfohexadecanoylamino)methyl]cyclohexanecarbonyl]amino]propanoyl]amino]ethoxy]ethoxy]acetyl]amino]ethoxy]ethoxy]acetyl],
N{Epsilon-22}-[2-[2-[2-[[2-[2-[2-[[(2R)-3-sulfo-2-[[4-[(16-sulfohexadecanoylamino)methyl]cyclohexanecarbonyl]amino]propanoyl]amino]ethoxy]ethoxy]acetyl]amino]ethoxyethoxy]acetyl],
N{Epsilon-30}-[2-[2-[2-[[2-[2-[2-[[(2R)-3-sulfo-2-[[4-[(16-sulfohexadecanoylamino)methyl]cyclohexanecarbonyl]amino]propanoyl]amino]ethoxy]ethoxy]acetyl]amino]ethoxy]ethoxyacetyl]-[Aib8,Lys8,Lys22,Arg26,Lys30,Arg34]-GLP-1-(7-37)-peptide Chem. 24

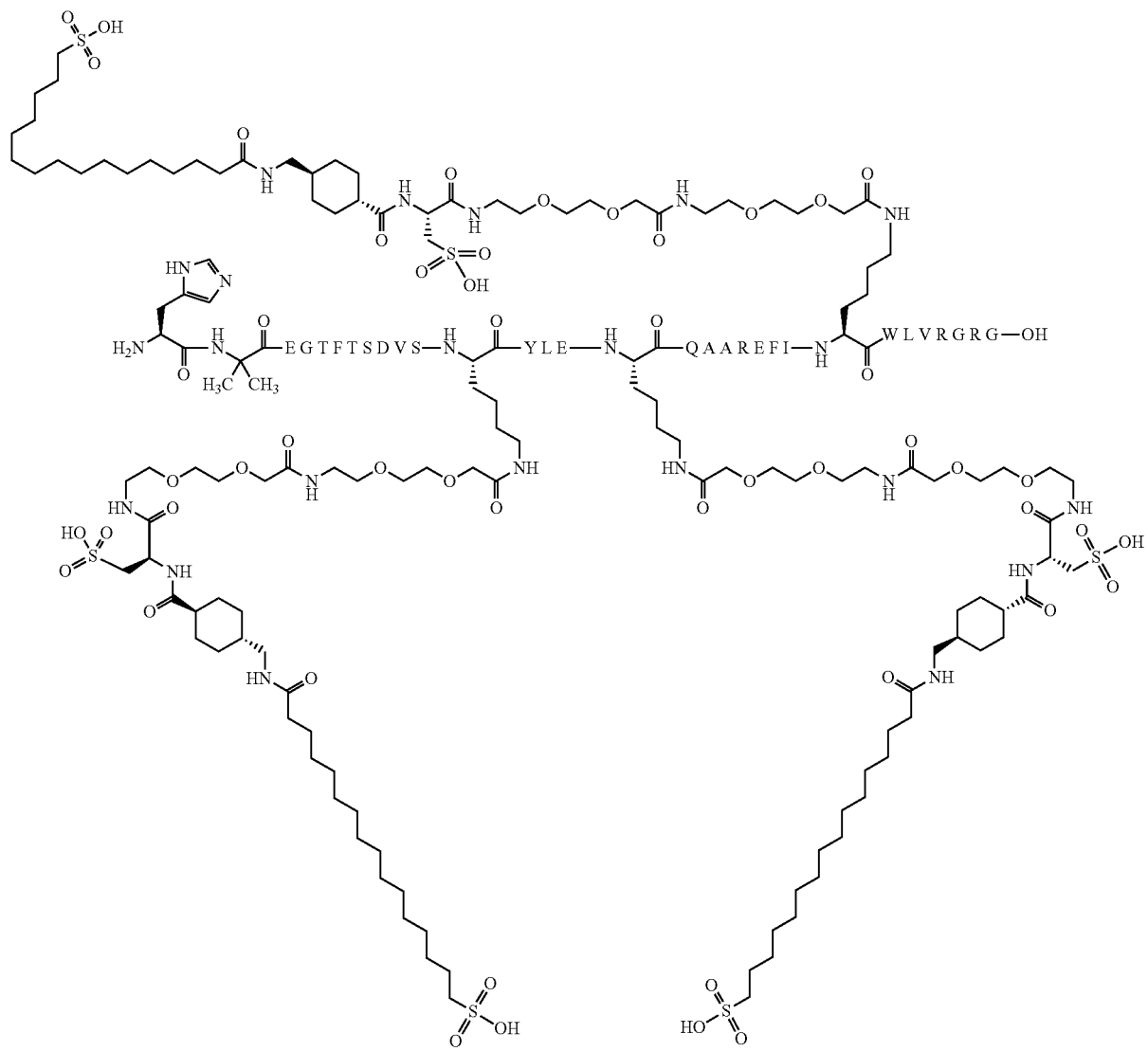

The peptide is SEQ ID NO: 2.
Synthesis method: SPPS_L; SC_L; SC_M_1; SC_M_2; SC_M_3; CP_M1

LCMS01v01: Rt=3.3 min, m/4=1574; m/5=1259

UPLC02v01: Rt=9.3 min

Example 5

N{Epsilon-18}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl], N{Epsilon-27}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl], N{Epsilon-37}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Aib8, Lys18,Glu22,Arg26,Lys27,Arg34,Lys37]-GLP-1-(7-37)-peptide Chem. 25

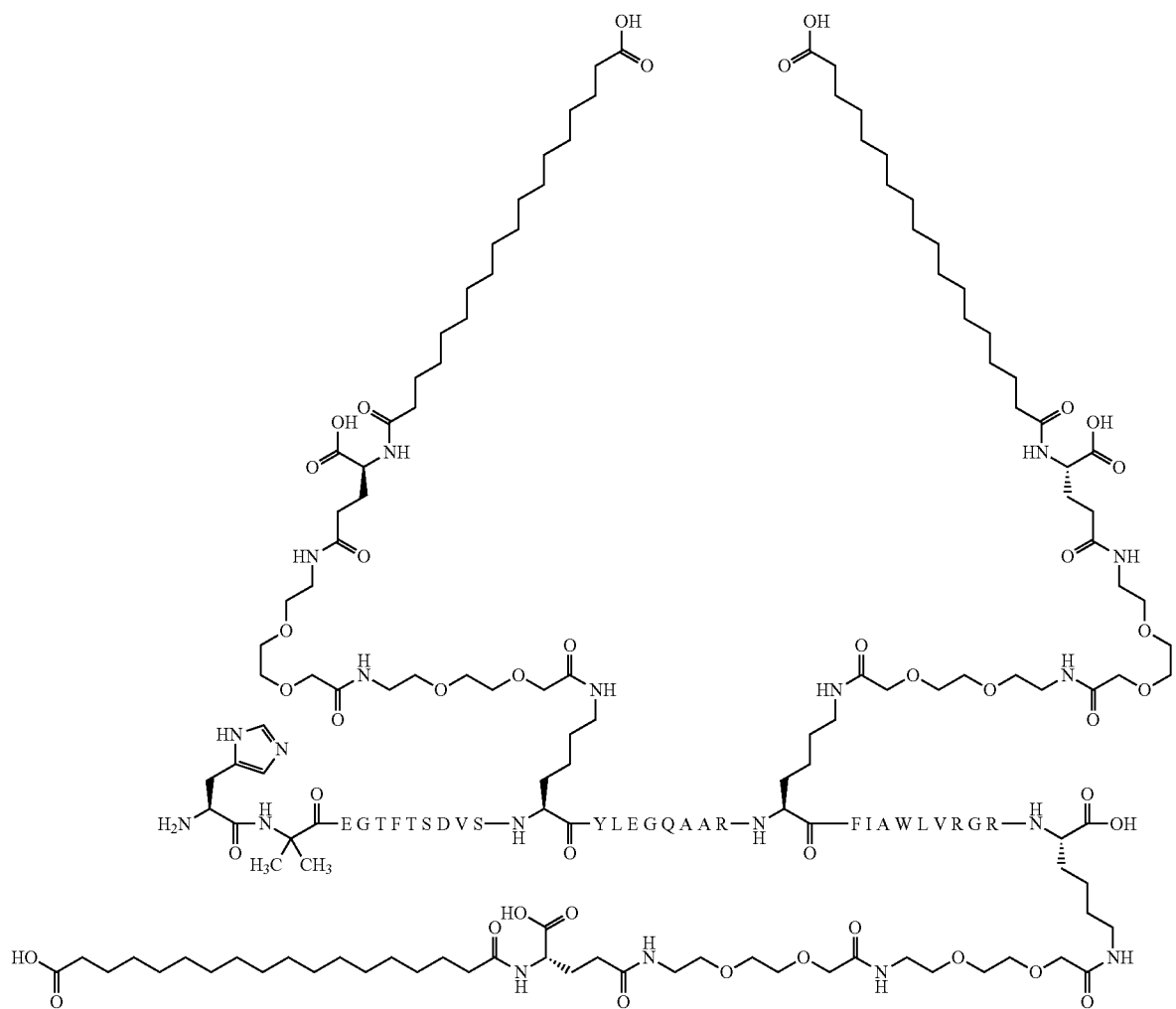

The peptide is SEQ ID NO: 4.

Synthesis method: SPPS_P; SC_L; CP_M1

LCMS01v01: Rt=2.9 min, m/3=1920; m/4=1440; m/5=1152

UPLC02v01: Rt=11.4 min

Example 6

N{Epsilon-18}-[(2S)-2-amino-6-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]hexanoyl],
N{Epsilon-27}-[(2S)-2-amino-6-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]hexanoyl],
N{Epsilon-37}-[(2S)-2-amino-6-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]hexanoyl]-[Aib8,Lys8,Glu22,Arg26,Lys27,Arg34,Lys37]-GLP-1-(7-37)-peptide Chem. 26

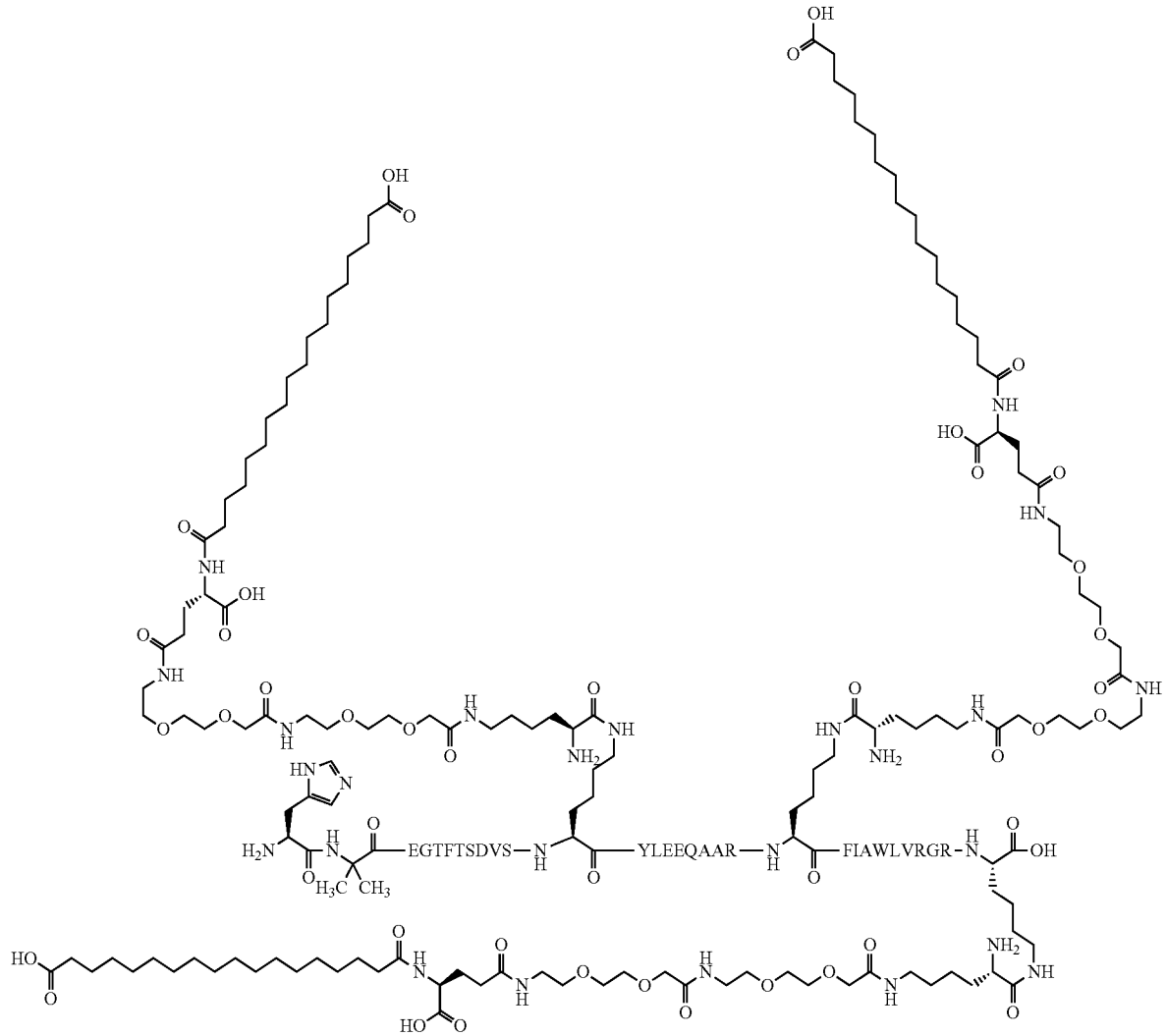

The peptide is SEQ ID NO: 4.
Synthesis method: SPPS_P; SC_L; CP_M1
LCMS01v01: Rt=2.7 min, m/4=1536; m/5=1229; m/6=1024; m/7=878
UPLC02v01: Rt=9.3 min

Example 7

N{Epsilon-18}-[2-[2-[2-[[4-carboxy-4-[[2-[2-[2-(17-carboxyheptadecanoylamino)ethoxy]ethoxy]acetyl]amino]butanoyl]amino]ethoxy]ethoxy]acetyl],N{Epsilon-27}-[2-[2-[2-[[(4S)-4-carboxy-4-[[2-[2-[2-(17-carboxyheptadecanoylamino)ethoxy]ethoxy]acetyl]amino]butanoyl]amino]ethoxy]ethoxy]acetyl],N{Epsilon-37}-[2-[2-[2-[[(4S)-4-carboxy-4-[[2-[2-[2-(17-carboxyheptadecanoylamino)ethoxy]ethoxy]acetyl]amino]butanoyl]amino]ethoxy]ethoxy]acetyl]-[Aib8, Lys18,Glu22,Arg26,Lys27,Arg34,Lys37]-GLP-1-(7-37)-peptide Chem. 27

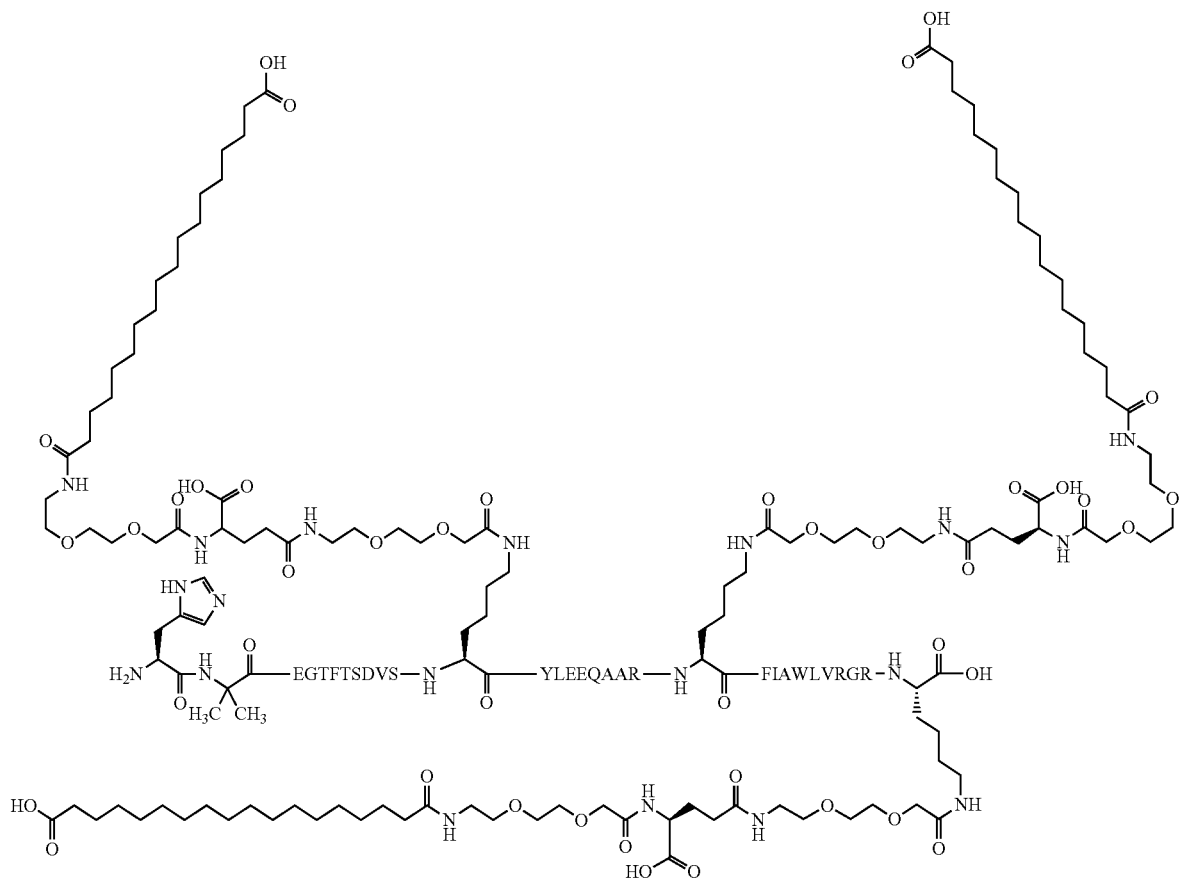

The peptide is SEQ ID NO: 4.

Synthesis method: SPPS_P; SC_L; CP_M1

LCMS01v01: Rt=3.0 min, m/3=1920; m/4=1440; m/5=1152

UPLC02v01: Rt=10.7 min

Example 8

N{Epsilon-18}-[(2S)-2-[[(2S)-2-[[(2S)-2-[[(2S)-2-[[(2S)-2-[[(2S)-2-[[(4S)-4-carboxy-4-(17-carboxy-heptadecanoylamino)butanoyl]amino]-3-hydroxy-propanoyl]amino]-3-hydroxypropanoyl]amino]-3-hydroxypropanoyl]amino]-3-hydroxypropanoyl]amino]-3-hydroxypropanoyl]amino]-3-hydroxypropanoyl], N{Epsilon-26}-[(2S)-2-[[(2S)-2-[[(2S)-2-[[(2S)-2-[[(2S)-2-[[(2S)-2-[[(4S)-4-carboxy-4-(17-carboxyheptadecanoylamino)butanoyl]amino]-3-hydroxypropanoyl]amino]-3-hydroxypropanoyl]amino]-3-hydroxypropanoyl]amino]-3-hydroxypropanoyl]amino]-3-hydroxypropanoyl]amino]-3-hydroxypropanoyl], N{Epsilon-37}-[(2S)-2-[[(2S)-2-[[(2S)-2-[[(2S)-2-[[(2S)-2-[[(2S)-2-[[(4S)-4-carboxy-4-(17-carboxy-heptadecanoylamino)butanoyl]amino]-3-hydroxy-propanoyl]amino]-3-hydroxypropanoyl]amino]-3-hydroxypropanoyl]amino]-3-hydroxypropanoyl]amino]-3-hydroxypropanoyl]amino]-3-hydroxypropanoyl]-[Aib8,Lys18,Arg34,Lys37]-GLP-1-(7-37)-peptide Chem. 28

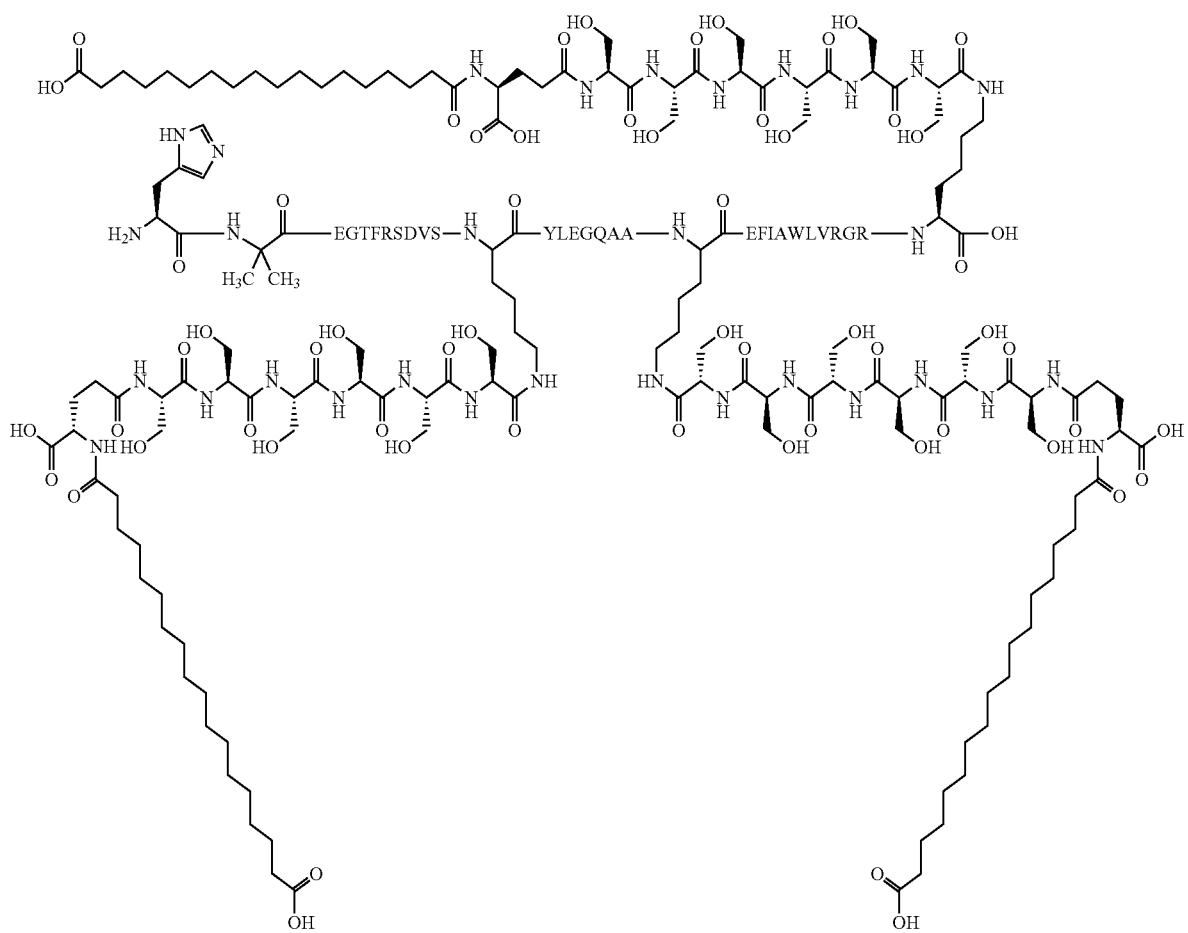

The peptide is SEQ ID NO: 3.
Synthesis method: SPPS_P; SC_P; CP_M1
MALDI01v01: calc. m/z: 6354. found m/z: 6350.
UPLC02v01: Rt=10.5 min

Example 9

N{Epsilon-18}-[(2S)-2-[[(2S)-2-[[(2S)-2-[[(2S)-2-[[(2S)-2-[[(2S)-2-[[(4S)-4-carboxy-4-(17-carboxy-heptadecanoylamino)butanoyl]amino]-3-hydroxy-propanoyl]amino]-3-hydroxypropanoyl]amino]-3-hydroxypropanoyl]amino]-3-hydroxypropanoyl]amino]-3-hydroxypropanoyl]amino]-3-hydroxypropanoyl], N{Epsilon-27}-[(2S)-2-[[(2S)-2-[[(2S)-2-[[(2S)-2-[[(2S)-2-[[(2S)-2-[[(4S)-4-carboxy-4-(17-carboxyheptadecanoylamino)butanoyl]amino]-3-hydroxypropanoyl]amino]-3-hydroxypropanoyl]amino]-3-hydroxypropanoyl]amino]-3-hydroxypropanoyl]amino]-3-hydroxypropanoyl]amino]-3-hydroxypropanoyl], N{Epsilon-37}-[(2S)-2-[[(2S)-2-[[(2S)-2-[[(2S)-2-[[(2S)-2-[[(2S)-2-[[(4S)-4-carboxy-4-(17-carboxy-heptadecanoylamino)butanoyl]amino]-3-hydroxy-propanoyl]amino]-3-hydroxypropanoyl]amino]-3-hydroxypropanoyl]amino]-3-hydroxypropanoyl]amino]-3-hydroxypropanoyl]amino]-3-hydroxypropanoyl]-[Aib8,Lys18,Arg26,Lys27,Arg34,Lys37]-GLP-1-(7-37)-peptide

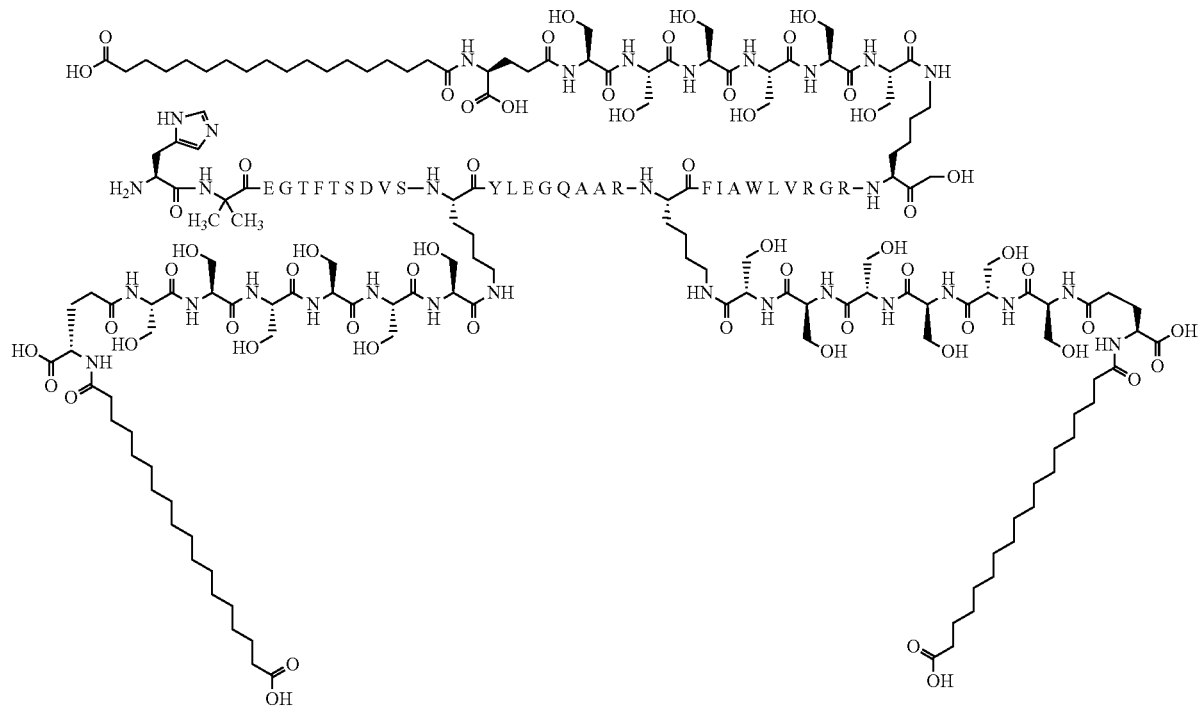

Chem. 29

The peptide is SEQ ID NO: 5.

Synthesis method: SPPS_P; SC_P; CP_M1

MALDI01v01: calc. m/z: 6381. found m/z: 6381.

UPLC02v01: Rt=10.1 min

Example 10

N{Epsilon-27}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl],
N{Epsilon-30}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl],
N{Epsilon-37}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Aib8,Glu22,Arg26,Lys27,Lys30,Arg34,Lys37]-GLP-1-(7-37)-peptide Chem. 30

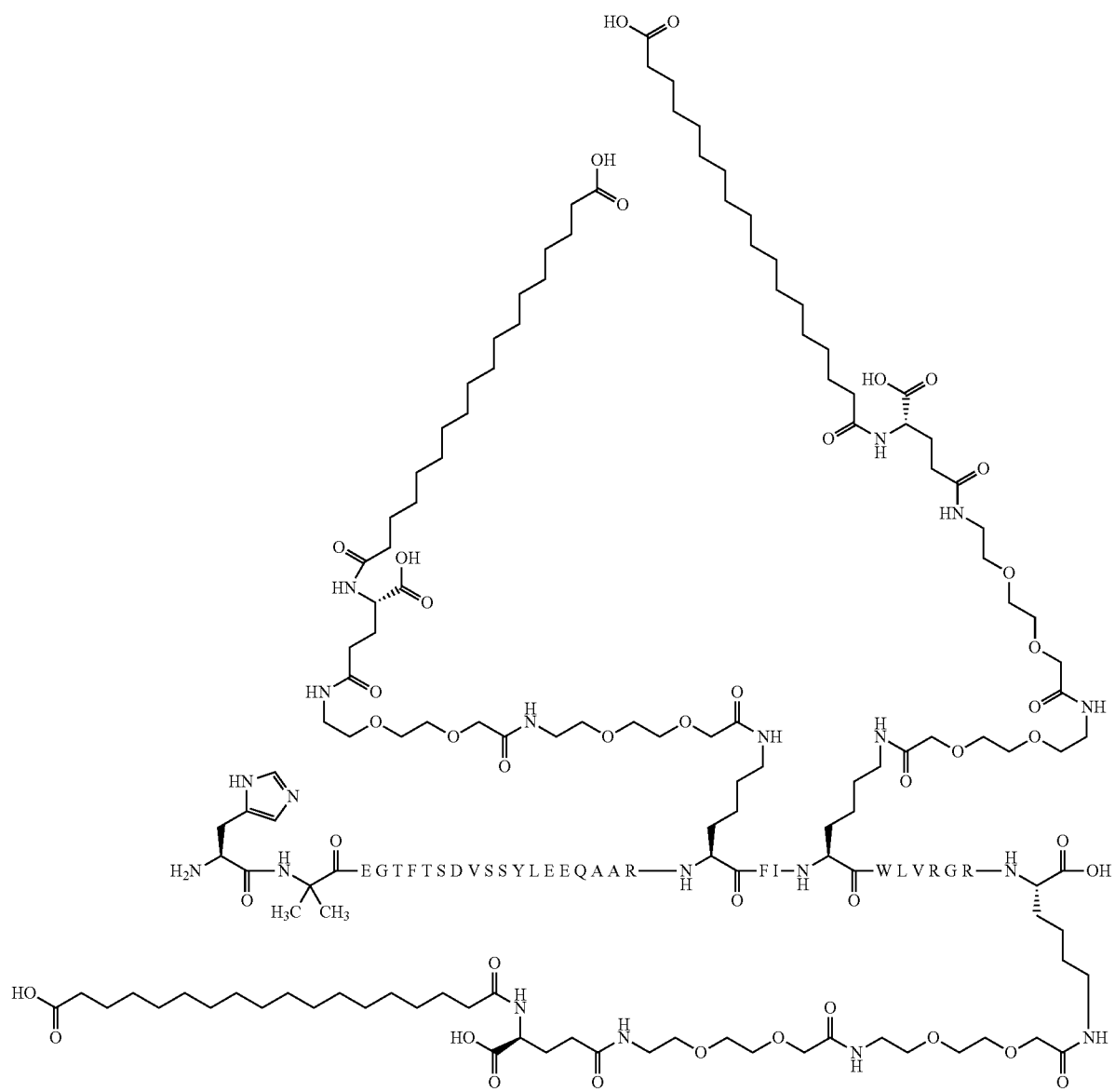

The peptide is SEQ ID NO: 6.
Synthesis method: SPPS_P; SC_L; CP_M1
LCMS01v01: Rt=2.6 min, m/3=1925; m/4=1444; m/5=1155; m/6=963
UPLC02v01: Rt=10.6 min Example 11

N{Epsilon-26}-[(2S)-2-amino-6-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]hexanoyl],
N{Epsilon-30}-[(2S)-2-amino-6-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]hexanoyl],
N{Epsilon-37}-[(2S)-2-amino-6-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]hexanoyl]-[Aib8,Glu22,Lys30,Arg34,Lys37]-GLP-1-(7-37)-peptide Chem. 31

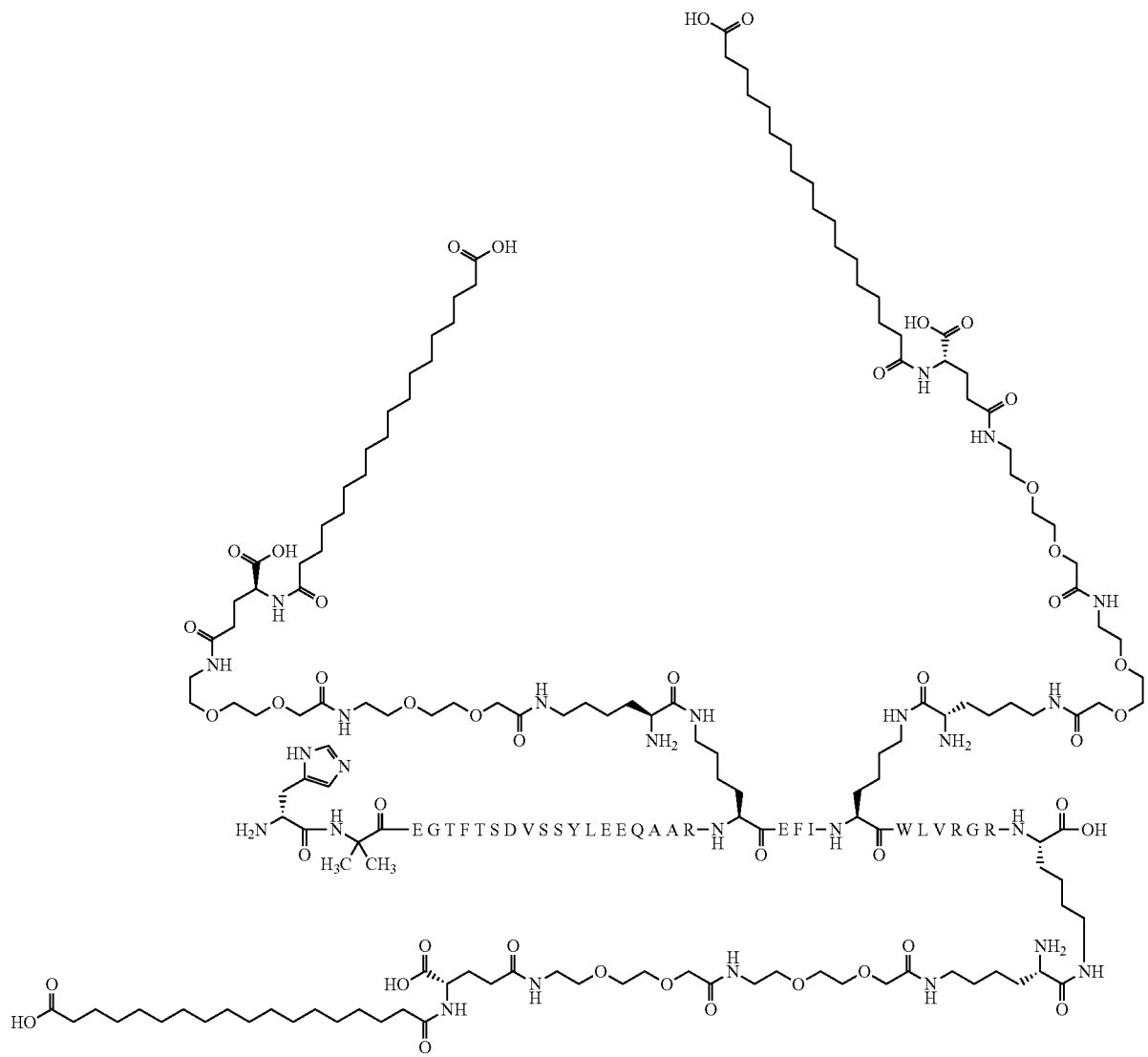

The peptide is SEQ ID NO: 7.
Synthesis method: SPPS_L; SC_L; CP_M1
LCMS01v01: Rt=2.5 min, m/4=1533; m/5=1227; m/6=1022 m/7=877
UPLC02v01: Rt=9.8 min

Example 12

N{Epsilon-26}-[(2S)-2-amino-6-[[2-[2-[2-[[2-[2-[2-[[(2R)-3-sulfo-2-(16-sulfohexadecanoylamino)propanoyl]amino]ethoxy]ethoxy]acetyl]amino]ethoxy]ethoxy]acetyl]amino]hexanoyl], N{Epsilon-30}-[(2S)-2-amino-6-[[2-[2-[2-[[2-[2-[2-[[(2R)-3-sulfo-2-(16-sulfohexadecanoylamino)propanoyl]amino]ethoxy]ethoxy]acetyl]amino]ethoxy]ethoxy]acetyl]amino]hexanoyl], N{Epsilon-37}-[(2S)-2-amino-6-[[2-[2-[2-[[2-[2-[2-[[(2R)-3-sulfo-2-(16-sulfohexadecanoylamino)propanoyl]amino]ethoxy]ethoxy]acetyl]amino]ethoxy]ethoxy]acetyl]amino]hexanoyl]-[Aib8,Glu22,Lys30,Arg34,Lys37]-GLP-1-(7-37)-peptide Chem. 32

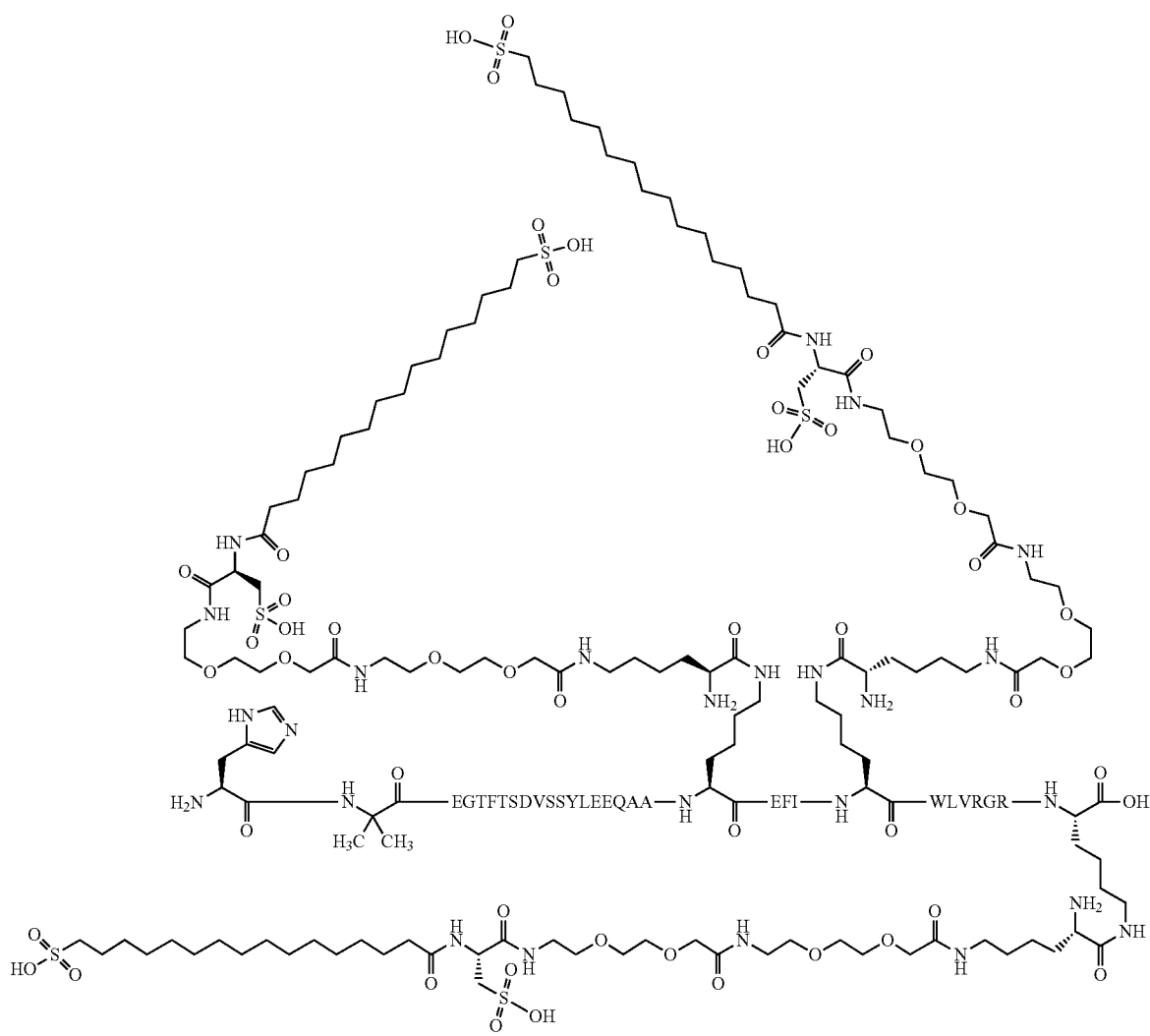

The peptide is SEQ ID NO: 7.
Synthesis method: SPPS_P; SC_L; SC_M_2; SC_M_3; CP_M1
LCMS01v01: Rt=3.0 min, m/4=1566; m/5=1253; m/6=1045; m/7=896
UPLC02v01: Rt=8.4 min

Example 13

N{Epsilon-18}-[2-[2-[2-[[2-[2-[2-[[(2S)-2-amino-6-(16-sulfohexadecanoylamino)hexanoyl]amino]ethoxy]ethoxy]acetyl]amino]ethoxy]ethoxy]acetyl], N{Epsilon-22}-[2-[2-[2-[[2-[2-[2-[[(2S)-2-amino-6-(16-sulfohexadecanoylamino)hexanoyl]amino]ethoxy]ethoxy]acetyl]amino]ethoxy]ethoxy]acetyl], N{Epsilon-30}-[2-[2-[2-[[2-[2-[2-[[(2S)-2-amino-6-(16-sulfohexadecanoylamino)hexanoyl]amino]ethoxy]ethoxy]acetyl]amino]ethoxy]ethoxy]acetyl]-[Aib8,Lys18,Lys22,Arg26,Lys30,Arg34]-GLP-1-(7-37)-peptide Chem. 33

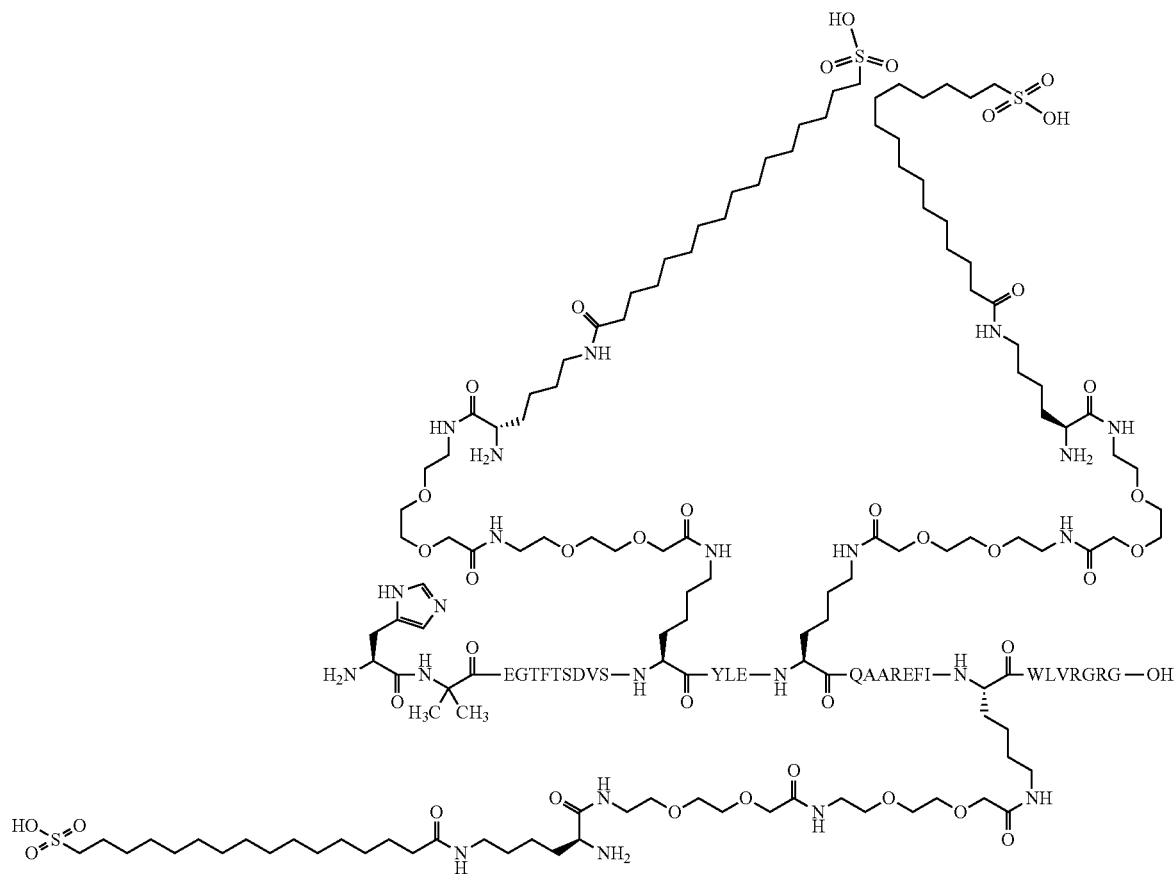

The peptide is SEQ ID NO: 2.

Synthesis method: SPPS_L; SC_L; SC_M_3; CP_M1

LCMS01v01: Rt=2.3 min, m/3=1936; m/4=1452; m/5=1162; m/6=969; m/7=830; m/8=727;

UPLC02v01: Rt=8.5 min

Example 14

N{Epsilon-18}-[2-[2-[2-[[2-[2-[2-[[(2S)-2-amino-6-[[(2 S)-2-amino-6-(16-sulfohexadecanoylamino)hexanoyl]amino]hexanoyl]amino]ethoxy]ethoxy]acetyl]amino]ethoxy]ethoxyacetyl], N{Epsilon-22}-[2-[2-[2-[[2-[2-[2-[[(2S)-2-amino-6-[[(2S)-2-amino-6-(16-sulfohexadecanoylamino)hexanoyl]amino]hexanoyl]amino]ethoxy]ethoxy]acetyl]amino]ethoxy]ethoxy]acetyl], N{Epsilon-30}-[2-[2-[2-[[2-[2-[2-[[(2S)-2-amino-6-[[(2S)-2-amino-6-(16-sulfohexadecanoylamino)hexanoyl]amino]hexanoyl]amino]ethoxy]ethoxy]acetyl]amino]ethoxy]ethoxy]acetyl]-[Aib8,Lys18,Lys22,Arg26,Lys30,Arg34]-GLP-1-(7-37)-peptide Chem. 34

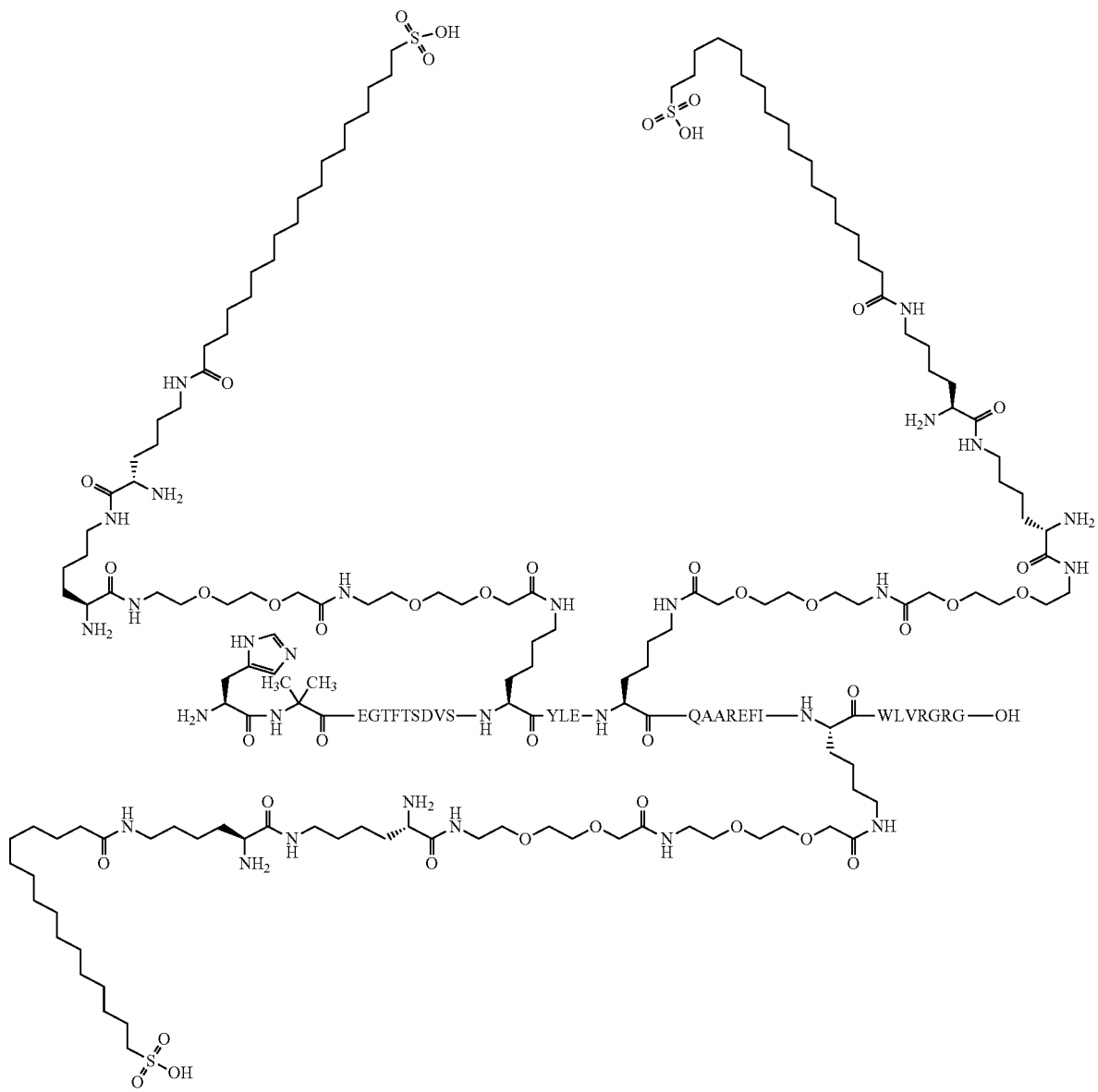

The peptide is SEQ ID NO: 2.
Synthesis method: SPPS_L; SC_L; SC_M_3; CP_M1
LCMS01v01: Rt=2.3 min, m/4=1548; m/5=1239; m/6=1033; m/7=885; m/8=775
UPLC02v01: Rt=7.7 min Example 15

N{Epsilon-18}-[2-[2-[2-[[2-[2-[2-[[2-[2-[2-[[2-[2-[2-[[2-[2-[2-[[(2S)-2-amino-6-[[(2S)-2-amino-6-(19-carboxynonadecanoylamino)hexanoyl]amino]hexanoyl]amino]ethoxy]ethoxy]acetyl]amino]ethoxy]ethoxy]acetyl]amino]ethoxy]ethoxy]acetyl]amino]ethoxy]ethoxy]acetyl], N{Epsilon-22}-[2-[2-[2-[[2-[2-[2-[[2-[2-[2-[[2-[2-[2-[[2-[2-[2-[[(2S)-2-amino-6-[[(2S)-2-amino-6-(19-carboxynonadecanoylamino)hexanoyl]amino]hexanoyl]amino]ethoxy]ethoxy]acetyl]amino]ethoxy]ethoxy]acetyl]amino]ethoxy]ethoxy]acetyl]amino]ethoxy]ethoxy]acetyl], N{Epsilon-30}-[2-[2-[2-[[2-[2-[2-[[2-[2-[2-[[2-[2-[2-[[2-[2-[2-[[(2S)-2-amino-6-[[(2S)-2-amino-6-(19-carboxynonadecanoylamino)hexanoyl]amino]hexanoyl]amino]ethoxy]ethoxy]acetyl]amino]ethoxy]ethoxy]acetyl]amino]ethoxy]ethoxy]acetyl]amino]ethoxy]ethoxy]acetyl]-[Aib8,Lys18,Lys22,Arg26,Lys30,Arg34]-GLP-1-(7-37)-peptide

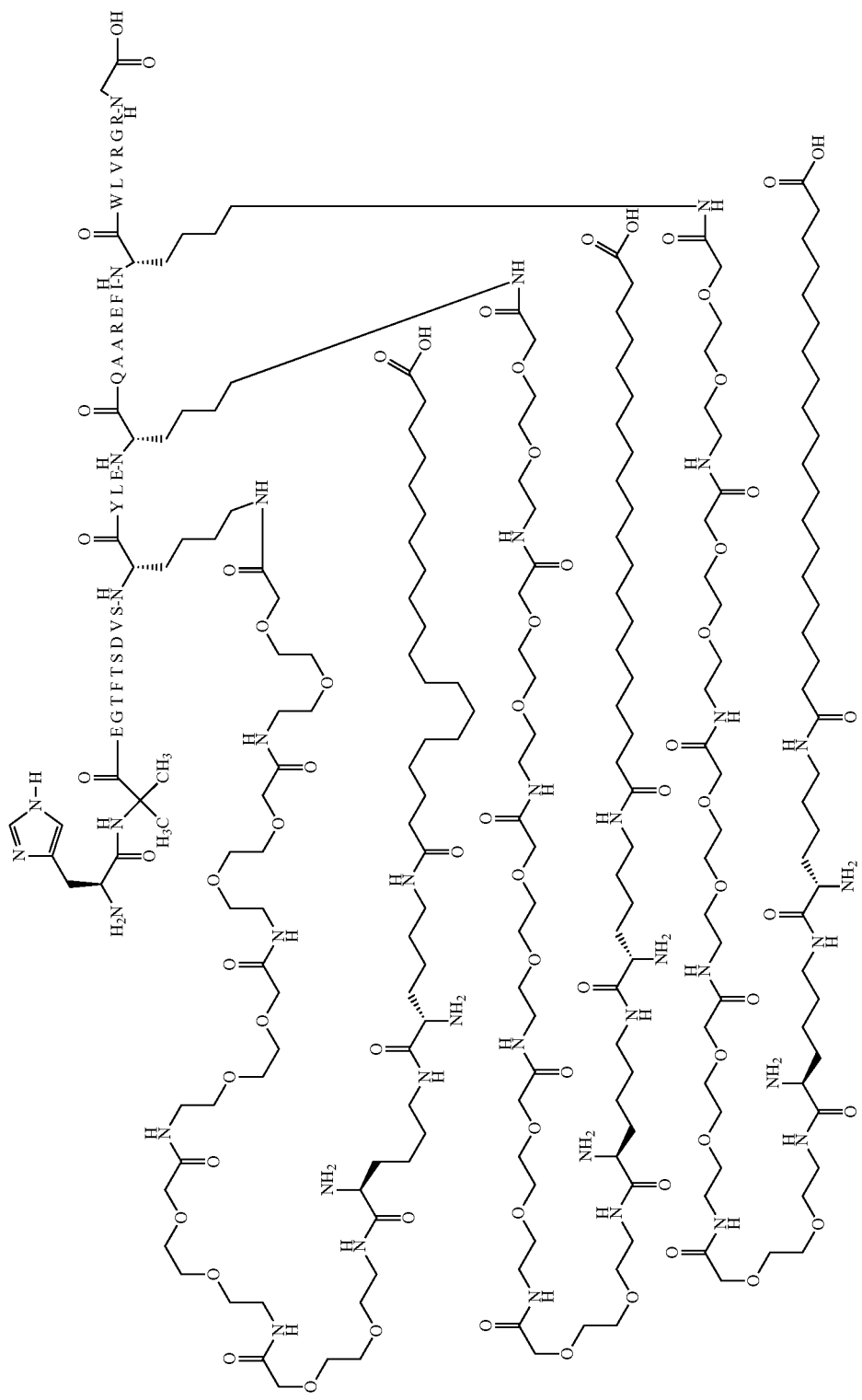
Chem. 35

The peptide is SEQ ID NO: 2.
Synthesis method: SPPS_P; SC_L; CP_M1
LCMS01: Rt=2.27 min; m/4=1879; m/5=1503
UPLC02v01: Rt=9.41 min Example 16

N{Epsilon-18}-[2-[2-[2-[[2-[2-[2-[[2-[2-[2-[[2-[2-[2-[[2-[2-[2-[[(2S)-2-amino-6-[[(2S)-2-amino-6-(17-carboxyheptadecanoylamino)hexanoyl]amino]hexanoyl]amino]ethoxy]ethoxy]acetyl]amino]ethoxy]ethoxy]acetyl]amino]ethoxy]ethoxy]acetyl]amino]ethoxy]ethoxy]acetyl], N{Epsilon-22}-[2-[2-[2-[[2-[2-[2-[[2-[2-[2-[[2-[2-[2-[[2-[2-[2-[[(2S)-2-amino-6-[[(2S)-2-amino-6-(17-carboxyheptadecanoylamino)hexanoyl]amino]hexanoyl]amino]ethoxy]ethoxy]acetyl]amino]ethoxy]ethoxy]acetyl]amino]ethoxy]ethoxy]acetyl]amino]ethoxy]ethoxy]acetyl], N{Epsilon-30}-[2-[2-[2-[[2-[2-[2-[[2-[2-[2-[[2-[2-[2-[[2-[2-[2-[[(2S)-2-amino-6-[[(2S)-2-amino-6-(17-carboxyheptadecanoylamino)hexanoyl]amino]hexanoyl]amino]ethoxy]ethoxy]acetyl]amino]ethoxy]ethoxy]acetyl]amino]ethoxy]ethoxy]acetyl]amino]ethoxy]ethoxy]acetyl]-[Aib8,Lys18,Lys22,Arg26,Lys30,Arg34]-GLP-1-(7-37)-peptide Example 17

N{Epsilon-18}-[2-[2-[2-[[2-[2-[2-[[2-[2-[2-[[2-[2-[2-[[2-[2-[2-[[(2S)-2-amino-6-[[(2S)-2-amino-6-[[(2S)-2-amino-6-(17-carboxyheptadecanoylamino)hexanoyl]amino]hexanoyl]amino]hexanoyl]amino]ethoxy]ethoxy]acetyl]amino]ethoxy]ethoxy]acetyl]amino]ethoxy]ethoxy]acetyl]amino]ethoxy]ethoxy]acetyl], N{Epsilon-22}-[2-[2-[2-[[2-[2-[2-[[2-[2-[2-[[2-[2-[2-[[(2S)-2-amino-6-[[(2S)-2-amino-6-[[(2S)-2-amino-6-(17-carboxyheptadecanoylamino)hexanoyl]amino]hexanoyl]amino]hexanoyl]amino]ethoxy]ethoxy]acetyl]amino]ethoxy]ethoxy]acetyl]amino]ethoxy]ethoxy]acetyl]amino]ethoxy]ethoxy]acetyl], N{Epsilon-30}-[2-[2-[2-[[2-[2-[2-[[2-[2-[2-[[2-[2-[2-[[(2S)- 2-amino-6-[[(2S)-2-amino-6-[[(2S)-2-amino-6-(17-carboxyheptadecanoylamino)hexanoyl]amino]hexanoyl]amino]hexanoyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl]-[Aib8,Lys18,Lys22,Arg26,Lys30,Arg34]-GLP-1-(7-37)-peptide Chem. 36

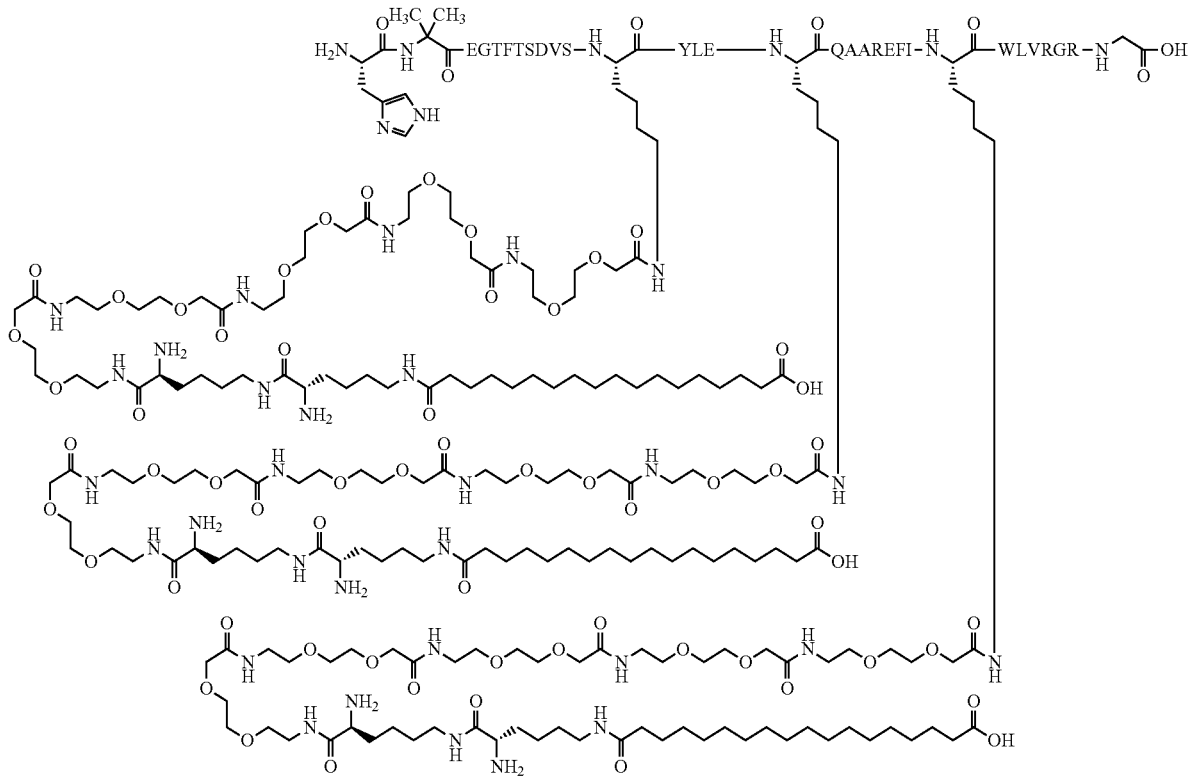

The peptide is SEQ ID NO: 2.
Synthesis method: SPPS_P; SC_L; CP_M1
LCMS01: Rt=2.08 min; m/4=1859; m/5=1487
UPLC02v01: Rt=8.50 min

[Chem. 37]
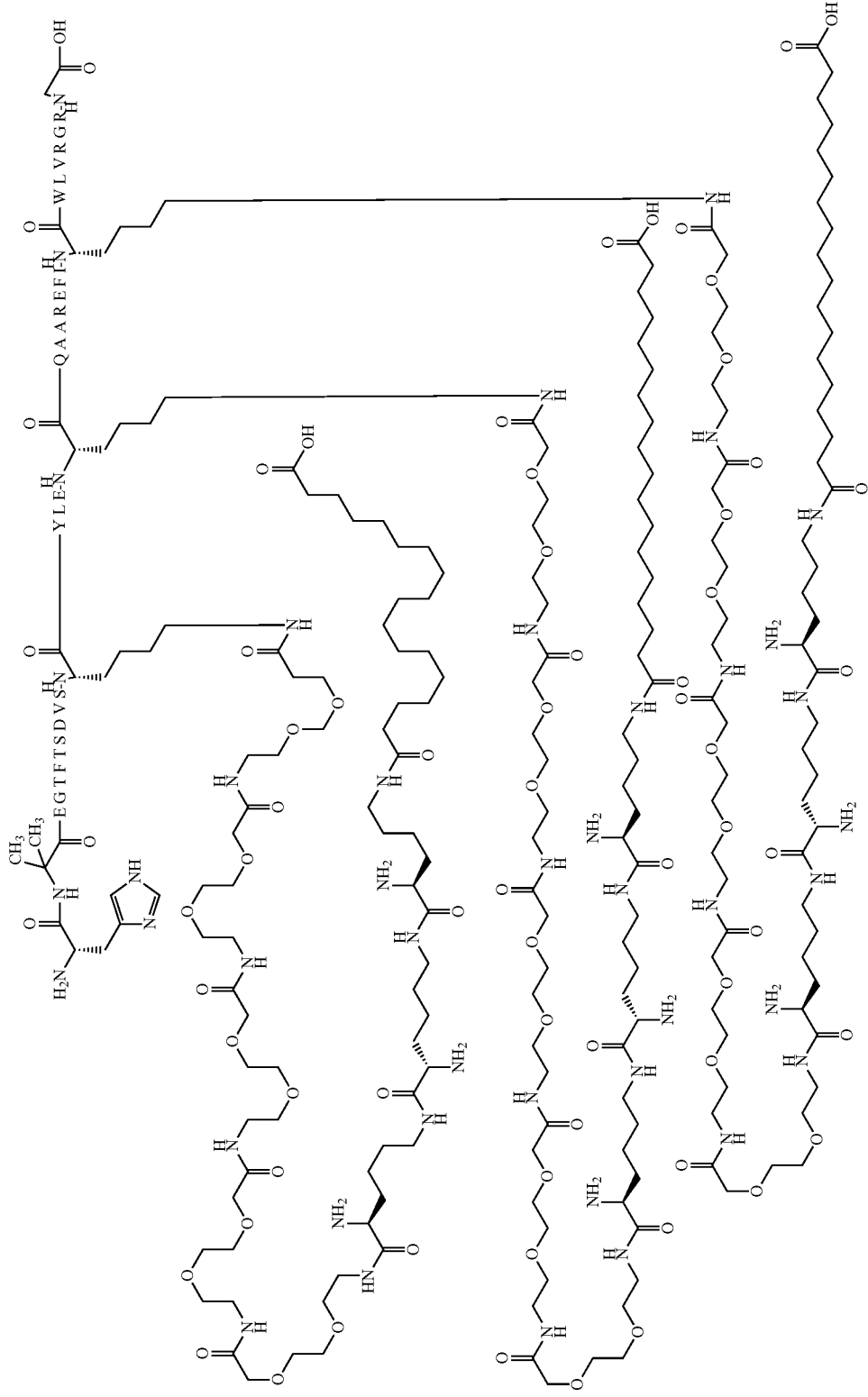

The peptide is SEQ ID NO: 2.
Synthesis method: SPPS_P; SC_L; CP_M1
LCMS01: Rt=1.92 min; m/4=1955; m/5=1564
UPLC02v01: Rt=8.08 min Example 18

N{Epsilon-18}-[2-[2-[2-[[2-[2-[2-[[2-[2-[2-[[2-[2-[2-[[(2S)-2-amino-6-[[(2S)-2-amino-6-[4-(16-sulfohexadecanoylamino)butanoylamino]hexanoyl]amino]hexanoyl]amino]ethoxy]ethoxy]acetyl]amino]ethoxy]ethoxy]acetyl]amino]ethoxy]ethoxy]acetyl], N{Epsilon-22}-[2-[2-[2-[[2-[2-[2-[[2-[2-[2-[[2-[2-[2-[[(2S)-2-amino-6-[[(2S)-2-amino-6-[4-(16-sulfohexadecanoylamino)butanoylamino]hexanoyl]amino]hexanoyl]amino]ethoxy]ethoxy]acetyl]amino]ethoxy]ethoxy]acetyl]amino]ethoxy]ethoxy]acetyl]amino]ethoxy]ethoxy]acetyl], N{Epsilon-30}-[2-[2-[2-[[2-[2-[2-[[2-[2-[2-[[2-[2-[2-[[(2S)-2-amino-6-[[(2S)-2-amino-6-[4-(16-sulfohexadecanoylamino)butanoylamino]hexanoyl]amino]hexanoyl]amino]ethoxy]ethoxy]acetyl]amino]ethoxy]ethoxy]acetyl]amino]ethoxy]ethoxy]acetyl]-[Aib8,Lys18,Lys22,Arg26,Lys30,Arg34]-GLP-1-(7-37)-peptide Chem. 38

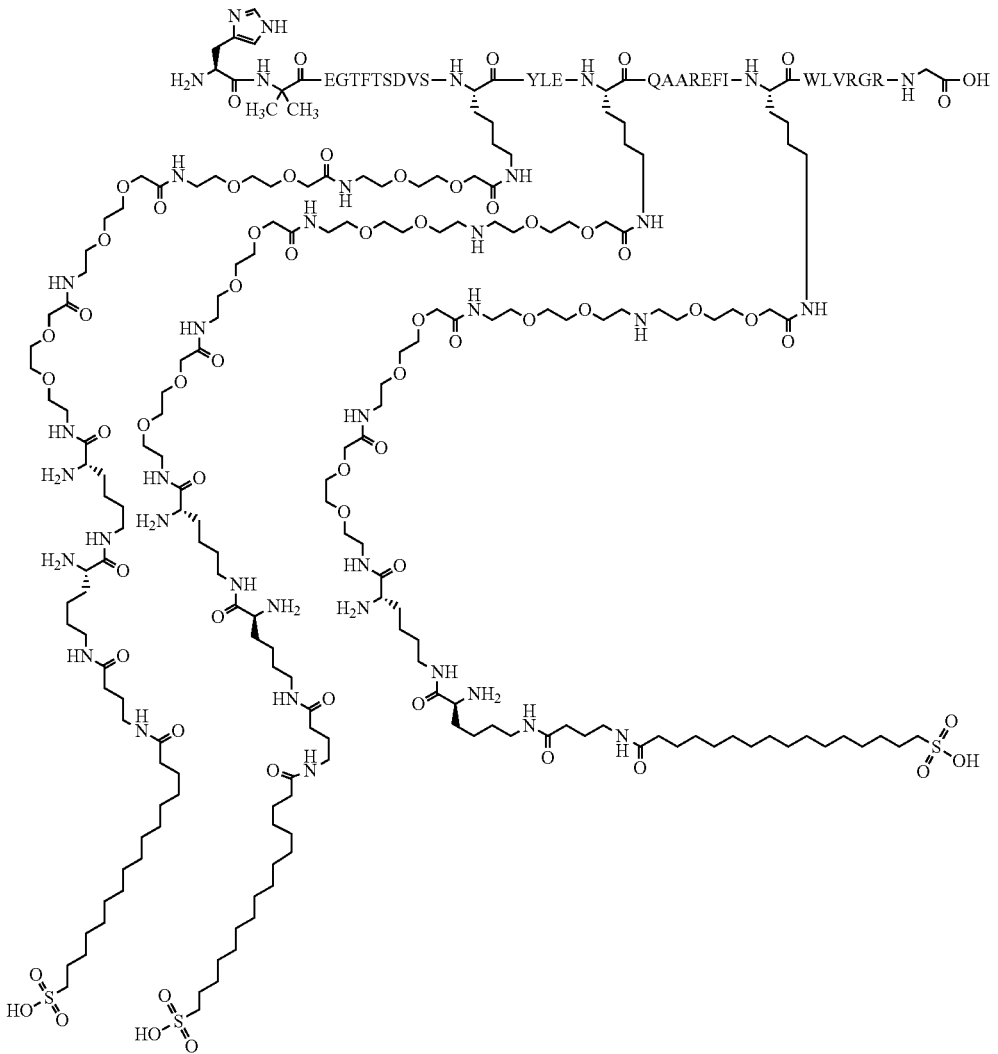

The peptide is SEQ ID NO: 2.
Synthesis method: SPPS_L; SC_L; SC_M_3; CP_M1

LCMS01: Rt=1.88 min; m/4=1830; m/5=1464
UPLC02v01: Rt=8.4 min

Example 19

N{Epsilon-18}-[2-[2-[2-[[2-[2-[2-[[2-[2-[2-[[2-[2-[2-[[(2S)-2-amino-6-[[(2S)-2-amino-6-[6-(16-sulfo-hexadecanoylamino)hexanoylamino]hexanoyl]amino]hexanoyl]amino]ethoxy]ethoxy]acetyl]amino]ethoxy]ethoxy]acetyl]amino]ethoxy]ethoxy]acetyl],
N{Epsilon-22}-[2-[2-[2-[[2-[2-[2-[[2-[2-[2-[[2-[2-[2-[[(2S)-2-amino-6-[[(2S)-2-amino-6-[6-(16-sulfo-hexadecanoylamino)hexanoylamino]hexanoyl]amino]hexanoyl]amino]ethoxy]ethoxy]acetyl]amino]ethoxy]ethoxy]acetyl]amino]ethoxy]ethoxy]acetyl],
N{Epsilon-30}-[2-[2-[2-[[2-[2-[2-[[2-[2-[2-[[2-[2-[2-[[(2S)-2-amino-6-[[(2S)-2-amino-6-[6-(16-sulfo-hexadecanoylamino)hexanoylamino]hexanoyl]amino]hexanoyl]amino]ethoxy]ethoxy]acetyl]amino]ethoxy]ethoxy]acetyl]amino]ethoxy]ethoxy]acetyl]amino]ethoxy]ethoxy]acetyl]-[Aib8,Lys18,Lys22,Arg26,Lys30,Arg34]-GLP-1-(7-37)-peptide

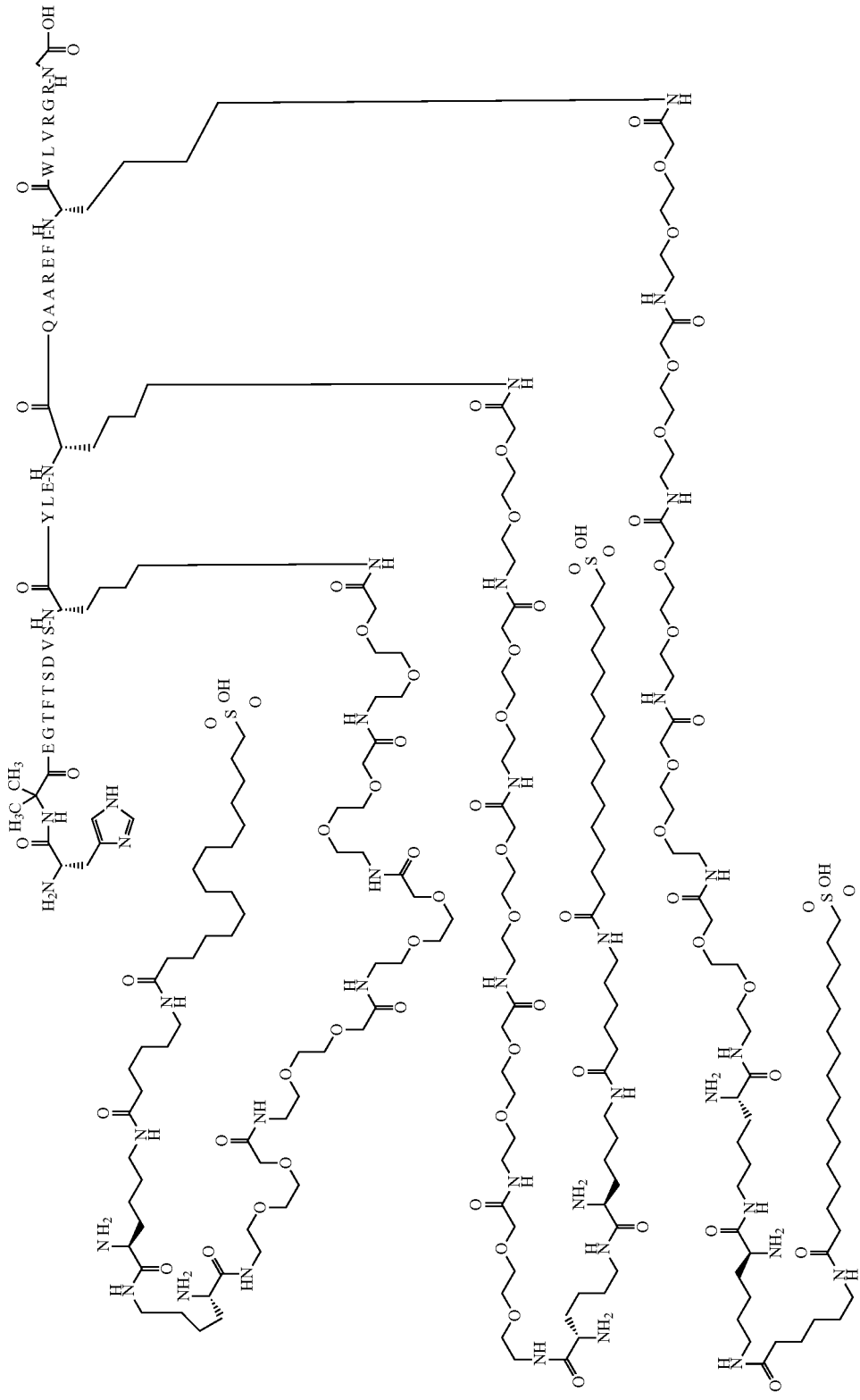
Chem. 39

The peptide is SEQ ID NO: 2.
Synthesis method: SPPS_L; SC_L; SC_M_3; CP_M1
LCMS01: Rt=1.94 min; m/4=1851; m/5=1481
UPLC02v01: Rt=8.6 min Example 20

N{Epsilon-18}-[2-[2-[2-[[2-[2-[2-[[2-[2-[2-[[2-[2-[2-[[2-[2-[2-[[(2S)-2-amino-6-[[(2S)-2-amino-6-[6-(16-sulfohexadecanoylamino)hexanoylamino]hexanoyl]amino]hexanoyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl], N{Epsilon-22}-[2-[2-[2-[[2-[2-[2-[[2-[2-[2-[[2-[2-[2-[[2-[2-[2-[[(2S)-2-amino-6-[[(2S)-2-amino-6-[6-(16-sulfohexadecanoylamino)hexanoylamino]hexanoyl]amino]hexanoyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl], N{Epsilon-30}-[2-[2-[2-[[2-[2-[2-[[2-[2-[2-[[2-[2-[2-[[2-[2-[2-[[(2S)-2-amino-6-[[(2S)-2-amino-6-[6-(16-sulfohexadecanoylamino)hexanoylamino]hexanoyl]amino]hexanoyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl]-[Aib8,Lys18,Lys22,Arg26,Lys30,Arg34]-GLP-1-(7-37)-peptide

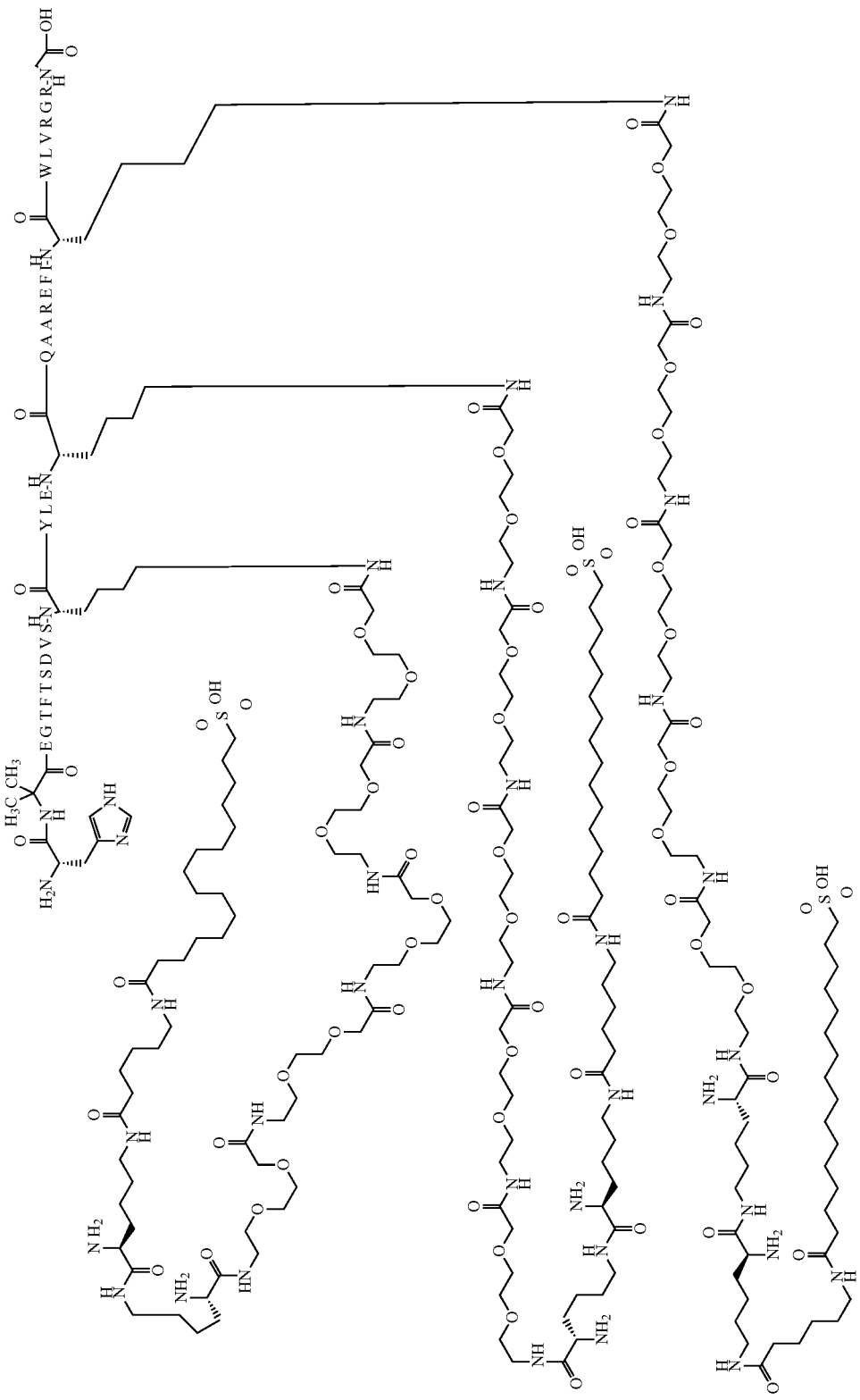
Chem. 40

The peptide is SEQ ID NO: 2.
Synthesis method: SPPS_L; SC_L; SC_M_3; CP_M1
LCMS01: Rt=1.93 min; m/4=1960; m/5=1568
UPLC02v01: Rt=8.5 min Example 21

N{Epsilon-18}-[2-[2-[2-[[2-[2-[2-[[2-[2-[2-[[2-[2-
[2-[[2-[2-[2-[[(2S)-2-amino-6-[[(2S)-2-amino-6-[4-
(16-sulfohexadecanoylamino)butanoylamino]
hexanoyl]amino]hexanoyl]amino]ethoxy]ethoxy]
acetyl]amino]ethoxy]ethoxy]acetyl]amino]ethoxy]
ethoxy]acetyl]amino]ethoxy]ethoxy]acetyl]amino]
ethoxy]ethoxy]acetyl], N{Epsilon-22}-[2-[2-[2-[[2-
[2-[2-[[2-[2-[2-[[2-[2-[2-[[2-[2-[2-[[(2S)-2-amino-6-
[[(2S)-2-amino-6-[4-(16-sulfohexadecanoylamino)
butanoylamino]hexanoyl]amino]hexanoyl]amino]
ethoxy]ethoxy]acetyl]amino]ethoxy]ethoxy]acetyl]
amino]ethoxy]ethoxy]acetyl]amino]ethoxy]ethoxy]
acetyl]amino]ethoxy]ethoxy]acetyl], N{Epsilon-
30}-[2-[2-[2-[[2-[2-[2-[[2-[2-[2-[[2-[2-[2-[[2-[2-[2-
[[(2S)-2-amino-6-[[(2S)-2-amino-6-[4-(16-
sulfohexadecanoylamino)butanoylamino]hexanoyl]
amino]hexanoyl]amino]ethoxy]ethoxy]acetyl]amino]
ethoxy]ethoxy]acetyl]amino]ethoxy]ethoxy]acetyl]
amino]ethoxy]ethoxy]acetyl]amino]ethoxy]ethoxy]
acetyl]-[Aib8,Lys18,Lys22,Arg26,Lys30,Arg34]-
GLP-1-(7-37)-peptide Pharmacological Methods Example 22

In Vitro Potency

The purpose of this example is to test the activity, or potency, of the GLP-1 derivatives in vitro. The in vitro potency is the measure of human GLP-1 receptor activation in a whole cell assay.

The potencies of the GLP-1 derivatives of Examples 1-21 were determined as described below. Semaglutide was included for comparison.

Principle

In vitro potency was determined by measuring the response of the human GLP-1 receptor in a reporter gene assay. The assay was performed in a stably transfected BHK cell line that expresses the human GLP-1 receptor and contains the DNA for the cAMP response element (CRE) coupled to a promoter and the gene for firefly luciferase (CRE luciferase). When the human GLP-1 receptor is activated it results in the production of cAMP, which in turn results in the luciferase protein being expressed. When assay incubation is completed the luciferase substrate (luciferin) is added and the enzyme converts luciferin to oxyluciferin to produce bioluminescence. The luminescence is measured as the readout for the assay.

Cell Culture and Preparation

The cells used in this assay (clone FCW467-12A/KZ10-1) were BHK cells with BHKTS13 as a parent cell line. The Chem. 41

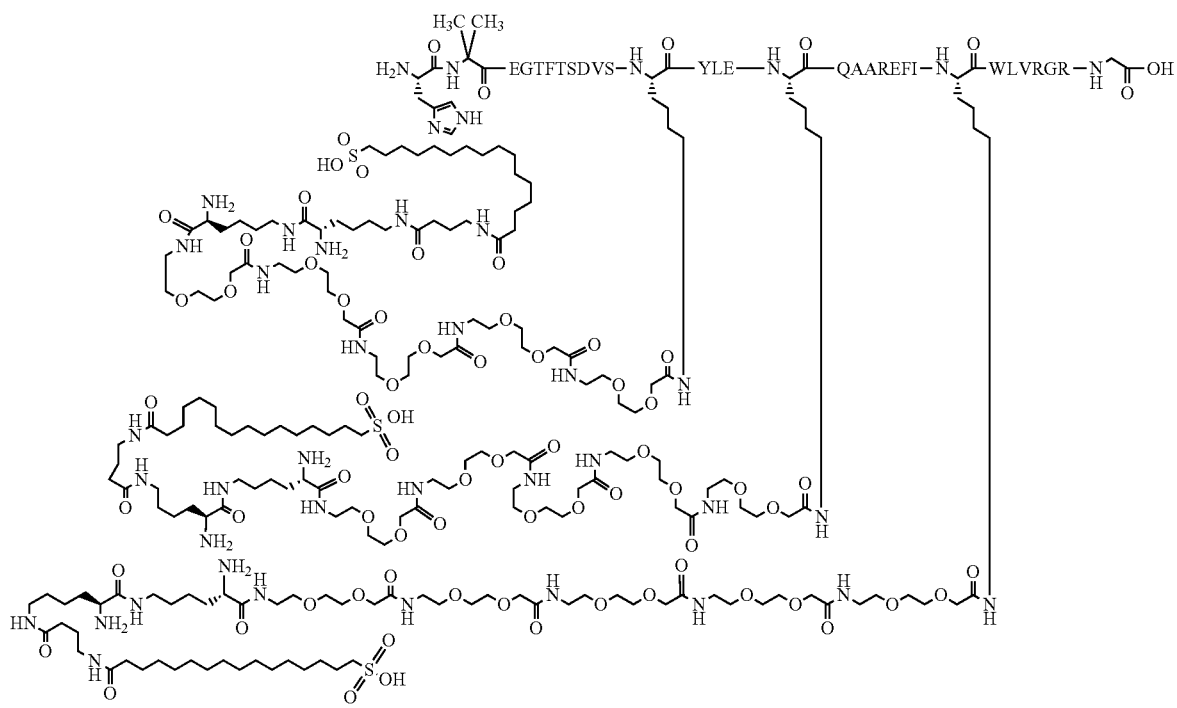

The peptide is SEQ ID NO: 2.
Synthesis method: SPPS_L; SC_L; SC_M_3; CP_M1
LCMS01: Rt=1.89 min; m/4=1939; m/5=1552
UPLC02v01: Rt=8.3 min cells were derived from a clone (FCW467-12A) that expresses the human GLP-1 receptor and were established by further transfection with CRE luciferase to obtain the current clone.

The cells were cultured at 5% $CO_2$ in Cell Culture Medium. They were aliquoted and stored in liquid nitrogen. Before each assay an aliquot is taken up and washed twice in PBS before being suspended at the desired concentration in the assay specific buffer. For 96-well plates the suspension was made to give a final concentration of $5 \times 10^3$ cells/well.

Materials

The following chemicals were used in the assay: Pluronic F-68 (10%) (Gibco 2404), human serum albumin (HSA) (Sigma A9511), ovalbumin (Sigma A5503), DMEM w/o phenol red (Gibco 11880-028), 1 M Hepes (Gibco 15630), Glutamax 100× (Gibco 35050) and steadylite plus (PerkinElmer 6016757).

Buffers

Cell Culture Medium consisted of DMEM medium with 10% FBS (Fetal Bovine Serum; Invitrogen 16140-071), 1 mg/ml G418 (Invitrogen 15140-122), 240 nM MTX (methotrexate; Sigma M9929) and 1% pen/strep (penicillin/streptomycin; Invitrogen 15140-122).

Assay Medium consisted of DMEM w/o phenol red, 10 mM Hepes and 1× Glutamax. The Assay Buffer consisted of 2% ovalbumin and 0.2% Pluronic F-68 in Assay Medium.

Procedure

1) Cell stocks were thawed in a 37° C. water bath.
2) Cells were washed three times in PBS.
3) The cells were counted and adjusted to $5 \times 10^3$ cells/50 µl ($1 \times 10^5$ cells/ml) in Assay Medium. A 50 µl aliquot of cells was transferred to each well in the assay plate.
4) Stocks of the test compounds and reference compounds were diluted to a concentration of 0.2 pM in Assay Buffer. Compounds were diluted 10-fold to give the following concentrations: $2 \times 10^{-7}$ M, $2 \times 10^{-8}$ M; $2 \times 10^{-9}$ M, $2 \times 10^{-10}$ M, $2 \times 10^{-11}$ M, $2 \times 10^{-12}$ M, $2 \times 10^{-13}$ M, and $2 \times 10^{-14}$ M.
5) A 50 µl aliquot of compound or blank was transferred from the dilution plate to the assay plate. Compounds were tested at the following final concentrations: $1 \times 10^{-7}$ M, $1 \times 10^{-8}$ M; $1 \times 10^{-9}$ M, $1 \times 10^{-10}$ M, $1 \times 10^{-11}$ M, $1 \times 10^{-12}$ M, $1 \times 10^{-13}$ M, and $1 \times 10^{-14}$ M.
6) The assay plate was incubated for 3 h in a 5% $CO_2$ incubator at 37° C.
7) The assay plate was removed from the incubator and allowed to stand at room temperature for 15 min.
8) A 100 µl aliquot of steadylite plus reagent was added to each well of the assay plate (reagent was light sensitive).
9) Each assay plate was covered with aluminum foil to protect it from light and shaken for 30 min at room temperature.
10) Each assay plate was read in a Packard TopCount NXT instrument.

Calculations and Results

The data from the TopCount instrument were transferred to GraphPad Prism software. The software performs a non-linear regression (log(agonist) vs response). $EC_{50}$ values which were calculated by the software and reported in pM are shown in Table 1 below.

A minimum of two replicates was measured for each sample. The reported values are averages of the replicates.

TABLE 1

| In vitro potency | |
| --- | --- |
| Example no. | $EC_{50}$ (pM) |
| 1 | 67 |
| 2 | 20 |
| 3 | 33 |

TABLE 1-continued

| In vitro potency | |
| --- | --- |
| Example no. | $EC_{50}$ (pM) |
| 4 | 14 |
| 5 | 40 |
| 6 | 12 |
| 7 | 76 |
| 8 | 102 |
| 9 | 67 |
| 10 | 26 |
| 11 | 85 |
| 12 | 99 |
| 13 | 26 |
| 14 | 18 |
| 15 | 82 |
| 16 | 14 |
| 17 | 18 |
| 18 | 116 |
| 19 | 19 |
| 20 | 27 |
| 21 | 15 |
| semaglutide | 8.3 |

All compounds have potency data that confirms that they are GLP-1 receptor agonists.

Example 23

GLP-1 Receptor Binding

The purpose of this example is to test the receptor binding of the GLP-1 derivatives in vitro. The receptor binding is a measure of affinity of a derivative for the human GLP-1 receptor.

Principle

The receptor binding of the GLP-1 derivatives of Examples 1-21 to the human GLP-1 receptor was measured in a competitive binding assay. In this type of assay a labelled ligand (in this case $^{125}$I-GLP-1) is bound to the receptor. Each derivative is added in a series of concentrations to isolated membranes containing the human GLP-1 receptor and displacement of the labelled ligand is monitored. The receptor binding is reported as the concentration at which half of the labelled ligand is displaced from the receptor, the $IC_{50}$ value. Semaglutide was included as comparative compound. In order to test the binding of the derivatives to albumin, the assay is performed in a low concentration of serum albumin (max. 0.001% final assay concentration as well as in the presence of a considerably higher concentration of serum albumin (2.0% final assay concentration). An increase of the $IC_{50}$ value in the presence of serum albumin indicates an affinity to serum albumin and represents a method to predict a protracted pharmacokinetic profile of the test substance in animal models.

Materials

The following chemicals were used in the assay: Human serum albumin (HSA) (Sigma A1653), DMEM w/o phenol red (Gibco 11880-028), Pen/strep (Invitrogen 15140-122), G418 (Invitrogen 10131-027), 1 M Hepes (Gibco 15630), EDTA (Invitrogen 15575-038), PBS (Invitrogen 14190-094), fetal calf serum (Invitrogen 16140-071), EGTA, $MgCl_2$ (Merck 1.05832.1000), Tween 20 (Amresco 0850C335), SPA particles (wheat germ agglutinin (WGA) SPA beads, Perkin Elmer RPNQ0001), [$^{125}$I]-GLP-1]-(7-36) $NH_2$ (produced in-house), OptiPlate™-96 (Packard 6005290).

Buffer 1 consisted of 20 mM Na-HEPES plus 10 mM EDTA and pH was adjusted to 7.4. Buffer 2 consisted of 20 mM Na-HEPES plus 0.1 mM EDTA and pH was adjusted to 7.4. Assay buffer consisted of 50 mM HEPES supplemented with 5 mM EGTA, 5 mM $MgCl_2$, 0.005% Tween 20 and pH was adjusted to 7.4. An 8% albumin stock consisted of HSA dissolved at 8% (w/v) in assay buffer. An 0.02% albumin stock consisted of HSA dissolved at 0.02% (w/v) in assay buffer.

Cell Culture and Membrane Preparation

The cells used in this assay (clone FCW467-12A) were BHK cells with BHKTS13 as a parent cell line. The cells express the human GLP-1 receptor.

The cells were grown at 5% $CO_2$ in DMEM, 10% fetal calf serum, 1% Pen/Strep (Penicillin/Streptomycin) and 1.0 mg/ml of the selection marker G418.

To make a membrane preparation the cells were grown to approximately 80% confluence. The cells were washed twice in phosphate-buffered saline and harvested. The cells were pelleted using a brief centrifugation and the cell pellet was kept on ice. The cell pellet was homogenised with ULTRA-THURRAX™ dispersing instrument for 20-30 seconds in a suitable amount of buffer 1 (e.g., 10 ml). The homogenate was centrifuged for 15 minutes. The pellet was re-suspended (homogenised) in 10 ml buffer 2 and centrifuged. This step was repeated once more. The resulting pellet was re-suspended in buffer 2 and the protein concentration was determined. The membranes were aliquoted and stored at minus 80° C.

Procedure

1. For the receptor binding assay in the presence of low HSA (0.005%) 50 µl of the assay buffer was added to each well of an assay plate. Assay continued with step 3.
2. For the receptor binding assay in the presence of high HSA (2%) 50 µl of the 8% albumin stock was added to each well of an assay plate. Assay continued with step 3.
3. Test compounds were serially diluted to give the following concentrations: $8\times10^{-7}$ M, $8\times10^{-8}$ M, $8\times10^{-9}$ M, $8\times10^{-10}$ M, $8\times10^{-11}$ M, $8\times10^{-12}$ M and $8\times10^{-13}$ M. Twenty-five µl were added to appropriate wells in the assay plate.
4. Cell membrane aliquots were thawed and diluted to their working concentration. Fifty µl were added to each well in the assay plate.
5. WGA SPA beads were suspended in assay buffer at 20 mg/ml. The suspension was diluted to 10 mg/ml in assay buffer just prior to addition to the assay plate. Fifty µl were added to each well in the assay plate.
6. The incubation was started by adding 25 µl of 480 pM solution of [$^{125}$I]-GLP-1]-(7-36)$NH_2$ to each well of the assay plate. A 25 µl aliquot was reserved for measuring total counts/well.
7. The assay plate was incubated for 2 h at 30° C.
8. The assay plate was centrifuged for 10 min.
9. The assay plate was read in a Packard TopCount NXT instrument.

Calculations

The data from the TopCount instrument were transferred to GraphPad Prism software. The software averaged the values for the replicates and performed a non-linear regression. $IC_{50}$ values were calculated by the software and reported in nM.

Results

The following results were obtained:

TABLE 2

| | GLP-1 receptor binding | |
|---|---|---|
| Example no. | Low HSA $IC_{50}$ (nM) | High HSA $IC_{50}$ (nM) |
| 1 | 2.3 | 289 |
| 2 | 1.4 | 290 |
| 3 | 3.8 | 647 |
| 4 | 1.6 | 351 |
| 5 | 0.60 | >1000 |
| 6 | 0.40 | >1000 |
| 7 | 0.70 | >1000 |
| 8 | 4.5 | 745 |
| 9 | 1.7 | >1000 |
| 10 | 0.82 | 188 |
| 11 | 8.7 | >1000 |
| 12 | 5.0 | 214 |
| 13 | 0.23 | 84 |
| 14 | 0.19 | 100 |
| 15 | 11 | 426 |
| 16 | 0.40 | 381 |
| 17 | 0.08 | 143 |
| 18 | 0.10 | 19 |
| 19 | 0.15 | 49 |
| 20 | 0.36 | 100 |
| 21 | 0.24 | 96 |
| semaglutide | 0.55 | 321 |

All compounds show a very good binding to the GLP-1 receptor in the absence of albumin.

Example 24

Pharmacokinetic Study in Minipigs

The purpose of this study is to determine the protraction in vivo of the GLP-1 derivatives after i.v. administration to minipigs, i.e. the prolongation of their time in the body and thereby their time of action. This is done in a pharmacokinetic (PK) study, where the terminal half-life of the derivative in question is determined. By terminal half-life is meant the time it takes to halve a certain plasma concentration in the terminal elimination phase.

Each of the derivatives of Examples 1, 2, 3, 4, 8, 10, 12, and 14 were dosed with 2 nmol/kg, and the derivatives of Examples 6 and 17 were dosed with 5 nmol/kg. The derivative of Example 2 was tested a second time dosed with 100 nmol/kg. Semaglutide was included for comparison (1.5 nmol/kg).

Male Göttingen minipigs were obtained from Ellegaard Göttingen Minipigs (Dalmose, Denmark) approximately 7-14 months of age and weighing approximately 16-35 kg were used in the studies. The minipigs were housed either individually (pigs with permanent catheters) or in a group and fed restrictedly once or twice daily with SDS minipig diet (Special Diets Services, Essex, UK).

After at least 2 weeks of acclimatisation two permanent central venous catheters were implanted in vena cava caudalis or cranialis in each animal. The animals were allowed 1 week recovery after the surgery, and were then used for repeated pharmacokinetic studies with a suitable wash-out period between successive GLP-1 derivative dosings.

The GLP-1 derivatives of Examples 1, 2, 3, 4, 6, 8, 10, and 12 were dissolved in 50 mM sodium phosphate, 145 mM sodium chloride, 0.05% tween 80, pH 7.4 to a concentration of usually from 20-60 nmol/ml. The derivative of Example 14 was formulated in 2 mM sodium acetate, 250 mM glycerol, 0.025% tween 20, pH 4. The derivative of Example 17 was formulated in 2 mM sodium acetate, 250 mM glycerol, 0.025% polysorbate 20, pH 4. Intravenous injections (the volume corresponding to for example 0.050-0.125 ml/kg) of the compounds were given through one catheter or through the venflon, and blood was sampled at predefined time points for up till 25 days post dosing (preferably through the other catheter or by venipuncture). Blood samples (for example 0.8 ml) were collected in EDTA buffer (8 mM) and then centrifuged at 4° C. and 1942G for 10 minutes.

Plasma was pipetted into Micronic tubes on dry ice, and kept at −20° C. until analysed for plasma concentration of the respective GLP-1 compound using LOCI. Individual plasma concentration-time profiles were analyzed by a non-compartmental pharmacokinetic method in Phoenix v. 6.2 (Pharsight Inc., Mountain View, Calif., USA), or other relevant software for PK analysis, and the resulting terminal half-lives (harmonic mean) determined. The terminal half-life of the derivative of Example 2 is the arithmetic mean of two determinations with different dosages, as explained above.

Results

The following results were obtained:

TABLE 3

| Pharmacokinetic study in minipigs (i.v.) | |
|---|---|
| Example no. | Terminal half-live (h) |
| 1 | 162 |
| 2 | 140 |
| 3 | 120 |
| 4 | 120 |
| 6 | 103 |
| 8 | 138 |
| 10 | 158 |
| 12 | 111 |
| 14 | 140 |
| 17 | 143 |
| semaglutide | 55 |

The tested derivatives of the invention have very long terminal half-lives (around twice that of semaglutide or longer).

Example 25

Pharmacodynamic Study in Db/Db Mice

The purpose of the study is to verify the acute effect of the GLP-1 derivatives on blood glucose (BG) and body weight (BW) in a diabetic setting.

The GLP-1 derivatives of Examples 1, 2, 10, 14, 15, and 17-20 were tested in a single-dose study in an obese, diabetic mouse model (db/db mice) as described in the following. The derivatives were tested at a dose of either 100 nmol/kg (Examples 1, 2, 10, and 14) or 10 nmol/kg (Examples 15, and 17-20).

Six db/db mice per compound to be tested (from Taconic, Denmark), fed from birth with the diet NIH31 (NIH 31M Rodent Diet, commercially available from Taconic Farms, Inc., US, see www.taconic.com), were enrolled for the study at the age of approximately 10 weeks. The mice were given free access to standard chow (e.g. Altromin 1324, Brogaarden, Gentofte, Denmark) and tap water and kept at 24° C. After 1-2 weeks of acclimatisation, the basal blood glucose was assessed twice on two consecutive days (i.e. at 9 am). The mice were allocated to treatment groups based on matching blood glucose levels and body weights. The mice were used in experiments with a duration of 120 hours, and were re-used for up to 2 times. After the last experiment the mice were euthanised.

The animals were grouped to receive treatment as follows: Vehicle, s.c. or GLP-1 derivative, 10 or 100 nmol/kg, s.c., where vehicle was 50 mM sodium phosphate, 70 mM sodium chloride, 0.05% polysorbate 80, pH 7.4 (Example 1, 2, and 10); or 2 mM acetate, sodium; 250 mM glycerol; 0.025% polysorbate 20, pH 4 (Examples 14, 15, and 17-20).

The GLP-1 derivative was dissolved in the vehicle, to a dosing concentration of 1.7 or 17 nmol/ml. Animals were dosed once, at the start of the experiment, s.c. with a dose-volume of 6 ml/kg (i.e. 300 µl per 50 g mouse).

On the day of dosing, blood glucose was assessed at time −½h (8.30 am), the mice were weighed after this. The GLP-1 derivative was dosed at approximately 9 am (time 0). On the day of dosing, blood glucose was assessed at times 1, 2, 4 and 8 h (10 am, 11 am, 1 pm and 5 pm) after dosing.

On the following days, the blood glucose was assessed at time 24 h, 48 h, 72 h, and 96 h. On each day, the mice were weighed following blood glucose sampling.

The mice were weighed individually on a digital weighing scale.

Samples for the measurement of blood glucose were obtained from the tail tip capillary of conscious mice. Blood, 10 µl, was collected into heparinised capillaries and transferred to 500 µl glucose buffer (EKF system solution, Eppendorf, Germany). The glucose concentration was measured using the glucose oxidase method (glucose analyser Biosen 5040, EKF Diagnostic, GmbH, Barleben, Germany). The samples were kept at room temperature for up to 1 h until analysis. If analysis had to be postponed, samples were kept at 4° C. for a maximum of 24 h.

The data are presented as percent change in blood glucose or body weight measured at the 48 h time point. For example, the percent change in blood glucose level at 48 h for each individual is calculated as follows: [[(blood glucose level at 48 h)-(basal blood glucose level)]/(basal blood glucose level)]×100%, where basal blood glucose level refers to the level before the administration of any treatment—and similarly for the body weight change. A negative value refers to a % reduction.

The following results were obtained (averages of all individual determinations corresponding to the respective treatment):

TABLE 4

| Effect on blood glucose and body weight in db/db mice | | |
|---|---|---|
| Example no. | % change in blood glucose 48 h | % change in body weight 48 h |
| 1 | −16.3 | −2.8 |
| 2 | −37.0 | −4.9 |
| 10 | −13.0 | −1.8 |
| 14 | −63.6 | −7.2 |
| 15 | 3.6 | −3.8 |
| 17 | −3.8 | −1.4 |
| 18 | −0.2 | −2.2 |
| 19 | −12.5 | −2.4 |
| 20 | −22 | −0.5 |

All derivatives tested at the given doses showed effect in vivo by decreasing blood glucose as well as body weight after 48 h. The only apparent exception is the compound of Example 15, which showed efficacy after 24 hours (change by −9.8% in blood glucose), but caused a slight increase in blood glucose after 48 hours.

Example 26

Pharmacodynamic Study in LYD Pig

The purpose of this experiment is to investigate the effect of GLP-1 derivatives on food intake in pigs. This is done in a pharmacodynamic (PD) study as described below, in which food intake is measured from 1 to 4 days after administration of a single dose of the GLP-1 derivative, as compared to a vehicle-treated control group.

Female Landrace Yorkshire Duroc (LYD) pigs, approximately 3 months of age, weighing approximately 30-35 kg are used (n=3-4 per group). The animals are housed in a group for approximately 1 week during acclimatisation to the animal facilities. During the experimental period the animals are placed in individual pens at least 2 days before dosing and during the entire experiment for measurement of individual food intake. The animals are fed ad libitum with pig food (Svinefoder, Danish Top, or HRC Sow and Weaner Diet) at all times both during the acclimatisation and the experimental period. Food intake is monitored either on line by logging the weight of food every 15 minutes, or manually. The weight of food is recorded daily for each animal (24 h periods) from day −2 to day 6 (120 hour) after dose, administration inclusive.

The GLP-1 derivatives are first dissolved in a phosphate buffer (50 mM phosphate, 0.05% tween 80, pH 8; or 50 mM phosphate, 145 mM sodium chloride, 0.05% tween 80, pH 7.4) at the desired concentration (such as 12, 40, 120, 400 or 1200 nmol/ml corresponding to doses of 10, 15, or 30 nmol/kg). The phosphate buffer serves as vehicle. Animals are dosed with a single subcutaneous dose of the GLP-1 derivative or vehicle (usual dose volume 0.025 ml/kg) on the morning of day 1, and food intake is measured for 1-4 days after dosing. On the last day of each study, 1-4 days after dosing, a blood sample for measurement of plasma exposure of the GLP-1 derivative is taken from the jugular/anterior vena cava. The animals are re-used for three experiments. Plasma content of the GLP-1 derivatives is analysed using LOCI.

Food intake is calculated as mean 24 h food intake in 24 h intervals (0-24 h, 24-48 h, 48-72 h, and 72-96 h) and may, e.g., be indicated as percentage of the food intake of the vehicle group in the same time interval.

Statistical comparisons of the food intake in the 24 hour intervals in the vehicle vs.

GLP-1 derivative group are done using two-way-ANOVA repeated measures, followed by Bonferroni post-test.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A derivative of a GLP-1 peptide,
wherein the GLP-1 peptide comprises a first, a second, and a third K residue at positions corresponding to positions (18, 22, 30), (18, 26, 37), (18, 27, 37), (26, 30, 37), or (27, 30, 37) of GLP-1(7-37) (SEQ ID NO: 1), and has the general formula I, $$Xaa_7\text{-}Xaa_8\text{-}Glu\text{-}Gly\text{-}Thr\text{-}Xaa_{12}\text{-}Thr\text{-}Ser\text{-}Asp\text{-}Xaa_{16}\text{-}\\Ser\text{-}Xaa_{18}\text{-}Xaa_{19}\text{-}Xaa_{20}\text{-}Glu\text{-}Xaa_{22}\text{-}Xaa_{23}\text{-}Ala\text{-}\\Xaa_{25}\text{-}Xaa_{26}\text{-}Xaa_{27}\text{-}Phe\text{-}Ile\text{-}Xaa_{30}\text{-}Xaa_{31}\text{-}Leu\text{-}\\Xaa_{33}\text{-}Xaa_{34}\text{-}Xaa_{35}\text{-}Xaa_{36}\text{-}Xaa_{37},$$  Formula I:

wherein $Xaa_7$ is L-histidine; $Xaa_8$ is Aib; $Xaa_{12}$ is Phe; $Xaa_{16}$ is Val; $Xaa_{18}$ is Ser or Lys; $Xaa_{19}$ is Tyr; $Xaa_{20}$ is Leu; $Xaa_{22}$ is Gly, Lys or Glu; $Xaa_{23}$ is Gln; $Xaa_{25}$ is Ala; $Xaa_{26}$ is Arg or Lys; $Xaa_{27}$ is Glu or Lys; $Xaa_{30}$ is Ala or Lys; $Xaa_{31}$ is Trp; $Xaa_{33}$ is Val; $Xaa_{34}$ is Arg; $Xaa_{35}$ is Gly; $Xaa_{36}$ is Arg; and $Xaa_{37}$ is Gly or Lys;
wherein said derivative comprises
a first, a second, and a third protracting moiety selected from formula Chem. 1, Chem. 1a, and formula Chem. 2:

HOOC—(CH$_2$)$_{16}$—CO—*,  Chem. 1:

HOOC—(CH$_2$)$_{18}$—CO—*, and  Chem. 1a:

HO$_3$S—(CH$_2$)$_{15}$—CO—*; and  Chem. 2:

a first, a second, and a third linker, each linker comprising a *—CO group and an *—NH group;
wherein each protracting moiety is attached at its *—CO end to the *—NH end of the respective linker, and each linker is attached at its *—CO end to the epsilon amino group of the respective K residue of the GLP-1 peptide; or a pharmaceutically acceptable salt, amide, or ester thereof.

2. The derivative of claim 1, wherein each of the first, second, and third protracting moiety is of formula Chem. 1.

3. The derivative of claim 1, wherein each of the first, second, and third protracting moiety is of formula Chem. 1a.

4. The derivative of claim 1, wherein each of the first, second, and third protracting moiety is of formula Chem. 2.

5. The derivative of claim 1, wherein the linker comprises at least one linker element selected from formula Chem. 3, Chem. 4, Chem. 5, Chem. 6, Chem. 7, Chem. 8, and Chem. 9:

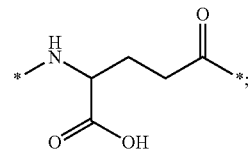

Chem. 3

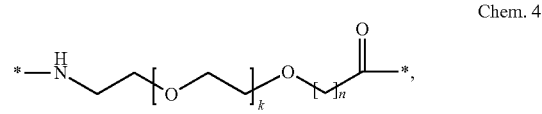

Chem. 4 wherein k is an integer in the range of 1-5, and n is an integer in the range of 1-5;

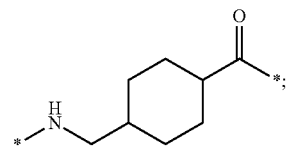

Chem. 5

Chem. 6

*—NH—(CH$_2$)$_q$—CH[(CH$_2$)$_w$—NH$_2$]—CO—*, wherein q is an integer in the range of 0-5, and w is an integer in the range of 0-5, with the provisos that when w is 0 q is an integer in the range of 1-5, and when q is 0 w is an integer in the range of 1-5;

Chem. 7

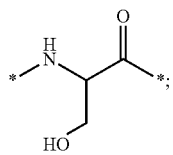

Chem. 8

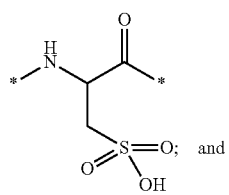

Chem. 9

*—NH—(CH$_2$)$_s$—CH$_2$—CO—*, in which s is an integer in the range of 2-4.

6. A derivative of a GLP-1 peptide, wherein the GLP-1 peptide comprises i) (8Aib, 18K, 22K, 26R, 30K, 34R); ii) (8Aib, 18K, 34R, 37K); iii) (8Aib, 18K, 22E, 26R, 27K, 34R, 37K); iv) (8Aib, 18K, 26R, 27K, 34R, 37K); v) (8Aib, 22E, 26R, 27K, 30K, 34R, 37K); vi) (8Aib, 22E, 30K, 34R, 37K); vii) (18K, 22K, 30K); viii) (18K, 37K); ix) (18K, 27K, 37K); x) (27K, 30K, 37K); or xi) (30K, 37K); wherein in viii) and xi) the amino acid at the position corresponding to position 26 in GLP-1(7-37) (SEQ ID NO: 1) is K, wherein said derivative comprises a first, a second, and a third protracting moiety selected from formula Chem. 1, Chem. 1a, and formula Chem. 2:

| HOOC—(CH$_2$)$_{16}$—CO—*, | Chem. 1: |
|---|---|
| HOOC—(CH$_2$)$_{18}$—CO—*, and | Chem. 1a: |
| HO$_3$S—(CH$_2$)$_{15}$—CO—*; and | Chem. 2: | a first, a second, and a third linker, each linker comprising a *—CO group and an *—NH group;

wherein each protracting moiety is attached at its *—CO end to the *—NH end of the respective linker, and each linker is attached at its *—CO end to the epsilon amino group of the respective K residue of the GLP-1 peptide;

or a pharmaceutically acceptable salt, amide, or ester thereof.

7. A derivative of a GLP-1 peptide, wherein the GLP-1 peptide is selected from the following : i) (8Aib, 18K, 22K, 26R, 30K, 34R) (SEQ ID NO: 2); ii) (8Aib, 18K, 34R, 37K) (SEQ ID NO: 3); iii) (8Aib, 18K, 22E, 26R, 27K, 34R, 37K) (SEQ ID NO: 4); iv) (8Aib, 18K, 26R, 27K, 34R, 37K) (SEQ ID NO: 5); v) (8Aib, 22E, 26R, 27K, 30K, 34R, 37K) (SEQ ID NO: 6); and vi) (8Aib, 22E, 30K, 34R, 37K) (SEQ ID NO: 7), wherein said derivative comprises a first, a second, and a third protracting moiety selected from formula Chem. 1, Chem. 1a, and formula Chem. 2:

| HOOC—(CH$_2$)$_{16}$—CO—*, | Chem. 1: |
|---|---|
| HOOC—(CH$_2$)$_{18}$—CO—*, and | Chem. 1a: |
| HO$_3$S—(CH$_2$)$_{15}$—CO—*; and | Chem. 2: | a first, a second, and a third linker, each linker comprising a *—CO group and an *—NH group;

wherein each protracting moiety is attached at its *—CO end to the *—NH end of the respective linker, and each linker is attached at its *—CO end to the epsilon amino group of the respective K residue of the GLP-1 peptide;

or a pharmaceutically acceptable salt, amide, or ester thereof.

8. A GLP-1 derivative selected from the following: Chem.

Chem. 21
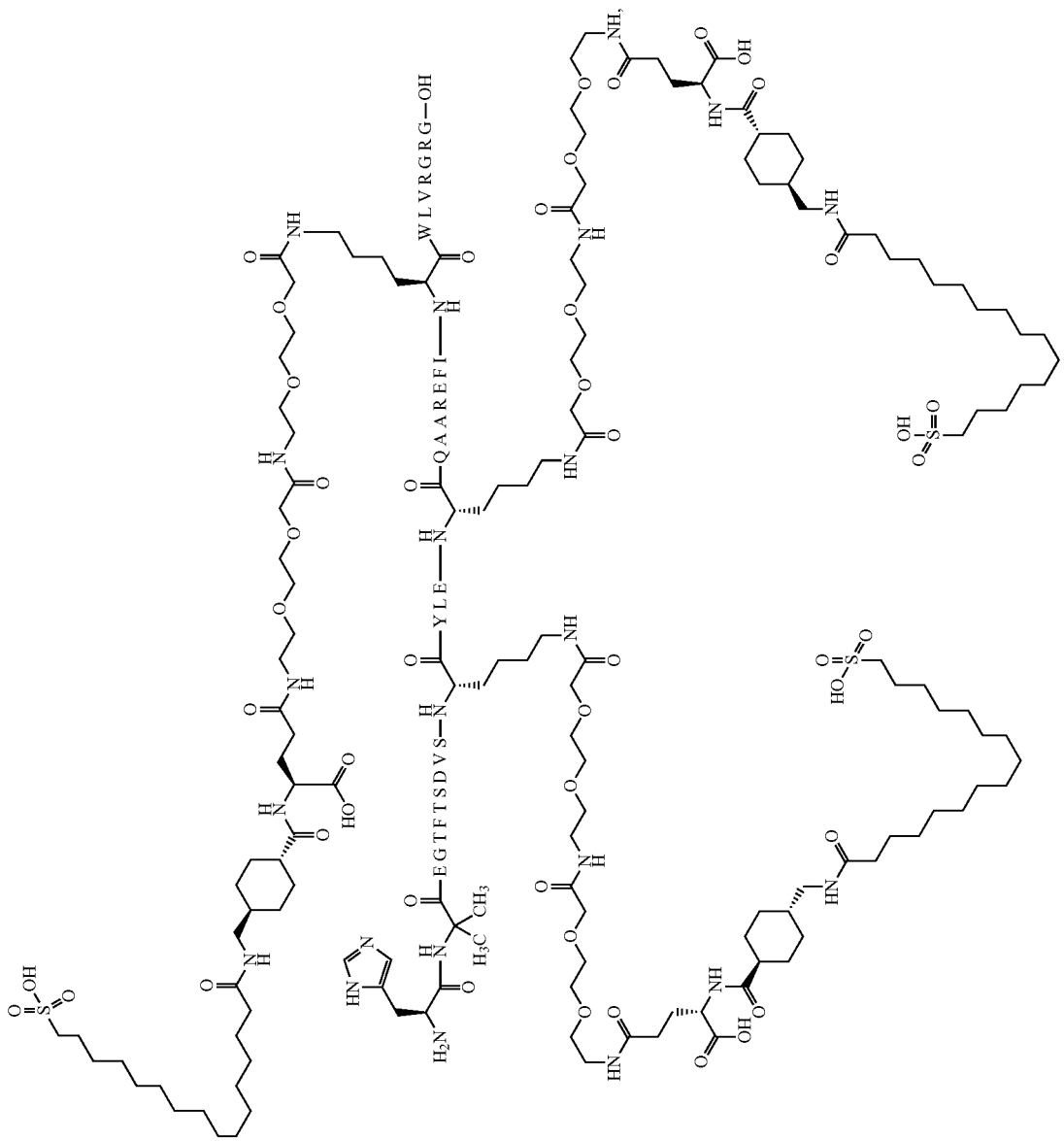

Chem. 22
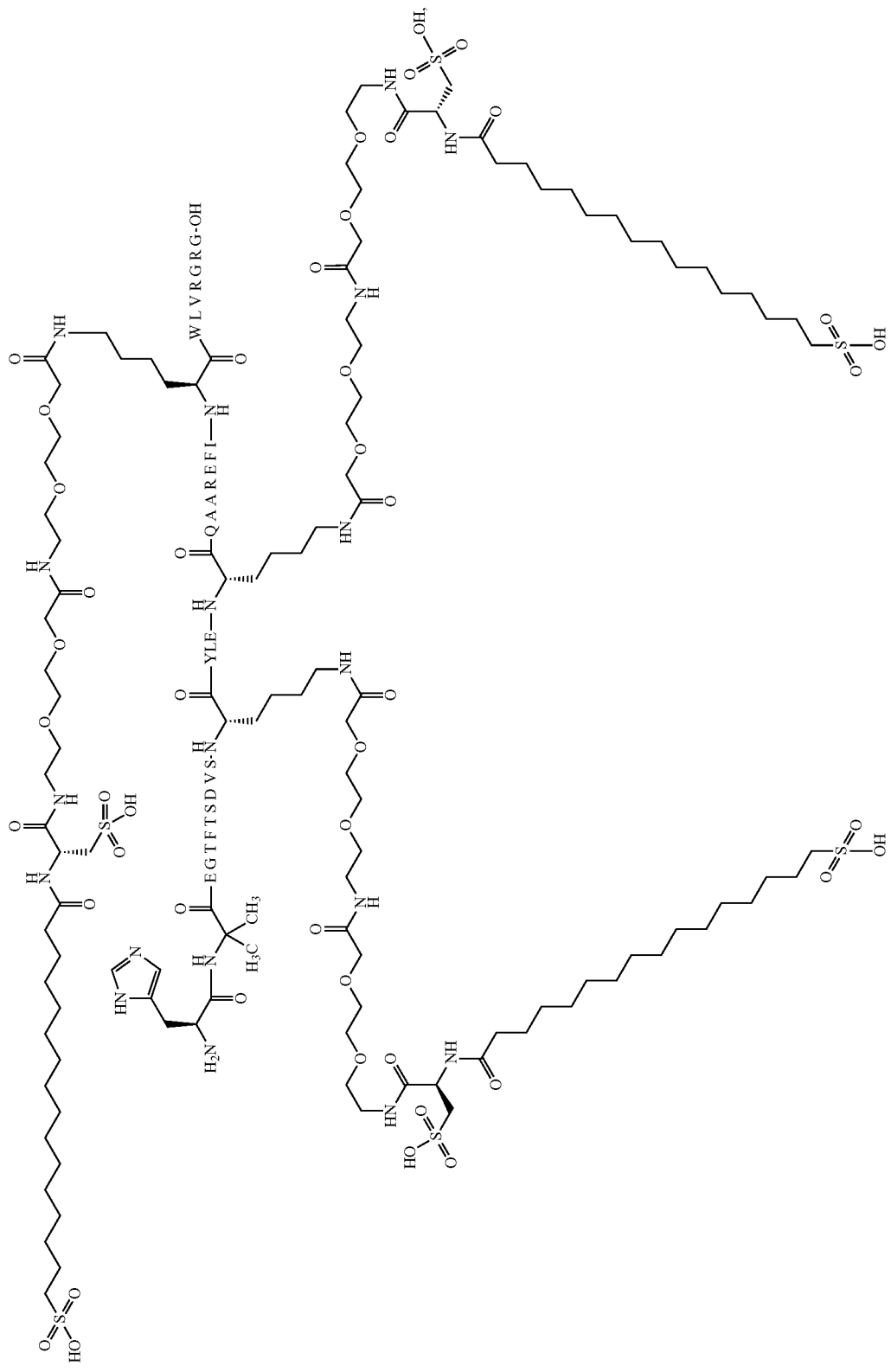

Chem. 23
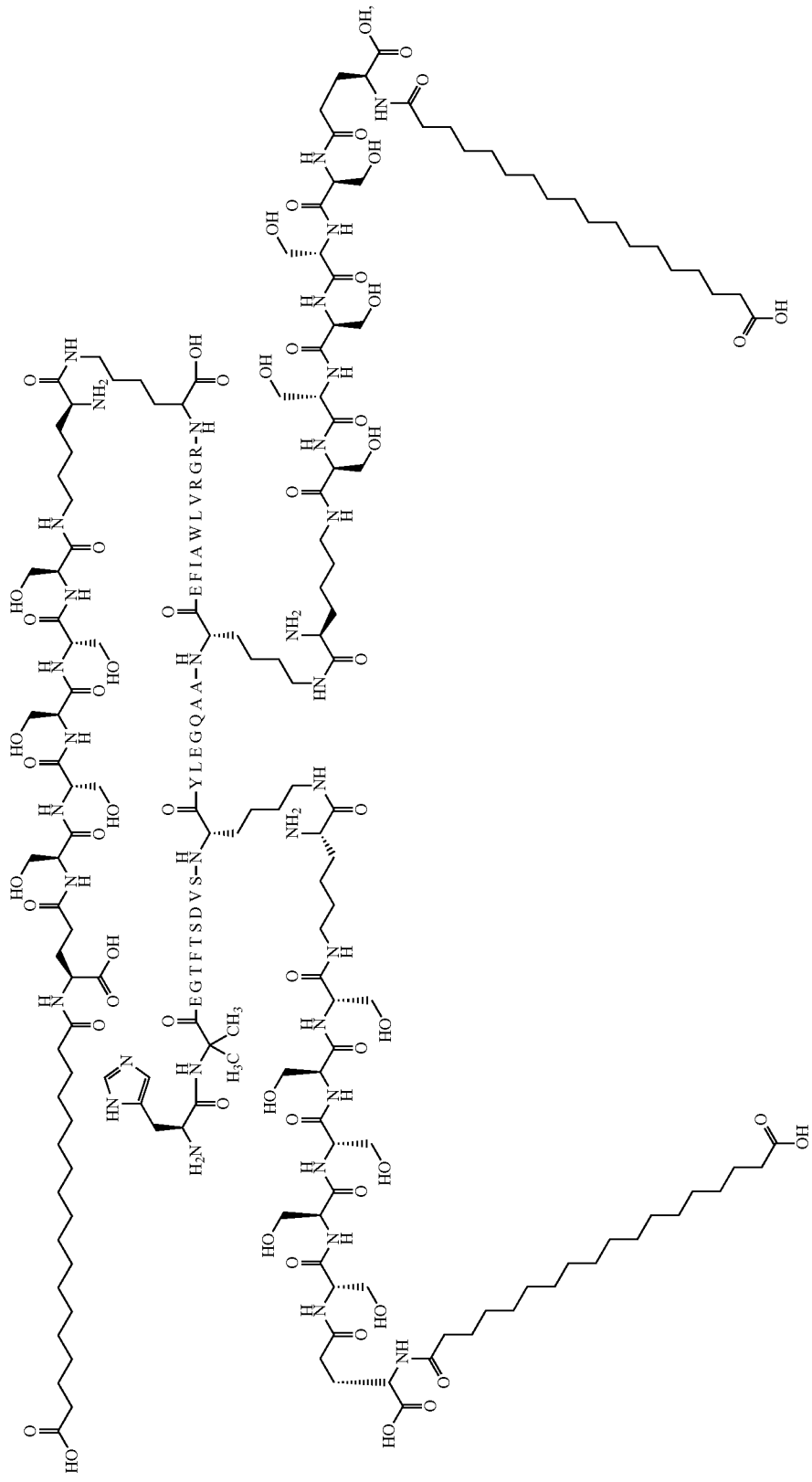

Chem. 24
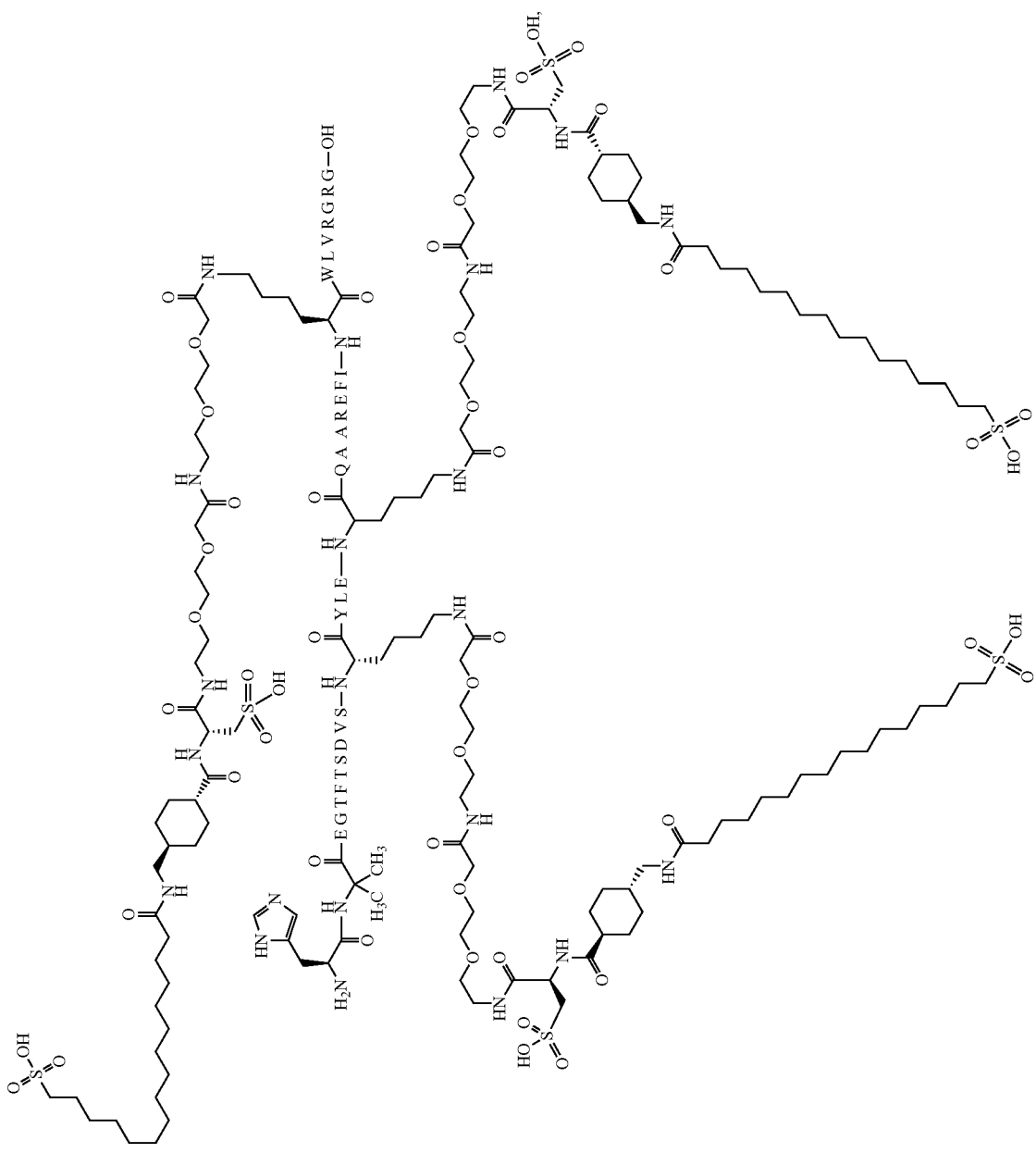

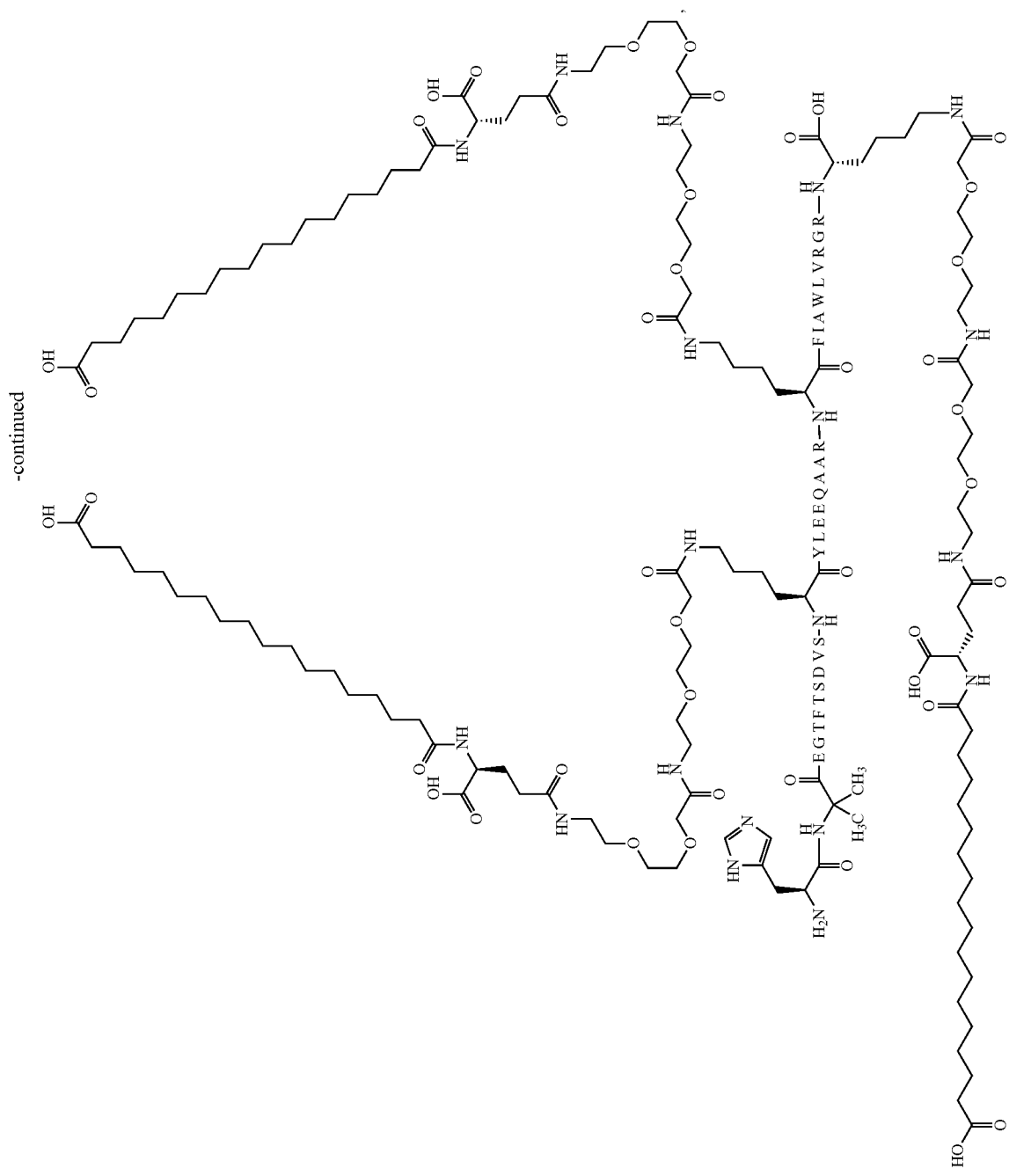

Chem. 26
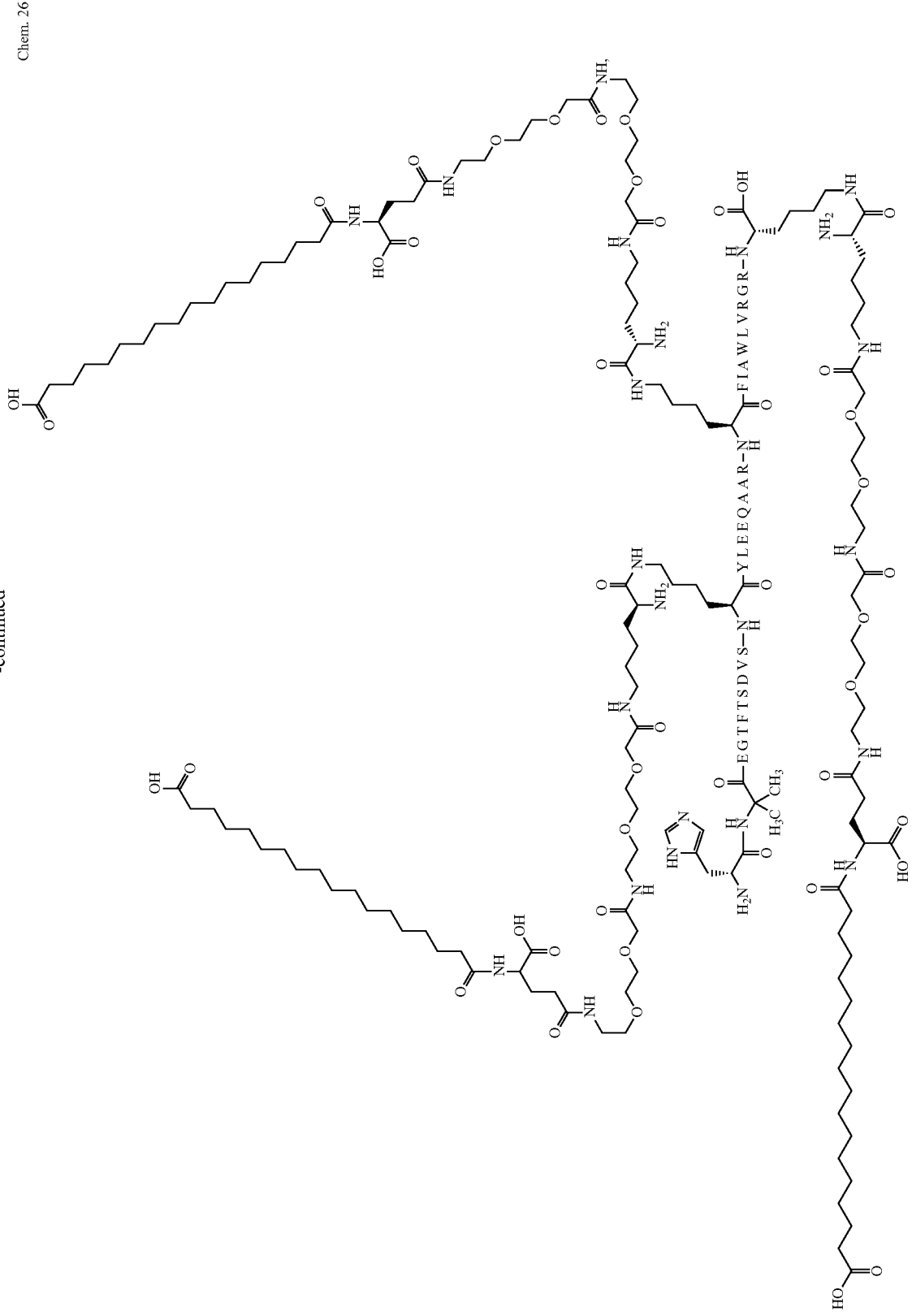

-continued
Chem. 27
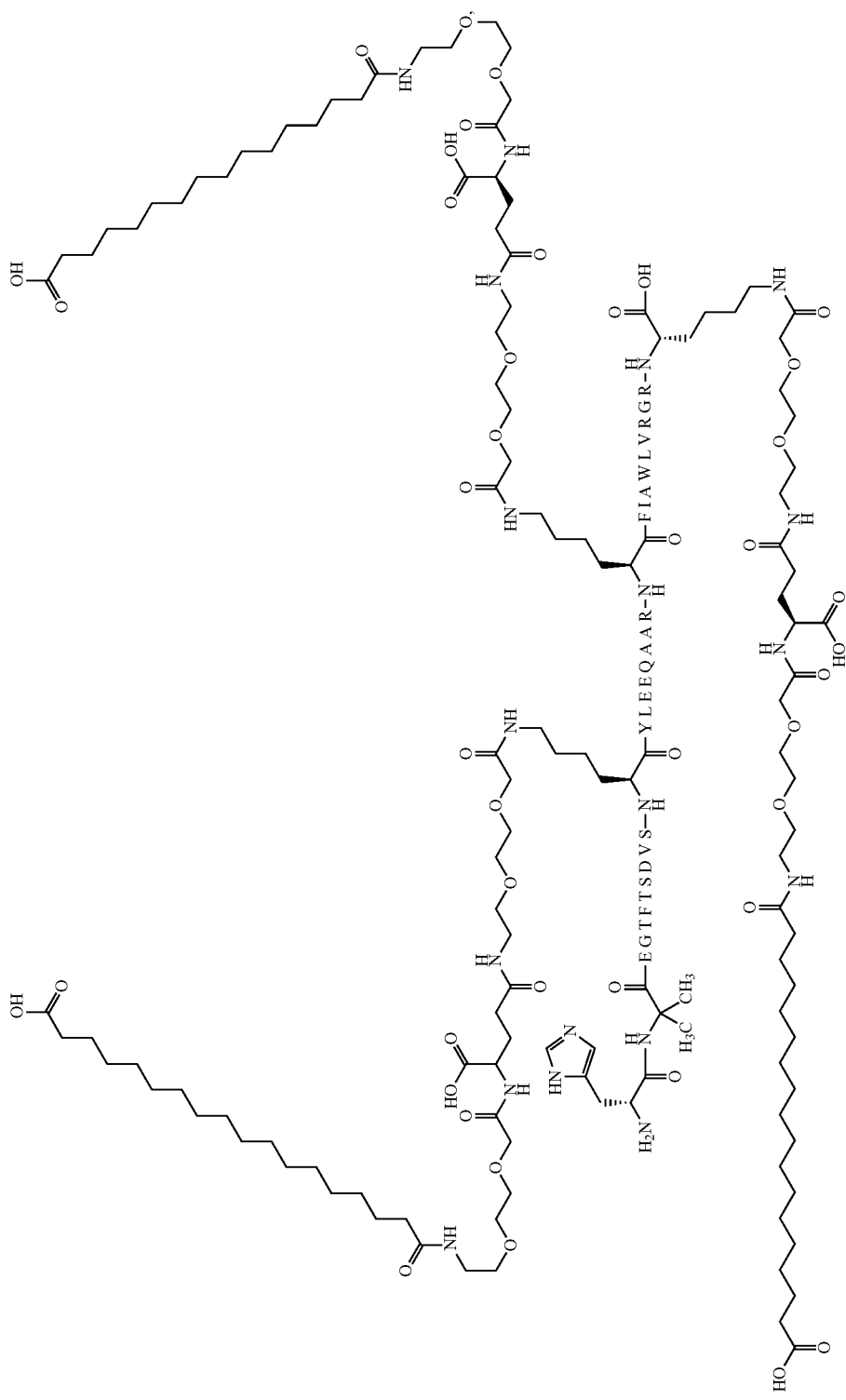

[Chem. 28]
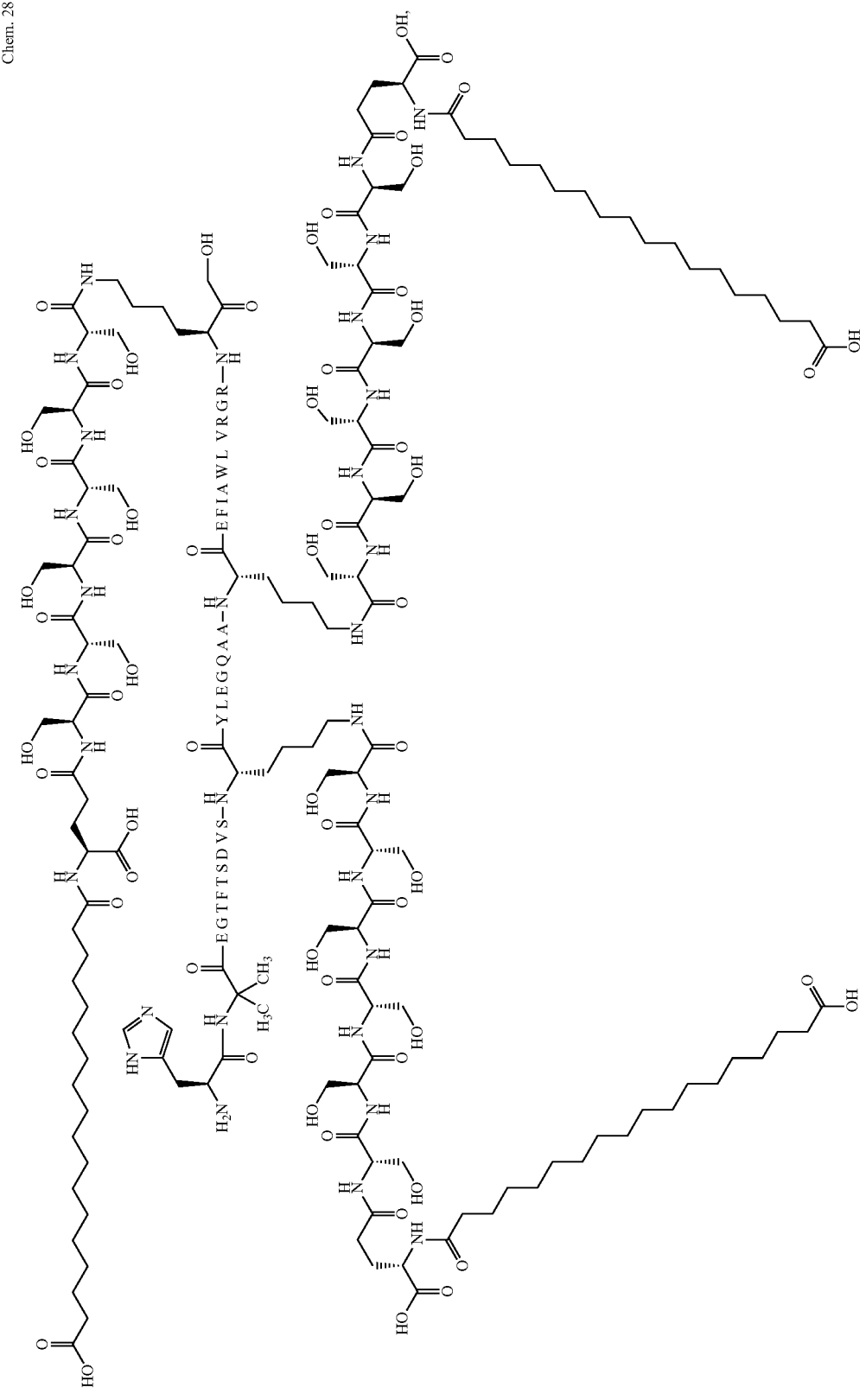

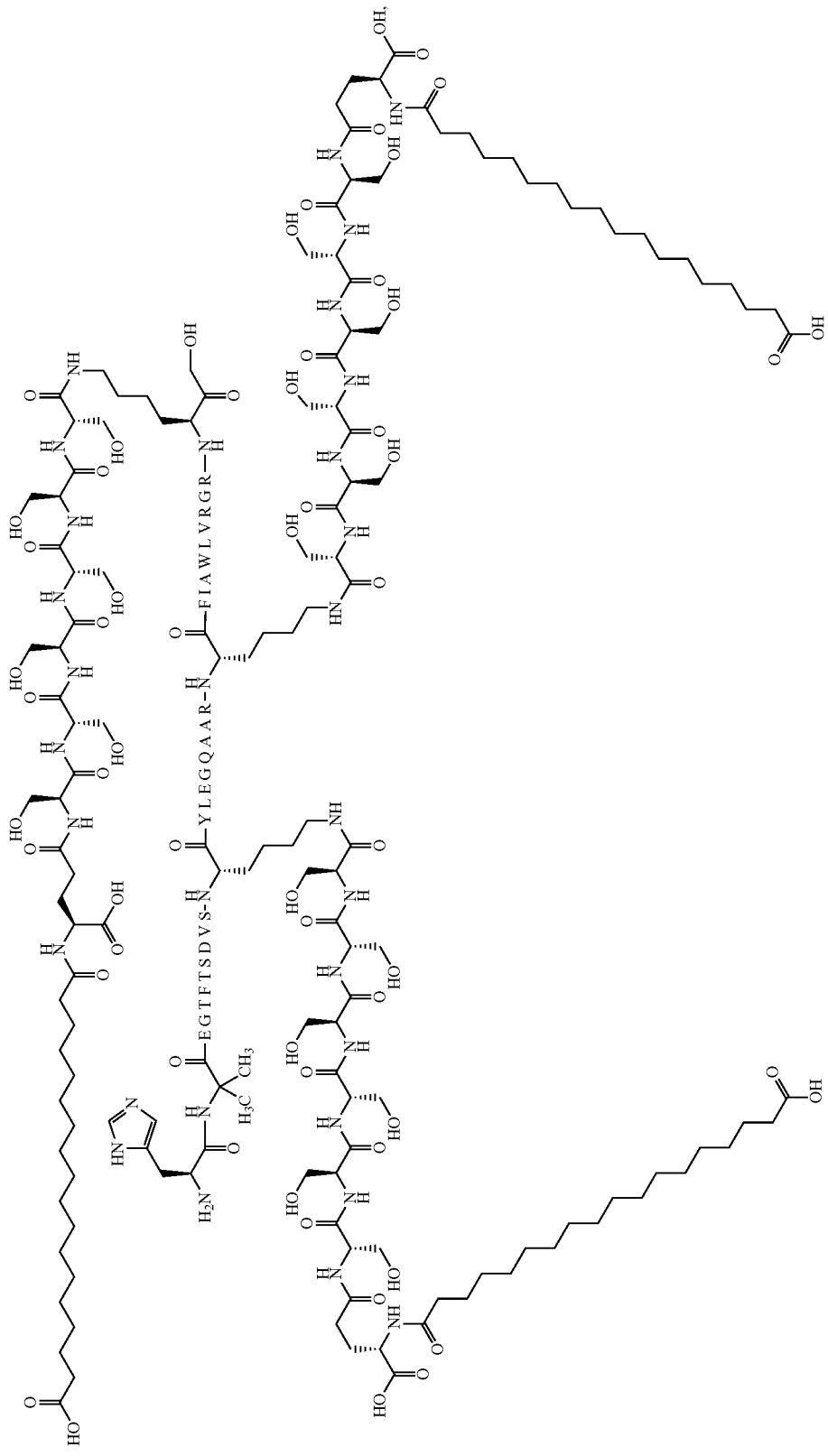
Chem. 29

Chem. 30
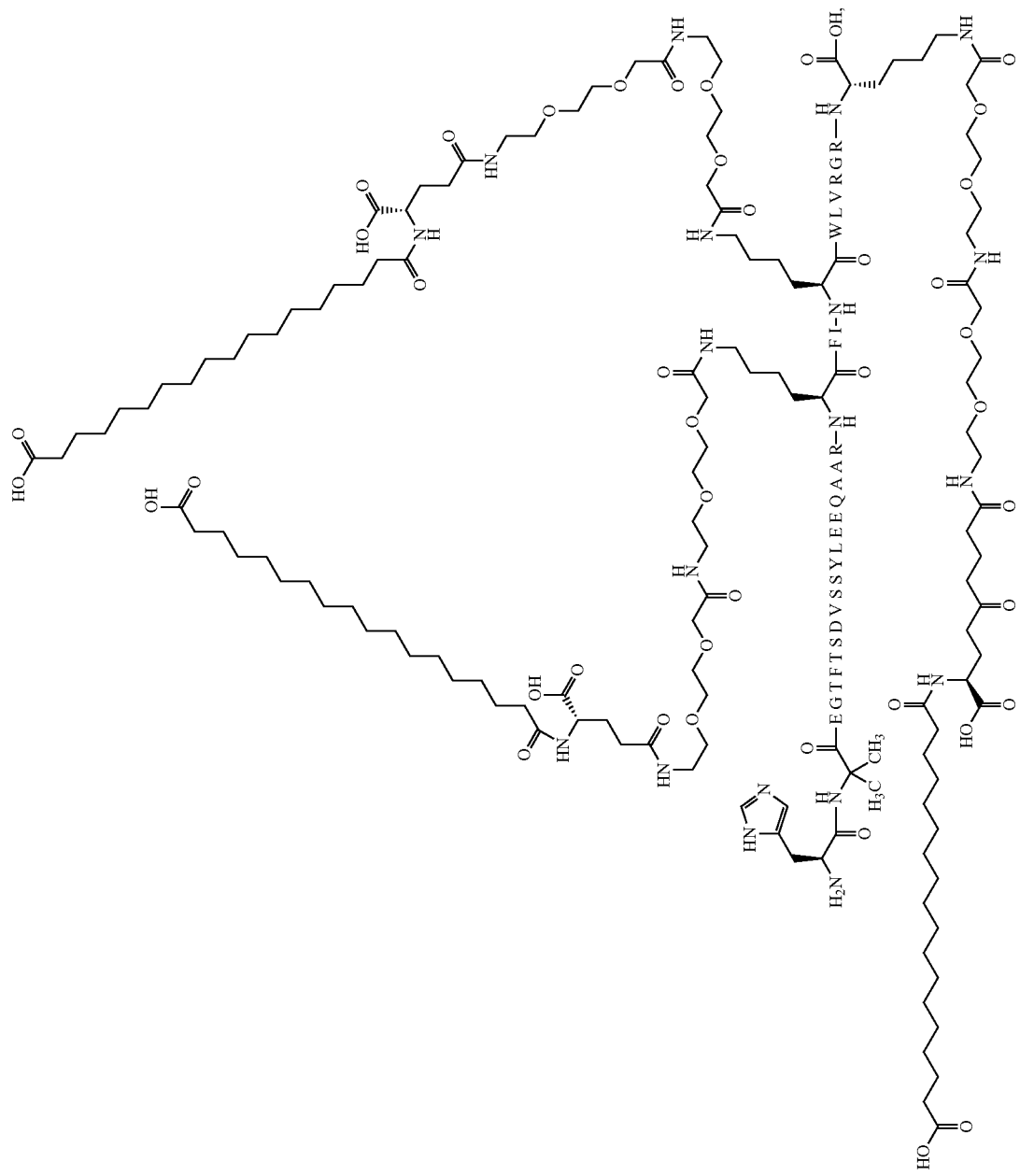

Chem. 31
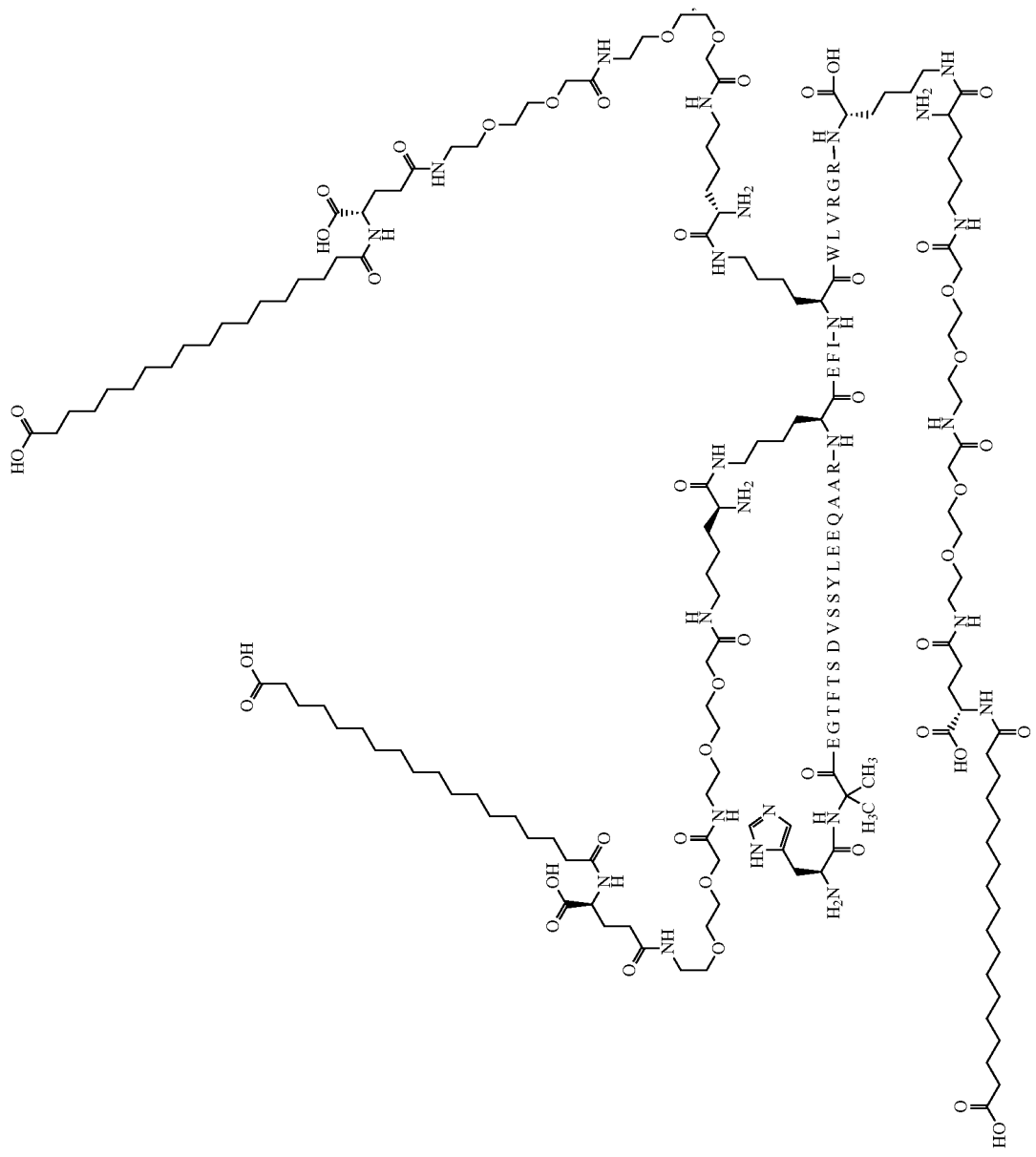

Chem. 32
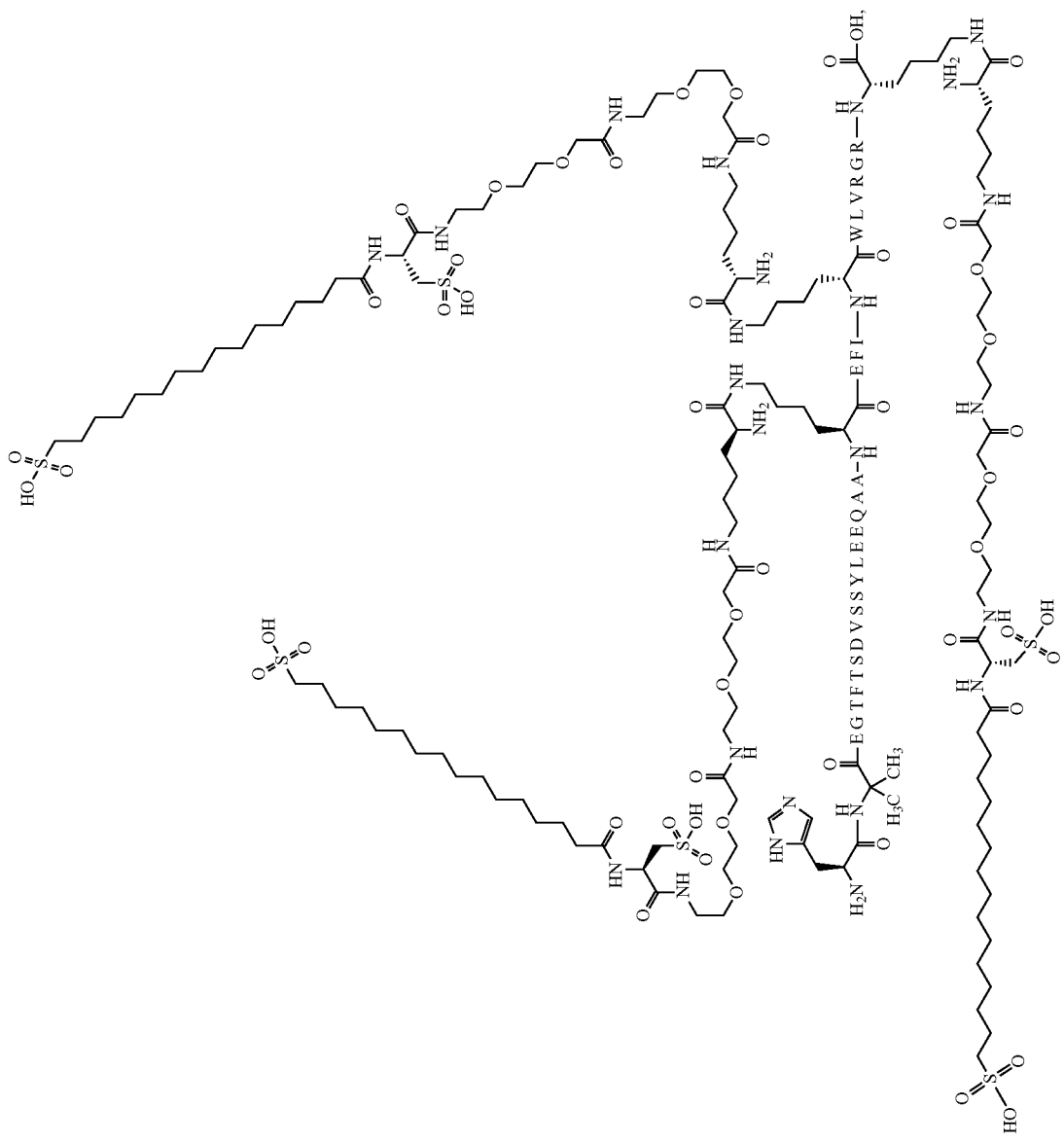

Chem. 33
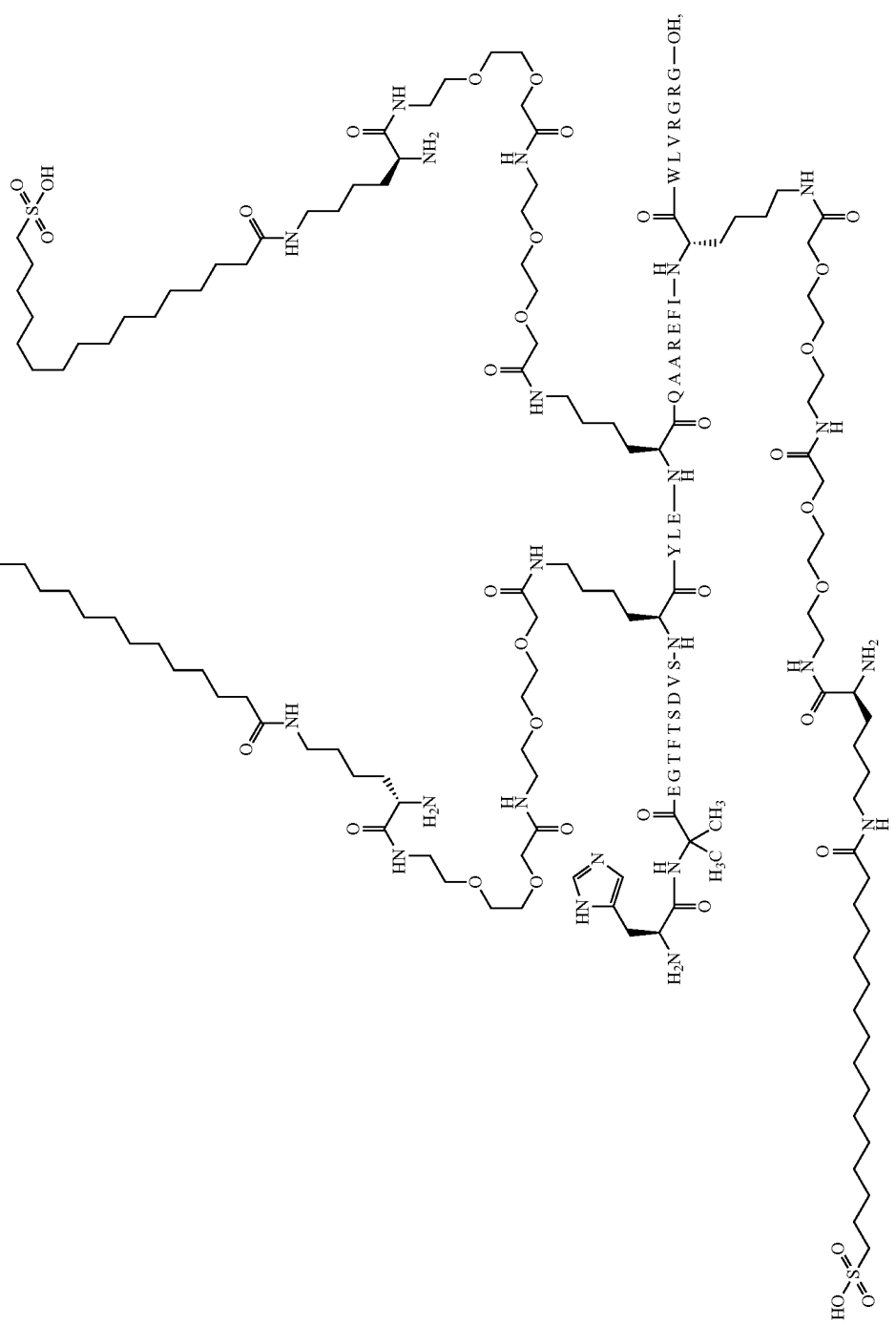

Chem. 34
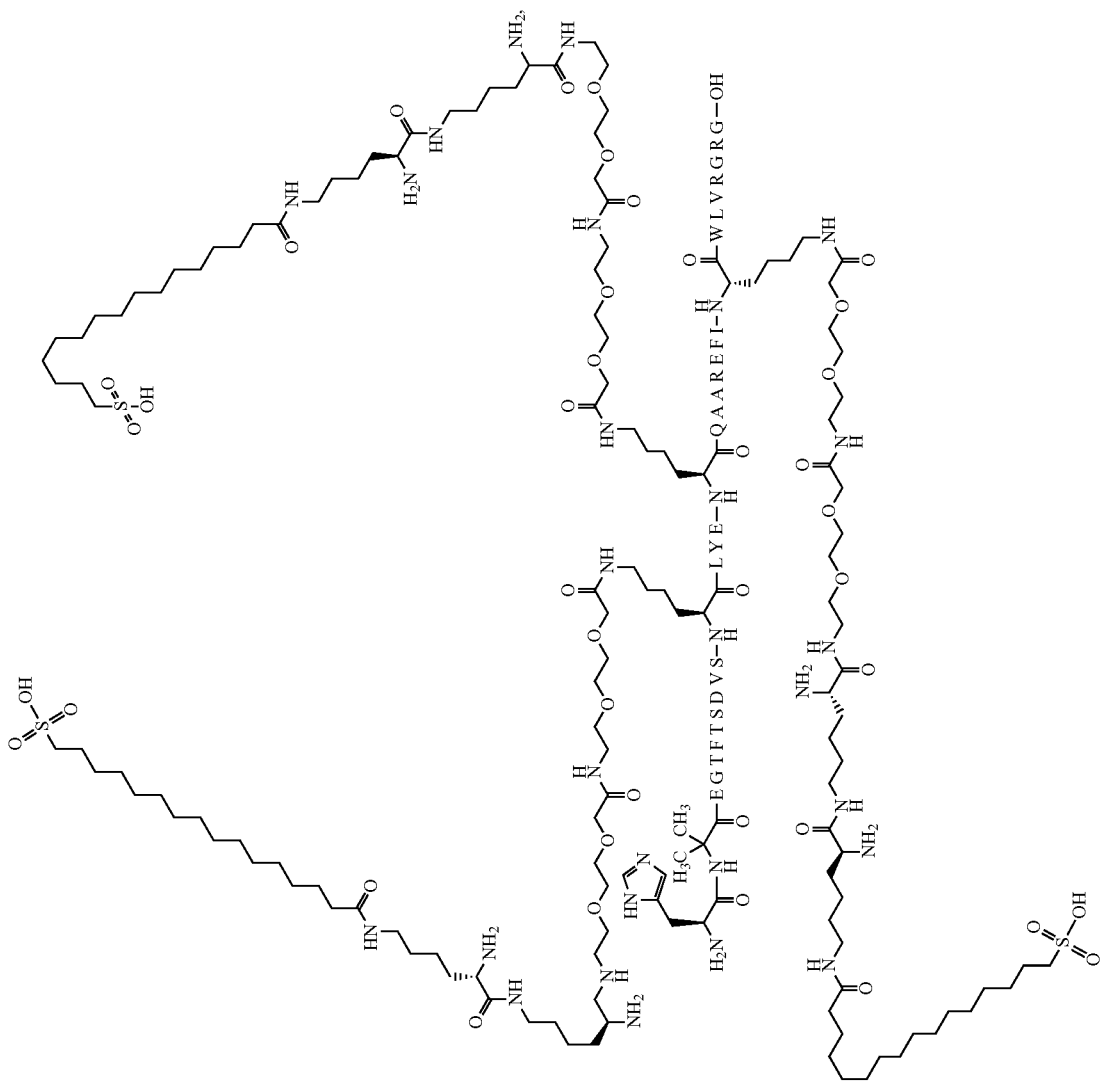

Chem. 35
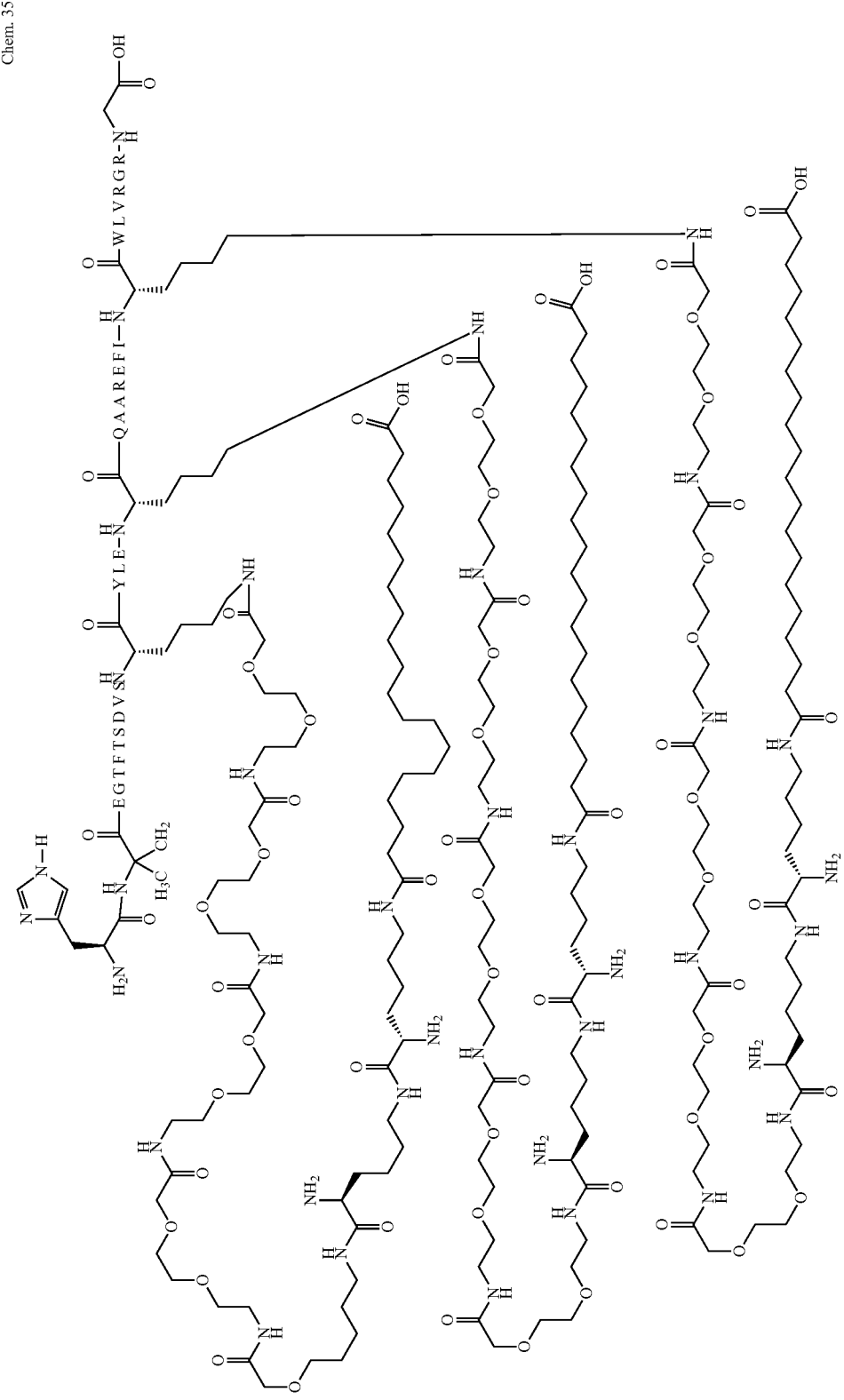

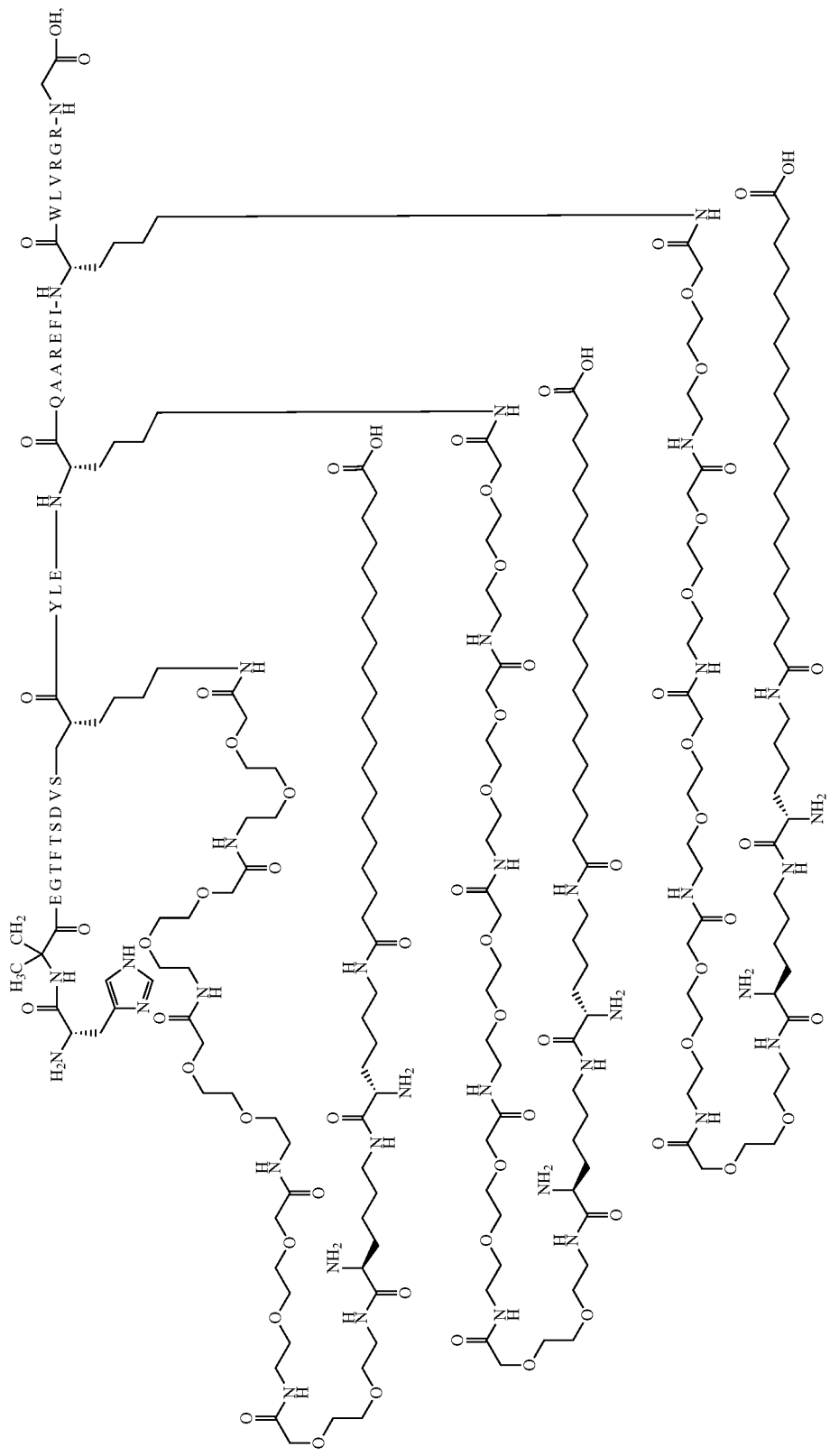

-continued
Chem. 37
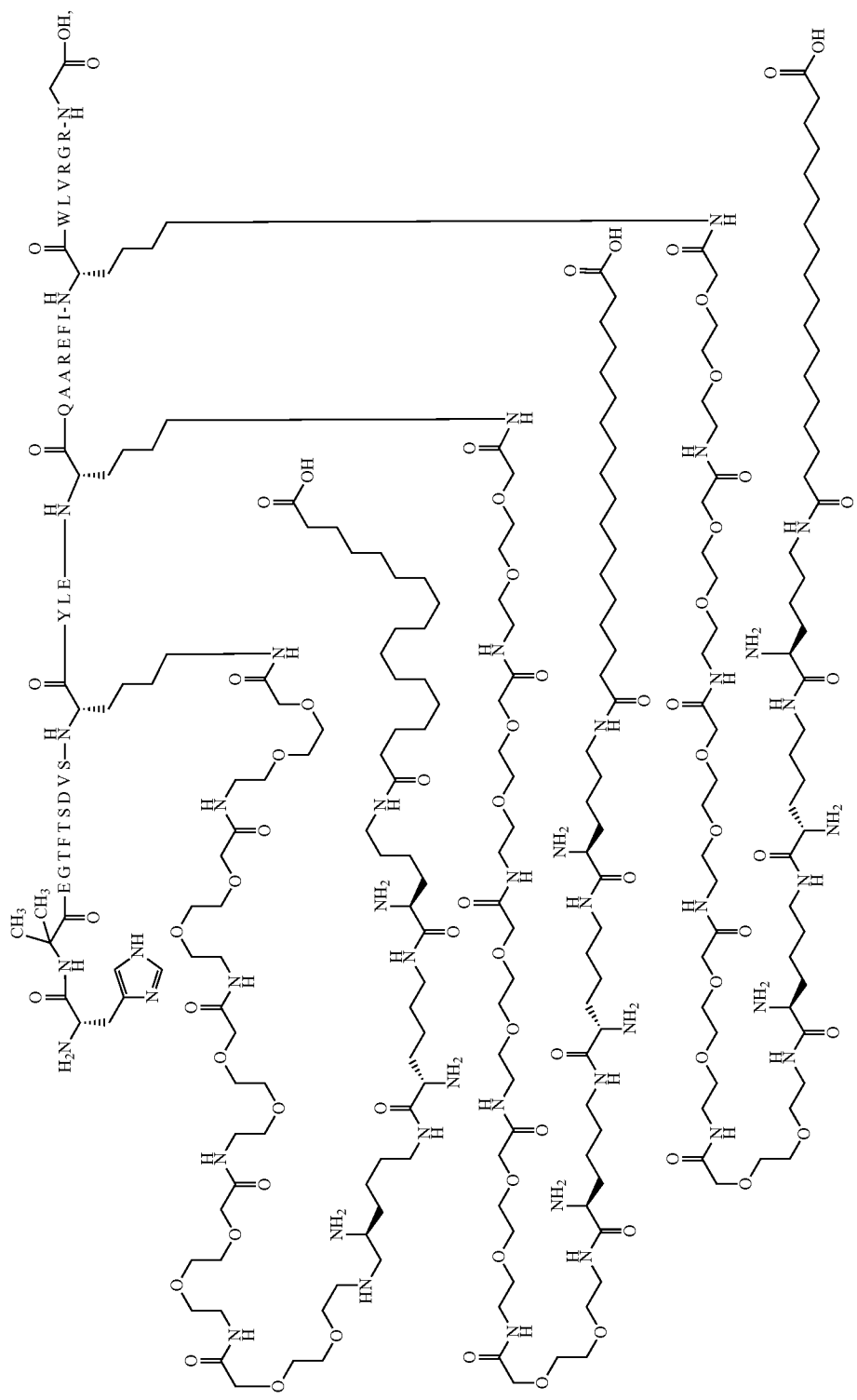

-continued
Chem. 38
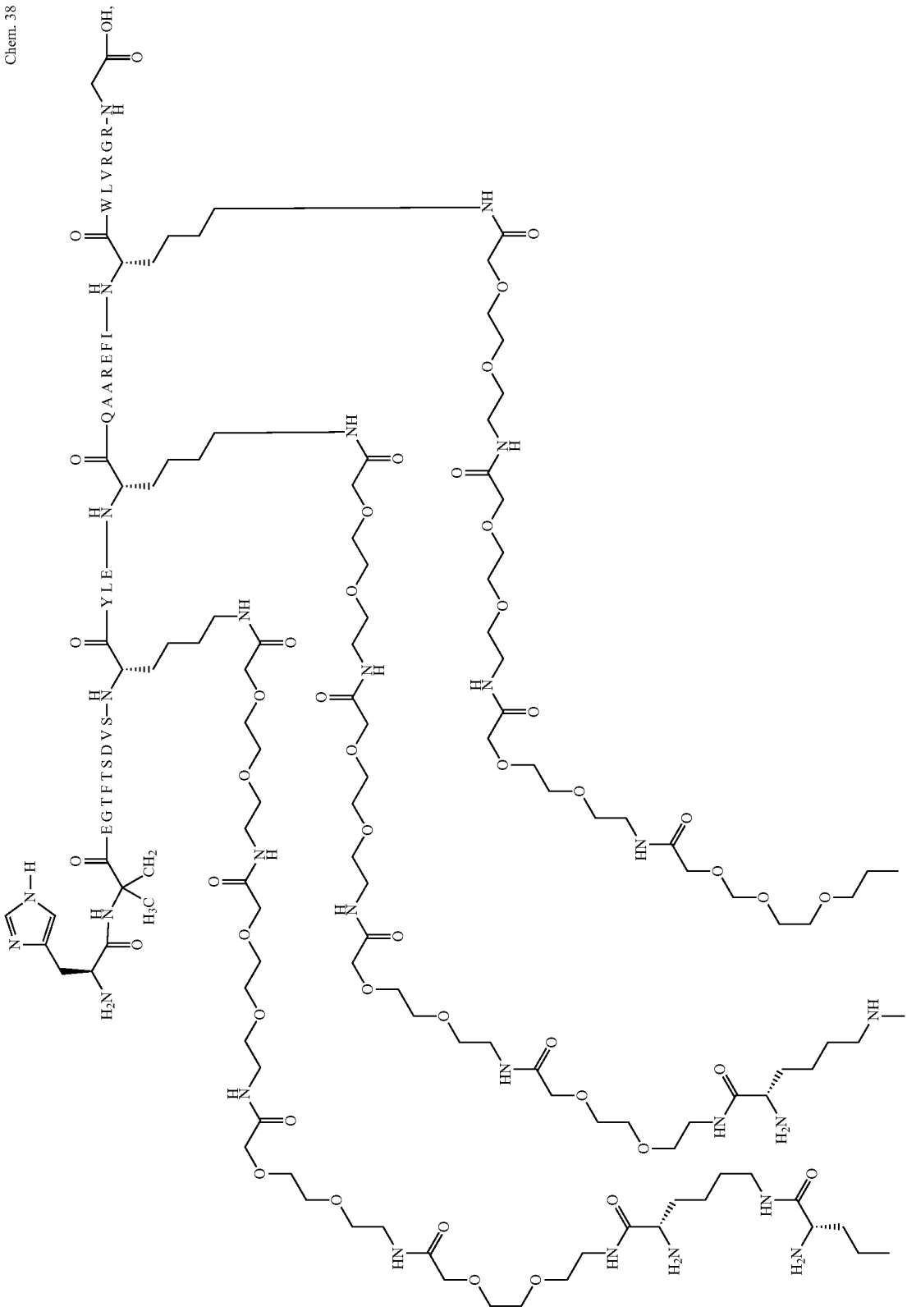

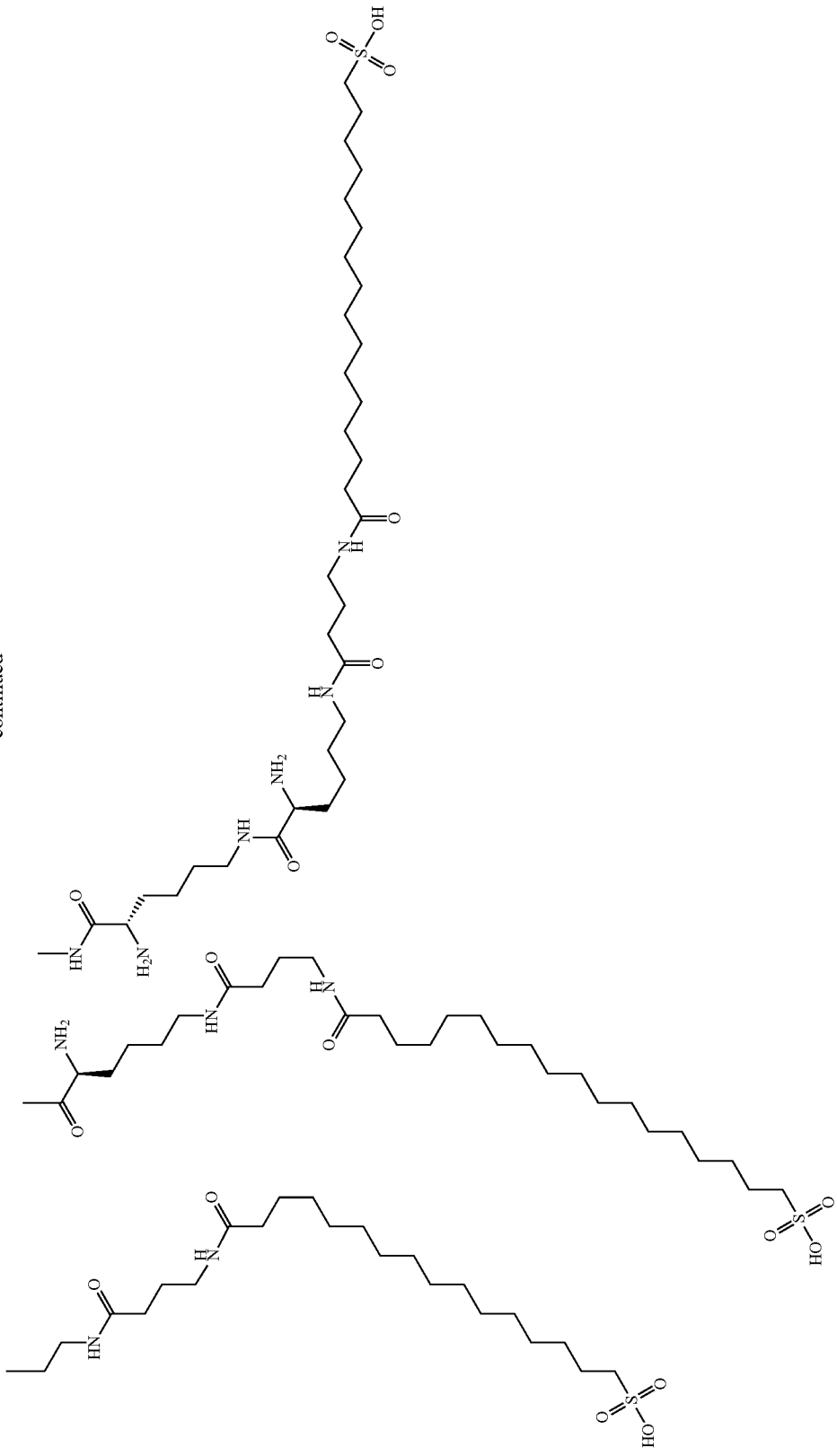

-continued
Chem. 39
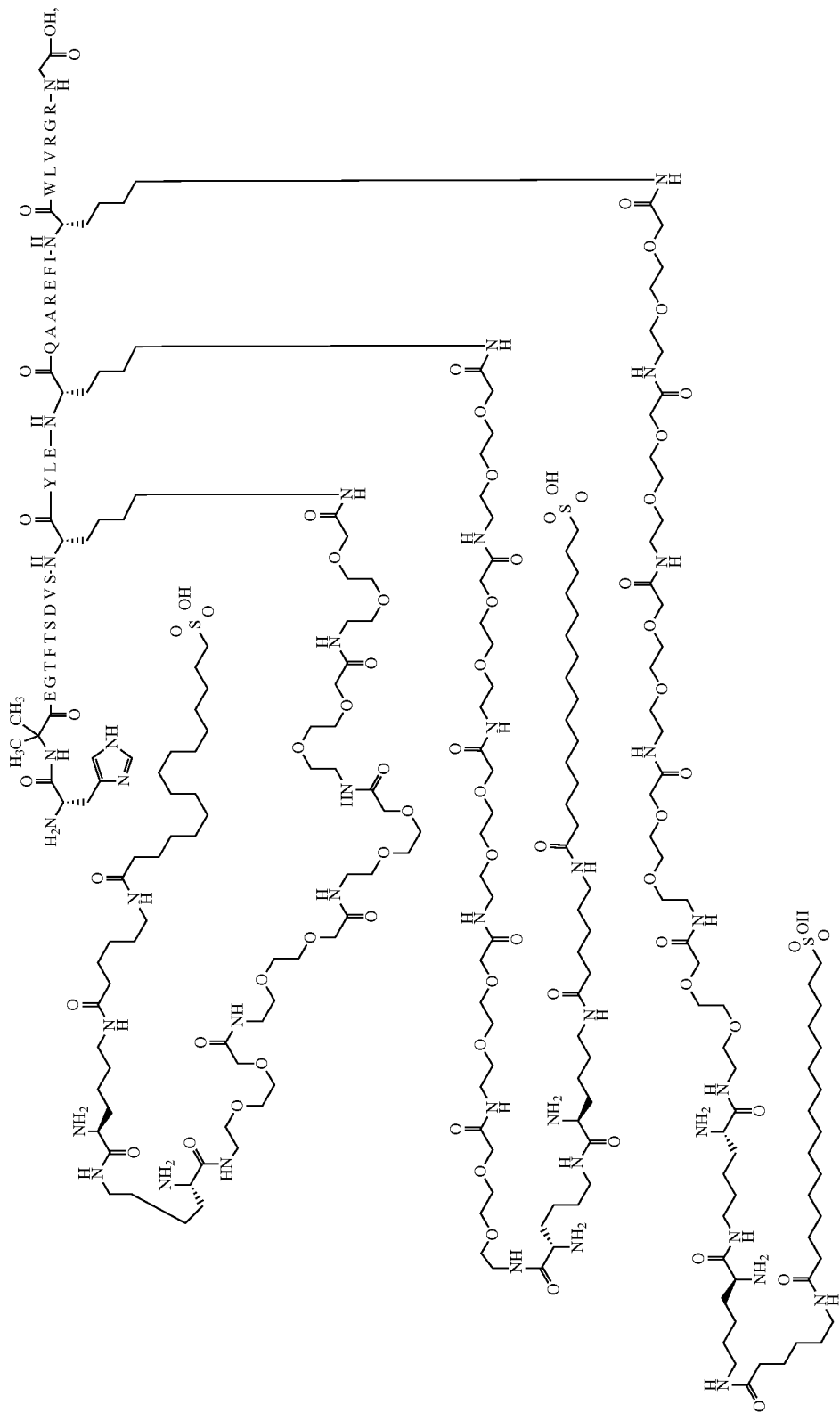

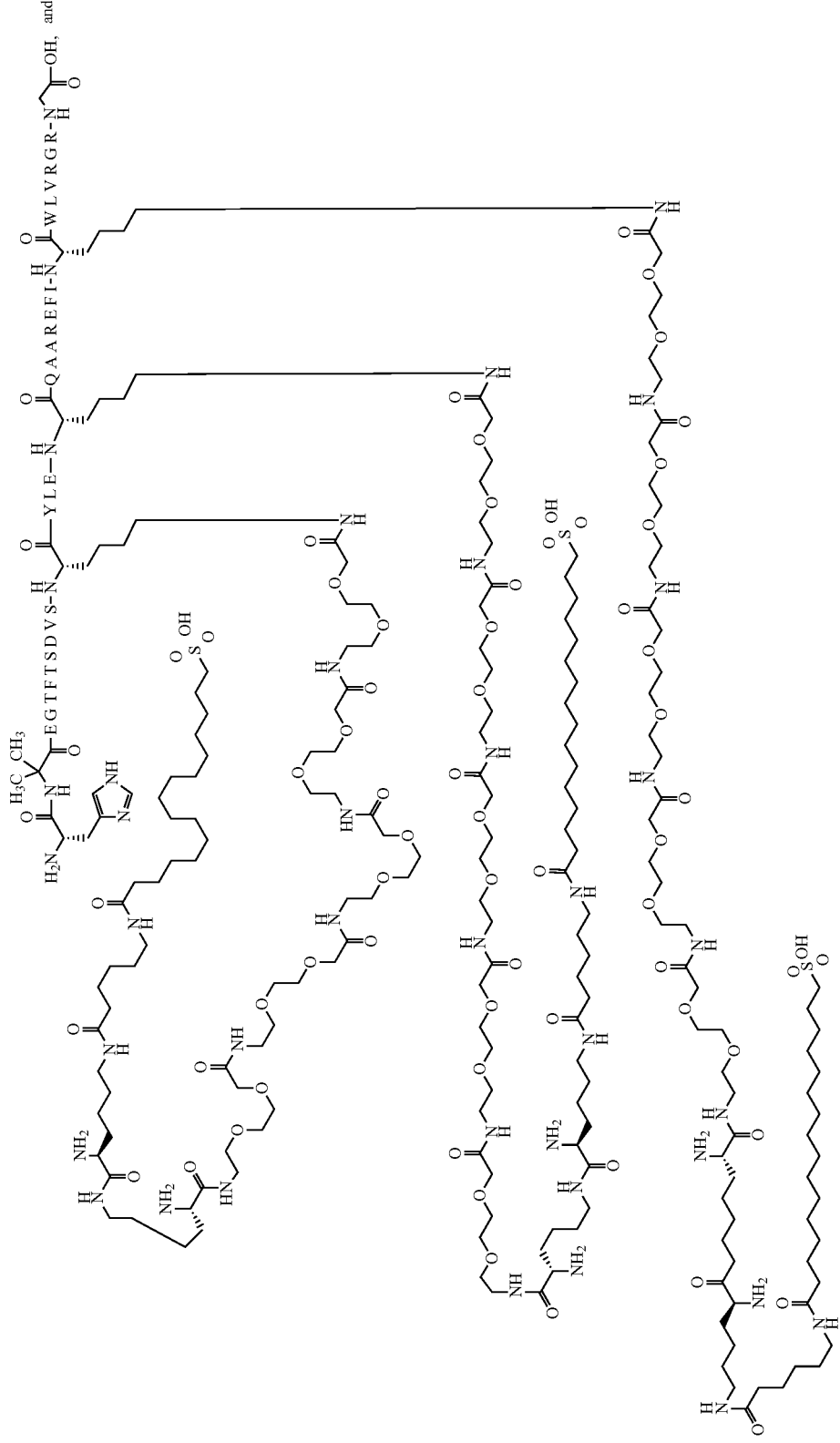

Chem. 41
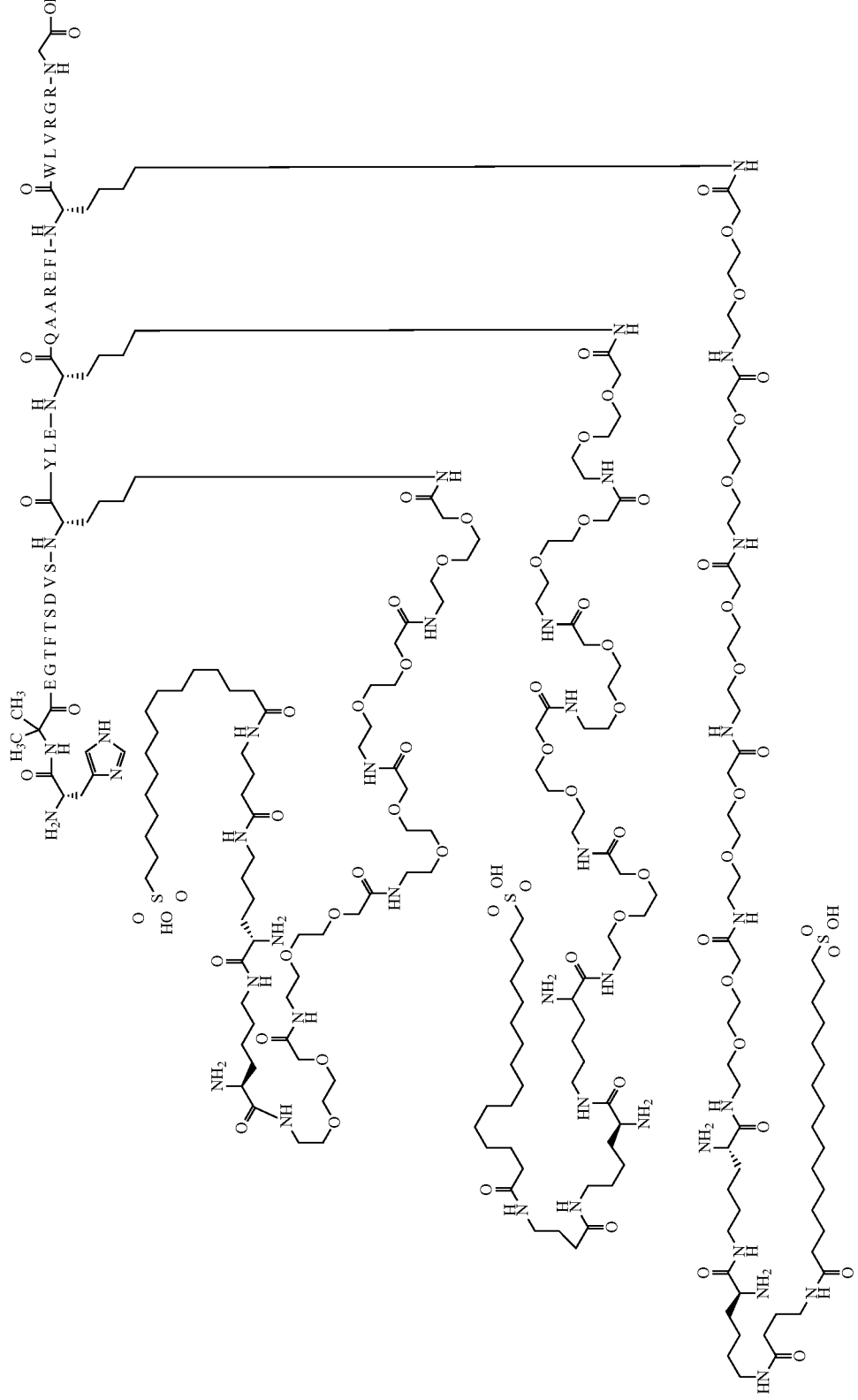

or a pharmaceutically acceptable salt, amide, or ester thereof.

9. An intermediate product in the form of a GLP-1 analogue, which comprises the following amino acid changes when compared to GLP-1(7-37) (SEQ ID NO: 1): vii) (18K, 22K, 30K); viii) (18K, 37K); ix) (18K, 27K, 37K); x) (27K, 30K, 37K); or xi) (30K, 37K);

wherein in embodiment viii) and xi) the amino acid at the position corresponding to position 26 in GLP-1(7-37) (SEQ ID NO: 1) is K.

10. An intermediate product in the form of a GLP-1 analogue, which comprises the following amino acid changes when compared to GLP-1 (7-37) (SEQ ID NO: 1): i) (8Aib, 18K, 22K, 26R, 30K, 34R); ii) (8Aib, 18K, 34R, 37K); iii) (8Aib, 18K, 22E, 26R, 27K, 34R, 37K); iv) (8Aib, 18K, 26R, 27K, 34R, 37K); v) (8Aib, 22E, 26R, 27K, 30K, 34R, 37K); or vi) (8Aib, 22E, 30K, 34R, 37K).

11. An intermediate product in the form of a GLP-1 analogue, selected from the following analogues of GLP-1 (7-37) (SEQ ID NO: 1): i) (8Aib, 18K, 22K, 26R, 30K, 34R) (SEQ ID NO: 2); ii) (8Aib, 18K, 34R, 37K) (SEQ ID NO: 3); iii) (8Aib, 18K, 22E, 26R, 27K, 34R, 37K) (SEQ ID NO: 4); iv) (8Aib, 18K, 26R, 27K, 34R, 37K) (SEQ ID NO: 5); v) (8Aib, 22E, 26R, 27K, 30K, 34R, 37K) (SEQ ID NO: 6); and vi) (8Aib, 22E, 30K, 34R, 37K) (SEQ ID NO: 7).

12. A pharmaceutical composition comprising a derivative according to claim 1, and a pharmaceutically acceptable excipient.

13. A method for
(i) treating hyperglycemia, type 2 diabetes, impaired glucose tolerance, type 1 diabetes, non-insulin dependent diabetes, MODY (maturity onset diabetes of the young), p gestational diabetes,
(ii) reduction of HbA1C;
(iii) delaying diabetic disease progression, delaying the progression of impaired glucose tolerance (IGT) to insulin requiring type 2 diabetes, delaying insulin resistance, or delaying the progression of non-insulin requiring type 2 diabetes to insulin requiring type 2 diabetes; or
(iv) treating an eating disorder , by decreasing food intake, reducing body weight, suppressing appetite, or inducing satiety;

said method comprising administering to said subject an effective amount of the pharmaceutical composition of claim 12.

* * * * *

UNITED STATES PATENT AND TRADEMARK OFFICE
CERTIFICATE OF CORRECTION

PATENT NO. : 10,266,577 B2
APPLICATION NO. : 14/909543
DATED : April 23, 2019
INVENTOR(S) : Per Sauerberg et al.

Page 1 of 3

It is certified that error appears in the above-identified patent and that said Letters Patent is hereby corrected as shown below:

In the Claims
At Column 158, Claim number 8, Chem. 31, please replace with the following structure:

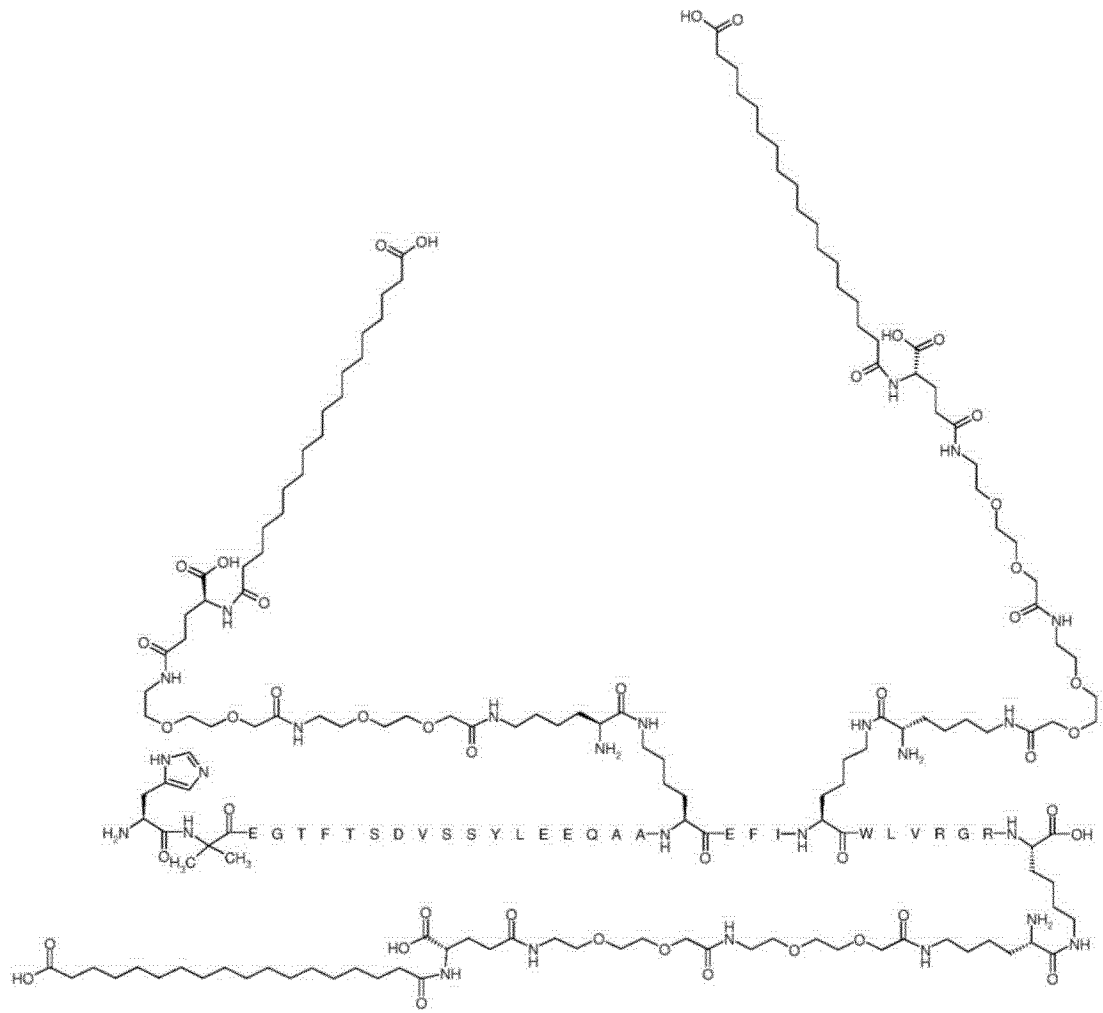

Signed and Sealed this
Tenth Day of September, 2019

Andrei Iancu
*Director of the United States Patent and Trademark Office*

CERTIFICATE OF CORRECTION (continued)

At Column 163, Claim number 8, Chem. 34, please replace with the following structure:

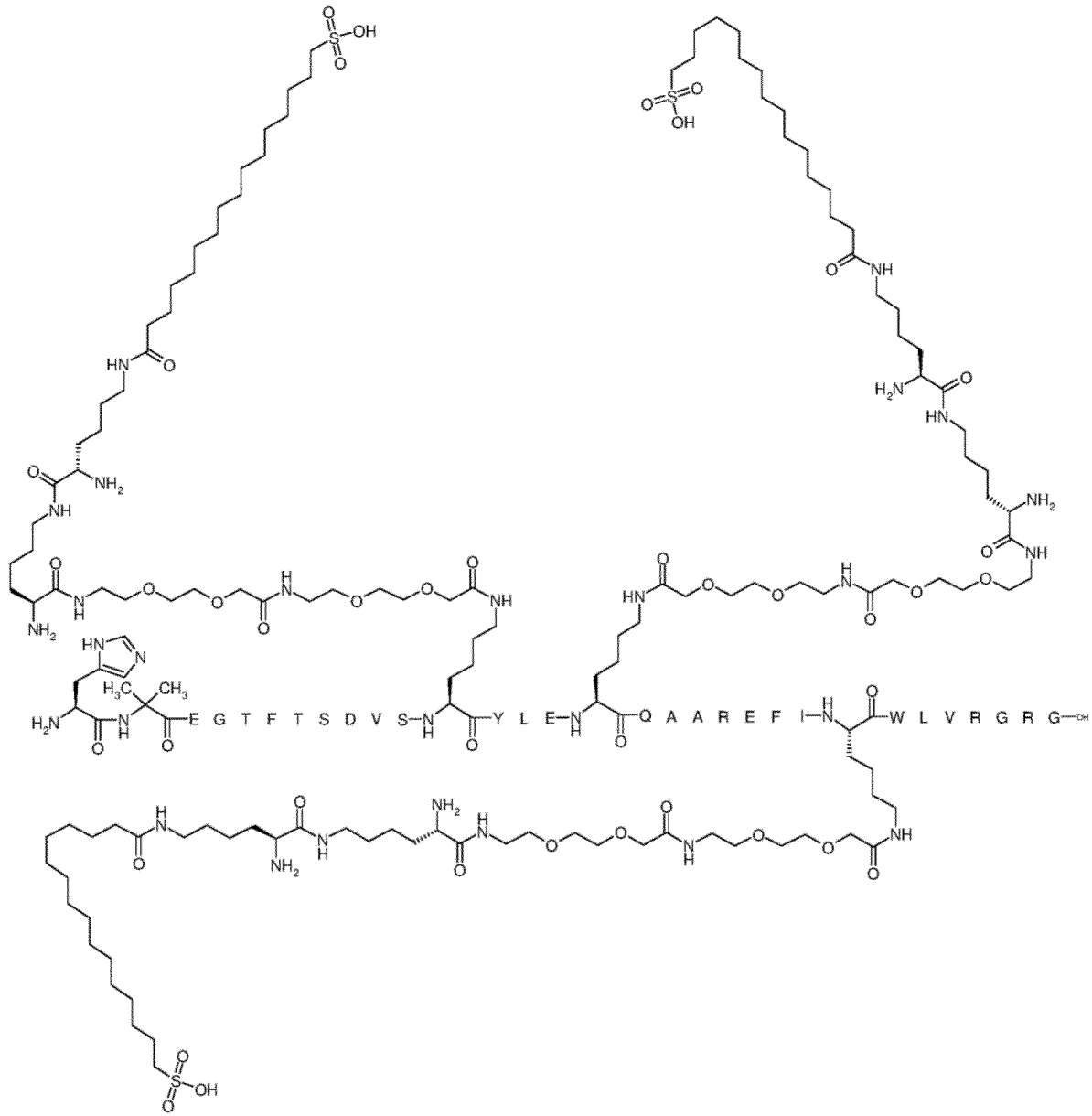

CERTIFICATE OF CORRECTION (continued)

At Column 167, Claim number 8, Chem. 36, please replace with the following structure:

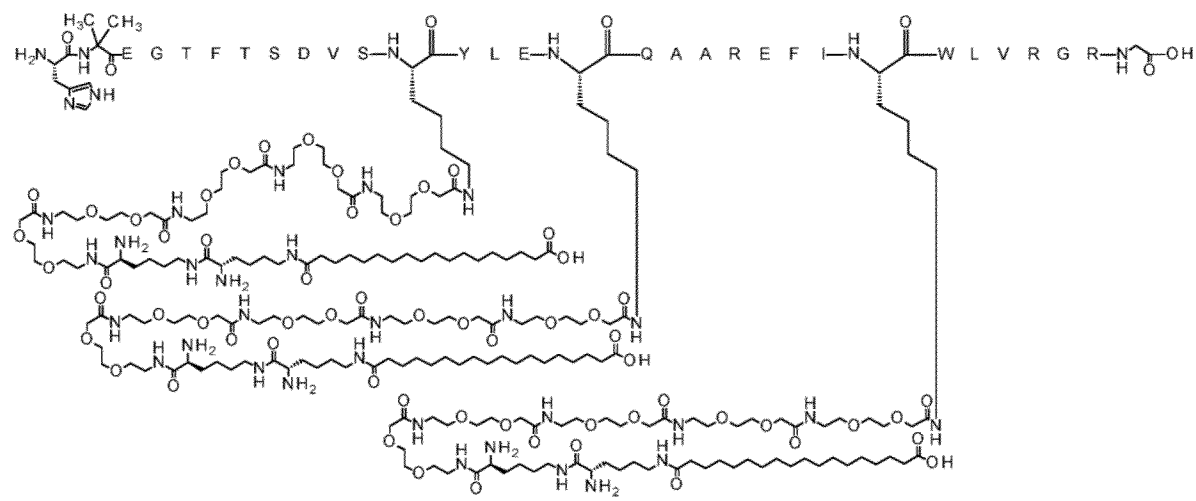

UNITED STATES PATENT AND TRADEMARK OFFICE
CERTIFICATE OF CORRECTION

PATENT NO. : 10,266,577 B2  
APPLICATION NO. : 14/909543  
DATED : April 23, 2019  
INVENTOR(S) : Per Sauerberg Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 73 days.

Signed and Sealed this  
Seventeenth Day of March, 2020

Andrei Iancu  
*Director of the United States Patent and Trademark Office*